(12) United States Patent
Brode, III et al.

(10) Patent No.: US 6,599,730 B1
(45) Date of Patent: *Jul. 29, 2003

(54) SUBTILISIN 309 VARIANTS HAVING DECREASED ADSORPTION AND INCREASED HYDROLYSIS

(75) Inventors: Philip Frederick Brode, III, Cincinnati, OH (US); Bobby Lee Barnett, Cincinnati, OH (US); Donn Nelton Rubingh, Cincinnati, OH (US); Chanchal Kamur Ghosh, West Chester, OH (US)

(73) Assignee: Procter & Gamble Company, Cincinnati, OH (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/400,068

(22) Filed: Mar. 7, 1995

Related U.S. Application Data

(63) Continuation-in-part of application No. 08/237,938, filed on May 2, 1994, now abandoned.

(51) Int. Cl.⁷ ............................ C12N 9/56; C12N 15/57; C12N 15/74; C11D 3/386
(52) U.S. Cl. .................. 435/221; 435/69.1; 435/252.3; 435/320.1; 435/471; 510/392; 536/23.2
(58) Field of Search ............................. 435/221, 69.1; 536/23.2; 510/320, 326

(56) References Cited

U.S. PATENT DOCUMENTS

| | | | |
|---|---|---|---|
| 4,760,025 A | | 7/1988 | Estell et al. .............. 435/222 |
| 4,908,773 A | | 3/1990 | Pantoliano et al. ......... 364/496 |
| 4,914,031 A | | 4/1990 | Zukowsky et al. ......... 435/222 |
| 4,980,288 A | | 12/1990 | Bryan et al. .............. 435/222 |
| 4,990,452 A | | 2/1991 | Bryan et al. .............. 435/222 |
| 5,013,657 A | | 5/1991 | Bryan et al. ............. 435/172.3 |
| 5,116,741 A | | 5/1992 | Bryan et al. ................ 435/87 |
| 5,118,623 A | * | 6/1992 | Boguslawski et al. ...... 510/374 |
| 5,155,033 A | * | 10/1992 | Estell et al. .............. 435/221 |
| 5,182,204 A | * | 1/1993 | Estell et al. .............. 435/222 |
| 5,185,258 A | * | 2/1993 | Caldwell et al. ........... 435/220 |
| 5,208,158 A | * | 5/1993 | Bech et al. .............. 435/219 |
| 5,217,878 A | * | 6/1993 | van Eekelen et al. ...... 435/69.1 |
| 5,240,632 A | * | 8/1993 | Brumbaugh ................ 252/95 |
| 5,244,791 A | * | 9/1993 | Estell ..................... 435/68.1 |
| 5,246,849 A | | 9/1993 | Bryan et al. .............. 435/220 |
| 5,260,207 A | * | 11/1993 | Pantoliano et al. ......... 435/221 |

FOREIGN PATENT DOCUMENTS

| | | |
|---|---|---|
| AU | 8772281 | 11/1987 |
| EP | 0 251 446 A2 * | 4/1987 |
| EP | 0 260 105 | 3/1988 |
| EP | 0 328 229 A1 * | 8/1989 |
| EP | 0 357 157 A1 * | 3/1990 |
| EP | 0 380 362 | 8/1990 |
| EP | 0 398 539 | 11/1990 |
| EP | 0 405 901 A1 | 1/1991 |
| EP | 0 405 902 A1 | 1/1991 |
| WO | 87/04461 | 7/1987 |
| WO | 87/05050 | 8/1987 |
| WO | WO 88/08033 A1 * | 10/1988 |
| WO | 89/06279 | 1/1989 |
| WO | WO 89/07642 * | 8/1989 |
| WO | 91/00345 | 1/1991 |
| WO | WO 91/14420 A1 * | 11/1991 |
| WO | WO 92/02615 A1 * | 2/1992 |
| WO | WO 92/08778 A1 * | 5/1992 |
| WO | 92/11357 | 7/1992 |
| WO | WO 92/11357 A1 * | 7/1992 |
| WO | WO 94/02618 A1 * | 2/1994 |
| WO | 94/02618 | 2/1994 |
| WO | WO 95/07991 A2 * | 3/1995 |
| WO | 95/07991 | 3/1995 |
| WO | WO 95/30010 A1 * | 4/1995 |
| WO | WO 95/30011 A1 * | 4/1995 |
| WO | WO 88/08028 A1 * | 10/1998 |

OTHER PUBLICATIONS

Thomas, P. G., et al., 1985, "Tailoring the pH dependence of enzyme catalysis using protein engineering to change a single amino acid at BPN' position 99: D99S reduces pKa", Nature, vol. 318, pp. 375–376.*

Russell, A. J. & Fersht, A. R., 1987, "Rational modification of enzyme catalysis by engineering surface charge", Nature, vol. 328, pp. 496–500.*

(List continued on next page.)

*Primary Examiner*—Ponnathapu Achutamurthy
*Assistant Examiner*—William W. Moore
(74) *Attorney, Agent, or Firm*—Frank Taffy; Len Lewis; Steve W. Miller

(57) ABSTRACT

The present invention relates to subtilisin 309 variants having a modified amino acid sequence of wild-type subtilisin 309 amino acid sequence, the wild-type amino acid sequence comprising a first loop region, a second loop region, a third loop region, a fourth loop region, a fifth loop region and a sixth loop region; wherein the modified amino acid sequence comprises different amino acids than that occurring in wild-type subtilisin 309 (i.e., substitution) at specifically identified positions in one or more of the loop regions whereby the subtilisin 309 variant has decreased adsorption to, and increased hydrolysis of, an insoluble substrate as compared to the wild-type subtilisin 309. The present invention also relates to DNA sequence encoding such subtilisin 309 variants. The present invention also relates to compositions comprising such subtilisin 309 variants for cleaning a variety of surfaces.

(List continued on next page.)

94 Claims, 2 Drawing Sheets

U.S. PATENT DOCUMENTS

| | | | | |
|---|---|---|---|---|
| 5,275,945 | A | * 1/1994 | Hsiao et al. | 435/221 |
| RE34,606 | E | * 5/1994 | Estell et al. | 510/392 |
| 5,310,675 | A | * 5/1994 | Estell et al. | 435/320.1 |
| 5,316,941 | A | * 5/1994 | Estell et al. | 435/252.3 |
| 5,324,653 | A | * 6/1994 | van Eekelen et al. | 435/221 |
| 5,336,611 | A | * 8/1994 | van Eekelen et al. | 435/221 |
| 5,340,735 | A | * 8/1994 | Christianson et al. | 435/221 |
| 5,346,823 | A | * 9/1994 | Estell et al. | 435/221 |
| 5,352,603 | A | * 10/1994 | Vetter et al. | 435/221 |
| 5,371,008 | A | * 12/1994 | Carter et al. | 435/222 |
| 5,371,190 | A | * 12/1994 | Carter et al. | 530/350 |
| 5,389,307 | A | * 2/1995 | Lindegaard et al. | 510/320 |
| 5,397,705 | A | * 3/1995 | Zukowski et al. | 435/221 |
| 5,403,737 | A | * 4/1995 | Abrahmsen et al. | 435/252.3 |
| 5,441,882 | A | * 8/1995 | Estell et al. | 435/222 |
| 5,453,372 | A | * 9/1995 | Vetter et al. | 435/222 |
| 5,470,733 | A | * 11/1995 | Bryan et al. | 435/222 |
| 5,472,855 | A | * 12/1995 | Carter et al. | 435/68.1 |
| 5,482,849 | A | * 1/1996 | Branner et al. | 435/222 |
| 5,500,364 | A | * 3/1996 | Christianson et al. | 435/221 |
| 5,567,601 | A | * 10/1996 | Bryan et al. | 435/222 |
| 5,629,173 | A | * 5/1997 | Abrahmsen et al. | 435/68.1 |
| 5,631,217 | A | * 5/1997 | Branner et al. | 510/320 |
| 5,652,136 | A | * 7/1997 | Carter et al. | 435/252.3 |
| 5,665,587 | A | * 9/1997 | Aaslyng et al. | 435/221 |
| 5,677,272 | A | * 10/1997 | Ghosh et al. | 510/306 |
| 5,679,630 | A | * 10/1997 | Baeck et al. | 510/305 |
| 5,700,676 | A | * 12/1997 | Bott et al. | 435/221 |
| 5,707,848 | A | * 1/1998 | Bryan et al. | 435/6 |
| 5,736,512 | A | * 4/1998 | Abrahmsen et al. | 514/12 |
| 5,741,664 | A | * 4/1998 | Ballinger et al. | 435/221 |
| 5,741,694 | A | * 4/1998 | Hastrup et al. | 435/221 |
| 5,763,257 | A | * 6/1998 | Bott et al. | 435/221 |
| 5,801,038 | A | * 9/1998 | Bott et al. | 435/221 |
| 5,801,039 | A | * 9/1998 | Maurer et al. | 435/221 |
| 5,955,340 | A | * 9/1999 | Bott et al. | 435/221 |
| 5,972,682 | A | * 10/1999 | Bott et al. | 435/221 |
| 5,985,639 | A | * 11/1999 | Christianson et al. | 435/221 |
| 6,197,567 | B1 | * 3/2001 | Aaslyng et al. | 435/221 |
| 6,197,589 | B1 | * 3/2001 | Maurer et al. | 435/471 |
| 6,271,012 | B1 | * 8/2001 | van Eekelen et al. | 435/221 |
| 6,287,841 | B1 | * 9/2001 | Mulleners et al. | 435/221 |

OTHER PUBLICATIONS

Abrahmsén, L., J. Tom, J. Burnier, K. A. Butcher, A. Kossiakoff and J. A. Wells, "Engineering Subtilisin and Its Substrates for Efficient Ligation of Peptide Bonds in Aqueous Solution", Biochemistry, vol. 30, No. 17, pp. 4151–4159 (no month identified 1991).

Arnold, F.H., "Engineering Enzymes for Non–aqueous Solvents", TibTech, vol. 8, pp. 244–249 (Sep. 1990).

Braxton, S. and J. A. Wells, "The Importance of a Distal Hydrogen Bonding Group in Stabilizing the Transition State in Subtilisin BPN'", The Journal of Biological Chemistry, vol. 266, No. 18, pp. 11797–11800 (Jun. 1991).

Brode, P. F., III and D. S. Rauch, "Subtilisin BPN': Activity on an Immobilized Substrate", Langmuir, vol. 8, No. 5, pp. 1325–1329 (no month identified 1992).

Brode, P.F. III, C.R. Erwin, D.S. Rauch, E.S. Wang, J.M. Armpriester, B.L. Barnett, M.D. Bauer, P.R. Green, D.A. Thaman, and D.N. Rubingh, "Surface Active Variants of Subtilisin BPN': Interfacial Hydrolysis", Abstract, Keystone Symposium (Mar. 6–11, 1994).

Carter, P., L. Abrahmsén, and J. A. Wells, "Probing the Mechansim and Improving the Rate of Substrate–Assisted Catalysis in Subtilisin BPN'", Biochemistry, vol. 30, No. 25, pp. 6142–6148 (no month identified 1991).

Carter, P. and J. A. Wells, "Functional Interaction Among Catalytic Residues in Subtilisin BPN'", Proteins: Structure, Function, and Genetics, vol. 7, pp. 335–342, (no month identified 1990).

Cunningham, B. C. and J. A. Wells, "Improvement in the Alkaline Stability of Subtilisin Using An Efficient Random Mutagenesis and Screening Procedure", Protein Engineering, vol. 1, No. 4, pp. 319–325 (no month identified 1987).

Egmond, M. R., W. P. Antheunisse, P. Ravestein, A. T. A. Mooren and J. de Vlieg, "Engineering Surface Charges In A Subtilisin", First International Symposium on Subtilisin Enzymes, Hamburg, Germany, (Sep. 1992).

Estell, D.A., "Engineering Enzymes for Improved Performance in Industrial Applications", Journal of Biotechnology, vol. 28, No. 1, pp. 25–30 (Jan. 1993).

Hopp, T. P. and K. R. Woods, "Prediction of Protein Antigenic Determinants From Amino Acid Sequences", Proc. Natl. Acad. Sci. USA, vol. 78, No. 6, pp. 3824–3828 (Jun. 1981).

Mitchinson, C. and J.A. Wells, "Protein Engineering of Disulfide Bonds in Subtilisin BPN'", Biochemistry, vol. 28, No. 11, pp. 4807–4815 (no month identified 1989).

Mizushima, N., D. Spellmeyer, S. Hirono, D. Pearlman and P. Kollman, "Free Energy Perturbation Calculations on Binding and Catalysis ater Mutating Threonin 220 in Subtilisin", Journal of Biological Chemistry, vol. 266, No. 18, pp. 11801–11809 (Jun. 1991).

Pantoliano, M.W., M. Whitlow, J.F. Wood, S.W. Dodd, K.D. Hardman, M.L. Rollence and P.N. Bryan, "Large Increases in General Stability for Subtilisin BPN' through Incremental Changes in the Free Energy of Unfolding", Biochemistry, vol. 28, No. 18, pp. 7205–7213 (no month identified 1989).

Russell, A. J. and A. R. Fersht, "Rational Modification of Enzyme Catalysis by Engineering Surface Charge", Nature, vol. 328, pp. 496–500 (Aug. 1987).

Siezen, R.J., W.M. de Vos, J.A.M. Leunissen and B.W. Dijkstra, "Homology Modelling and Protein Engineering Strategy of Subtilases, the Family of Subtilisin–like Serine Proteinases", Prot. Eng., vol. 4, No. 7, pp. 719–737 (no month identified 1991).

Sternberg, M. J. E., F. R. F. Hayes, A. J. Russell, P. G. Thomas and A. R. Fersht, "Prediction of Electrostatic Effects of Engineering of Protein Charges", Nature, vol. 330, pp. 86–88 (Nov. 1987).

Wells, J.A., B.C. Cunningham, T.P. Graycar and D.A. Estell, "Recruitment of Substrate–specificity Properties from One Enzyme into a Related One by Protein Engineering", Proc. Natl. Acad. Sci., USA,, vol. 84, pp. 5167–5171 (Aug. 1987).

Wells, J.A. and D.A. Estell, "Subtilisin–An Enzyme Designed to be Engineered", TIBS 13, pp. 291–297 (Aug. 1988).

Wong, C.–H., S.–T. Chen, W. J. Hennen, J. A. Bibbs, Y.–F. Wang, J. L.–C. Liu, M. W. Pantoliano, M. Whitlow and P. N. Bryan, "Enzymes in Organic Synthesis: Use of Subtilisin and a Highly Stable Mutant Derived from Multiple Site–Specific Mutations", J. Am. Chem. Soc., vol. 112, No. 3, pp. 945–953 (no month identified 1990).

* cited by examiner

Comparison of subtilisin sequences from:

B.amyloliquefaciens

B.lentus

```
161
SSSTVGYPGKYPSVIAVGAVDSSNQRASFSSVGPELDVMA
       170              180            190
***ISYPARYANAMAVGATDQNNNRASFSQYGAGLDIVA
201
PGVSIQSTLPGNKYGAYNGTSMASPHVAGAAALILSKHPN
      210              220           230
PGVNVQSTYPGSTYASLNGTSMATPHVAGAAALVKQKNPS
241
WTNTQVRSSLENTTTKLGDSFYYGKGLINVQAAAQ
      250              260           270
WSNVQIRNHLKNTATSLGSTNLYGSGLVNAEAATR
```

FIG 1/B

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 269 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:1:

```
Ala Gln Ser Val Pro Trp Gly Ile Ser Arg Val Gln Ala Pro Ala Ala
 1               5                  10                  15

His Asn Arg Gly Leu Thr Gly Ser Gly Val Lys Val Ala Val Leu Asp
                20                  25                  30

Thr Gly Ile Ser Thr His Pro Asp Leu Asn Ile Arg Gly Gly Ala Ser
            35                  40                  45

Phe Val Pro Gly Glu Pro Ser Thr Gln Asp Gly Asn Gly His Gly Thr
        50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
                100                 105                 110

Gly Asn Asn Gly Met His Val Ala Asn Leu Ser Leu Gly Ser Pro Ser
            115                 120                 125

Pro Ser Ala Thr Leu Glu Gln Ala Val Asn Ser Ala Thr Ser Arg Gly
```

```
                            130                 135                 140
Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
                180                 185                 190

Val Ala Pro Gly Val Asn Val Gln Ser Thr Tyr Pro Gly Ser Thr Tyr
                195                 200                 205

Ala Ser Leu Asn Gly Thr Ser Met Ala Thr Pro His Val Ala Gly Ala
                210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
                260                 265
```

(2) INFORMATION FOR SEQ ID NO:2:

(i) SEQUENCE CHARACTERISTICS:
        (A) LENGTH: 275 amino acids
        (B) TYPE: amino acid
        (D) TOPOLOGY: linear (ii) MOLECULE TYPE: protein (xi) SEQUENCE DESCRIPTION: SEQ ID NO:2:

```
Ala Gln Ser Val Pro Tyr Gly Val Ser Gln Ile Lys Ala Pro Ala Leu
1                   5                   10                  15

His Ser Gln Gly Tyr Thr Gly Ser Asn Val Lys Val Ala Val Ile Asp
                20                  25                  30

Ser Gly Ile Asp Ser Ser His Pro Asp Leu Lys Val Ala Gly Gly Ala
                35                  40                  45

Ser Met Val Pro Ser Glu Thr Asn Pro Phe Gln Asp Asn Asn Ser His
                50                  55                  60

Gly Thr His Val Ala Gly Thr Val Ala Ala Leu Asn Asn Ser Ile Gly
65                  70                  75                  80

Val Leu Gly Val Ala Pro Ser Ala Ser Leu Tyr Ala Val Lys Val Leu
                85                  90                  95

Gly Ala Asp Gly Ser Gly Gln Tyr Ser Trp Ile Ile Asn Gly Ile Glu
                100                 105                 110

Trp Ala Ile Ala Asn Asn Met Asp Val Ile Asn Met Ser Leu Gly Gly
                115                 120                 125

Pro Ser Gly Ser Ala Ala Leu Lys Ala Ala Val Asp Lys Ala Val Ala
130                 135                 140

Ser Gly Val Val Val Ala Ala Ala Gly Asn Glu Gly Thr Ser Gly
145                 150                 155                 160

Ser Ser Ser Thr Val Gly Tyr Pro Gly Lys Tyr Pro Ser Val Ile Ala
                165                 170                 175

Val Gly Ala Val Asp Ser Ser Asn Gln Arg Ala Ser Phe Ser Ser Val
                180                 185                 190

Gly Pro Glu Leu Asp Val Met Ala Pro Gly Val Ser Ile Gln Ser Thr
                195                 200                 205

Leu Pro Gly Asn Lys Tyr Gly Ala Tyr Asn Gly Thr Ser Met Ala Ser
                210                 215                 220
```

```
Pro His Val Ala Gly Ala Ala Ala Leu Ile Leu Ser Lys His Pro Asn
225             230             235             240

Trp Thr Asn Thr Gln Val Arg Ser Ser Leu Glu Asn Thr Thr Thr Lys
            245             250             255

Leu Gly Asp Ser Phe Tyr Tyr Gly Lys Gly Leu Ile Asn Val Gln Ala
            260             265             270

Ala Ala Gln
    275
```

SUBTILISIN 309 VARIANTS HAVING DECREASED ADSORPTION AND INCREASED HYDROLYSIS

This is a continuation-in-part of application Ser. No. 08/237,938, filed on May 2, 1994, now abandoned.

TECHNICAL FIELD

The present invention relates to novel enzyme variants useful in a variety of cleaning compositions, and the genes encoding such enzyme variants.

BACKGROUND

Enzymes make up the largest class of naturally occurring proteins. Each class of enzyme generally catalyzes (accelerates a reaction without being consumed) a different kind of chemical reaction. One class of enzymes known as proteases, are known for their ability to hydrolyze (break down a compound into two or more simpler compounds with the uptake of the H and OH parts of a water molecule on either side of the chemical bond cleaved) other proteins. This ability to hydrolyze proteins has been taken advantage of by incorporating naturally occurring and protein engineered proteases as an additive to laundry detergent preparations. Many stains on clothes are proteinaceous and widespecificity proteases can substantially improve removal of such stains.

Unfortunately, the efficacy level of these proteins in their natural, bacterial environment, frequently does not translate into the relatively unnatural wash environment. Specifically, protease characteristics such as thermal stability, pH stability, oxidative stability and substrate specificity are not necessarily optimized for utilization outside the natural environment of the enzyme.

The amino acid sequence of the protease determines the characteristics of the protease. A change of the amino acid sequence of the protease may alter the properties of the enzyme to varying degrees, or may even inactivate the enzyme, depending upon the location, nature and/or magnitude of the change in the amino acid sequence. Several approaches have been taken to alter the wild-type amino acid sequence of proteases in an attempt to improve their properties, with the goal of increasing the efficacy of the protease in the wash environment. These approaches include altering the amino acid sequence to enhance thermal stability and to improve oxidation stability under quite diverse conditions.

Despite the variety of approaches described in the art, there is a continuing need for new effective variants of proteases useful for cleaning a variety of surfaces.

OBJECTS OF THE PRESENT INVENTION

It is an object of the present invention to provide subtilisin 309 enzyme variants having improved hydrolysis versus the wild-type of the enzyme.

It is also an object of the present invention to provide cleaning compositions comprising these subtilisin 309 enzyme variants.

SUMMARY

The present invention relates to subtilisin 309 variants having a modified amino acid sequence of wild-type subtilisin 309 amino acid sequence, the wild-type amino acid sequence comprising a first loop region, a second loop region, a third loop region, a fourth loop region, a fifth loop region and a sixth loop region; wherein the modified amino acid sequence comprises different amino acids than that occurring in wild-type subtilisin 309 (i.e., substitution) at specifically identified positions in one or more of the loop regions whereby the subtilisin 309 variant has decreased adsorption to, and increased hydrolysis of, an insoluble substrate as compared to the wild-type subtilisin 309. The present invention also relates to DNA sequences encoding such subtilisin 309 variants. The present invention also relates to compositions comprising such subtilisin 309 variants for cleaning a variety of surfaces.

BRIEF DESCRIPTION OF THE DRAWINGS

FIG. 1A and FIG. 1B depict the amino acid sequences of subtilisin BPN' and subtilisin 309. The top line represents the amino acid sequence of subtilisin BPN' (SEQ ID NO:2), which is derived from *Bacillus amyloliquefaciens;* the bottom line represents the amino acid sequence of subtilisin 309 (SEQ ID NO:1), which is derived from *Bacillus lentus.* The symbol * in the sequence for subtilisin 309 denotes the absence of specific amino acid residues as compared to subtilisin BPN'.

DESCRIPTION

I. Subtilisin 309 Variants

This invention pertains to subtilisin enzymes, in particular subtilisin 309, that have been modified by mutating the various nucleotide sequences that code for the enzyme, thereby modifying the amino acid sequence of the enzyme. The modified subtilisin enzymes (hereinafter, "subtilisin 309 variants") of the present invention have decreased adsorption to and increased hydrolysis of an insoluble substrate as compared to the wild-type subtilisin. The present invention also pertains to the mutant genes encoding for such subtilisin 309 variants.

Figure 1:
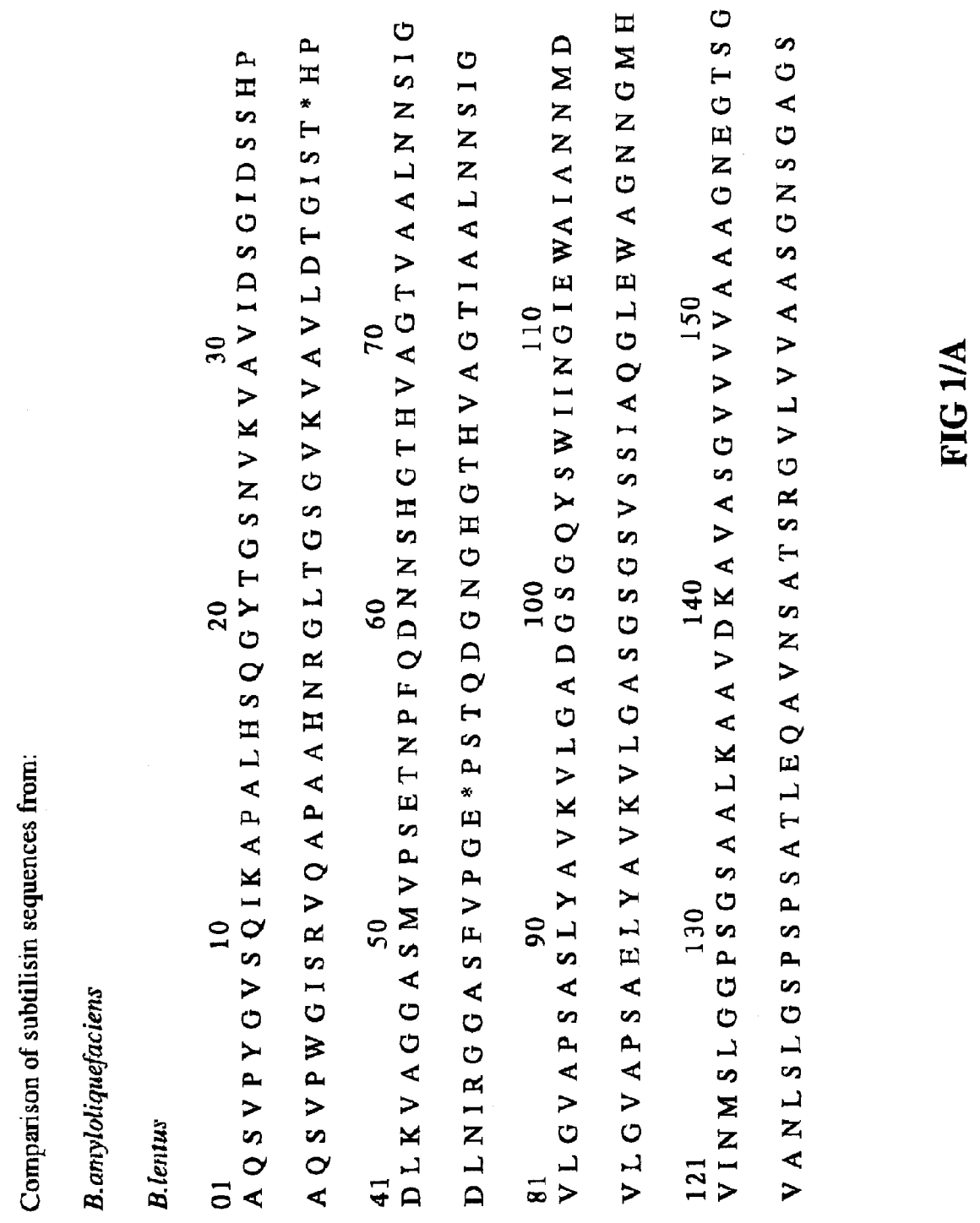

When refering to the amino acid sequence of native subtilisin 309 (having 269 amino acid residues), the amino acid sequence of subtilisin BPN' (having 275 amino acid residues) is frequently used as the standard. The use of "BPN' numbering" has become the coventional method for identifying residue positions in all subtilisins. The amino acid sequences for native subtilisin BPN' and native subtilisin 309 are set forth in FIGS. 1A and 1B. The symbol '*' in the sequence for subtilisin 309 in FIGS. 1A and 1B denotes the absence of specific amino acid residues compared to native subtilisin BPN'. However, for purposes of discussion herein, reference to amino acid positions shall be based on "true" subtilisin 309 numbering (e.g., refer to SEQ ID NO:1, discussed below).

The subtilisin 309 enzymes of this invention belong to a class of enzymes known as proteases. A protease is a catalyst for the cleavage of peptide bonds. One type of protease is a serine protease. A serine protease is distinguished by the fact that there is an essential serine residue at the active site.

The observation that an enzyme's rate of hydrolysis of soluble substrates increases with enzyme concentration is well documented. It would therefore seem plausible that for surface bound substrates, such as is encountered in many cleaning applications, the rate of hydrolysis would increase with increasing surface concentration. This has been shown to be the case. (Brode, P. F. III and D. S. Rauch, LANGMUIR, "Subtilisin BPN': Activity on an Immobilized Substrate", Vol. 8, pp. 1325–1329 (1992)). In fact, a linear dependence of rate upon surface concentration was found for insoluble substrates when the surface concentration of the enzyme was varied. (Rubingh, D. N. and M. D. Bauer, "Catalysis of Hydrolysis by Proteases at the Protein-Solution Interface," in POLYMER SOLUTIONS, BLENDS AND INTERFACES, Ed. by I. Noda and D. N. Ribingh, Elsevier, p. 464 (1992)). Surprisingly, when seeking to apply this principle in the search for variant proteases which give better cleaning performance, we did not find that enzymes which adsorb more give better performance. In fact, we surprisingly determined the opposite to be the case: decreased adsorption by an enzyme to a substrate resulted in increased hydrolysis of the substrate (i.e., better cleaning performance).

While not wishing to be bound by theory, it is believed that improved performance, when comparing one variant to another, is a result of the fact that enzymes which adsorb less are also less tightly bound and therefore more highly mobile on the surface from which the insoluble protein substrate is to be removed. At comparable enzyme solution concentrations, this increased mobility is sufficient to outweigh any advantage that is conferred by delivering a higher concentration of enzyme to the surface.

The mutations described herein are designed to change (i.e., decrease) the adsorption of the enzyme to surface-bound soils. In subtilisin 309, certain amino acids form exterior loops on the enzyme molecule. For purposes of discussion, these loops shall be referred to as the first, second, third, fourth and fifth loop regions. Specifically, positions 57–64 form the first loop region; positions 93–105 form the second loop region; positions 124–131 form the third loop region; positions 152–161 form the fourth loop region; position 181–185 form the fifth loop region; and positions 193–214 form the sixth loop region (position numbering analagous to positions in the amino acid sequence for wild-type subtilisin 309 (SEQ ID NO:1)).

It believed that these loop regions play a significant role in the adsorption of the enzyme molecule to a surface-bound peptide, and specific mutations in one or more of these loop regions will have a significant effect on this adsorption. While not wishing to be bound by theory, it is believed that the loop regions are important to the adsorption of the subtilisin 309 molecule for at least two reasons. First, the amino acids which comprise the loop regions can make close contacts with any surfaces to which the molecule is exposed. Second, the proximity of the loop regions to the active-site and binding pocket of the subtilisin 309 molecule gives them a role in the catalytically productive adsorption of the enzyme to surface-bound substrates (peptides/protein soils).

The following is a list of abbreviations used herein to described amino acids:

| Amino Acid | Three-letter Abbreviation | One-letter Symbol |
|---|---|---|
| Alanine | Ala | A |
| Arginine | Arg | R |
| Asparagine | Asn | N |
| Aspartic Acid | Asp | D |
| Asparagine or Aspartic Acid | Asp | D |
| Cysteine | Cys | C |
| Glutamine | Gln | Q |
| Glutamic Acid | Glu | E |
| Glutamine or Glutamic Acid | Glx | Z |
| Glycine | Gly | G |
| Histidine | His | H |
| Isoleucine | Ile | I |

-continued

| Amino Acid | Three-letter Abbreviation | One-letter Symbol |
|---|---|---|
| Leucine | Leu | L |
| Lysine | Lys | K |
| Methionine | Met | M |
| Phenylalanine | Phe | F |
| Proline | Phe | F |
| Serine | Ser | S |
| Threonine | Thr | T |
| Tryptophan | Trp | W |
| Tyrosine | Tyr | Y |
| Valine | Val | V |
| No amino acid at position | Xaa | * |

As used herein, "variant" means an enzyme having an amino acid sequence which differs from that of wild-type.

As used herein, "mutant subtilisin 309 DNA sequence" means a DNA sequence coding for a subtilisin 309 variant.

As used herein, "wild-type subtilisin 309" refers to an enzyme represented by SEQ ID NO:1. The amino acid sequence for subtilisin 309 is further described in World Patent Publication 89/06279 (1989), incorporated herein by reference. See also, World Patent Publication 94/02618, published Feb. 3, 1994 by Mulleners et al.

As used herein, the term "subtilisin 309 wild-type amino acid sequence" encompasses SEQ ID NO:1 as well as SEQ ID NO:1 having modifications to the amino acid sequence other than at any of positions 57–64, 93–105, 124–131, 152–161, 181–185 and 193–214.

As used herein, "more hydrophilic amino acid" refers to any other amino acid having greater hydrophilicity than a subject amino acid with reference to the hydrophilicity table below. The following hydrophilicity table (Table 1) lists amino acids in descending order of increasing hydrophilicity (see Hopp, T. P., and Woods, K. R., "Prediction of Protein Antigenic Determinants from Amino Acid Sequences", PROCEEDINGS OF THE NATIONAL ACADEMY OF SCIENCE USA, Vol. 78, pp. 3824–3828, 1981, incorporated herein by reference).

TABLE 1

| Amino Acid | Hydrophilicity Value |
|---|---|
| Trp | −3.4 |
| Phe | −2.5 |
| Tyr | −2.3 |
| Leu, Ile | −1.8 |
| Val | −1.5 |
| Met | −1.3 |
| Cys | −1.0 |
| Ala, His | −0.5 |
| Thr | −0.4 |
| Pro, Gly | −0.0 |
| Gln, Asn | 0.2 |
| Ser | 0.3 |
| Arg$^+$, Lys$^+$, Glu$^-$, Asp$^-$ | 3.0 |

Table 1 also indicates which amino acids carry a charge (this characteristic being based on a pH of from about 8–9). The positively charged amino acids are Arg and Lys, the negatively charged amino acids are Glu and Asp, and the remaining amino acids are neutral. In a preferred embodiment of the present invention, the substituting amino acid is either neutral or negatively charged, more preferably negatively charged (i.e., Glu or Asp).

Therefore, for example, the statement "substitute Gln with an equally or more hydrophilic amino acid which is neutral or has a negative charge" means Gln would be substituted with Asn (which is equally hydrophilic to Gln), or Ser, Glu or Asp (which are more hydrophilic than Gln); each of which are neutral or have a negative charge, and have a greater hydrophilicity value as compared to Gln. Likewise, the statement "substitute Pro with a more hydrophilic amino acid which is neutral or has a negative charge" means Pro would be substituted with Gln, Asn, Ser, Glu or Asp.

A. Loop Region 6 Substitution Variants

1. Variants comprising at least one amino acid substitution

In one embodiment of the present invention, the subtilisin 309 variant has a modified amino acid sequence of subtilisin 309 wild-type amino acid sequence, wherein the modified amino acid sequence comprises a substitution at one or more of positions 193, 194, 195, 196, 197, 199, 200, 201, 202, 203, 204, 205, 206, 207, 208, 209, 210, 211, 212, 213 or 214; whereby the subtilisin 309 variant has decreased adsorption to, and increased hydrolysis of, an insoluble substrate as compared to the wild-type subtilisin 309. Preferably, the positions having a substituted amino acid are 193, 194, 195, 196, 199, 201, 202, 203, 204, 205, 206 or 209; more preferably, 194, 195, 196, 199 or 201.

Preferably, the substituting amino acid for position 193 is Ala, Asn, Asp, Cys, Gln, Glu, Gly, His, Pro, Ser or Thr.

Preferably, the substituting amino acid for position 194 is Asn, Asp, Gln, Glu, Gly, His, Pro, Ser or Thr.

Preferably, the substituting amino acid for position 195 is Asn, Asp, Gln, Glu, Gly, Ser.

Preferably, the substituting amino acid for position 196 is Asn, Asp, Gln, Glu, Pro or Ser.

Preferably, the substituting amino acid for position 197 is Ala, Asp, Cys, Gln, Glu, Gly, His, Met, Pro or Ser.

Preferably, the substituting amino acid for position 199 is Ala, Asn, Asp, Cys, Gln, Glu, Gly, His, Met, Pro, Ser or Thr.

Preferably, the substituting amino acid for position 200 Asn, Asp, Glu or Ser.

Preferably, the substituting amino acid for position 201 is Asp or Glu.

Preferably, the substituting amino acid for position 202 is Asn, Asp, Gln, Glu, Gly, Pro or Ser.

Preferably, the substituting amino acid for position 203 is Ala, Asn, Asp, Gln, His, Ile, Met, Pro or Ser.

Preferably, the substituting amino acid for position 204 is Asn, Asp, Gln, Glu, Gly or Ser.

Preferably, the substituting amino acid for position 205 is Asn, Asp, Gln, Glu, Pro or Ser.

Preferably, the substituting amino acid for position 206 is Asp or Glu.

Preferably, the substituting amino acid for position 207 is Asn, Asp, Gln, Glu, Gly, Pro or Ser.

Preferably, the substituting amino acid for position 208 is Ala, Asn, Asp, Cys, Gln, Glu, Gly, His, Ile, Leu, Met, Pro or Val.

Preferably, the substituting amino acid for position 209 is Asn, Asp, gln, Glu, gly, His, Pro, Ser or Thr.

Preferably, the substituting amino acid for position 210 is Asp or Glu.

Preferably, the substituting amino acid for position 211 is Ala, Asn, Asp, Cys, Gln, Gly, His, Ile, Met, Pro, Ser, Thr or Val.

Preferably, the substituting amino acid for position 212 is Glu.

Preferably, the substituting amino acid for position 213 is Asn, Asp, Gln, Glu, Pro or Ser.

Preferably, the substituting amino acid for position 214 is Asn, Asp, Gln, Glu, Gly, Pro or Ser.

More preferably, the substituting amino acid for any positions 193, 194, 195, 196, 197, 199, 201, 202, 203, 204, 205, 206, 207, 208, 209, 210, 211, 212, 213 and 214 is, with reference to Table 1, is neutral or negatively charged and equally or more hydrophilic, preferably more hydrophilic, than the amino acid at the subject position in wild-type subtilisin 309.

More preferably still, the substituting amino acid for any of positions 193, 194, 195, 196, 197, 199, 200, 201, 202, 204, 205, 206, 207, 208, 209, 210, 212, 213 and 214 is Asp or Glu; and the substituting amino acid for positions 203 and 211 is Asp.

2. Variants comprising at least two amino acid substitutions

In another embodiment of the present invention, the subtilisin 309 variant has a modified amino acid sequence of subtilisin 309 wild-type amino acid sequence, wherein the modified amino acid sequence comprises a substitution at two or more of positions 193, 194, 195, 196, 197, 198, 199, 200, 201, 202, 203, 204, 205, 206, 207, 208, 209, 210, 211, 212, 213 or 214; whereby the subtilisin 309 variant has decreased adsorption to, and increased hydrolysis of, an insoluble substrate as compared to wild-type subtilisin 309. Preferably, the positions having a substituting amino acid are 193, 194, 195, 199, 201, 202, 203, 204, 205, 206, or 209; more preferably, positions 194, 195, 196, 211 or 213.

Preferably, the substituting amino acid for position 193 is Ala, Asn, Asp, Cys, Gln, Glu, Gly, His, Met, Pro, Ser or Thr.

Preferably, the substituting amino acid for position 194 is Asn, Asp, Gln, Glu, Gly, His, Pro, Ser or Thr.

Preferably, the substituting amino acid for position 195 is Asn, Asp, Gln, Glu, Gly or Ser.

Preferably, the substituting amino acid for position 196 is Asn, Asp, Gln, Glu, Pro or Ser.

Preferably, the substituting amino acid for position 197 is Ala, Asn, Asp, Cys, Gln, Glu, Gly, His, Met, Pro, Ser, or Thr.

Preferably, the substituting amino acid for position 198 is Asp, Gln, Glu or Ser.

Preferably, the substituting amino acid for position 199 is Ala, Asn, Asp, Cys, Gln, Glu, Gly, His, Met, Pro, Ser or Thr.

Preferably, the substituting amino acid for position 200 Asn, Asp, Glu or Ser.

Preferably, the substituting amino acid for position 201 is Asp or Glu.

Preferably, the substituting amino acid for position 202 is Asn, Asp, Gln, Glu, Gly, Pro or Ser.

Preferably, the substituting amino acid for position 203 is Ala, Asn, Asp, Cys, Gln, Glu, Gly, His, Ile, Met, Pro, Ser, or Thr.

Preferably, the substituting amino acid for position 204 is Asn, Asp, Gln, Glu, Gly or Ser.

Preferably, the substituting amino acid for position 205 is Asn, Asp, Gln, Glu, Pro or Ser.

Preferably, the substituting amino acid for position 206 is Asp or Glu.

Preferably, the substituting amino acid for position 207 is Asn, Asp, Gln, Glu, Gly, Pro or Ser.

Preferably, the substituting amino acid for position 208 is Ala, Asn, Asp, Cys, Gln, Glu, Gly, His, Ile, Leu, Met, Pro or Val.

Preferably, the substituting amino acid for position 209 is Asn, Asp, Gln, Glu, Gly, His, Pro, Ser or Thr.

Preferably, the substituting amino acid for position 210 is Asp or Glu.

Preferably, the substituting amino acid for position 211 is Ala, Asn, Asp, Cys, Gln, Glu, Gly, His, Ile, Met, Pro, Ser, Thr or Val.

Preferably, the substituting amino acid for position 212 is Asp, Gln, Glu or Ser. However, if position 211 is substituted with Asn, Glu or Val, then position 212 is not substituted with Asp;

Preferably, the substituting amino acid for position 213 is Asn, Asp, Gln, Glu, Pro or Ser.

Preferably, the substituting amino acid for position 214 is Asn, Asp, Gln, Glu, Gly, Pro or Ser.

More preferably, the substituting amino acid for any positions 193, 194, 195, 196, 197, 198, 199, 200, 201, 202, 203, 204, 205, 206, 207, 208, 209, 210, 211, 212, 213 and 214 is, with reference to Table 1, is neutral or negatively charged and equally or more hydrophilic, preferably more hydrophilic, than the amino acid at the subject position in wild-type subtilisin 309.

More preferably still, the substituting amino acid for any of positions 193, 194, 195, 196, 197, 198, 199, 200, 201, 202, 203, 204, 205, 206, 207, 208, 209, 210, 211, 212, 213 or 214 is Asp or Glu.

3. Variants comprising at least three amino acid substitutions

In another embodiment of the present invention, the subtilisin 309 variant has a modified amino acid sequence of subtilisin 309 wild-type amino acid sequence, wherein the modified amino acid sequence comprises a substitution at three or more of positions 193, 194, 195, 196, 197, 198, 199, 200, 201, 202, 203, 204, 205, 206, 207, 208, 209, 210, 211, 212, 213 or 214; whereby the subtilisin 309 variant has decreased adsorption to, and increased hydrolysis of, an insoluble substrate as compared to wild-type subtilisin 309. Preferably, the positions having a substituting amino acid are 193, 194, 195, 199, 201, 202, 203, 204, 205, 206, or 209; more preferably, positions 194, 195, 196, 211 or 213.

Preferably, the substituting amino acid for position 193 is Ala, Asn, Asp, Cys, Gln, Glu, Gly, His, Met, Pro, Ser or Thr.

Preferably, the substituting amino acid for position 194 is Asn, Asp, Gln, Glu, Gly, His, Pro, Ser or Thr.

Preferably, the substituting amino acid for position 195 is Asn, Asp, Gln, Glu, Gly or Ser.

Preferably, the substituting amino acid for position 196 is Asn, Asp, Gln, Glu, Pro or Ser.

Preferably, the substituting amino acid for position 197 is Ala, Asn, Asp, Cys, Gln, Glu, Gly, His, Met, Pro, Ser, or Thr.

Preferably, the substituting amino acid for position 198 is Asp, Gln, Glu or Ser.

Preferably, the substituting amino acid for position 199 is Ala, Asn, Asp, Cys, Gln, Glu, Gly, His, Met, Pro, Ser or Thr.

Preferably, the substituting amino acid for position 200 Asn, Asp, Glu or Ser.

Preferably, the substituting amino acid for position 201 is Asp or Glu.

Preferably, the substituting amino acid for position 202 is Asn, Asp, Gln, Glu, Gly, Pro or Ser.

Preferably, the substituting amino acid for position 203 is Ala, Asn, Asp, Cys, Gln, Glu, Gly, His, Ile, Leu, Met, Pro, Ser, Thr, or Val.

Preferably, the substituting amino acid for position 204 is Asn, Asp, Gln, Glu, Gly or Ser.

Preferably, the substituting amino acid for position 205 is Asn, Asp, Gln, Glu, Pro or Ser.

Preferably, the substituting amino acid for position 206 is Asp or Glu.

Preferably, the substituting amino acid for position 207 is Asn, Asp, Gln, Glu, Gly, Pro or Ser.

Preferably, the substituting amino acid for position 208 is Ala, Asn, Asp, Cys, Gln, Glu, Gly, His, Ile, Leu, Met, Pro, Thr or Val.

Preferably, the substituting amino acid for position 209 is Asn, Asp, Gln, Glu, Gly, His, Pro, Ser or Thr.

Preferably, the substituting amino acid for position 210 is Asp or Glu.

Preferably, the substituting amino acid for position 211 is Ala, Asn, Asp, Cys, Gln, Glu, Gly, His, Ile, Met, Pro, Ser, Thr or Val.

Preferably, the substituting amino acid for position 212 is Asp, Gln, Glu or Ser.

Preferably, the substituting amino acid for position 213 is Asn, Asp, Gln, Glu, Pro or Ser.

Preferably, the substituting amino acid for position 214 is Asn, Asp, Gln, Glu, Gly, Pro or Ser.

More preferably, the substituting amino acid for any positions 193, 194, 195, 196, 197, 198, 199, 200, 201, 202, 203, 204, 205, 206, 207, 208, 209, 210, 211, 212, 213 or 214 is, with reference to Table 1, is neutral or negatively charged and equally or more hydrophilic, preferably more hydrophilic, than the amino acid at the subject position in wild-type subtilisin 309.

More preferably still, the substituting amino acid for any of positions 193, 194, 195, 196, 197, 198, 199, 200, 201, 202, 203, 204, 205, 206, 207, 208, 209, 210, 211, 212, 213 or 214 is Asp or Glu.

B. Multi-Loop Regions Substitution Variants

In another embodiment of the present invention, the subtilisin 309 variant has a modified amino acid sequence of subtilisin 309 wild-type amino acid sequence, wherein the modified amino acid sequence comprises a substitution at one or more positions in one or more of the first, second, third, fourth, or fifth loop regions; whereby the subtilisin 309 variant has decreased adsorption to, and increased hydrolysis of, an insoluble substrate as compared to wild-type subtilisin 309.

In another embodiment of the present invention, the subtilisin 309 variant further comprises one or more substitutions to the sixth loop region.

In a preferred embodiment of the present invention, the substituting amino acid for one or more of the positions in one or more of the loop regions is, with reference to Table 1, neutral or negatively charged and equally or more hydrophilic, preferably more hydrophilic, than the amino acid at the subject position in the wild-type amino acid sequence.

1. Substitutions in the First Loop Region

When a substitution occurs in the first loop region, the substitution occurs at one or more of positions 57, 58, 59, 60, 61, 63, or 64.

When a substitution occurs at position 57, the substituting amino acid is Asn, Asp, Glu or Ser.

When a substitution occurs at position 58, the substituting amino acid is Glu.

When a substitution occurs at position 59, the substituting amino acid is Asn, Asp, Gln, Glu, Pro or Ser.

When a substitution occurs at position 60, the substituting amino acid is Asp, Gln, Glu or Ser.

When a substitution occurs at position 61, the substituting amino acid is Asn, Asp, Gln, Glu, Pro or Ser.

When a substitution occurs at position 63, the substituting amino acid is Asn, Asp, Gln, Glu, Pro or Ser.

When a substitution occurs at position 64, the substituting amino acid is Asn, Asp, Gln, Glu, Gly, Pro or Ser.

2. Substitutions in the Second Loop Region

When a substitution occurs in the second loop region, the substitution occurs at one or more of positions 93, 94, 95, 96, 97, 98, 99, 100, 101, 102, 103, 104, or 105.

When a substitution occurs at position 93, the substituting amino acid is Ala, Asn, Asp, Cys, Gln, Glu, Gly, His, Met, Pro, Ser or Thr.

When a substitution occurs at position 94, the substituting amino acid is Ala, Asn, Asp, Cys, Gln, Glu, Gly, His, Ile, Met, Pro, Ser, Thr or Val.

When a substitution occurs at position 95, the substituting amino acid is Asn, Asp, Gln, Glu, Pro or Ser.

When a substitution occurs at position 96, the substituting amino acid is Asn, Asp, Gln, Glu, Gly, His, Pro, Ser or Thr.

When a substitution occurs at position 97, the substituting amino acid is Asp or Glu.

When a substitution occurs at position 98, the substituting amino acid is Asn, Asp, Gln, Glu, Pro or Ser.

When a substitution occurs at position 99, the substituting amino acid is Asp or Glu.

When a substitution occurs at position 100, the substituting amino acid is Asn, Asp, Gln, Glu, Pro or Ser.

When a substitution occurs at position 101, the substituting amino acid is Asp or Glu.

When a substitution occurs at position 102, the substituting amino acid is Ala, Asn, Asp, Cys, Gln, Glu, Gly, His, Met, Pro, Ser or Thr.

When a substitution occurs at position 103, the substituting amino acid is Asp or Glu.

When a substitution occurs at position 104, the substituting amino acid is Asp or Glu.

When a substitution occurs at position 105, the substituting amino acid is Ala, Asn, Asp, Cys, Gln, Glu, Gly, His, Leu, Met, Pro, Ser, Thr or Val.

3. Substitutions in the Third Loop Region

When a substitution occurs in the third loop region, the substitution occurs at one or more of positions 124, 125, 126, 127, 128, 129, 130 or 131.

When a substitution occurs at position 124, the substituting amino acid is Ala, Asn, Asp, Cys, Gln, Glu, Gly, His, Ile, Met, Pro, Ser, Thr or Val.

When a substitution occurs at position 125, the substituting amino acid is Asn, Asp, Gln, Glu, Pro or Ser.

When a substitution occurs at position 126, the substituting amino acid is Asp or Glu.

When a substitution occurs at position 127, the substituting amino acid is Asn, Asp, Gln, Glu, Gly or Ser.

When a substitution occurs at position 128, the substituting amino acid is Asp or Glu.

When a substitution occurs at position 129, the substituting amino acid is Asn, Asp, Gln, Glu, Gly or Ser.

When a substitution occurs at position 130, the substituting amino acid is Asp or Glu.

When a substitution occurs at position 131, the substituting amino acid is Asn, Asp, Gln, Glu, Gly, His, Pro, Ser, Thr.

4. Substitutions in the Fourth Loop Region

When a substitution occurs in the fourth loop region, the substitution occurs at one or more of positions 152, 153, 154, 155, 156, 157, 158, 159, 160 or 161.

When a substitution occurs at position 152, the substituting amino acid is Asn, Asp, Gln, Glu, Pro or Ser.

When a substitution occurs at position 153, the substituting amino acid is Asp, Gln, Glu or Ser.

When a substitution occurs at position 154, the substituting amino acid is Asp or Glu.

When a substitution occurs at position 155, the substituting amino acid is Asn, Asp, Gln, Glu, Pro or Ser.

When a substitution occurs at position 156, the substituting amino acid is Asn, Asp, Gln, Glu, Gly, His, Pro, Ser or Thr.

When a substitution occurs at position 157, the substituting amino acid is Asn, Asp, Gln, Glu, Pro or Ser.

When a substitution occurs at position 158, the substituting amino acid is Asp or Glu.

When a substitution occurs at position 159, the substituting amino acid is Ala, Asn, Asp, Cys, Gln, Glu, Gly, His, Leu, Met, Pro, Ser, Thr or Val.

When a substitution occurs at position 160, the substituting amino acid is Asp or Glu.

When a substitution occurs at position 161, the substituting amino acid is Ala, Asn, Asp, Cys, Gln, Glu, Gly, His, Ile, Leu, Met, Pro, Ser, Thr or Val.

5. Substitutions in the Fifth Loop Region

When a substitution occurs in the fifth loop region, the substitution occurs at one or more of positions 181, 182, 183, 184 or 185.

When a substitution occurs at position 181, the substituting amino acid is Asn, Asp, Gln, Glu, Gly, His, Pro, Ser or Thr.

When a substitution occurs at position 182, the substituting amino acid is Asp or Glu.

When a substitution occurs at position 183, the substituting amino acid is Ala, Asn, Asp, Cys, Gln, Glu, Gly, His, Ile, Leu, Met, Pro, Ser, Thr, Tyr or Val.

When a substitution occurs at position 184, the substituting amino acid is Asp or Glu.

When a substitution occurs at position 185, the substituting amino acid is Asn, Asp, Glu or Ser.

6. Substitutions in the Sixth Loop Region

When a substitution occurs in the sixth loop region, in conjunction with one or more substitutions in one or more of the preceding five loop regions, the substitution occurs at one or more of positions 193, 194, 195, 196, 197, 198, 199, 200, 201, 202, 203, 204, 205, 206, 207, 208, 209, 210, 211, 212, 213 or 214.

When a substitution occurs at position 193, the substituting amino acid is Ala, Asn, Asp, Cys, Gln, Glu, Gly, His, Met, Pro, Ser or Thr.

When a substitution occurs at position 194, the substituting amino acid is Asn, Asp, Gln, Glu, Gly, His, Pro, Ser or Thr.

When a substitution occurs at position 195, the substituting amino acid is Asn, Asp, Gln, Glu, Gly or Ser.

When a substitution occurs at position 196, the substituting amino acid is Asn, Asp, Gln, Glu, Pro or Ser.

When a substitution occurs at position 197, the substituting amino acid is Ala, Asn, Asp, Cys, Gln, Glu, Gly, His, Met, Pro, Ser or Thr.

When a substitution occurs at position 198, the substituting amino acid is Asp, Gln, Glu or Ser.

When a substitution occurs at position 199, the substituting amino acid is Ala, Asn, Asp, Cys, Gln, Glu, His, Met, Pro, Ser or Thr.

When a substitution occurs at position 200, the substituting amino acid is Asn, Asp, Glu or Ser.

When a substitution occurs at position 201, the substituting amino acid is Asp or Glu.

When a substitution occurs at position 202, the substituting amino acid is Asn, Asp, Gln, Glu, Gly, Pro or Ser.

When a substitution occurs at position 203, the substituting amino acid is Ala, Asn, Asp, Cys, Gln, Glu, Gly, His, Ile, Leu, Met, Pro, Ser, Thr or Val.

When a substitution occurs at position 204, the substituting amino acid is Asn, Asp, Gln, Glu, Gly or Ser.

When a substitution occurs at position 205, the substituting amino acid is Asn, Asp, Gln, Glu, Pro or Ser.

When a substitution occurs at position 206, the substituting amino acid is Asp or Glu.

When a substitution occurs at position 207, the substituting amino acid is Asn, Asp, Gln, Glu, Gly, Pro or Ser.

When a substitution occurs at position 208, the substituting amino acid is Ala, Asn, Asp, Cys, Gln, Glu, Gly, His, Ile, Leu, Met, Pro, Ser, Thr or Val.

When a substitution occurs at position 209, the substituting amino acid is Asn, Asp, Gln, Glu, Glly, His, Pro, Ser or Thr.

When a substitution occurs at position 210, the substituting amino acid is Asp or Glu.

When a substitution occurs at position 211, the substituting amino acid is Ala, Asn, Asp, Cys, Gln, Glu, Gly, His, Ile, Met, Pro, Ser, Thr or Val.

When a substitution occurs at position 212, the substituting amino acid is Asp, Gln, Glu or Ser.

When a substitution occurs at position 213, the substituting amino acid is Asn, Asp, Gln, Glu, Pro or Ser.

When a substitution occurs at position 214, the substituting amino acid is Asn, Asp, Gln, Glu, Gly, Pro or Ser.

C. Additional Substitutions at Positions Other Than the Loop Regions

As indicated hereinbefore, in addition to the one or more substitutions made to the first, second, third, fourth, fifth and/or sixth loop regions of wild-type subtilisin 309, substitutions may be made at positions other than positions in such loop regions (hereafter referred to as "additional substitution"). In another embodiment of the present invention, the subtilisin 309 variant has a modified amino acid sequence of subtilisin 309 wild-type amino acid sequence wherein, in addition to being substituted at one or more positions in one or more of the above-discussed loop regions, there is substitution at position 74. The additional substitution may occur at position 74 alone (preferred), or in combination with one or more additional substitutions.

Where the additional substitution to the subtilisin 309 variant is at position 74 alone, the substitution is preferably with Asn, Asp, Glu, Gly, His, Lys, Phe or Pro. Particularly preferred is where the substitution is with Asp or His.

Where there is more than one additional substitution to the subtilisin 309 variant, preferred is where the additional substitutions occur at position 74 in combination with one or more of the following residues: 97, 99, 101, 102, 105 and 121. Preferred additional substitution combinations include the following: 74/97; 74/99; 74/101; 74/102; 74/105; 74/121; 74/97/99; 74/97/101; 74/97/102; 74/99/101; 74/99/102; 74/101/102; 74/102/105; 74/102/121; 74/105/121; 74/97/99/101; 74/97/99/102; 74/97/101/102; 74/99/101/102; 74/101/102/121; 74/102/105/121; 74/97/99/101/102; 74/97/101/102/121 and/or 74/97/99/101/102/121. Most preferred additional substitution combinations include the following: 74/97; 74/102; 74/97/102; 74/101/102; 74/102/105; 74/99/102/102; 74/97/99/101/102 and 74/99/102.

Preferably, the additional substitutions to be made at each of the identified amino acid residue positions include but are not limited to substitutions at position 74 including Asp, His, Glu, Gly, Phe, Lys, Pro and Asn; substitutions at position 97 including Asp. Thr, Asn, Gln, Gly and Ser; substitutions at position 99 including Gly, Asp, Lys, Leu, Ala, Glu and Ser; substitutions at position 101 including Gln, Thr, Asp, Glu, Tyr, Lys, Gly, Arg and Ser; substitutions at position 102 including Ser, Tyr, Ile, Leu, M, Ala, W, Asp, Thr, Gly and Val; substitutions at position 105 including Val, Leu, M, Tyr, Gly, Glu, Phe, Thr, Ser, Ala and Ile; and substitutions at position 121 including Asn, Thr, Ile and Ser. The specifically preferred amino acid(s) to be substituted at each such position are designated below in Table 2. Although specific amino acids are shown in Table 2, it should be understood that any amino acid may be substituted at the identified residues. As indicated herein before, these substitutions are in addition to the one or more substitutions at one or more of the loop regions, discussed above.

TABLE 2

| Amino Acid Residue | Preferred Amino Acid to be Substituted/Inserted |
|---|---|
| 74 | Asp, His |
| 97 | Asp, Thr, Asn, Gly |
| 99 | Arg, Gly, Asp, Lys, Leu, Ala, Glu |
| 101 | Ala, Gln, Thr, Asp, Glu, Tyr, Lys, Gly, Arg |
| 102 | Ile, Tyr, Ser, Leu, Ala, Thr, Gly |
| 105 | Val, Leu, Tyr, Gly, Phe, Thr, Ser, Ala |
| 121 | Ser, Thr, Ile |

D. Preparation of Enzyme Variants

EXAMPLE 1

Mutant 309 DNA Sequences

A phagemid (pJMA602) containing the wild type subtilisin 309 (i.e., savinase) gene is constructed. The 2.8 Kbp Pvu II restriction enzyme fragment of plasmid pUC119, (Vieira, J. and Messing, J., "Production of Single-Stranded Plasmid DNA", 153 METHODS IN ENZYMOLOGY 3–11 (1989)) is cloned into the Pvu II site of plasmid pUB110 (Bacillus Genetic Stock Center, Columbus, Ohio 1E9). The pUC119-pUB110 hybrid plasmid is named pJMA601. Into the BamH I restriction site of pJMA601 is cloned the polymerase chain reation-amplified 309 (savinase) gene from *Bacillus lentus* chromosomal DNA (National Collections of Industrial and Marine Bacteria *Bacillus lentus* 10309) giving phagemid pJMA602. Phagemid pJMA602 is transformed into *Escherichia coli* ung-strain CJ236 and a single stranded uracil-containing DNA template is produced using the VCSM13 helper phage (Kunkel, T. A., J. D. Roberts and R. A. Zakour, "Rapid and efficient site-specific mutagenesis without phenotypic selection", METHODS IN ENZYMOLOGY, Vol. 154, pp. 367–382, (1987); as modified by Yuckenberg, P. D., F. Witney, J. Geisselsoder and J. McClary, "Site-directed in vitro mutagenesis using uracil-containing DNA and phagemid vectors", DIRECTED MUTAGENESIS—A PRACTICAL APPROACH, ed. M. J. McPherson, pp. 27–48, (1991); both of which are incorporated herein by reference). A single primer site-directed mutagenesis modification of the method of Zoller and Smith (Zoller, M. J., and M. Smith, "Oligonucleotide-directed metagenesis using M13-derived vectors: an efficient and general procedure for the production of point mutations in any fragment of DNA", NUCLEIC ACIDS RESEARCH, Vol. 10, pp. 6487–6500, (1982), incorporated herein by reference) is used to produce all mutants (basically as presented by Yuckenberg, et al., 1991, above). Oligonucleotides are made using an Applied Biosystem Inc. 380B DNA synthesizer. Mutagenesis reaction products are transformed into *Escherichia coli* strain MM294 (American Type Culture Collection *E. Coli.* 33625). All mutants are confirmed by DNA sequencing and the isolated DNA is transformed into the *Bacillus subtilis* expression strain BG2036 (Yang, M. Y., E. Ferrari and D. J. Henner, (1984), "Cloning of the Neutral Protease Gene of *Bacillus subtilis* and the Use of the Cloned Gene to Create an In Vitro-derived Deletion Mutation", JOURNAL OF BACTERIOLOGY, Vol. 160, pp. 15–21). For some of the mutants a modified pJMA602 with a frameshift-stop codon mutation in the corresponding loop is used to produce the uracil template. Oligonucleotides are designed to restore the proper reading frame at position 203 and also encoded for random substitutions at positions 57, 58, 59, 60, 61, 63, 64, 93, 94, 95, 96, 97, 98, 99, 100, 101, 102, 103, 104, 105, 124, 125, 126, 127, 128, 129, 130, 131, 152, 153, 154, 155, 156, 157, 158, 159, 160, 161, 181, 182, 183, 184, 185, 193, 194, 195, 196, 197, 198, 199, 200, 201, 202, 203, 204, 205, 206, 207, 208, 209, 210, 211, 212, 213 and 214 (equimolar and/or variable mixtures of all four nucleotides for all three bases at these codons). Mutations that correct for the frameshift-stop and produce a functional enzyme are identified by their ability to digest casein. The random substitutions are determined by DNA sequencing.

EXAMPLE 2

Fermentation

The *Bacillus subtilis* cells (BG2036) containing a subtilisin mutant of interest are grown to mid-log phase in a one liter culture of LB-glucose broth and inoculated into a Biostat ED fermenter (B. Braun Biotech, Inc., Allentown, Pa.) in a total volume of 10 liters. The fermentation media contains Yeast Extract, starch, antifoam, buffers and trace minerals (see FERMENTATION: A PRACTICAL APPROACH, Ed. B. McNeil and L. M. Harvey, 1990). The broth is kept at a constant pH of 7.0 during the fermentation run. Chloramphenical is added for antibiotic selection of mutagenized plasmid. The cells are grown overnight at 37° C. to an $A_{600}$ of about 60 and harvested.

EXAMPLE 3

Purification

The fermentation broth is taken through the following steps to obtain pure enzyme. The broth is cleared of *Bacillus subtilis* cells by centrifugation, and clarified by removing fine particulates with a 100K cutoff membrane. This is followed by concentration on a 10K cutoff membrane, and flow dialysis to reduce the ionic strength and adjust the pH to 5.5 using 0.025M MES buffer (2-(N-morpholino) ethanesulfonic acid). The enzyme is further purified by loading it onto either a cation exchange chromatography column or an affinity adsorption chromatography column and eluting it from the column with a NaCl or a propylene glycol gradient (see Scopes, R. K., PROTEIN PURIFICATION PRINCIPLES AND PRACTICE, Springer-Verlag, New York (1984), incorporated herein by reference).

The pNA assay (DelMar, E. G., C. Largman, J. W. Brodrick and M. C. Geokas, ANAL. BIOCHEM., Vol. 99, pp. 316–320, (1979), incorporated herein by reference) is used to determine the active enzyme concentration for fractions collected during gradient elution. This assay measures the rate at which p-nitroaniline is released as the enzyme hydrolyzes the soluble synthetic substrate, succinyl-alanine-alanine-proline-phenylalanine-p-nitroanilide (sAAPF-pNA). The rate of production of yellow color from the hydrolysis reaction is measured at 410 nm on a spectrophotometer and is proportional to the active enzyme concentration. In addition, absorbance measurements at 280 nm are used to determine the total protein concentration. The active enzyme/total-protein ratio gives the enzyme purity, and is used to identify fractions to be pooled for the stock solution.

To avoid autolysis of the enzyme during storage, an equal weight of propylene glycol is added to the pooled fractions obtained from the chromatography column. Upon completion of the purification procedure the purity of the stock enzyme solution is checked with SDS-PAGE (sodium dodecyl sulfate polyacrylamide gel electrophoresis) and the absolute enzyme concentration is determined via an active site titration method using trypsin inhibitor type II-T: turkey egg white purchased from Sigma Chemical Company (St. Louis, Mo.). The measured conversion factors will show which changes made in the enzyme molecule at the various positions result in the enzyme variant having increased activity over the wild-type, against the soluble substrate pNA.

In preparation for use, the enzyme stock solution is eluted through a Sephadex-G25 (Pharmacia, Piscataway, N.J.) size exclusion column to remove the propylene glycol and exchange the buffer. The MES buffer in the enzyme stock solution is exchanged for 0.1 M Tris buffer (Tris (hydroxymethylaminomethane) containing 0.01M $CaCl_2$ and pH adjusted to 8.6 with HCl. All experiments are carried out at pH 8.6 in Tris buffer thermostated at 25° C.

E. Characterization of Enzyme Variants

EXAMPLE 4

Model Surface Preparation

Aminopropyl controlled pore glass (CPG) purchased from CPG Inc. (Fairfield, N.J.) is used as a support for covalently attaching the sAAPF-pNA substrate purchased from Bachem, Inc. (Torrence, Calif.). The reaction is carried out in dimethyl sulfoxide and (1-ethyl-3-[3-(dimethylamino) propyl] carbodiimide hydrochloride) (EDC) is used as a coupling agent. Upon completion (monitored by pNA assay), the excess solvent is removed, and the CPG:sAAPF-pNA is rinsed with dimethyl sulfoxide (DMSO) and doubly-distilled water. This is followed by oven drying with a $N_2$ purge at about 70° C. The reaction scheme and preparation of the immobilized substrate are conducted as described by Brode, P. F. III, and D. S. Rauch, "Subtilisin BPN': Activity on an Immobilized Substrate," LANGMUIR, Vol. 8, p. 1325–1329, (1992), incorporated herein by reference.

The CPG surface will have 62,000±7,000 pNA molecules/ $\mu m^2$. The surface area will remain unchanged from the value of 50.0 m²/g reported by CPG Inc. for the CPG as received. This suggests that the procedure used to add sAAPF-pNA to CPG does not damage the porous structure (mean diameter is 486 Å).

EXAMPLE 5

Surface Hydrolysis Assay

Using CPG:sAAPF-pNA, adsorption of an enzyme variant and hydrolysis of a CPG-bound peptide can be measured in a single experiment. A small volume of enzyme variant stock solution is added to a flask containing Tris buffer and CPG:sAAPF-pNA which has been degassed. The flask is shaken on a wrist-action shaker for a period of 90 minutes during which the shaker is stopped at various time intervals (for example, every 2 minutes during the early stages of adsorption hydrolysis—e.g., the first 20 minutes—and every 10 minutes towards the end of the experiment). The CPG:sAAPF-pNA is allowed to settle and the solution is sampled. Both the experimental procedure and the calculation of the adsorption and hydrolysis are conducted as described by Brode et al., 1991, above.

All enzymes are monitored for stability against autolysis and should show no appreciable autolytic loss over the time course of this experiment. Therefore, enzyme adsorption can be determined by measuring solution depletion. The difference between the initial enzyme variant concentration and the concentration measured at each individual time point gives the amount of enzyme variant adsorbed. The amount of pNA hydrolyzed from the surface is measured by taking an absorbance reading on an aliquot of the sample at 410 nm. The total amount of pNA hydrolyzed is calculated by adding the amount sampled and the amount remaining in the flask. This value is corrected by subtracting the amount of pNA that is hydrolyzed by Tris buffer at pH 8.6 when no enzyme is present. This base-hydrolysis ranges from 7–29% of the total hydrolysis depending on the efficiency of the enzyme.

EXAMPLE 6

Soluble Substrate Kinetic Analysis

The rates of hydrolysis of the soluble substrate sAAPF-pNA are monitored by measuring the adsorbance increase as a function of time at 410 nm on a DU-70 spectrophotometer. The enzyme concentration is held constant and is prepared to be in the range of 6–10 nanomolar while the substrate concentration is varied from 90–700 µM sAAPF-pNA for each kinetic determination. An adsorbance data point is taken each second over a period of 900 seconds and the data are transferred to a LOTUS™ spreadsheet (Lotus Development Corporation, Cambridge, Mass.). Analysis for kinetic parameters is conducted by the standard Lineweaver Burk analysis in which the data in the initial part of the run (generally the first minute) are fit to a linear regression curve to give $v_o$. The $v_o$ and $s_o$ data are plotted in the standard inverse fashion to give $K_M$ and $k_{cat}$.

F. Example Subtilisin 309 Variants

Subtilisin 309 variants of the present invention which have decreased adsorption to and increased hydrolysis of surface bound substrates are exemplified in Tables 3–38, below. In describing the specific mutations, the original amino acid occurring in wild-type is given first, the position number second, and the substituted amino acid third.

TABLE 3

Loop 1-Single Mutation Variants

Gln57Asn
Gln57Asp
Gln57Glu
Gln57Ser
Asp58Glu
Gly59Asn
Gly59Asp
Gly59Gln
Gly59Glu
Gly59Pro
Gly59Ser
Asn60Asp
Asn60Gln
Asn60Glu
Asn60Ser
Gly61Asn
Gly61Asp
Gly61Gln
Gly61Glu
Gly61Pro
Gly61Ser
Gly63Asn
Gly63Asp
Gly63Gln
Gly63Glu
Gly63Pro
Gly63Ser
Thr64Asn
Thr64Asp
Thr64Gln
Thr64Glu
Thr64Gly
Thr64Pro
Thr64Ser

TABLE 4

Loop 1-Double Mutation Variants

Gln57Ser + Asn60Glu
Asp58Glu + Gly61Gln
Gly59Ser + Gly63Ser
Asn60Ser + Gly61Ser
Gly63Asn + Thr64Asp
Gly59Asn + Thr64Glu
Asn60Glu + Gly63Ser
Asn60Gln + Gly63Gln
Asn60Asp + Gly63Ser
Asp58Glu + Gly63Gln
Gln57Asp + Thr64Gly
Gln57Glu + Gly63Gln
Asn60Glu + Gly63Asn
Gly61Gln + Gly63Asn
Asp58Glu + Gly59Asn
Asp58Glu + Thr64Pro
Gly61Asn + Gly63Asn
Asp58Glu + Gly61Pro
Asn60Glu + Gly63Gln
Asn60Asp + Gly61Gln
Asp58Glu + Asn60Ser
Gln57Asn + Gly59Glu
Asn60Glu + Gly61Pro
Gly61Asn + Thr64Gln
Asp58Glu + Thr64Ser
Asn60Asp + Thr64Gln
Gly59Glu + Gly63Ser
Gln57Asn + Gly61Ser
Gly61Ser + Thr64Asn
Gln57Asp + Gly61Asn
Gly59Glu + Gly63Pro
Asn60Gln + Gly61Ser
Gly61Pro + Gly63Ser
Gly59Asp + Gly63Asn
Gly63Gln + Thr64Asn

TABLE 4-continued

| Loop 1-Double Mutation Variants |
|---|
| Gln57Glu + Gly59Gln |
| Gln57Asp + Gly59Pro |
| Gln57Glu + Gly61Ser |
| Gln57Asp + Gly63Gln |
| Asp58Glu + Gly61Asn |
| Gly59Asn + Asn60Glu |
| Gly61Gln + Thr64Glu |
| Gln57Glu + Gly61Gln |
| Asp58Glu + Gly63Ser |
| Gly59Glu + Gly63Asn |
| Gly61Ser + Thr64Asp |
| Gly59Ser + Thr64Asp |
| Gln57Glu + Gly63Pro |
| Gly59Ser + Thr64Glu |
| Asn60Gln + Gly63Pro |
| Gln57Asn + Asn60Asp |

TABLE 5

| Loop 1-Triple Mutation Variants |
|---|
| Gly59Pro + Gly63Gln + Thr64Glu |
| Gln57Ser + Gly59Asn + Gly63Pro |
| Gly59Pro + Asn60Asp + Thr64Asn |
| Gln57Glu + Gly59Asn + Gly63Pro |
| Gln57Asp + Gly63Pro + Thr64Asn |
| Gln57Ser + Asn60Glu + Thr64Gly |
| Gln57Ser + Asn60Ser + Gly63Ser |
| Gly61Ser + Gly63Ser + Thr64Gln |
| Gln57Glu + Gly61Pro + Thr64Gly |
| Asp58Glu + Gly63Pro + Thr64Gly |
| Gln57Asn + Asp58Glu + Gly61Pro |
| Asp58Glu + Gly59Ser + Thr64Pro |
| Gln57Asn + Gly59Glu + Gly61Ser |
| Gly59Glu + Gly61Gln + Thr64Asn |
| Gln57Asp + Asn60Gln + Thr64Gly |
| Asn60Glu + Gly61Gln + Thr64Gly |
| Gln57Asp + Gly59Pro + Gly63Pro |
| Gln57Asn + Gly63Asn + Thr64Gly |
| Gln57Ser + Gly59Asp + Gly61Ser |
| Gly61Gln + Gly63Asn + Thr64Pro |
| Gln57Glu + Gly59Pro + Thr64Ser |
| Asn60Asp + Gly63Gln + Thr64Gly |
| Asp58Glu + Gly63Asn + Thr64Gln |
| Asp58Glu + Gly61Gln + Gly63Gln |
| Gln57Asp + Gly61Pro + Thr64Gln |
| Asp58Glu + Gly59Asn + Gly61Ser |
| Asp58Glu + Gly59Ser + Asn60Ser |
| Gln57Asn + Gly61Pro + Thr64Gly |
| Gly59Glu + Gly61Pro + Gly63Pro |
| Gly59Glu + Gly61Gln + Gly63Asn |
| Gly59Glu + Gly61Pro + Gly63Gln |
| Gly59Glu + Gly61Pro + Thr64Asn |
| Gln57Asn + Asp58Glu + Thr64Gln |

TABLE 6

| Loop 1-Quadruple Mutation Variants |
|---|
| Gly59Gln + Asn60Asp + Gly61Pro + Gly63Pro |
| Gly59Ser + Asn60Gln + Gly63Ser + Thr64Asp |
| Gly59Pro + Asn60Ser + Gly61Ser + Gly63Gln |
| Gln57Glu + Gly59Pro + Asn60Ser + Gly61Pro |
| Gln57Glu + Asn60Gln + Gly63Asn + Thr64Gly |
| Gln57Ser + Gly59Ser + Asn60Asp + Gly61Ser |
| Gln57Ser + Asn60Glu + Gly61Pro + Thr64Pro |
| Asn60Gln + Gly61Pro + Gly63Gln + Thr64Asp |
| Asn60Glu + Gly61Gln + Gly63Asn + Thr64Pro |
| Gln57Glu + Gly59Gln + Gly61Pro + Thr64Gln |
| Gln57Asn + Asp58Glu + Gly59Ser + Asn60Gln |
| Asp58Glu + Asn60Ser + Gly63Ser + Thr64Ser |
| Gln57Glu + Gly59Pro + Gly63Gln + Thr64Ser |

TABLE 6-continued

| Loop 1-Quadruple Mutation Variants |
|---|
| Asp58Glu + Gly59Ser + Asn60Ser + Gly63Ser |
| Gly59Asn + Asn60Asp + Gly61Ser + Thr64Gln |
| Gln57Glu + Asp58Glu + Gly59Gln + Gly61Gln |
| Gln57Glu + Asp58Glu + Asn60Ser + Thr64Pro |
| Gln57Asp + Asp58Glu + Gly61Ser + Gly63Pro |
| Gln57Asp + Asp58Glu + Asn60Gln + Gly61Gln |
| Gln57Ser + Asp58Glu + Gly59Glu + Asn60Gln |
| Asp58Glu + Gly59Asp + Gly61Ser + Gly63Gln |
| Gly59Glu + Asn60Asp + Gly61Asn + Gly63Asn |
| Gly59Asp + Asn60Asp + Gly61Asn + Gly63Gln |
| Gly59Glu + Asn60Asp + Gly61Pro + Thr64Ser |
| Asp58Glu + Gly59Glu + Asn60Asp + Thr64Gly |
| Asp58Glu + Gly59Glu + Asn60Asp + Gly61Pro |
| Asp58Glu + Gly59Glu + Asn60Glu + Gly61Asn |

TABLE 7

| Loop 2-Single Mutation Variants |
|---|
| Val 93Ala |
| Val 93Asn |
| Val 93Asp |
| Val 93Cys |
| Val 93Gln |
| Val 93Glu |
| Val 93Gly |
| Val 93His |
| Val 93Met |
| Val 93Pro |
| Val 93Ser |
| Val 93Thr |
| Leu 94Ala |
| Leu 94Asn |
| Leu 94Asp |
| Leu 94Cys |
| Leu 94Gln |
| Leu 94Glu |
| Leu 94Gly |
| Leu 94His |
| Leu 94Ile |
| Leu 94Met |
| Leu 94Pro |
| Leu 94Ser |
| Leu 94Thr |
| Leu 94Val |
| Gly 95Asn |
| Gly 95Asp |
| Gly 95Gln |
| Gly 95Glu |
| Gly 95Pro |
| Gly 95Ser |
| Ala 96Asn |
| Ala 96Asp |
| Ala 96Gln |
| Ala 96Glu |
| Ala 96Gly |
| Ala 96His |
| Ala 96Pro |
| Ala 96Ser |
| Ala 96Thr |
| Ser 97Asp |
| Ser 97Glu |
| Gly 98Asn |
| Gly 98Asp |
| Gly 98Gln |
| Gly 98Glu |
| Gly 98Pro |
| Gly 98Ser |
| Ser 99Asp |
| Ser 99Glu |
| Gly100Asn |
| Gly100Asp |
| Gly100Gln |
| Gly100Glu |

TABLE 7-continued

Loop 2-Single Mutation Variants

Gly100Pro
Gly100Ser
Ser101Asp
Ser101Glu
Val102Ala
Val102Asn
Val102Asp
Val102Cys
Val102Gln
Val102Glu
Val102Gly
Val102His
Val102Met
Val102Pro
Val102Ser
Val102Thr
Ser103Asp
Ser103Glu
Ser104Asp
Ser104Glu
Ile105Ala
Ile105Asn
Ile105Asp
Ile105Cys
Ile105Gln
Ile105Glu
Ile105Gly
Ile105His
Ile105Leu
Ile105Met
Ile105Pro
Ile105Ser
Ile105Thr
Ile105Val

TABLE 8

Loop 2-Double Mutation Variants

Val 93Gln + Ser 99Glu
Gly 95Ser + Gly 98Gln
Ser101Asp + Ile105Ala
Leu 94Ser + Gly 95Ser
Leu 94Pro + Ser101Asp
Gly 98Gln + Ser103Asp
Ser 97Asp + Tyr102Gln
Tyr102Cys + Ile105Met
Val 93Pro + Gly 98Gln
Ser 99Glu + Gly100Pro
Ser103Asp + Ile105Leu
Ser 97Asp + Gly 98Gln
Val 93Ser + Ser 99Asp
Leu 94Ser + Gly 98Glu
Gly 95Glu + Tyr102Met
Gly 95Asn + Ser103Glu
Gly 98Ser + Tyr102Thr
Gly 98Gln + Tyr102Cys
Leu 94Ile + Ile105Gln
Leu 94Asp + Gly100Gln
Ala 96Gly + Ser101Asp
Ser101Glu + Ile105Gln
Gly 95Gln + Ile105Ser
Val 93Gln + Gly100Pro
Val 93Met + Ser104Asp
Gly 98Pro + Ser101Asp
Val 93Pro + Ile105His
Gly 95Asp + Gly100Ser
Tyr102Cys + Ile105Leu
Gly100Asn + Ile105Met
Gly 98Asn + Ser101Glu
Ser 99Glu + Ile105Gln
Val 93Thr + Tyr102Thr
Gly 98Ser + Ser104Glu
Gly 95Asn + Ser104Glu

TABLE 8-continued

Loop 2-Double Mutation Variants

Val 93Pro + Ser103Glu
Gly 95Asn + Tyr102Ile
Leu 94Pro + Gly 98Asp
Leu 94His + Gly 98Asp
Val 93Asn + Tyr102Thr
Tyr102Ala + Ser103Asp
Gly 98Pro + Ser103Glu
Leu 94Cys + Tyr102Leu
Val 93Gly + Gly 98Ser
Gly100Gln + Tyr102Ser
Val 93Thr + Gly100Asn
Gly 98Asn + Ile105Pro
Val 93Asp + Leu 94Ala
Leu 94Gly + Ser104Glu
Val 93Met + Ser101Asp
Val 93Met + Ser 97Glu
Ala 96Pro + Ile105Asn
Ser 97Glu + Gly 98Pro
Ala 96Thr + Ser 99Glu
Val 93Asn + Gly100Asn
Gly 95Gln + Gly 98Pro
Gly 95Asn + Ala 96His
Val 93Ser + Ser103Asp
Gly 98Gln + Ile105Pro
Val 93Cys + Ile105Glu

TABLE 9

Loop 2-Triple Mutation Variants

Val 93Gln + Leu 94Thr + Ser 99Glu
Leu 94Met + Gly 95Gln + Ser104Asp
Ser 99Glu + Tyr102Met + Ile105Thr
Val 93Thr + Leu 94Thr + Ile105Cys
Leu 94Asp + Ala 96Thr + Gly 98Asn
Val 93Met + Gly 95Gln + Ser103Asp
Val 93Cys + Ala 96Pro + Ser 99Glu
Leu 94Asp + Ala 96Gly + Gly100Gln
Leu 94His + Gly 98Gln + Ser 99Glu
Gly 95Pro + Ser101Asp + Tyr102Gln
Leu 94Asn + Gly 95Gln + Ser101Asp
Leu 94His + Gly 98Pro + Ser104Glu
Leu 94Thr + Ala 96Asn + Gly100Pro
Gly 95Ser + Gly 98Ser + Tyr102Glu
Ala 96Thr + Ser 97Asp + Tyr102Thr
Leu 94Asn + Gly100Ser + Ser101Glu
Leu 94Met + Gly 98Gln + Gly100Asn
Val 93Pro + Ala 96Glu + Ile105Ala
Val 93Cys + Gly 95Glu + Tyr102Leu
Leu 94Cys + Gly 95Ser + Ser 97Asp
Gly 95Gln + Ser101Glu + Tyr102His
Val 93Gln + Gly 95Glu + Ile105Gln
Val 93Gly + Ser 99Asp + Ile105Gly
Gly 95Asn + Gly 98Glu + Ile105Val
Ser 97Glu + Gly 98Pro + Tyr102Thr
Val 93Glu + Leu 94Ile + Gly100Gln
Ala 96Pro + Ser101Asp + Ile105Pro
Gly 98Pro + Ser103Asp + Ile105Val
Ala 96Gln + Ser 99Asp + Tyr102Ser
Ser 97Asp + Gly 98Ser + Ile105Asn
Val 93Gln + Gly 98Asn + Tyr102Leu
Leu 94Gly + Tyr102Pro + Ser103Glu
Val 93Thr + Gly100Gln + Ser104Glu
Val 93Gly + Gly100Gln + Ser103Glu
Ala 96Thr + Gly100Ser + Ser103Glu
Gly100Asn + Ser101Glu + Ile105Thr
Gly 95Asp + Tyr102Gly + Ile105Met
Val 93Cys + Ala 96Thr + Ile105Cys
Ala 96Gly + Gly 98Asp + Ser 99Asp
Gly 95Ser + Ser 97Asp + Gly 98Asp
Leu 94Asn + Ser103Glu + Ser104Asp
Tyr102Val + Ser103Glu + Ser104Glu
Ser 99Asp + Gly100Glu + Ile105Met
Ser 97Asp + Gly 98Asp + Ser 99Glu

TABLE 9-continued

| Loop 2-Triple Mutation Variants |
|---|
| Gly 95Asn + Ser101Glu + Ser103Glu |
| Ser101Glu + Tyr102Asn + Ser103Glu |
| Leu 94Asp + Ser 99Glu + Gly100Gln |
| Gly100Asp + Ser101Glu + Ser104Glu |
| Leu 94Asp + Gly 98Glu + Ile105Cys |
| Gly 95Glu + Ser 97Glu + Tyr102Asn |
| Tyr102Thr + Ser103Glu + Ile105Glu |
| Gly 95Asp + Ser 99Glu + Gly100Gln |
| Gly 95Glu + Ser 99Glu + Tyr102Met |
| Val 93Gln + Ser 97Asp + Ser 99Glu |
| Gly100Glu + Ser101Asp + Ser103Asp |
| Val 93Asp + Ser103Glu + Ser104Glu |
| Val 93Asp + Ser 99Asp + Gly100Asp |
| Ala 96Gln + Gly100Asp + Ser104Asp |
| Val 93Asp + Ser101Glu + Ile105Asp |
| Leu 94Asp + Ser 99Glu + Ser101Glu |

TABLE 10

| Loop 2-Quadruple Mutation Variants |
|---|
| Leu 94Asn + Ser 97Glu + Tyr102Asn + Ile105Met |
| Leu 94Pro + Gly 95Glu + Gly100Gln + Tyr102Ala |
| Val 93Cys + Leu 94Met + Gly 95Pro + Ala 96Gln |
| Gly 95Pro + Ser 97Glu + Tyr102Gln + Ile105Leu |
| Gly 95Asp + Gly100Pro + Tyr102Val + Ile105Cys |
| Ala 96Thr + Gly100Asp + Tyr102Ala + Ile105Asn |
| Val 93Asn + Leu 94Cys + Ser101Asp + Tyr102Val |
| Val 93Asn + Gly 95Asn + Ser104Asp + Ile105Val |
| Leu 94Ser + Gly 98Pro + Ser103Glu + Ile105Val |
| Val 93Asn + Leu 94His + Gly 95Asn + Ile105Asn |
| Ala 96Ser + Gly 98Asn + Ser 99Glu + Tyr102Gly |
| Val 93Asn + Gly 98Asn + Tyr102Ile + Ile105Asp |
| Val 93Asn + Tyr102Asn + Ser103Asp + Ile105Ser |
| Ala 96Ser + Gly100Ser + Ser101Asp + Tyr102Pro |
| Leu 94Pro + Ala 96Ser + Ser101Asp + Tyr102Ser |
| Val 93Met + Ala 96Thr + Ser104Asp + Ile105Gln |
| Val 93Met + Leu 94Ala + Gly 95Pro + Ser104Glu |
| Val 93Cys + Gly 95Pro + Ala 96Glu + Tyr102Val |
| Gly 95Asn + Ala 96Asn + Ser104Glu + Ile105Pro |
| Val 93Asn + Leu 94Asn + Gly 98Glu + Ser 99Glu |
| Leu 94His + Gly 98Glu + Ser 99Glu + Tyr102Ser |
| Gly 95Pro + Gly 98Glu + Ser 99Asp + Ile105Gly |
| Val 93Ala + Ala 96Ser + Ser103Glu + Ser104Glu |
| Leu 94Gly + Ser 97Asp + Gly 98Asp + Ser 99Glu |
| Val 93Cys + Leu 94Asp + Gly 95Asn + Gly100Glu |
| Val 93Ser + Ser101Glu + Ser103Asp + Ser104Asp |
| Ala 96Ser + Ser101Glu + Tyr102Gln + Ser103Asp |
| Val 93Thr + Gly100Asn + Ser101Glu + Ser103Asp |
| Val 93Asn + Leu 94Glu + Gly 95Glu + Ser 99Glu |
| Leu 94Asp + Ala 96Gly + Ser 99Glu + Ile105Cys |
| Leu 94Ala + Ser101Glu + Ser104Asp + Ile105Ser |
| Ala 96His + Ser101Glu + Ser104Glu + Ile105Ala |
| Val 93Gly + Gly100Pro + Ser101Glu + Ser104Asp |
| Gly 95Gln + Ser101Glu + Ser104Asp + Ile105Met |
| Gly 98Gln + Ser101Glu + Ser104Glu + Ile105Asn |
| Val 93Gly + Ser101Asp + Tyr102Glu + Ile105Asp |
| Ser101Asp + Tyr102Val + Ser104Glu + Ile105Glu |
| Val 93Cys + Gly 95Asp + Gly 98Asp + Gly100Pro |
| Gly 95Asp + Ser 97Glu + Tyr102Ala + Ile105Cys |
| Val 93Thr + Gly 95Glu + Ala 96Asn + Ser 99Asp |
| Val 93Cys + Gly 95Asp + Ser 99Glu + Ile105Val |
| Val 93Cys + Ser101Asp + Ser103Glu + Ile105Asp |
| Ala 96His + Ser 97Glu + Ser 99Asp + Ile105Asn |
| Ala 96Asn + Ser 97Glu + Ser 99Glu + Tyr102Pro |
| Val 93Cys + Ser 97Glu + Ser 99Asp + Ile105His |
| Val 93Ser + Ser 97Glu + Gly 98Gln + Ser 99Glu |
| Gly 95Asn + Ser 97Asp + Ser 99Glu + Gly100Glu |
| Val 93Met + Gly100Asp + Tyr102Asp + Ser103Asp |
| Leu 94Gly + Ser101Asp + Tyr102Ala + Ile105Glu |
| Ser 97Glu + Gly 98Asp + Gly100Asp + Tyr102Gly |
| Leu 94Ser + Ser 99Glu + Gly100Glu + Ser104Glu |
| Val 93Asn + Ser 99Glu + Gly100Glu + Ser104Asp |
| Val 93Ala + Ser 99Glu + Gly100Asp + Ser104Asp |

TABLE 10-continued

| Loop 2-Quadruple Mutation Variants |
|---|
| Leu 94Cys + Gly 95Ser + Ser 99Asp + Ser101Glu |
| Gly 95Ser + Ala 96Thr + Ser 99Glu + Ser101Asp |
| Leu 94Cys + Ala 96Ser + Ser 99Asp + Ser101Asp |
| Ser 99Asp + Ser101Glu + Tyr102Asn + Ile105Val |
| Val 93Glu + Gly 95Pro + Ser101Glu + Ser103Asp |
| Val 93Ala + Gly 95Asp + Ser 99Asp + Ser101Glu |
| Ser 99Glu + Ser101Glu + Tyr102Pro + Ser104Glu |

TABLE 11

| Loop 3-Single Mutation Variants |
|---|
| Leu124Ala |
| Leu124Asn |
| Leu124Asp |
| Leu124Cys |
| Leu124Gln |
| Leu124Glu |
| Leu124Gly |
| Leu124His |
| Leu124Ile |
| Leu124Met |
| Leu124Pro |
| Leu124Ser |
| Leu124Thr |
| Leu124Val |
| Gly125Asn |
| Gly125Asp |
| Gly125Gln |
| Gly125Glu |
| Gly125Pro |
| Gly125Ser |
| Ser126Asp |
| Ser126Glu |
| Pro127Asn |
| Pro127Asp |
| Pro127Gln |
| Pro127Glu |
| Pro127Gly |
| Pro127Ser |
| Ser128Asp |
| Ser128Glu |
| Pro129Asn |
| Pro129Asp |
| Pro129Gln |
| Pro129Glu |
| Pro129Gly |
| Pro129Ser |
| Ser130Asp |
| Ser130Glu |
| Ala131Asn |
| Ala131Asp |
| Ala131Gln |
| Ala131Glu |
| Ala131Gly |
| Ala131His |
| Ala131Pro |
| Ala131Ser |
| Ala131Thr |

TABLE 12

| Loop 3-Double Mutation Variants |
|---|
| Leu124Gln + Ser128Glu |
| Gly125Ser + Ser126Glu |
| Gly125Ser + Ser128Glu |
| Pro127Gly + Ser130Glu |
| Leu124Thr + Ser126Glu |
| Ser126Glu + Pro129Ser |
| Gly125Gln + Ser128Glu |
| Pro127Ser + Ser130Glu |

TABLE 12-continued

Loop 3-Double Mutation Variants

Gly125Glu + Pro127Asn
Pro129Gln + Ser130Glu
Gly125Asp + Ala131His
Pro127Gly + Ala131Glu
Leu124His + Ser126Asp
Pro127Gly + Pro129Asp
Ser126Glu + Ala131Gln
Leu124Asp + Ala131Pro
Gly125Pro + Pro127Glu
Gly125Ser + Ser126Asp
Leu124Gln + Ala131Asn
Gly125Asp + Pro129Ser
Pro129Asn + Ala131Asp
Pro127Asn + Ser128Asp
Pro129Gly + Ala131Glu
Pro127Ser + Pro129Asp
Pro127Ser + Ser128Glu
Leu124Gly + Ser130Glu
Gly125Asn + Ser130Asp
Leu124Glu + Pro127Asn
Ser130Glu + Ala131Gly
Ser130Asp + Ala131Thr
Leu124Gln + Ser128Asp
Leu124Ser + Ala131Pro
Pro129Ser + Ser130Glu
Gly125Gln + Pro127Asp
Leu124Cys + Ala131Thr
Gly125Gln + Pro129Gln
Leu124Met + Ala131Gln
Gly125Gln + Ala131Asp
Ser128Glu + Ala131Asn
Ser130Glu + Ala131Pro
Gly125Pro + Ala131Ser
Pro127Ser + Pro129Asn
Ser126Glu + Pro127Gln
Pro127Ser + Ser130Asp
Pro127Gly + Ser128Asp
Gly125Glu + Pro127Ser
Leu124Cys + Pro129Asn
Gly125Gln + Pro129Glu
Gly125Asn + Ala131Asp
Gly125Ser + Pro129Gln
Ser126Asp + Pro129Gln
Leu124Val + Pro129Asn
Leu124His + Ser126Glu
Pro127Glu + Ala131Gly
Leu124Thr + Gly125Pro
Leu124His + Ser130Glu
Gly125Asn + Ser126Asp
Pro129Asn + Ala131Pro
Pro127Gln + Pro129Asn
Leu124Gly + Pro129Glu

TABLE 13

Loop 3-Triple Mutation Variants

Gly125Gln + Ser126Glu + Ala131His
Ser126Asp + Pro127Ser + Ala131His
Leu124Val + Ser130Asp + Ala131Asn
Leu124Gln + Ser126Glu + Ala131Ser
Gly125Ser + Pro129Glu + Ala131Gly
Leu124Ser + Pro127Asp + Ala131Gln
Pro127Ser + Ser128Asp + Ala131His
Leu124Thr + Pro127Glu + Ala131Ser
Leu124Gln + Ser126Glu + Ala131Asn
Gly125Asn + Pro127Glu + Ala131Gln
Gly125Gln + Ser126Asp + Pro127Gln
Pro127Asn + Ser130Asp + Ala131Thr
Gly125Asn + Pro127Glu + Pro129Asn
Leu124Thr + Ser128Asp + Ala131Gln
Gly125Ser + Pro129Gln + Ala131Glu
Pro127Gln + Pro129Asn + Ser130Glu
Leu124Ile + Gly125Gln + Ser130Glu

TABLE 13-continued

Loop 3-Triple Mutation Variants

Pro129Asn + Ser130Glu + Ala131Gly
Leu124Ser + Gly125Ser + Pro129Gln
Leu124Asn + Gly125Gln + Ser128Asp
Leu124Gln + Pro127Ser + Ser130Asp
Gly125Ser + Pro127Ser + Ala131Asp
Gly125Ser + Ser128Glu + Pro129Gln
Pro127Asn + Ser128Asp + Ala131Gly
Leu124Thr + Gly125Ser + Ala131Asn
Gly125Gln + Pro129Ser + Ser130Asp
Gly125Pro + Ser126Glu + Pro129Asn
Pro129Gly + Ser130Asp + Ala131Pro
Gly125Asn + Ser126Asp + Pro129Gly
Gly125Asp + Ser126Asp + Ala131Asn
Gly125Glu + Ser126Glu + Ala131Ser
Gly125Glu + Ser126Asp + Ala131His
Gly125Gln + Ser128Glu + Pro129Glu
Ser128Glu + Pro129Glu + Ala131Gly
Leu124Cys + Ser128Glu + Pro129Asp
Pro127Gly + Ser128Glu + Pro129Glu
Pro127Gly + Ser128Asp + Pro129Asp
Leu124Asn + Ser128Glu + Pro129Asp
Ser126Glu + Pro127Asp + Ala131Asn
Ser126Glu + Pro127Glu + Pro129Gly
Leu124His + Ser126Asp + Pro127Glu
Ser126Asp + Pro127Glu + Pro129Gly
Pro127Asp + Ser128Asp + Pro129Asn
Pro127Asp + Ser128Glu + Ala131His
Pro127Glu + Ser128Asp + Ala131Pro
Leu124Ile + Pro127Glu + Ser128Glu
Pro129Asp + Ser130Asp + Ala131Gly
Leu124Pro + Pro129Glu + Ser130Glu
Ser126Asp + Pro127Glu + Ser128Asp
Ser126Glu + Pro127Asp + Ser128Asp
Pro129Glu + Ser130Asp + Ala131Glu
Leu124Asp + Gly125Asp + Ser126Asp
Leu124Ser + Ser126Asp + Ser128Asp
Ser126Glu + Ser128Asp + Pro129Asn
Gly125Asn + Ser126Glu + Ser128Glu
Ser126Glu + Ser128Glu + Ala131Thr
Leu124Asn + Ser126Glu + Ser128Glu
Ser126Glu + Ser128Glu + Pro129Glu
Gly125Glu + Ser126Glu + Ser128Asp
Ser128Asp + Pro129Ser + Ser130Glu

TABLE 14

Loop 3-Quadruple Mutation Variants

Gly125Gln + Ser126Glu + Pro127Ser + Ala131Ser
Gly125Asn + Pro127Ser + Ser130Asp + Ala131Asn
Leu124Ala + Pro127Gln + Ser128Glu + Ala131Pro
Gly125Pro + Pro127Ser + Pro129Ser + Ser130Glu
Gly125Asn + Pro129Asn + Ser130Asp + Ala131Gln
Gly125Asn + Pro129Asn + Ser130Glu + Ala131Pro
Leu124Ser + Ser126Glu + Pro129Gly + Ala131Gln
Gly125Asn + Ser126Glu + Pro127Gly + Ala131Ser
Leu124Ile + Ser128Asp + Pro129Gln + Ala131Ser
Leu124His + Gly125Ser + Pro129Gly + Ala131Asn
Leu124Ala + Gly125Glu + Pro127Gln + Pro129Gln
Leu124Ser + Gly125Glu + Ser126Asp + Pro129Ser
Gly125Glu + Ser126Glu + Pro127Gln + Ala131His
Leu124Met + Gly125Asp + Ser126Asp + Pro127Asn
Leu124Gln + Ser128Glu + Pro129Asp + Ala131Gln
Leu124Val + Ser128Glu + Pro129Glu + Ala131Asn
Pro127Ser + Ser128Asp + Pro129Asp + Ala131Thr
Leu124Ile + Ser128Glu + Pro129Asp + Ala131Ser
Gly125Ser + Ser126Glu + Pro127Glu + Ala131Gln
Leu124His + Gly125Gln + Ser130Glu + Ala131Glu
Leu124Thr + Gly125Gln + Ser130Asp + Ala131Asp
Leu124His + Pro127Glu + Ser128Glu + Ala131His
Gly125Ser + Pro127Asp + Ser128Asp + Pro129Gln
Leu124Asn + Ser126Glu + Pro127Asp + Ser128Asp
Pro127Gln + Ser128Glu + Pro129Asp + Ser130Asp
Gly125Pro + Ser128Asp + Pro129Glu + Ser130Glu

TABLE 14-continued

Loop 3-Quadruple Mutation Variants

Leu124Asn + Gly125Asp + Ser126Asp + Pro127Asp
Leu124Asp + Gly125Asp + Ser126Asp + Pro129Gln
Leu124Asp + Gly125Glu + Ser126Asp + Pro129Gly
Gly125Gln + Ser126Glu + Ser128Glu + Ala131Thr
Leu124Asn + Ser126Glu + Pro127Gln + Ser128Asp
Leu124Met + Gly125Pro + Ser126Asp + Ser128Glu
Leu124Asn + Gly125Ser + Ser126Asp + Ser128Asp
Leu124Val + Ser126Glu + Ser128Glu + Pro129Asp
Leu124Cys + Ser126Asp + Ser128Glu + Pro129Glu
Ser126Asp + Pro127Asp + Pro129Glu + Ala131Ser
Gly125Asn + Ser126Glu + Pro127Glu + Pro129Glu
Leu124Ser + Ser126Asp + Pro127Asp + Pro129Asp
Gly125Asp + Ser126Glu + Ser128Asp + Pro129Ser
Leu124Val + Gly125Asp + Ser126Glu + Ser128Glu
Gly125Glu + Ser126Glu + Ser128Asp + Pro129Asn
Gly125Glu + Ser126Asp + Pro127Ser + Ser128Asp
Leu124Met + Ser128Glu + Ser130Glu + Ala131Ser
Leu124Cys + Ser128Glu + Pro129Ser + Ser130Asp
Gly125Gln + Ser128Glu + Ser130Glu + Ala131His
Leu124Met + Pro127Gln + Ser128Glu + Ser130Glu
Leu124Gly + Ser126Asp + Pro129Glu + Ser130Asp
Gly125Asn + Ser126Glu + Pro129Glu + Ser130Glu
Leu124Gly + Gly125Asp + Pro127Asp + Pro129Gly
Ser126Asp + Ser128Asp + Ser130Glu + Ala131Gln
Gly125Pro + Ser126Asp + Ser128Glu + Ser130Asp
Ser126Asp + Pro127Gly + Ser128Glu + Ser130Glu
Ser126Glu + Pro127Gly + Ser128Asp + Ser130Glu
Ser126Asp + Ser128Asp + Pro129Ser + Ser130Asp
Ser126Glu + Ser128Asp + Ser130Asp + Ala131His
Ser126Glu + Ser128Glu + Ser130Glu + Ala131Ser
Gly125Pro + Ser126Glu + Ser128Glu + Ser130Asp
Leu124Val + Ser126Asp + Ser128Glu + Ser130Asp
Gly125Gln + Ser126Glu + Ser128Asp + Ser130Glu
Ser126Glu + Ser128Asp + Pro129Gly + Ser130Glu

TABLE 15

Loop 4-Single Mutation Variants

Gly152Asn
Gly152Asp
Gly152Gln
Gly152Glu
Gly152Pro
Gly152Ser
Asn153Asp
Asn153Gln
Asn153Glu
Asn153Ser
Ser154Asp
Ser154Glu
Gly155Asn
Gly155Asp
Gly155Gln
Gly155Glu
Gly155Pro
Gly155Ser
Ala156Asn
Ala156Asp
Ala156Gln
Ala156Glu
Ala156Gly
Ala156His
Ala156Pro
Ala156Ser
Ala156Thr
Gly157Asn
Gly157Asp
Gly157Gln
Gly157Glu
Gly157Pro
Gly157Ser
Ser158Asp
Ser158Glu

TABLE 15-continued

Loop 4-Single Mutation Variants

Ile159Ala
Ile159Asn
Ile159Asp
Ile159Cys
Ile159Gln
Ile159Glu
Ile159Gly
Ile159His
Ile159Leu
Ile159Met
Ile159Pro
Ile159Ser
Ile159Thr
Ile159Val
Ser160Asp
Ser160Glu
Tyr161Ala
Tyr161Asn
Tyr161Asp
Tyr161Cys
Tyr161Gln
Tyr161Glu
Tyr161Gly
Tyr161His
Tyr161Ile
Tyr161Leu
Tyr161Met
Tyr161Pro
Tyr161Ser
Tyr161Thr
Tyr161Val

TABLE 16

Loop 4-Double Mutation Variants

Ser154Glu + Gly155Asn
Ser154Asp + Gly157Gln
Ser154Glu + Ile159His
Gly152Gln + Gly157Asp
Ser154Glu + Gly155Ser
Asn153Ser + Ser154Glu
Ala156Asn + Ser160Glu
Ala156Thr + Ser158Glu
Asn153Glu + Gly157Ser
Gly155Asn + Ala156Asp
Ile159Gly + Tyr161Gly
Gly155Ser + Tyr161Glu
Ser154Asp + Gly155Pro
Gly155Asp + Ala156Ser
Gly152Glu + Asn153Ser
Ser158Glu + Ile159Asn
Asn153Asp + Ala156His
Ser154Glu + Tyr161Cys
Ile159Leu + Tyr161Asn
Gly157Asp + Ile159Gly
Ser158Asp + Ile159Gly
Gly152Pro + Gly155Glu
Gly155Gln + Ser160Asp
Gly152Asp + Tyr161Met
Ser154Glu + Gly155Gln
Gly155Glu + Tyr161Ala
Ala156Ser + Ser160Asp
Ala156Glu + Tyr161Leu
Gly152Pro + Gly157Asn
Ser158Glu + Ile159Ser
Gly157Asp + Tyr161Thr
Ser158Asp + Ile159Cys
Gly155Pro + Tyr161Ala
Gly152Asp + Tyr161Ala
Ala156His + Ile159Asn
Ser154Asp + Ala156His
Gly157Pro + Ser158Asp
Asn153Ser + Ile159Cys

TABLE 16-continued

| Loop 4-Double Mutation Variants |
|---|
| Ser154Asp + Ala156Ser |
| Ser154Glu + Tyr161Ala |
| Ile159Leu + Tyr161Ala |
| Gly152Glu + Gly155Gln |
| Ala156Pro + Gly157Glu |
| Asn153Asp + Tyr161His |
| Ala156Gln + Ile159Asn |
| Gly152Pro + Ser154Asp |
| Gly155Gln + Ala156Asp |
| Ala156Ser + Ile159Gly |
| Asn153Asp + Gly157Gln |
| Ile159Leu + Ser160Asp |
| Gly155Glu + Ile159Gln |
| Ser160Asp + Tyr161Thr |
| Ser158Asp + Ile159Gln |
| Ser154Glu + Gly157Asn |
| Ala156Gly + Ile159His |
| Ala156Ser + Ser158Asp |
| Asn153Gln + Gly155Glu |
| Gly155Asn + Ser158Glu |
| Ser158Glu + Ile159Pro |
| Ser158Asp + Ile159Leu |

TABLE 17

| Loop 4-Triple Mutation Variants |
|---|
| Ala156Asn + Gly157Asn + Tyr161Cys |
| Gly152Gln + Gly155Glu + Tyr161Asn |
| Gly152Gln + Asn153Gln + Ser154Glu |
| Gly155Ser + Ser158Glu + Tyr161Gln |
| Gly152Glu + Asn153Ser + Ala156Ser |
| Gly152Glu + Ile159Pro + Tyr161Asn |
| Gly152Asp + Gly157Gln + Tyr161Met |
| Gly155Asn + Ile159Thr + Tyr161His |
| Asn153Ser + Gly155Ser + Ser158Glu |
| Gly152Ser + Gly155Pro + Ser158Glu |
| Gly152Pro + Gly157Gln + Ser160Asp |
| Gly152Gln + Ser154Asp + Tyr161Met |
| Ala156Pro + Ile159Asn + Tyr161Ile |
| Ile159Asn + Ser160Glu + Tyr161Ser |
| Gly152Asp + Ile159Ala + Tyr161Cys |
| Asn153Gln + Ile159Ala + Ser160Glu |
| Asn153Asp + Gly155Pro + Tyr161Asn |
| Gly155Asn + Ala156Thr + Ser158Asp |
| Gly152Gln + Ser154Asp + Tyr161Gln |
| Gly157Ser + Ser158Asp + Tyr161Pro |
| Ser154Glu + Gly155Ser + Ile159Cys |
| Gly155Gln + Ala156Asn + Ser158Asp |
| Gly155Asn + Gly157Asn + Ile159Ala |
| Gly157Asn + Ser158Glu + Ile159His |
| Asn153Ser + Ile159Leu + Ser160Glu |
| Ala156Gln + Gly157Asp + Tyr161Asn |
| Gly155Asn + Ala156His + Tyr161Val |
| Asn153Gln + Ala156Asp + Ile159Gly |
| Ala156His + Ser160Glu + Tyr161His |
| Ala156Gln + Ser160Asp + Tyr161Ala |
| Gly152Asp + Gly157Gln + Ile159Gly |
| Asn153Glu + Ala156Pro + Ile159Ala |
| Gly152Gln + Gly155Asn + Ala156Thr |
| Asn153Gln + Ile159Met + Ser160Glu |
| Gly152Asp + Ala156Pro + Tyr161Cys |
| Gly152Ser + Ser154Glu + Tyr161Val |
| Gly155Asp + Gly157Ser + Tyr161Asn |
| Asn153Glu + Ser154Asp + Gly155Ser |
| Asn153Glu + Ser154Asp + Ala156Pro |
| Gly157Asn + Ser160Asp + Tyr161Asp |
| Gly152Glu + Asn153Asp + Tyr161Met |
| Gly152Asp + Asn153Asp + Ile159Leu |
| Ala156Asp + Gly157Glu + Tyr161Thr |
| Asn153Ser + Ser154Glu + Gly155Asp |
| Ser154Asp + Gly155Asp + Ala156Pro |
| Asn153Ser + Ser154Asp + Gly155Glu |
| Ser154Glu + Gly155Asp + Tyr161Ala |

TABLE 17-continued

| Loop 4-Triple Mutation Variants |
|---|
| Gly157Asp + Ser158Glu + Tyr161Met |
| Gly155Gln + Gly157Asp + Ser158Glu |
| Ala156His + Gly157Glu + Ser158Asp |
| Gly155Asp + Ala156Glu + Gly157Asp |
| Ser154Asp + Ala156Glu + Tyr161Cys |
| Ser154Asp + Ala156Glu + Ile159Pro |
| Ser154Asp + Ala156Glu + Ile159Asn |
| Gly152Pro + Ala156Glu + Ser158Glu |
| Gly155Asn + Ala156Glu + Ser158Glu |
| Asn153Glu + Gly155Asp + Ile159Pro |
| Gly152Glu + Ile159Cys + Ser160Asp |
| Gly152Glu + Ser154Glu + Gly157Gln |
| Gly152Glu + Ser154Glu + Gly155Asn |

TABLE 18

| Loop 4-Quadruple Mutation Variants |
|---|
| Ala156Pro + Ile159Pro + Ser160Glu + Tyr161Thr |
| Asn153Gln + Gly157Asn + Ile159Gln + Ser160Asp |
| Asn153Gln + Ala156Gly + Gly157Glu + Ile159Asn |
| Gly152Asn + Ile159Gln + Ser160Asp + Tyr161Met |
| Gly152Pro + Ser154Glu + Gly157Pro + Ile159Ala |
| Ala156Ser + Gly157Ser + Ile159Gln + Tyr161Glu |
| Asn153Ser + Gly157Ser + Ile159Ala + Ser160Asp |
| Gly155Gln + Ser158Asp + Ile159Gly + Tyr161Met |
| Gly152Ser + Ser154Asp + Ala156Gln + Ile159Cys |
| Ala156His + Gly157Pro + Ser158Glu + Tyr161Met |
| Ala156Pro + Gly157Asn + Ile159Met + Ser160Asp |
| Ser154Glu + Gly155Asn + Ile159Met + Tyr161Ala |
| Gly152Ser + Ala156His + Gly157Pro + Ile159Gly |
| Asn153Ser + Ile159Leu + Ser160Glu + Tyr161Thr |
| Gly152Asn + Ser154Asp + Ala156Ser + Gly157Asn |
| Ser154Asp + Gly155Gln + Ile159Leu + Tyr161Thr |
| Asn153Ser + Ser154Asp + Gly155Asn + Ile159Met |
| Gly152Asn + Asn153Gln + Gly155Asn + Ile159Val |
| Asn153Glu + Ser154Glu + Gly157Asn + Ile159Leu |
| Asn153Glu + Ser154Asp + Gly155Pro + Ala156Ser |
| Ser154Asp + Gly155Asp + Ala156Gly + Gly157Asn |
| Gly152Ser + Gly157Asp + Ser158Asp + Ile159Ser |
| Gly155Pro + Gly157Asp + Ser158Asp + Ile159Pro |
| Ala156Glu + Gly157Glu + Ser158Glu + Tyr161Ile |
| Asn153Glu + Ser154Asp + Gly155Asp + Ala156Pro |
| Ser154Glu + Ala156Glu + Gly157Ser + Ile159Ser |
| Ala156Glu + Gly157Asn + Ser158Asp + Ile159Asn |
| Gly152Asn + Asn153Asp + Gly155Glu + Tyr161Gln |
| Gly152Pro + Asn153Asp + Gly155Glu + Gly157Gln |
| Gly152Asp + Ala156Pro + Ile159Val + Ser160Asp |
| Gly152Asp + Asn153Gln + Ile159Ala + Ser160Asp |
| Gly152Glu + Ser154Glu + Ile159Gln + Tyr161Cys |
| Gly152Glu + Ser154Asp + Gly157Pro + Tyr161Leu |
| Gly155Asp + Ala156Asp + Gly157Pro + Ser158Asp |
| Gly155Glu + Ala156Asp + Gly157Gln + Ser158Asp |
| Gly152Asp + Asn153Glu + Ile159Thr + Ser160Glu |
| Gly152Glu + Asn153Asp + Ile159Leu + Ser160Glu |
| Ala156Thr + Ser158Asp + Ser160Glu + Tyr161Cys |
| Ser158Glu + Ile159Met + Ser160Asp + Tyr161Pro |
| Ser158Glu + Ile159Cys + Ser160Glu + Tyr161Gly |
| Gly155Pro + Ser158Glu + Ile159Gln + Ser160Asp |
| Gly157Pro + Ser158Asp + Ser160Glu + Tyr161Met |
| Gly152Glu + Ser154Glu + Gly157Asn + Ser160Glu |
| Gly152Glu + Ser154Asp + Gly157Gln + Ser160Asp |
| Gly152Glu + Ser154Asp + Gly157Ser + Ser160Glu |
| Gly152Glu + Ala156Gly + Ser158Asp + Ser160Glu |
| Gly152Asp + Ser158Asp + Ile159Leu + Ser160Glu |
| Gly152Asp + Gly155Gln + Ser158Asp + Ser160Glu |
| Ala156Glu + Ser158Glu + Ser160Asp + Tyr161Gly |
| Gly157Asp + Ser158Glu + Ile159His + Ser160Glu |
| Gly152Asn + Ser154Glu + Gly155Asp + Ser158Asp |
| Asn153Glu + Ser154Asp + Gly157Pro + Ser160Glu |
| Asn153Asp + Ser154Asp + Ile159Ser + Ser160Glu |
| Asn153Asp + Ser154Asp + Ser160Asp + Tyr161Ile |
| Gly152Asn + Ser154Glu + Gly157Glu + Ser158Asp |
| Gly152Glu + Ala156Asp + Ser158Glu + Ile159Val |

TABLE 18-continued

| Loop 4-Quadruple Mutation Variants |
|---|
| Asn153Asp + Ser154Glu + Ala156Ser + Gly157Asp |
| Asn153Glu + Ser154Glu + Gly155Ser + Gly157Asp |
| Ser154Glu + Gly155Asp + Gly157Pro + Ser160Asp |
| Gly152Asp + Asn153Glu + Ser158Glu + Ile159Ala |

TABLE 19

| Loop 5-Single Mutation Variants |
|---|
| Ala181Asn |
| Ala181Asp |
| Ala181Gln |
| Ala181Glu |
| Ala181Gly |
| Ala181His |
| Ala181Pro |
| Ala181Ser |
| Ala181Thr |
| Ser182Asp |
| Ser182Glu |
| Phe183Ala |
| Phe183Asn |
| Phe183Asp |
| Phe183Cys |
| Phe183Gln |
| Phe183Glu |
| Phe183Gly |
| Phe183His |
| Phe183Ile |
| Phe183Leu |
| Phe183Met |
| Phe183Pro |
| Phe183Ser |
| Phe183Thr |
| Phe183Tyr |
| Phe183Val |
| Ser184Asp |
| Ser184Glu |
| Gln185Asn |
| Gln185Asp |
| Gln185Glu |
| Gln185Ser |

TABLE 20

| Loop 5-Double Mutation Variants |
|---|
| Ala181Asp + Phe183Gln |
| Ser182Asp + Gln185Asn |
| Phe183Met + Gln185Glu |
| Ser182Glu + Gln185Asn |
| Ala181Pro + Ser182Glu |
| Ala181Asn + Gln185Glu |
| Ser182Glu + Phe183Leu |
| Ala181Pro + Gln185Asp |
| Phe183Ser + Gln185Glu |
| Ala181Gln + Ser182Glu |
| Phe183Ile + Gln185Glu |
| Ala181Ser + Gln185Asp |
| Ala181Gln + Phe183Ser |
| Ala181Thr + Phe183Asn |
| Ala181Gly + Gln185Asp |
| Ala181His + Ser182Glu |
| Phe183Gln + Gln185Ser |
| Phe183Pro + Gln185Ser |
| Ala181Asn + Ser182Asp |
| Ala181Ser + Gln185Glu |
| Ala181Asn + Phe183Asn |
| Ala181His + Phe183Asp |
| Ala181Asn + Ser182Glu |
| Ser182Asp + Phe183His |
| Ala181Asp + Phe183Ile |

TABLE 20-continued

| Loop 5-Double Mutation Variants |
|---|
| Phe183Leu + Gln185Asp |
| Ser182Glu + Phe183Ser |
| Ala181His + Gln185Asp |
| Phe183Val + Gln185Asp |
| Ser182Asp + Phe183Thr |
| Phe183Gly + Gln185Asp |
| Ala181Thr + Gln185Glu |
| Ala181His + Gln185Glu |
| Ser182Asp + Phe183Val |
| Ala181Asp + Phe183Ser |
| Ser182Asp + Phe183Cys |
| Ala181Pro + Phe183Asp |
| Ala181Gly + Phe183Ala |
| Ala181Pro + Phe183Asn |
| Phe183Pro + Gln185Asp |
| Ser182Glu + Phe183Tyr |
| Phe183Cys + Gln185Ser |
| Ala181Thr + Ser182Glu |
| Ala181Pro + Phe183Ala |
| Ser182Glu + Phe183Thr |
| Ala181Pro + Phe183Pro |
| Ser182Glu + Gln185Ser |
| Ala181Gln + Ser182Asp |
| Phe183Gly + Gln185Glu |
| Ala181Gln + Gln185Asp |
| Phe183Ser + Gln185Asp |
| Ser182Asp + Phe183Met |
| Phe183Ala + Gln185Asn |
| Ala181Asp + Phe183His |
| Phe183Val + Gln185Glu |
| Ala181Ser + Ser182Glu |
| Ala181Asn + Phe183Pro |
| Phe183Tyr + Gln185Glu |
| Ala181Glu + Phe183Cys |
| Ser182Glu + Phe183Ile |

TABLE 21

| Loop 5 - Triple Mutation Variants |
|---|
| Ala181Glu + Phe183Val + Gln185Ser |
| Ala181Pro + Ser182Asp + Gln185Asn |
| Ala181Thr + Phe183His + Gln185Asp |
| Ser182Glu + Phe183Ala + Gln185Asn |
| Ala181Thr + Ser182Asp + Gln185Asn |
| Ala181Gln + Ser182Asp + Phe183Ala |
| Ser182Asp + Phe183Asn + Gln185Asn |
| Ala181Gln + Phe183Gln + Gln185Glu |
| Ser181Asp + Phe183Met + Gln185Asn |
| Ala181Pro + Ser182Glu + Phe183Gly |
| Ala181His + Phe183Ala + Gln185Ser |
| Ala181Ser + Ser182Glu + Gln185Asn |
| Ala181Gly + Phe183Ile + Gln185Glu |
| Ala181Asn + Phe183Tyr + Gln185Asn |
| Ser182Asp + Phe183Leu + Gln185Asn |
| Ser182Asp + Phe183Val + Gln185Asn |
| Ala181Glu + Phe183Leu + Gln185Ser |
| Ala181Glu + Phe183Tyr + Gln185Ser |
| Ala181Gln + Ser182Asp + Phe183Gly |
| Ala181Thr + Phe183Ile + Gln185Ser |
| Ala181Gln + Ser182Glu + Gln185Ser |
| Ala181Gln + Ser182Glu + Phe183His |
| Ala181Asp + Phe183Ala + Gln185Asn |
| Ala181Thr + Ser182Asp + Phe183Thr |
| Ala181Ser + Phe183Pro + Gln185Glu |
| Ser182Glu + Phe183Ala + Gln185Ser |
| Ala181Asn + Phe183Cys + Gln185Ser |
| Ala181Pro + Phe183Thr + Gln185Asp |
| Ala181Thr + Phe183Val + Gln185Asn |
| Ala181Gln + Ser182Asp + Gln185Ser |
| Ala181Asn + Ser182Asp + Gln185Ser |
| Ser182Asp + Phe183Thr + Gln185Ser |
| Ala181Ser + Phe183Asp + Gln185Asn |
| Ser182Asp + Phe183Thr + Gln185Asn |

TABLE 21-continued

| Loop 5 - Triple Mutation Variants |
|---|
| Ala181Gly + Phe183Asn + Gln185Ser |
| Ala181Asp + Phe183Met + Gln185Ser |
| Ala181Asp + Phe183Pro + Gln185Asn |
| Ala181Gly + Ser182Asp + Phe183Gly |
| Ala181Gln + Ser182Glu + Gln185Asn |
| Ala181Thr + Ser182Asp + Gln185Ser |
| Ala181Asn + Phe183Asn + Gln185Asp |
| Ala181Thr + Phe183Asp + Gln185Ser |
| Ala181Gln + Phe183Ser + Gln185Ser |
| Ser182Asp + Phe183Gly + Gln185Ser |
| Ala181Gly + Ser182Glu + Phe183Leu |
| Ala181Asn + Ser182Glu + Gln185Asn |
| Ala181Glu + Ser182Glu + Phe183Ser |
| Ala181Glu + Ser182Glu + Phe183Gly |
| Ala181Glu + Ser182Glu + Phe183Leu |
| Ala181Glu + Ser182Glu + Phe183Val |
| Ala181Glu + Ser182Asp + Phe183Met |
| Ala181Asp + Ser182Asp + Phe183Met |
| Ala181Asp + Ser182Asp + Phe183Cys |
| Ala181Glu + Ser182Asp + Gln185Asn |
| Ala181Asp + Ser182Asp + Gln185Asn |
| Ala181Glu + Ser182Glu + Phe183Asn |
| Ala181Asp + Ser182Glu + Phe183Ser |
| Ala181Glu + Ser182Asp + Gln185Ser |
| Ala181Glu + Ser182Glu + Phe183Thr |
| Ala181Glu + Ser182Asp + Phe183Leu |

TABLE 22

| Loop 5 - Quadruple Mutation Variants |
|---|
| Ala181Ser + Ser182Asp + Phe183Ala + Gln185Ser |
| Ala181Ser + Ser182Glu + Phe183Pro + Gln185Ser |
| Ala181Gly + Ser182Asp + Phe183Gly + Gln185Asn |
| Ala181Gly + Ser182Glu + Phe183Pro + Gln185Ser |
| Ala181Thr + Ser182Glu + Phe183Thr + Gln185Ser |
| Ala181Gly + Ser182Glu + Phe183Thr + Gln185Ser |
| Ala181His + Ser182Glu + Phe183His + Gln185Asn |
| Ala181Gly + Ser182Glu + Phe183Ser + Gln185Ser |
| Ala181Gln + Ser182Glu + Phe183His + Gln185Asn |
| Ala181Asn + Ser182Glu + Phe183Cys + Gln185Ser |
| Ala181Pro + Ser182Glu + Phe183Met + Gln185Ser |
| Ala181Gln + Ser182Asp + Phe183Gln + Gln185Asn |
| Ala181Thr + Ser182Asp + Phe183His + Gln185Asn |
| Ala181Gly + Ser182Glu + Phe183Leu + Gln185Ser |
| Ala181Asn + Ser182Asp + Phe183Ile + Gln185Ser |
| Ala181Gly + Ser182Asp + Phe183Ala + Gln185Ser |
| Ala181Asn + Ser182Asp + Phe183Ser + Gln185Asn |
| Ala181Asn + Ser182Glu + Phe183Gly + Gln185Ser |
| Ala181Asn + Ser182Glu + Phe183Met + Gln185Asn |
| Ala181His + Ser182Glu + Phe183Asn + Gln185Asn |
| Ala181Gly + Ser182Glu + Phe183Tyr + Gln185Asn |
| Ala181Asn + Ser182Asp + Phe183Asn + Gln185Asn |
| Ala181Glu + Ser182Glu + Phe183Asn + Gln185Asn |
| Ala181Asp + Ser182Glu + Phe183Ile + Gln185Asn |
| Ala181Glu + Ser182Asp + Phe183Gln + Gln185Asn |
| Ala181Asp + Ser182Asp + Phe183His + Gln185Asn |
| Ala181Glu + Ser182Asp + Phe183Ser + Gln185Asn |
| Ala181Glu + Ser182Asp + Phe183Leu + Gln185Asn |
| Ala181Glu + Ser182Asp + Phe183Leu + Gln185Ser |
| Ala181Asp + Ser182Glu + Phe183Thr + Gln185Ser |
| Ala181Asp + Ser182Asp + Phe183Gln + Gln185Asn |
| Ala181Asp + Ser182Asp + Phe183Ala + Gln185Asn |
| Ala181Asp + Ser182Glu + Phe183Ala + Gln185Asn |
| Ala181Glu + Ser182Asp + Phe183Met + Gln185Ser |
| Ala181Glu + Ser182Glu + Phe183Thr + Gln185Asn |
| Ala181Asp + Ser182Asp + Phe183Gly + Gln185Ser |
| Ala181Glu + Ser182Asp + Phe183Ala + Gln185Asn |
| Ala181His + Ser182Glu + Phe183Glu + Gln185Asn |
| Ala181Ser + Ser182Asp + Phe183Glu + Gln185Ser |
| Ala181Ser + Ser182Asp + Phe183Asp + Gln185Ser |
| Ala181Pro + Ser182Glu + Phe183Asp + Gln185Ser |
| Ala181Asp + Ser182Asp + Phe183Asp + Gln185Asn |
| Ala181Glu + Ser182Asp + Phe183Glu + Gln185Ser |

TABLE 22-continued

| Loop 5 - Quadruple Mutation Variants |
|---|
| Ala181Ser + Ser182Asp + Phe183Glu + Gln185Glu |
| Ala181Gly + Ser182Glu + Phe183Glu + Gln185Glu |
| Ala181Gln + Ser182Glu + Phe183Asp + Gln185Asp |
| Ala181Ser + Ser182Asp + Phe183Asp + Gln185Asp |
| Ala181Thr + Ser182Asp + Phe183Asp + Gln185Asp |
| Ala181Pro + Ser182Asp + Phe183Glu + Gln185Asp |
| Ala181Asn + Ser182Glu + Phe183Asp + Gln185Asp |
| Ala181Thr + Ser182Asp + Phe183Asp + Gln185Glu |
| Ala181Pro + Ser182Glu + Phe183Glu + Gln185Glu |
| Ala181Asn + Ser182Asp + Phe183Asp + Gln185Glu |
| Ala181Thr + Ser182Glu + Phe183Asp + Gln185Asp |
| Ala181His + Ser182Glu + Phe183Glu + Gln185Glu |
| Ala181Glu + Ser182Glu + Phe183Ser + Gln185Glu |
| Ala181Glu + Ser182Glu + Phe183Val + Gln185Glu |
| Ala181Asp + Ser182Glu + Phe183Pro + Gln185Glu |
| Ala181Glu + Ser182Glu + Phe183Thr + Gln185Asp |
| Ala181Asp + Ser182Asp + Phe183Cys + Gln185Glu |

TABLE 23

| Loop 6 - Single Mutation Variants |
|---|
| Val193Ala |
| Val193Asn |
| Val193Asp |
| Val193Cys |
| Val193Gln |
| Val193Glu |
| Val193Gly |
| Val193His |
| Val193Met |
| Val193Pro |
| Val193Ser |
| Val193Thr |
| Ala194Asn |
| Ala194Asp |
| Ala194Gln |
| Ala194Glu |
| Ala194Gly |
| Ala194His |
| Ala194Pro |
| Ala194Ser |
| Ala194Thr |
| Pro195Asn |
| Pro195Asp |
| Pro195Gln |
| Pro195Glu |
| Pro195Gly |
| Pro195Ser |
| Gly196Asn |
| Gly196Asp |
| Gly196Gln |
| Gly196Glu |
| Gly196Pro |
| Gly196Ser |
| Val197Ala |
| Val197Asp |
| Val197Cys |
| Val197Gln |
| Val197Glu |
| Val197Gly |
| Val197His |
| Val197Met |
| Val197Pro |
| Val197Ser |
| Val199Ala |
| Val199Asn |
| Val199Asp |
| Val199Cys |
| Val199Gln |
| Val199Glu |
| Val199Gly |
| Val199His |
| Val199Met |

TABLE 23-continued

| Loop 6 - Single Mutation Variants |
|---|
| Val199Pro |
| Val199Ser |
| Val199Thr |
| Gln200Asn |
| Gln200Ser |
| Ser201Asp |
| Ser201Glu |
| Thr202Asn |
| Thr202Asp |
| Thr202Gln |
| Thr202Glu |
| Thr202Gly |
| Thr202Pro |
| Thr202Ser |
| Tyr203Ala |
| Tyr203Asn |
| Tyr203Asp |
| Tyr203Gln |
| Tyr203His |
| Tyr203Ile |
| Tyr203Met |
| Tyr203Pro |
| Tyr203Ser |
| Pro204Asn |
| Pro204Asp |
| Pro204Gln |
| Pro204Glu |
| Pro204Gly |
| Pro204Ser |
| Gly205Asn |
| Gly205Asp |
| Gly205Gln |
| Gly205Glu |
| Gly205Pro |
| Gly205Ser |
| Ser206Asp |
| Ser206Glu |
| Thr207Asn |
| Thr207Gln |
| Thr207Glu |
| Thr207Gly |
| Thr207Pro |
| Thr207Ser |
| Tyr208Ala |
| Tyr208Asn |
| Tyr208Asp |
| Tyr208Cys |
| Tyr208Gln |
| Tyr208Glu |
| Tyr208Gly |
| Tyr208His |
| Tyr208Ile |
| Tyr208Leu |
| Tyr208Met |
| Tyr208Pro |
| Tyr208Val |
| Ala209Asn |
| Ala209Asp |
| Ala209Gln |
| Ala209Glu |
| Ala209Gly |
| Ala209His |
| Ala209Pro |
| Ala209Ser |
| Ala209Thr |
| Ser210Asp |
| Ser210Glu |
| Leu211Ala |
| Leu211Asn |
| Leu211Asp |
| Leu211Cys |
| Leu211Gln |
| Leu211Gly |
| Leu211His |
| Leu211Ile |
| Leu211Met |
| Leu211Pro |
| Leu211Ser |
| Leu211Thr |
| Leu211Val |
| Asn212Glu |
| Gly213Asn |
| Gly213Asp |
| Gly213Gln |
| Gly213Glu |
| Gly213Pro |
| Gly213Ser |
| Thr214Asn |
| Thr214Asp |
| Thr214Gln |
| Thr214Glu |
| Thr214Gly |
| Thr214Pro |
| Thr214Ser |

TABLE 24

| Loop 6 - Double Mutation Variants |
|---|
| Gly196Asn + Ala209Asp |
| Val199Ser + Tyr208Asn |
| Pro195Asn + Thr207Asp |
| Val197Ala + Asn212Asp |
| Asn198Gln + Thr207Ser |
| Val199Gly + Tyr208Ile |
| Gly196Asn + Ala209Pro |
| Val199Gly + Gln200Ser |
| Pro195Ser + Gly205Gln |
| Val199Ser + Leu211Asp |
| Gly196Gln + Val197Asn |
| Thr202Asn + Thr214Glu |
| Ala194Thr + Thr202Pro |
| Val199Asn + Ser210Glu |
| Thr202Ser + Asn212Gln |
| Ser210Asp + Thr214Asn |
| Pro195Gly + Asn212Asp |
| Asn198Gln + Tyr208Gln |
| Val197Asn + Thr214Glu |
| Tyr208Asp + Leu211Gln |
| Thr202Ser + Ser210Glu |
| Val197Cys + Ser210Glu |
| Gln200Glu + Tyr203Gly |
| Ala209Thr + Leu211Glu |
| Val197Ser + Gln200Glu |
| Thr202Gly + Ser210Glu |
| Gln200Ser + Gly213Pro |
| Gly196Ser + Thr207Gly |
| Pro204Gln + Ser210Glu |
| Val199Cys + Pro204Gly |
| Gly213Pro + Thr214Pro |
| Gly196Asn + Ser210Glu |
| Thr207Gln + Ser210Glu |
| Val199Met + Gln200Asp |
| Thr202Ser + Tyr203Ile |
| Pro195Ser + Asn212Ser |
| Val197Glu + Tyr208Gln |
| Asn198Glu + Leu211Cys |
| Gly196Gln + Ser206Glu |
| Ala194Ser + Thr214Ser |
| Val197Ser + Tyr203Ala |
| Ser210Asp + Gly213Pro |
| Tyr203His + Gly213Asp |
| Val197Ser + Val197Ser |
| Ala209Pro + Ser210Asp |
| Thr207Asp + Thr214Ser |
| Thr207Gly + Ala209His |
| Pro195Asn + Asn198Asp |
| Val197Pro + Ser206Asp |
| Gal200Ser + Asn212Asp |
| Val197Thr + Asn212Asp |
| Gln200Asn + Thr214Glu |

TABLE 24-continued

Loop 6 - Double Mutation Variants

Ala209Asp + Thr214Ser
Ala209Asn + Asn212Ser
Ala194Ser + Asn212Glu
Val197Glu + Gly213Asn
Tyr203Cys + Asn212Asp
Pro195Gln + Val197Cys
Asn198Ser + Tyr208Ala
Gly205Gln + Ala209Glu
Gly205Ser + Leu211Ser
Gly205Gln + Tyr208Ala
Ala194Ser + Asn198Asp
Ala195Thr + Pro195Ser
Val199Thr + Pro204Glu
Thr202Gln + Ser210Asp
Ser206Glu + Leu211His
Asn198Glu + Thr202Asn
Ser210Asp + Gly213Ser
Gly196Ser + Thr202Gln
Pro204Gln + Gly213Asp
Asn198Glu + Pro204Gly
Thr202Gly + Tyr208Met
Pro195Gly + Gly213Glu
Pro195Ser + Pro204Asp
Pro195Ser + Tyr203Thr
Ala194Asn + Tyr203Pro
Ala194Pro + Gln200Asp
Pro204Asp + Gly205Asn
Gly196Pro + Asn198Gln
Thr207Ser + Leu211Gly
Pro195Ser + Leu211Ile
Pro204Glu + Leu211Gly
Val199Ser + Tyr208Ala
Gly196Ser + Ser210Asp
Ala194Thr + Leu211Gly
Thr207Ser + Ser210Glu
Gly196Pro + Thr207Glu
Pro204Glu + Leu211Met
Pro195Asn + Asn198Ser
Tyr203Met + Thr207Gln
Pro204Gly + Ala209Glu
Val197Glu + Asn212Ser
Pro195Ser + Ala209Pro
Gly196Ser + Leu211Gly
Gly205Pro + Leu211Met
Val197Gln + Pro204Ser
Val199Asn + Ser206Asp
Val197Asp + Thr214Asn
Gly196Gln + Thr214Gly
Pro204Asn + Asn212Gln
Val199Asn + Gln200Asn
Pro195Gly + Leu211Gly
Tyr203Cys + Pro204Ser
Gln200Asp + Leu211Cys
Asn198Gln + Ser210Glu
Ala198Gly + Gln200Glu
Gly196Gln + Pro204Glu
Val197Pro + Thr202Asn
Ala194Gly + Val199Ala
Ala194Thr + Leu211Asn
Asn198Gln + Gly205Asp
Tyr203Asn + Leu211His
Asn212Asp + Gly213Gln
Asn198Gln + Ser206Asp
Val199Thr + Gln200Glu
Thr202Ser + Asn212Asp
Ala194Gly + Ser210Glu
Ser206Glu + Ala209Asn
Ala209Asp + Asn212Ser
Val199Gly + Asn212Ser
Ala194Pro + Gly213Asp
Gln200Asp + Pro204Gly
Val197Thr + Tyr203Ala
Asn198Gln + Leu211Pro
Pro195Gln + Leu211Gln
Gly196Gln + Thr214Glu
Pro195Asn + Ser210Glu
Thr207Asn + Leu211Asp

TABLE 24-continued

Loop 6 - Double Mutation Variants

Ser210Glu + Gly213Pro
Gly205Pro + Thr207Asp
Gln200Glu + Thr202Gln
Thr202Ser + Gly213Asp
Pro204Gln + Thr214Gln
Gly196Ser + Gln200Asp
Val197Ser + Gln200Asp
Thr202Pro + Thr207Asp
Tyr203Thr + Tyr208His
Pro195Gln + Thr202Asn
Val197Asn + Asn212Asp
Val197Met + Thr202Gln
Val197Met + Thr202Pro
Ala209Glu + Leu211Met
Gly196Asn + Val199His
Ala194Gly + Ser206Glu
Gly196Asn + Pro204Asn
Gly196Asn + Gln200Glu
Val197Ser + Ser210Asp
Pro195Gln + Pro204Gln
Ala194His + Asn198Gln
Val197Cys + Asn212Gln
Asn198Glu + Ala209Ser
Ala194Gln + Val199Pro
Asn198Asp + Val199Gln
Asn198Asp + Thr214Pro
Pro204Asn + Tyr208Asp
Tyr203Ser + Tyr208Leu
Gly196Gln + Ala209Asp
Ser206Glu + Asn212Gln
Thr207Ser + Ala209His
Val197Thr + Ser210Asp
Tyr208Gln + Ser210Asp
Asn198Ser + Ser210Glu
Gly196Ser + Thr214Asp
Ala194Gln + Thr202Asn
Pro195Gly + Thr214Asn
Leu211Thr + Thr214Asp
Pro195Ser + Asn198Glu
Gly196Ser + Gly205Ser
Ala194His + Thr208Asn
Thr207Gly + Tyr208Met
Ala194Ser + Val197His

TABLE 25

Loop 6 - Triple Mutation Variants

Ala194Thr + Ser206Glu + Tyr208Cys
Gly196Asn + Tyr203Pro + Ala209Gly
Pro195Gly + Asn198Ser + Thr207Glu
Pro195Gly + Gly205Gln + Gly213Ser
Tyr203Leu + Pro204Gln + Gly205Gln
Gly196Gln + Val197Asn + Ser206Asp
Leu211Ser + Gly213Ser + Thr214Gln
Pro195Asn + Pro204Glu + Gly205Gln
Asn198Asp + Thr202Gly + Gly213Gln
Tyr203Ala + Leu211His + Thr214Gln
Ala194Thr + Val197Ser + Val199Gly
Ala194Gln + Thr207Asp + Thr214Ser
Gly196Asn + Pro204Gln + Ala209Asn
Thr202Pro + Tyr208Asp + Leu211Ile
Val197Gly + Ala209Gln + Asn212Gln
Gly196Ser + Gly205Asp + Leu211Thr
Ala194Ser + Val197Pro + Asn198Asp
Gly196Asn + Asn198Gln + Leu211Ser
Ala194Thr + Ala209His + Thr214Asp
Ala194Pro + Pro195Ser + Asn212Asp
Thr202Ser + Tyr203Gln + Ser210Asp
Thr202Ser + Tyr203Leu + Thr214Glu
Ala194Ser + Pro195Gly + Leu211Val
Ala194Pro + Thr207Glu + Leu211Ala
Gly196Asn + Ser206Glu + Leu211Gly
Gly196Ser + Gly205Ser + Ser210Asp

TABLE 25-continued

Loop 6 - Triple Mutation Variants

Ala194Thr + Val197Gly + Leu211Ser
Pro204Glu + Ala209His + Thr214Pro
Gly196Ser + Gly205Asp + Leu211His
Val197Cys + Thr202Gly + Thr207Gln
Asn198Ser + Pro204Gly + Gly213Asp
Ala194Gly + Ala209Pro + Ser210Asp
Gly196Pro + Tyr203Val + Tyr208Cys
Val199Ala + Thr207Asn + Tyr208Val
Tyr203Cys + Ser210Asp + Leu211Pro
Ala194Ser + Val197Ser + Gln200Asp
Ala194Asn + Pro195Gly + Leu211Ile
Val199Ser + Leu211Asn + Gly213Asp
Ala194Asn + Ser206Glu + Thr214Gly
Ala194Gly + Pro195Gly + Val197Asp
Pro195Gln + Ala209Ser + Ser210Asp
Val197Thr + Asn198Gln + Tyr203Leu
Val197Ala + Thr202Gln + Ser206Glu
Gly196Pro + Pro204Gly + Asn212Glu
Thr202Gly + Pro204Glu + Tyr208Ser
Gln200Ser + Thr202Pro + Pro204Ser
Gln200Glu + Tyr203Thr + Pro204Asn
Asn198Asp + Val199Asn + Pro204Asn
Ala194Pro + Pro195Gln + Val199Gly
Pro195Asn + Pro204Asn + Ser206Glu
Thr202Asn + Leu211Thr + Asn212Gln
Gly196Gln + Thr202Pro + Gly213Asp
Asn198Glu + Gln200Asn + Leu211Gly
Val199Gly + Thr202Gln + Gly213Glu
Tyr203Ser + Thr207Pro + Ser210Asp
Pro195Gly + Gly196Gln + Val197Glu
Pro195Gly + Thr207Gly + Tyr208Ser
Thr202Gly + Leu211Glu + Gly213Gln
Val197Gly + Thr202Pro + Asn212Glu
Gly196Gln + Gly205Asp + Ser206Glu
Pro195Gly + Val199Thr + Thr214Glu
Gly196Ser + Gln200Ser + Leu211Asp
Gly196Asn + Tyr208Glu + Thr214Pro
Tyr203Thr + Pro204Asn + Ser206Glu
Val199Thr + Thr202Asn + Tyr208Gly
Thr202Pro + Tyr203Thr + Pro204Glu
Gly196Gln + Asn212Asp + Thr214Gln
Pro195Gly + Thr202Gly + Asn212Ser
Pro195Gly + Tyr208Gln + Ser210Asp
Ala194Pro + Ser208Glu + Leu211Ser
Ala194His + Pro204Asn + Gly213Gln
Gly196Ser + Tyr208Met + Ser210Asp
Val197Glu + Val199Ser + Tyr203Asn
Thr202Gly + Ala209Asn + Asn212Asp
Val197Ser + Ser210Asp + Gly213Pro
Ala194Ser + Tyr208Ile + Asn212Glu
Ala194Gly + Asn198Gln + Ala209His
Ala194Ser + Thr207Pro + Gly213Glu
Val199Thr + Leu211Asp + Asn212Ser
Val199Pro + Thr202Ser + Leu211Asn
Ser206Glu + Tyr208Cys + Thr214Asn
Ala209Ser + Leu211Ile + Asn212Glu
Asn198Glu + Tyr208Ala + Ala209Ser
Ala194Pro + Asn198Asp + Gly213Gln
Ala194Asn + Pro195Ser + Leu211Glu
Gly196Pro + Pro204Gly + Gly205Pro
Tyr203Ile + Tyr208Thr + Ala209Glu
Gly196Gln + Thr202Gln + Asn212Asp
Ala194Asn + Val197Pro + Thr202Pro
Ala194Gln + Val199Gly + Ala209Asp
Ala194Ser + Pro195Gly + Asn212Gln
Pro195Gln + Tyr203Pro + Ser210Asp
Val197Thr + Thr202Gln + Tyr208Asn
Ala194Thr + Gly196Ser + Leu211Asn
Ala194Gly + Thr202Ser + Pro204Asp
Ala194Gly + Gly205Glu + Gly213Ser
Val199Pro + Thr207Pro + Tyr208Met
Ala194Pro + Asn198Glu + Ala209His
Tyr208Leu + Ser210Glu + Thr214Pro
Gly196Asn + Val199Ala + Gly205Asp
Gly196Pro + Gly205Glu + Tyr208Ser
Pro195Asn + Gly196Gln + Val197Cys
Asn198Ser + Gln200Glu + Leu211Asn
Thr202Ser + Tyr203Cys + Thr214Gln
Ala194Ser + Gly196Gln + Thr207Asp
Gly196Ser + Gly205Glu + Tyr208Ile
Tyr203Met + Gly205Asn + Gly213Pro
Pro204Gln + Gly205Asp + Ala209His
Gly205Asn + Leu211Asp + Thr214Ser
Tyr203Met + Ala209His + Leu211Met
Val199Asn + Thr202Ser + Gly213Glu
Val197Thr + Pro204Asp + Asn212Gln
Ala194Gly + Ser210Glu + Leu211Pro
Val197His + Ala209Gly + Ser210Asp
Gln200Glu + Thr202Gln + Tyr208His
Ala194Ser + Ser206Asp + Leu211Ala
Pro195Ser + Asn198Asp + Gly205Pro
Tyr203Pro + Thr207Asp + Thr214Pro
Pro195Ser + Val199His + Leu211Pro
Tyr203Met + Thr207Glu + Ala209His
Val197Cys + Gln200Asn + Ser206Glu
Val197Glu + Thr202Gln + Tyr208His
Pro195Gln + Val197Cys + Pro204Gly
Val199Pro + Gly205Ser + Gly213Asp
Ala194Thr + Thr207Ser + Ala209Glu
Val197Met + Gly205Pro + Tyr208Gly
Gly196Ser + Gly205Glu + Ala209Thr
Pro195Ser + Val199Thr + Gly205Ser
Ala194Ser + Asn198Asp + Gly213Ser
Asn198Glu + Val199Ser + Thr207Pro
Ala194Thr + Gly196Pro + Ser210Glu
Gly196Asn + Thr202Pro + Leu211Met
Tyr203Met + Asn212Asp + Thr214Ser
Tyr203Gly + Ala209Ser + Ser210Asp
Ala194Ser + Thr207Ser + Leu211Pro
Tyr208Cys + Gly213Asn + Thr214Pro
Val197Met + Pro204Glu + Gly213Ser
Gln200Ser + Tyr203Ala + Pro204Asp
Pro195Gly + Ser206Asp + Leu211Ile
Tyr203Gly + Try208Asp + Leu211Asn
Val197Thr + Ser206Glu + Thr214Pro
Tyr203Ala + Pro204Asn + Gly213Glu
Tyr208Ile + Ala209Gly + Leu211Gln
Asn198Ser + Pro204Gly + Asn212Glu
Ala194Gln + Val197Cys + Pro204Asn
Ala209Thr + Leu211Ser + Gly213Pro
Gly196Ser + Thr202Pro + Asn212Asp
Val197His + Tyr203Gln + Tyr208Cys
Val199Ser + Leu211Thr + Gly205Pro
Pro195Asn + Val197Asn + Thr202Pro
Val199Pro + Pro204Gly + Gly205Asn
Pro195Gly + Asn198Asp + Thr214Gly
Gln200Glu + Tyr203Ser + Asn212Gln
Pro195Gly + Val199Gln + Thr214Pro
Thr202Ser + Pro204Ser + Gly213Glu
Pro195Gly + Thr202Pro + Gly205Glu
Thr202Gln + Tyr203Gly + Ala209Asn
Pro195Asn + Gly196Gln + Asn212Asp
Thr202Gly + Tyr208Ile + Leu211Val
Asn198Glu + Tyr203Cys + Pro204Gly
Ala194Ser + Thr207Ser + Ser210Asp
Gln200Asp + Thr202Pro + Tyr203Ala
Val199Cys + Ala209Gln + Ser210Asp
Ala194Asn + Val199Cys + Leu211Pro
Gln200Ser + Ser210Glu + Leu211Asn
Tyr203Gln + Thr207Glu + Tyr208Ser
Ala194Thr + Thr202Asn + Thr207Gly
Pro195Gly + Gly196Gln + Ser210Asp
Gln200Ser + Pro204Gly + Ser206Glu
Ala194Asn + Gly196Gln + Asn198Glu
Val197Thr + Pro204Gln + Gly205Glu
Val199Ala + Gln200Asp + Gly213Asn
Val197Met + Tyr203Val + Gly213Pro
Ala194Gln + Tyr203Val + Thr214Glu
Val199Cys + Ala209His + Leu211Met
Thr202Gln + Tyr203Ile + Ala209Gln
Ala194Gly + Ser206Glu + Leu211Gly
Gly196Pro + Tyr208Gly + Ser210Glu

TABLE 25-continued

| Loop 6 - Triple Mutation Variants |
|---|
| Val197Gln + Thr202Gly + Gly205Asp |
| Val197Pro + Gly205Asp + Thr214Pro |

TABLE 26

| Loop 6 - Quadruple Mutation Variants |
|---|
| Pro195Asn + Val197Ala + Thr207Ser + Asn212Asp |
| Asn198Gln + Val199Gly + Tyr208Ile + Asn212Asp |
| Tyr203His + Leu211Pro + Asn212Gln + Gly213Gln |
| Ala194His + Asn198Ser + Thr202Asn + Ala209Asp |
| Gly196Gln + Asn198Ser + Thr202Ser + Pro204Glu |
| Pro195Gln + Asn198Gln + Gly205Glu + Ala209Pro |
| Val199His + Pro204Asp + Gly205Pro + Leu211Gly |
| Gly196Gln + Gly205Asn + Ser206Asp + Thr214Ser |
| Gln200Glu + Thr202Pro + Leu211Asn + Gly213Asn |
| Gly196Gln + Pro204Asn + Asn212Gln + Thr214Gly |
| Pro195Gly + Val199Asn + Gln200Asn + Leu211Gly |
| Pro195Gln + Pro204Ser + Gly205Glu + Tyr208Ile |
| Val199Ala + Tyr203Gln + Thr208Gly + Ser210Glu |
| Ala194His + Val199Ser + Pro204Asn + Gly205Glu |
| Gly196Pro + Asn198Asp + Gln200Asn + Ala209Pro |
| Pro195Gln + Gln200Asp + Tyr203Asn + Leu211Cys |
| Pro195Ser + Thr202Pro + Asn212Asp + Thr214Ser |
| Ala194Gly + Val197Glu + Tyr203Leu + Leu211Cys |
| Asn198Gln + Thr202Pro + Tyr208Met + Thr214Glu |
| Gly196Ser + Val199Ser + Gly205Gln + Ser210Glu |
| Tyr203Ala + Gly205Gln + Ser206Asp + Leu211Gln |
| Gly196Ser + Val199His + Gln200Asp + Thr207Ser |
| Pro195Gln + Gly196Gln + Gln200Glu + Tyr203Ser |
| Gly196Ser + Gln200Glu + Gly205Gln + Gly213Asn |
| Pro195Ser + Gly196Asn + Ser206Glu + Thr214Gly |
| Gly196Asn + Val199Asn + Ser206Glu + Tyr208Pro |
| Val197Gln + Gly205Ser + Ser210Glu + Thr214Ser |
| Pro195Asn + Gln200Glu + Gly205Asn + Leu211Pro |
| Tyr203Pro + Tyr208His + Leu211Val + Thr214Pro |
| Ala194His + Val199Ser + Thr202Gly + Tyr208Asp |
| Pro195Asn + Val199Asn + Ser206Asp + Gly213Ser |
| Ala194Ser + Pro195Asn + Val199Ala + Gly205Glu |
| Ala194Thr + Gly196Gln + Val199Gly + Tyr203Ile |
| Val199Ala + Ala209Asp + Leu211Val + Asn212Gln |
| Val197Gly + Asn198Ser + Tyr203Leu + Ser210Asp |
| Gln200Ser + Thr207Gly + Tyr208Thr + Ser210Asp |
| Pro204Gly + Gly205Asp + Thr207Asn + Tyr208Leu |
| Ala194Gln + Thr202Ser + Ala209Ser + Asn212Glu |
| Val197Met + Thr202Gly + Pro204Gly + Thr214Glu |
| Val199Ala + Pro204Gln + Gly205Asp + Tyr208Gly |
| Asn198Glu + Tyr208Cys + Ala209Gln + Leu211Val |
| Gln200Ser + Pro204Ser + Ala209Asn + Leu211Glu |
| Pro195Ser + Val197Thr + Gly205Gln + Thr214Pro |
| Pro195Asn + Thr202Asn + Gly205Asp + Tyr208Ser |
| Pro195Gly + Tyr203Pro + Leu211Ala + Asn212Glu |
| Thr202Gly + Pro204Asn + Gly205Asn + Gly213Gln |
| Val197Gly + Gln200Glu + Tyr208Ala + Asn212Ser |
| Ala194Ser + Pro195Ser + Tyr203Ala + Ala209Asp |
| Pro195Gln + Val197Thr + Val199Pro + Ala209His |
| Gly196Asn + Ser206Asp + Leu211His + Thr214Ser |
| Val197Asp + Tyr203His + Tyr208Cys + Thr214Gly |
| Ala194Gln + Pro195Asn + Ala209His + Ser210Asp |
| Val199Ser + Gln200Ser + Tyr203Asn + Ser206Asp |
| Ala194Asn + Pro195Gln + Ser206Glu + Gly213Ser |
| Pro195Ser + Tyr203Met + Ser206Asp + Gly213Gln |
| Ala194Gly + Val199Thr + Tyr208His + Gly213Pro |
| Ala194Pro + Val197Cys + Gln200Asp + Pro204Gly |
| Thr202Gln + Thr207Glu + Tyr208Cys + Leu211Pro |
| Gly196Gln + Asn198Glu + Tyr203Gln + Gly205Pro |
| Thr202Asn + Tyr203Pro + Gly205Ser + Gly213Glu |
| Pro195Asn + Asn198Ser + Ala209Gly + Leu211Thr |
| Asn198Asp + Gln200Ser + Tyr203Pro + Gly205Asn |
| Pro195Gln + Val199Gly + Tyr203Asn + Thr207Glu |
| Ala194Gln + Thr202Gln + Tyr203His + Tyr208His |
| Ala194Ser + Pro204Asp + Thr207Pro + Tyr208Thr |
| Asn198Gln + Val199Gln + Gln200Asn + Ala209Gln |
| Ala194Gly + Asn198Ser + Pro204Asp + Ala209His |

TABLE 26-continued

| Loop 6 - Quadruple Mutation Variants |
|---|
| Gly196Gln + Val197Thr + Ser206Glu + Ala209Pro |
| Gln200Ser + Thr202Pro + Tyr203Thr + Thr207Gly |
| Ala194Thr + Val197Gly + Gln200Asn + Thr207Asp |
| Val197Pro + Val199Asn + Gln200Glu + Leu211Ile |
| Gly196Pro + Pro204Ser + Ala209Ser + Leu211Gln |
| Pro195Gly + Gly196Gln + Asn198Gln + Tyr208Glu |
| Gln200Ser + Tyr203Met + Gly205Glu + Tyr208Asn |
| Ala194Gln + Pro195Gly + Ala209Gly + Ser210Glu |
| Gly196Asn + Val197Asn + Ser210Asp + Asn212Gln |
| Gly196Gln + Thr202Ser + Gly205Ser + Ser210Glu |
| Gln200Asn + Gly205Pro + Leu211Cys + Thr214Pro |
| Ala194Ser + Gly196Gln + Thr207Ser + Ser210Asp |
| Val197Gln + Thr202Pro + Tyr203Ala + Ser206Asp |
| Gly196Gln + Asn198Glu + Asn212Ser + Gly213Asn |
| Pro195Asn + Val197Gln + Gly205Gln + Leu211Glu |
| Thr207Glu + Tyr208Leu + Leu211Met + Gly213Gln |
| Pro195Ser + Val197Pro + Pro204Glu + Leu211Cys |
| Pro195Gly + Gly196Ser + Val199Gln + Thr214Asp |
| Val197Asn + Gly205Asn + Thr207Ser + Ser210Asp |
| Ala194His + Tyr203His + Gly205Pro + Ser206Glu |
| Pro195Asn + Asn198Gln + Val199Gln + Leu211Gln |
| Val197Pro + Thr202Gly + Pro204Gly + Thr207Ser |
| Thr202Pro + Tyr203Leu + Leu211Ala + Thr214Asp |
| Pro195Asn + Val199His + Tyr203Met + Thr207Glu |
| Val199Cys + Pro204Gly + Thr207Ser + Thr213Asp |
| Ala194Ser + Pro195Gln + Tyr203Thr + Tyr208Pro |
| Val199Cys + Tyr203Cys + Ser206Asp + Tyr208Ala |
| Val197Thr + Thr202Gln + Leu211Glu + Asn212Ser |
| Gly196Ser + Val199Pro + Ala209Gln + Leu211Asn |
| Ala194Gly + Ala209Gln + Asn212Asp + Thr214Gln |
| Ala194Gln + Thr207Asn + Ala209Pro + Leu211His |
| Gly196Ser + Val197Ser + Thr202Gln + Leu211Gln |
| Ala194Thr + Val197Ser + Thr202Pro + Thr207Pro |
| Gly196Pro + Thr202Pro + Gly205Glu + Gly213Pro |
| Ala194Pro + Pro195Gly + Val197Asn + Val199Cys |
| Thr202Gly + Thr207Ser + Tyr208Pro + Leu211Pro |
| Thr202Asn + Pro204Asp + Thr207Ser + Gly213Asn |
| Gly196Gln + Val197Cys + Tyr203Met + Ala209Asn |
| Gly196Gln + Ser206Glu + Thr207Ser + Gly213Pro |
| Pro195Ser + Val199Cys + Ser210Glu + Asn212Ser |
| Ala194Ser + Ser206Asp + Asn212Ser + Thr214Gln |
| Gly196Gln + Gln200Ser + Thr202Gln + Ala209Ser |
| Gly196Gln + Tyr203Thr + Thr207Gln + Asn212Glu |
| Ala194Pro + Thr202Gln + Tyr208Cys + Leu211Pro |
| Gln200Asp + Tyr203Cys + Leu211Gln + Asn212Gln |
| Gly196Asn + Tyr203Met + Leu211Asn + Gly213Asn |
| Pro195Gln + Gly196Asn + Gln200Ser + Thr202Gln |
| Thr202Pro + Tyr203Gly + Asn212Ser + Thr214Gly |
| Gln200Asp + Tyr203Thr + Pro204Gln + Gly205Ser |
| Gly196Asp + Thr202Pro + Pro204Asn + Ala209Ser |
| Gly196Ser + Gln200Ser + Pro204Gly + Ser210Asp |
| Ala194Gln + Gln200Asn + Thr202Ser + Gly205Gln |
| Pro195Gly + Gln200Asn + Thr207Asp + Ala209His |
| Gln200Asn + Thr202Ser + Tyr203Ala + Thr214Gly |
| Gln200Glu + Ala209Pro + Leu211Ile + Gly213Asn |
| Ala194Asn + Thr202Ser + Tyr203Met + Ser206Glu |
| Val197Asn + Asn198Ser + Thr207Gln + Thr214Glu |
| Val197Met + Gln200Ser + Pro204Glu + Ala209Pro |
| Gly196Asn + Val199Asn + Leu211Glu + Asn212Gln |
| Pro195Gln + Thr202Gln + Gly205Asp + Tyr208Asn |
| Thr202Pro + Ser206Asp + Leu211Ile + Gly213Ser |
| Gly196Ser + Gln200Glu + Thr202Gln + Tyr208Met |
| Asn198Glu + Tyr203Thr + Tyr208Asn + Gly213Gln |
| Asn198Ser + Ser210Glu + Leu211His + Thr214Pro |
| Gly196Ser + Val197Gly + Pro204Glu + Thr214Ser |
| Tyr203Met + Ser206Glu + Tyr208Ser + Ala209His |
| Gly196Gln + Gln200Ser + Leu211Cys + Gly213Pro |
| Ala194Gly + Val199Asn + Thr202Asn + Gly213Pro |
| Asn198Ser + Thr202Asn + Tyr203Gly + Ser210Glu |
| Val199Gln + Gln200Ser + Tyr203His + Thr214Asp |
| Thr202Gln + Ser206Asp + Thr207Ser + Thr214Gly |
| Ala194Thr + Tyr203Gln + Thr207Asp + Leu211Ile |
| Ala209Ser + Ser210Asp + Asn212Gln + Gly213Ser |
| Val197Ser + Tyr203Gly + Ser206Glu + Asn212Gln |
| Ala194Ser + Asn198Ser + Gly205Gln + Ser210Asp |
| Ala194Gln + Pro195Ser + Val197Gln + Pro204Asn |
| Ala194Gly + Asn198Ser + Ala209Glu + Thr214Asn |

TABLE 26-continued

| Loop 6 - Quadruple Mutation Variants |
|---|
| Val199Met + Ser206Asp + Gly213Asn + Thr214Ser |
| Thr202Gln + Gly205Ser + Leu211Asp + Asn212Glu |
| Pro195Ser + Ala209Glu + Gly213Asp + Thr214Asp |
| Thr202Gln + Thr207Pro + Gly213Glu + Thr214Asp |
| Ala194Ser + Thr207Pro + Ala209Glu + Ser210Glu |
| Gln200Asn + Thr202Gln + Ala209Glu + Ser210Glu |
| Gln200Ser + Ala209Asp + Ser210Asp + Asn212Gln |
| Gly205Asn + Ala209Asp + Ser210Glu + Asn212Gln |
| Pro204Gly + Leu211Gln + Asn212Glu + Gly213Asp |
| Tyr203Gly + Pro204Asp + Gly205Glu + Leu211Ala |
| Thr202Ser + Pro204Glu + Gly205Asp + Thr207Gln |
| Thr202Gly + Pro204Asp + Gly205Glu + Gly213Asn |
| Val199Gly + Ser210Asp + Leu211Asp + Asn212Gln |
| Gly196Pro + Thr202Ser + Gly205Asp + Ser206Glu |
| Val197Thr + Gly205Asp + ser206Glu + Gly213Gln |
| Pro204Asn + Gly205Glu + Ser206Gly + Asn212Ser |
| Ala194His + Gly205Asp + Ser206Asp + Leu211His |
| Pro195Asn + Ser206Gly + Thr207Asp + Asn212Ser |
| Tyr203Met + Ser206Gly + Thr207Glu + Leu211Gly |
| Gly196Gln + Pro204Asn + Ser206Asp + Thr207Glu |
| Ala194Thr + Val197Cys + Ser206Asp + Thr207Asp |
| Ala194Pro + Tyr208Asp + Ala209Asp + Gly213Gln |
| Gln200Asp + Tyr208Thr + Ala209Ser + Ser210Glu |
| Val199Asn + Gln200Asp + Thr202Gln + Ser210Asp |
| Ala194Ser + Gln200Glu + Thr202Gly + Ser210Glu |
| Val199Cys + Gln200Asp + Ala209Gln + Ser210Asp |
| Ala194Gln + Val197Asp + Tyr208Gln + Asn212Asp |
| Pro195Gly + Asn198Glu + Ser210Asp + Leu211Gln |
| Ala194Pro + Pro195Asn + Asn198Asp + Ser210Asp |
| Pro195Gln + Asn198Glu + Val199Ser + Ser210Asp |
| Val198His + Asn198Glu + Thr207Pro + Ser210Asp |
| Gly196Pro + Val197Gly + Asn198Asp + Ser210Gly |
| Asn198Glu + Ala209Gln + Leu211Gln + Thr214Pro |
| Gln200Glu + Tyr203Asn + Thr207Gln + Ala209Glu |
| Pro195Ser + Gly196Ser + Gln200Glu + Ala209Asp |
| Pro195Ser + Gln200Asp + Ala209Gly + Leu211Ala |

TABLE 27

| Loop 6 - Quintuple Mutation Variants |
|---|
| Val197Ala + Asn198Gln + Thr207Ser + Tyr208Ile + Asn212Asp |
| Ala194Gly + Gly196Ser + Val197Gly + Gln200Glu + Leu211Gly |
| Gln200Asp + Thr202Ser + Tyr203Ser + Pro204Ser + Asn212Ser |
| Pro195Ser + Val199Ala + Gly205Asn + Ser206Glu + Gly213Ser |
| Val199His + Pro204Asp + Gly205Pro + Leu211Gly + Thr214Ser |
| Ala194Gly + Thr207Pro + Ser210Glu + Leu211Cys + Gly213Gln |
| Pro195Asn + Gly196Pro + Asn198Ser + Thr202Gly + Gly213Asn |
| Gly196Ser + Val197Gln + Pro204Ser + Gly205Asp + Leu211Gly |
| Pro195Ser + Gly196Gln + Pro204Asn + Gly213Asp + Thr214Gly |
| Pro195Gly + Val199Asn + Gln200Asn + Ser210Glu + Leu211Gly |
| Val197Ser + Val199Gly + Tyr203Thr + Gly205Ser + Asn212Glu |
| Pro195Asn + Asn198Asp + Thr202Ser + Ala209His + Asn212Gln |
| Gly196Asn + Gly205Pro + Thr207Pro + Asn212Asp + Gly213Gln |
| Val197Gly + Asn198Asp + Val199His + Gly205Gln + Tyr208His |
| Tyr203Val + Thr207Gly + Ala209Ser + Asn212Glu + Gly213Gln |
| Ala194Thr + Pro195Gly + Gly196Ser + Tyr203Asn + Asn212Ser |
| Pro195Gln + Thr202Gly + Tyr203Leu + Pro204Gly + Ser210Asp |
| Pro195Asn + Val199Ala + Thr202Asn + Tyr208Pro + Ser210Asp |
| Ala194Pro + Pro195Gly + Asn198Glu + Pro204Asn + Tyr208Pro |
| Ala194Ser + Val197Thr + Asn198Ser + Thr202Pro + Asn212Ser |
| Gly196Ser + Val199Pro + Thr207Ser + Tyr208Thr + Asn212Gln |
| Gly205Glu + Tyr208Gly + Leu211Ile + Asn212Ser + Thr214Gly |
| Gln200Ser + Thr202Gly + Thr207Asp + Leu211Ser + Thr214Gln |
| Pro195Asn + Thr207Asp + Tyr208Asn + Asn212Ser + Gly213Asn |
| Pro195Asn + Tyr203Ser + Pro204Glu + Leu211Val + Asn212Gln |
| Gln200Asp + Gly205Ser + Tyr208Met + Leu211Asn + Asn212Ser |
| Ala194Ser + Val199Pro + Gly205Glu + Tyr208Met + Gly213Ser |
| Asn198Ser + Gln200Glu + Thr202Gly + Ala209Gln + Leu211Asn |
| Gly196Pro + Asn198Glu + Thr202Ser + Ala209Thr + Thr214Gly |
| Ala194Gln + Pro195Gly + Gly196Asn + Tyr203Ile + Thr214Pro |
| Pro195Gln + Val197Cys + Thr202Gln + Tyr203Cys + Tyr208His |
| Val199Pro + Pro204Gly + Gly205Ser + Thr207Ser + Gly213Asp |
| Tyr203Gly + Pro204Ser + Gly205Asn + Ala209Thr + Ser210Asp |

TABLE 27-continued

| Loop 6 - Quintuple Mutation Variants |
|---|
| Ala194Ser + Thr207Ser + Tyr208Cys + Leu211Pro + Thr213Pro |
| Pro195Gly + Val199His + Gly205Glu + Ala209Asn + Leu211Pro |
| Pro204Asn + Tyr208Ile + Ala209Gly + Leu211Gln + Gly213Glu |
| Ala194Gln + Val197Cys + Asn198Ser + Pro204Gly + Asn212Glu |
| Asn198Glu + Pro204Asn + Ala209Thr + Leu211Ser + Gly213Pro |
| Gly196Ser + Val199Ser + Pro204Asp + Thr207Gly + Tyr208Ile |
| Gln200Glu + Thr202Ser + Tyr203Ala + Pro204Gly + Tyr208Met |
| Asn198Gln + Thr202Pro + Gly205Asn + Thr207Glu + Thr214Pro |
| Gly196Ser + Val199Pro + Ala209Gln + Ser210Asp + Leu211Asn |
| Ala194Gly + Thr207Asn + Ala209Gln + Asn212Asp + Thr214Gln |
| Pro195Gly + Asn198Gln + Val199Thr + Tyr208His + Leu211Ile |
| Ala194Pro + Thr202Gly + Thr207Ser + Tyr208Pro + Leu211Pro |
| Gly196Ser + Val197Ala + Gln200Asn + Thr202Pro + Ser210Glu |
| Val197Gln + Thr202Asn + Tyr203Asn + Gly205Asp + Tyr208Ala |
| Gly196Pro + Tyr203Ile + Pro204Asn + Leu211Ala + Thr214Gln |
| Ala194Asn + Gln200Asn + Pro204Gln + Ala209Thr + Gly213Ser |
| Ala194His + Pro195Gly + Gln200Ser + Leu211Asn + Asn212Ser |
| Ala194Ser + Gly196Ser + Gln200Asn + Ser206Asp + Thr207Gly |
| Gly196Asn + Tyr203Asn + Tyr208Ala + Ala209Pro + Gly213Gln |
| Ala194Thr + Val199Asn + Tyr203Ser + Tyr208His + Asn212Asp |
| Val197Glu + Val199Ala + Tyr208Gln + Ala209Gly + Leu211Val |
| Gln200Asn + Thr202Ser + Tyr203Ala + Thr207Gln + Thr214Gly |
| Val197Asn + Asn198Ser + Thr202Pro + Thr207Gln + Thr214Glu |
| Pro195Gln + Asn198Glu + Gln200Ser + Tyr203Cys + Gly213Gln |
| Gly196Gln + Asn198Ser + Thr202Asn + Tyr203Ser + Gly205Pro |
| Ala194Thr + Thr207Pro + Tyr208Ile + Ala209Pro + Thr214Asn |
| Asn198Ser + Val199Pro + Thr202Asn + Tyr203Gly + Asn212Glu |
| Ala194Asn + Thr202Asn + Ser210Asp + Leu211Val + Asn212Ser |
| Val197Ser + Val199His + Thr202Asn + Ser210Asp + Leu211Cys |
| Gly196Pro + Val197Cys + Val199Met + Tyr203Ser + Leu211Asn |
| Ala194Gly + Gly196Pro + Val199His + Thr202Pro + Ser210Glu |
| Gly196Ser + Val197His + Asn198Glu + Thr202Pro + Asn212Ser |
| Ala194His + Gly196Asn + Val197Gln + Thr202Ser + Gly205Glu |
| Pro195Gly + Gly196Pro + Asn198Ser + Gln200Ser + Thr202Pro |
| Val197Asn + Asn198Asp + Gln200Asn + Thr202Gln + Tyr208Ala |
| Pro195Asn + Thr202Ser + Pro204Asp + Tyr208Ala + Ala209Ser |
| Tyr203His + Pro204Asn + Gly205Asp + Thr207Gln + Leu211Gly |
| Ala194Asn + Pro195Gln + Gly196Gln + Pro204Asn + Gly213Glu |
| Val197Thr + Val199His + Ser206Glu + Gly213Asn + Thr214Asn |
| Gly196Gln + Val197Asn + Tyr203Thr + Pro204Ser + Thr214Asp |
| Gly196Asn + Val199Gly + Gln200Ser + Tyr203Asn + Gly213Glu |
| Ala194Thr + Gln200Asn + Thr202Ser + Gly205Gln + Gly213Asp |
| Pro195Ser + Asn198Ser + Val199Gly + Tyr203Val + Thr207Glu |
| Ala194Asn + Pro195Gly + Thr202Gly + Tyr203Gly + Leu211Asp |
| Pro195Ser + Val197Ser + Tyr203Cys + Gly205Glu + Ala209Thr |
| Gly196Gln + Val197Gly + Gly205Ser + Tyr208Leu + Thr214Asp |
| Ala194Gln + Gly196Asn + Tyr203Pro + Pro204Ser + Gly213Asp |
| Gly196Gln + Thr202Gly + Tyr203Cys + Pro204Gln + Ser206Glu |
| Val197Pro + Val199Met + Tyr203Val + Pro204Gly + Thr214Asp |
| Gly196Pro + Gln200Asn + Tyr203Cys + Ala209Thr + Thr214Asn |
| Asn198Gln + Pro204Asn + Thr207Gln + GLy213Pro + Thr214Asp |
| Pro195Gly + Val197Ser + Val199Ala + Thr207Asp + Leu211Gly |
| Pro195Gln + Asn198Gln + Ser206Asp + Thr207Ser + Ala209Ser |
| Ala194Ser + Tyr203Leu + Ala209Asn + Ser210Asp + Thr214Ser |
| Val199His + Thr202Ser + Gly205Asn + Leu211Pro + Asn212Gln |
| Gly196Ser + Asn198Ser + Thr207Asn + Tyr208Gln + Ser210Glu |
| Pro195Asn + Asn198Gln + Thr207Ser + Gly213Asn + Thr214Gly |
| Gly196Gln + Gln200Ser + Pro204Asn + Gly205Gln + Gly213Asp |
| Pro204Asn + Ser206Glu + Tyr208Leu + Ala209Gly + Asn212Gln |
| Val197Thr + Val199Gly + Gln200Asp + The202Pro + Thr207Gly |
| Pro195Gln + Val199Ser + Thr202Asn + Gly205Asp + Ala209Gln |
| Gly196Gln + Tyr203Thr + Tyr208Cys + Leu211Ala + Thr214Glu |
| Asn198Gln + Gln200Ser + Pro204Gln + Asn212Ser + Gly213Pro |
| Val197Pro + Val199Asn + Thr202Gln + Tyr203Asn + Gly213Ser |
| Ala194Ser + Gln200Ser + Thr202Gln + Thr207Gln + Ala209Glu |
| Thr202Gly + Tyr203Thr + Tyr208Pro + Gly213Asp + Thr214Glu |
| Val197Gln + Pro204Gly + Gly205Ser + Ala209Glu + Ser210Asp |
| Ala194Ser + Val199Ala + Tyr208Ala + Ala209Glu + Ser210Glu |
| Val199Ala + Gln200Ser + Gly205Pro + Asn212Glu + Gly213Asp |
| Ala194Pro + Thr202Ser + Pro204Glu + Gly205Asp + Ala209Pro |
| Pro204Glu + Gly205Glu + Thr207Gly + Tyr208Ser + Leu211Ile |
| Pro195Gln + Val197Thr + Pro204Glu + Gly205Asp + Leu211Val |
| Val199His + Gly205Asp + Ser206Glu + Ala209Gln + Asn212Gln |
| Tyr203Ala + Gly205Glu + Ser206Asp + Tyr208Ile + Asn212Gln |
| Pro195Asn + Gly205Glu + Ser206Asp + Tyr208Ser + Ala209Ser |
| Val197His + Pro204Gly + Gly205Glu + Ser206Asp + Tyr208Cys |
| Thr202Asn + Pro204Ser + Gly205Asp + Ser206Asp + Tyr208Thr |

TABLE 27-continued

| Loop 6 - Quintuple Mutation Variants |
|---|
| Ala194Asn + Thr202Ser + Tyr203Gly + Ser206Glu + Thr207Glu |
| Pro195Ser + Gly196Gln + Val199Thr + Ser206Glu + Thr207Asp |
| Gly196Pro + Ser206Asp + Thr207Glu + Tyr208Thr + Leu211His |
| Ala194His + Gly196Gln + Pro204Asn + Tyr208Asp + Ala209Asp |
| Val199Ala + Tyr203Pro + Tyr208Asp + Ala209Asp + Asn212Gln |
| Val199Ala + Thr202Ser + Thr207Glu + Tyr208Asp + Thr214Ser |
| Gly196Asn + Thr202Gln + Pro204Ser + Thr207Asp + Tyr208Asp |
| Pro195Gln + Gln200Glu + Thr202Pro + Tyr203Pro + Ser210Asp |
| Gly196Pro + Val197Thr + Asn198Gln + Gln200Asp + Ser210Asp |
| Gly196Gln + Asn198Glu + Thr207Pro + Tyr208Ser + Ser210Glu |
| Ala194Pro + Asn198Glu + Thr207Pro + Ala209His + Ser210Glu |
| Asn198Glu + Val199Gln + Pro204Ser + Tyr208Asn + Ser210Asp |
| Pro195Gly + Asn198Glu + Thr207Gly + Tyr208Cys + Ser210Asp |
| Asn198Asp + Val199Thr + Leu211Asp + Asn212Ser + Thr214Gly |
| Gly196Pro + Asn198Gln + Gln200Glu + Tyr203Asn + Ala209Glu |
| Gly196Pro + Tyr203Thr + Pro204Asp + Ser206Asp + Ala209Gln |
| Pro195Asn + Gly196Pro + Asn198Asp + Ala209Pro + Asn212Glu |
| Pro195Asn + Gly196Gln + Gly205Asp + Thr207Glu + Leu211Thr |
| Thr202Asn + Pro204Asp + Thr207Asp + Tyr208Met + Thr214Pro |
| Tyr203Gly + Pro204Asp + Thr207Asp + Asn212Gln + Thr214Gly |
| Pro195Ser + Tyr203His + Pro204Gly + Thr207Asp + Gly213Gln |
| Asn198Glu + Gln200Glu + Tyr203Cys + Pro204Gly + Asn212Gln |
| Val197Glu + Val199Gly + Thr202Gly + Tyr203Ser + Gly213Glu |
| Pro204Gly + Thr207Asn + Ala209His + Ser210Asp + Asn212Asp |
| Pro195Gly + Gly196Gln + Thr202Gln + Ser210Asp + Asn212Asp |
| Thr202Asn + Tyr203Asn + Gly205Pro + Ser210Asp + Asn212Asp |
| Thr202Gln + Tyr203Gln + Ser210Asp + Asn212Asp + Gly213Gln |
| Gly196Ser + Ser210Asp + Leu211Gly + Asn212Asp + Thr214Gln |
| Gly196Pro + Ala209Ser + Ser210Glu + Leu211Asn + Asn212Asp |
| Gly205Ser + Ala209Pro + Ser210Glu + Asn212Asp + Thr214Pro |
| Pro195Gly + Tyr203Gly + Ser210Asp + Asn212Asp + Thr214Ser |
| Pro195Gln + Val197Asn + Val199Cys + Tyr208Gly + Ser210Asp |
| Val197Ser + Tyr203Gly + Pro204Gly + Thr207Ser + Tyr208Asp |
| Pro195Ser + Gly196Asn + Val197Asp + Val199Gly + Ser210Glu |
| Gly196Pro + Val197Asp + Thr202Pro + Ser210Gly + Thr214Pro |
| Val197Glu + Val199His + Tyr208Thr + Leu211Gln + Thr214Glu |
| Asn198Asp + Val199Asn + Thr207Asn + Ala209His + Gly213Asp |
| Val197His + Asn198Glu + Tyr203Gln + Tyr208Cys + Gly213Asp |
| Pro195Asn + Val197Asn + Asn198Glu + Thr202Pro + Gly213Asp |
| Pro195Ser + Asn198Glu + Tyr203Ser + Gly205Ser + Ala209Asp |
| Pro195GLy + Gly196Asn + Asn198Asp + Val199Met + Ala209Glu |
| Pro195Gln + Asn198Glu + Thr202Asn + Pro204Gly + Als209Asp |
| Val197Glu + Gln200Glu + Thr202Gly + Tyr208Ala + Gly213Gln |
| Val197Asp + Gln200Asp + Thr207Ser + Tyr208Ile + Ala209Ser |
| Val197Asp + Gln200Glu + Ala209Ser + Leu211Gly + Asn212Ser |
| Val197Glu + Gln200Asp + Thr202Asn + Gly205Gln + Asn212Gln |
| Ala194Pro + Gly196Pro + Val197Met + Gln200Glu + Asn212Asp |
| Gly196Gln + Gln200Glu + Thr202Pro + Tyr203Ile + Asn212Glu |
| Ala194His + Gln200Asp + Asn212Glu + Gly213Pro + Thr214Asn |
| Val199Pro + Gln200Glu + Pro204Gly + Asn212Glu + Gly213Ser |
| Asn198Ser + Gln200Asp + Gly205Pro + Thr207Ser + Asn212Glu |
| Ala194Asn + Gln200Asp + GLy205Asn + Tyr208Asn + Asn212Asp |
| Pro195Asn + GLn200Ser + Thr202Pro + Pro204Asp + Ala209Glu |
| Pro195Ser + Thr202Asn + Tyr202Cys + Pro204Glu + Ala209Asp |
| Ala194His + Asn198Ser + Thr202Asn + Pro204Glu + Ala209Asp |
| Ala194His + Pro204Asn + Ser206Glu + Ala209Glu + Thr214Ser |
| Pro195Gly + Val197Cys + Ser206Glu + Ala209Glu + Asn212Ser |
| Thr202Gly + Ser206Glu + Thr207Ser + Tyr208Met + Ala209Glu |
| Ala194Gly + Gln200Glu + Thr207Asp + Leu211Ser + Thr214Pro |
| Pro195Asn + Val199Ser + Gln200Glu + Gly205Asn + Thr207Asp |
| Ala194Gln + Asn198Gln + Gly205Pro + Ser210Asp + Gly213Asp |
| Gly196Ser + Thr207Gly + Ser210Glu + Leu211Thr + Gly213Asp |
| Asn198Gln + Pro204Gln + Thr207Asp + Tyr208Thr + Ser210Glu |
| Ala194Ser + Gly196Gln + Thr207Glu + Ser210Glu + Leu211Thr |
| Thr207Glu + Ser210Glu + Asn212Ser + Gly213Ser + Thr214Ser |
| Val197Cys + Thr207Glu + Ala209His + Ser210Glu + Thr214Asp |
| Asn198Glu + Val199Met + Tyr208Ala + Gly213Gln + Thr214Asp |
| Ala194Gln + Asn198Glu + Ala209Pro + Leu211His + Thr214Asp |
| Asn198Asp + Thr207Pro + Leu211Gly + Asn212Ser + Thr214Asp |
| Ala194Ser + Gly196Asn + Asn198Asp + Pro204Gln + Thr214Glu |

TABLE 28

| Loop 6 - Sextuple Mutation Variants |
|---|
| Ala194Gln + Val197Ser + Thr202Ser + Tyr203Ser + Ala209Ser + Asn212Asp |
| Pro195Ser + Val199Cys + Gly202Ser + Leu211Thr + Asn212Glu + Gly213Pro |
| Val197Thr + Asn198Ser + Val199Pro + Gln200Ser + Thr202Ser + Leu211Asn |
| Thr202Gly + Pro204Ser + Gly205Asn + Tyr208Asp + Gly213Gln + Thr214Pro |
| Val197Gly + Gln200Glu + Thr202Gly + Tyr208Ala + Leu211Val + Asn212Ser |
| Ala194Pro + Gly196Ser + Val199Cys + Tyr203Ala + Pro204Ser + Ala209Asp |
| Pro195Asn + Val199Pro + Thr202Asn + Tyr203Gly + Thr207Asp + Gly213Asn |
| Ala194Gln + Thr202Ser + Tyr203Ile + Pro204Asn + Gly205Asp + Tyr208Ser |
| Ala194Gln + Val197His + Ala209Ser + Ser210Asp + Leu211Gly + Asn212Gln |
| Thr202Gly + Gly205Pro + Ser210Asp + Leu211Ala + Gly213Ser + Thr214Gln |
| Ala194His + Gln200Ser + Thr202Gly + Pro204Ser + Tyr208His + Gly213Glu |
| Ala194Asn + Pro195Gln + Gly205Asn + Tyr208Ser + Leu211Val + Thr214Pro |
| Gly196Pro + Asn198Ser + Gln200Ser + Thr202Asn + Tyr208Ile + Thr214Glu |
| Pro195Asn + Gly205Pro + Thr207Gln + Ser210Glu + Leu211Asn + Gly213Pro |
| Ala194Ser + Val197Gly + Asn198Asp + Tyr203Cys + Gly205Gln + Leu211Met |
| Ala194Ser + Val197Asp + Val199Gln + Tyr203Cys + Gly205Ser + Gly213Gln |
| Ala194Pro + Thr202Gly + Thr207Ser + Tyr208Met + Leu211Pro + Gly213Glu |
| Ala194Thr + Pro195Asn + Gly196Gln + Gln200Ser + Thr202Asn + Pro204Glu |
| Ala194Gln + Gly196Asn + Val197Ser + Asn198Ser + Val199Thr + Ser210Glu |
| Gly196Ser + Val199Gly + Tyr203Ile + Pro204Asn + Leu211Asp + Thr214Gln |
| Ala194Asn + Gln200Asn + Pro204Gln + Ala209Thr + Leu211Asn + Gly213Ser |
| Ala194His + Pro195Gly + Gly196Asn + Gln200Ser + Tyr203Ser + Asn212Ser |
| Ala194Pro + Val197Met + Val199Asn + Thr202Ser + Ser206Asp + Thr207Asn |
| Pro195Gln + Thr202Pro + Gly205Asn + Ala209Pro + Asn212Ser + Thr214Asn |
| Pro195Asn + Asn198Glu + Val199His + Pro204Asn + Thr207Gly + Leu211Met |
| Gly196Ser + Pro204Asn + Thr207Pro + Asn212Asp + Gly213Ser + Thr214Pro |
| Ala194Ser + Pro195Ser + Val197Cys + Pro204Asn + Thr207Glu + Gly213Gln |
| Ala194His + Pro195Gly + Val197Gly + Val199Gln + Thr207Gly + Asn212Glu |
| Ala194Gln + Pro195Ser + Val197Ser + Tyr203Met + Leu211Glu + Gly213Asn |
| Ala194Asn + Gly196Asn + Pro204Asp + Thr207Pro + Tyr208Ser + Thr214Ser |
| Pro195Asn + Thr202Gly + Gly205Asp + Thr207Gln + Tyr208Thr + Ala209Asn |
| Ala194His + Pro195Gly + Val197His + Gly205Gln + Ala209Glu + Thr214Asn |
| Ala194Gln + Asn198Gln + Tyr203Met + Ala209Gln + Ser210Glu + Leu211Gly |
| Ala194Pro + Gly196Ser + Gln200Ser + Thr202Pro + Thr207Asp + Ala209Gly |
| Pro195Gln + Gly196Ser + Asn198Gln + Gly205Ser + Ser210Asp + Leu211Val |
| Asn198Gln + Val199Met + Gln200Glu + Thr202Gly + Gly205Asn + Try208Ala |
| Ala194Pro + Val199Ala + Pro204Asn + Thr207Gln + Leu211Glu + Gly213Ser |
| Gly196Pro + Val197Thr + Val199His + Gly205Asn + Ser206Asp + Thr207Asn |

TABLE 28-continued

| Loop 6 - Sextuple Mutation Variants |
| --- |
| Pro195Asn + Gly196Ser + Thr202Asn + Tyr203Gly + Leu211Asn + Asn212Glu |
| Ala194Ser + Pro195Gln + Val197Cys + Ser206Glu + Tyr208His + Asn212Gln |
| Pro195Gln + Gly196Pro + Val197Thr + Ser210Asp + Gly213Ser + Thr214Pro |
| Ala194Gly + Pro195Ser + Thr202Gly + Pro204Glu + Tyr208Thr + Gly213Pro |
| Ala194Asn + Pro195Asn + Gly196Asn + Gly205Pro + Ala209Asn + Ser210Asp |
| Pro195Ser + Val199Gln + Tyr208Asn + Ala209Gln + Leu211Gly + Gly213Gln |
| Asn198Asp + Val199Ala + Thr202Asn + Ala209Pro + Asn212Gln + Thr214Gly |
| Pro195Asn + Gly196Gln + Val199Pro + Ser206Glu + Tyr208Ala + Leu211Val |
| Ala194Gln + Pro195Ser + Asn198Asp + Val199Ser + Thr202Pro + Ala209Gln |
| Pro195Gly + Val199Met + Gly205Glu + Thr207Asn + Ala209Pro + Gly213Pro |
| Pro195Asn + Gly196Gln + Gln200Asp + Thr207Asn + Ala209Gly + Asn212Ser |
| Gly196Gln + Val197His + Thr207Asn + Ser210Asp + Leu211Ala + Gly213Gln |
| Ala194Gly + Val197Thr + Tyr203Met + Gly205Glu + Ala209Gly + Thr214Gly |
| Gln200Glu + Thr202Asn + Tyr203Gly + Thr207Asn + Asn212Gln + Gly213Pro |
| Gly196Asn + Thr202Ser + Pro204Glu + Leu211Pro + Gly213Ser + Thr214Asn |
| Pro195Gly + Val197Asn + Val199Gln + Gln200Asn + Thr207Gly + Asn212Ser |
| Pro195Gln + Gly196Pro + Val197His + Tyr203Gly + Ser206Asp + Thr214Ser |
| Gly196Gln + Tyr203His + Thr207Asn + Leu211Asn + Gly213Pro + Thr214Asp |
| Ala194Asn + Asn198Ser + Gln200Asn + Thr202Ser + Tyr203Ile + Ala209Thr |
| Ala194His + Val197Cyc + Gln200Ser + Tyr203Gly + Thr207Gly + Ala209His |
| Asn198Gln + Val199Thr + Gln200Asp + Pro204Asn + Asn212Ser + Gly213Gln |
| Gly196Pro + Tyr203Gln + Pro204Ser + Thr207Asn + Tyr208Met + Leu211Asp |
| Gly196Ser + Val197Met + Asn198Ser + Thr202Asn + Thr207Asp + Asn212Gln |
| Pro195Gly + Gly196Pro + Thr202Asn + Tyr203Ile + Gly213Asp + Thr214Asn |
| Pro195Gly + Gly196Pro + Gln200Glu + Pro204Ser + Tyr208Ile + Gly213Ser |
| Val199Ala + Thr202Gln + Gly205Ser + Ala209Asn + Ser210Glu + Leu211Cys |
| Ala194His + Pro195Ser + Val199Thr + Gln200Glu + Tyr203Pro + Tyr208Cys |
| Gly196Gln + Pro204Gly + Ser206Asp + Thr207Pro + Ala209Gln + Gly213Ser |
| Pro195Asn + Thr202Asn + Pro204Asn + Ala209Gln + Asn212Asp + Gly213Gln |
| Gly196Ser + Asn198Gln + Tyr203His + Asn212Ser + Gly213Asp + Thr214Gly |
| Ala194Gln + Val197Pro + Val199Gln + Gln200Asn + Tyr208Glu + Thr214Ser |
| Val199Cys + Gln200Asn + Pro204Gly + Ser206Asp + Thr207Ser + Asn212Ser |
| Ala196Gln + Gly196Gln + Val199His + Thr202Pro + Tyr203Thr + Gly205Ser |
| Asn198Gln + Val199Gly + Thr202Ser + Ser210Asp + Asn212Ser + Gly213Gln |
| Val199Thr + Gln200Asn + Pro204Ser + Tyr208Val + Asn212Gln + Thr214Asp |
| Ala194His + Gly196Gln + Val199Gln + Thr202Gly + Pro204Asp + Leu211Cys |
| Ala194Ser + Val197Gly + Pro204Gln + Ala209Pro + Ser210Glu + Thr214Gly |
| Ala194Gln + Gly196Pro + Tyr203Gln + Thr207Pro + Tyr208Pro + Ala209Asn |

TABLE 28-continued

| Loop 6 - Sextuple Mutation Variants |
| --- |
| Gly196Ser + Thr202Asn + Tyr208Ile + Ala209Gln + Leu211Ala + Gly213Glu |
| Pro195Asn + Gly196Pro + Val197Glu + Gln200Asn + Tyr203Ser + Tyr208Ser |
| Gly196Ser + Val199His + Gly205Asp + Tyr208Val + Ala209Gly + Thr214Pro |
| Val197Ser + Val199Met + Gln200Asn + Thr202Ser + Tyr208Cys + Gly213Gln |
| Ala194Ser + Gly196Gln + Val199Pro + Leu211Val + Gly213Glu + Thr214Gly |
| Ala194Gln + Asn198Gln + Val199Cys + Thr207Gly + Leu211Asp + Asn212Glu |
| Ala194Thr + Asn198Gln + Thr202Asn + Pro204Ser + Gly213Glu + Thr214Asp |
| Ala194Thr + Pro195Ser + Val199Ala + Ala209Glu + Ser210Glu + Leu211Cys |
| Tyr203Leu + Gly205Ser + Ala209Glu + Ser210Glu + Asn212Ser + Gly213Asn |
| Val197Glu + Asn198Glu + Tyr203Pro + Thr207Gly + Ala209Ser + Asn212Ser |
| Val197Asp + Asn198Asp + Val199His + Thr202Ser + Pro204Gln + Ala209Asn |
| Gly196Asn + Val197Glu + Asn198Asp + Gln200Ser + Pro204Asn + Thr207Gly |
| Pro195Gln + Thr202Ser + Tyr203Ser + Thr207Gln + Asn212Asp + Gly213Glu |
| Gly196Gln + Tyr203His + Gly205Ser + Leu211Asn + Asn212Asp + Gly213Glu |
| Asn198Ser + Gly205Ser + Tyr208Ile + Asn212Glu + Gly213Glu + Thr214Pro |
| Ala194Ser + Gly196Gln + Pro204Glu + Gly205Asp + Tyr208Asn + Thr214Asn |
| Ala194Ser + Pro195Gly + Val199Cys + Pro204Asp + Gly205Glu + Asn212Gln |
| Ala194Thr + Val199Pro + Aly205Asn + Ala209Gln + Ser210Glu + Leu211Asp |
| Thr202Gln + Thr207Gly + Ser210Asp + Leu211Glu + Gly213Gln + Thr214Ser |
| Thr202Gln + Gly205Asp + Ser206Glu + Tyr208Met + Gly213Gln + Thr214Asn |
| Ala194Gly + Gly205Glu + Ser206Glu + Ala209Gly + Leu211Gln + Thr214Gly |
| Gln200Ser + Thr202Ser + Tyr203Gly + Gly205Asp + Ser206Glu + Thr214Gln |
| Val197Asn + Thr202Ser + Gly205Glu + Ser206Glu + Ala209His + Thr214Ser |
| Ala194Gln + Thr202Ser + Tyr203Gly + Ser206Asp + Thr207Glu + Gly213Ser |
| Gly196Pro + Val199Gln + Tyr203Met + Ser206Glu + Thr207Asp + Ala209Thr |
| Pro195Gly + Gly196Pro + Thr202Ser + Pro204Gln + Tyr208Asp + Ala209Glu |
| Pro195Gln + Gly196Pro + Val197Pro + Gln200Asp + Gly205Ser + Ser210Asp |
| Gly196Ser + Asn198Glu + Gly205Pro + Ala209His + Ser210Glu + Asn212Gln |
| Ala194Thr + Asn198Asp + Thr202Ser + Tyr203Cys + Ala209Pro + Ser210Glu |
| Gly196Pro + Asn198Glu + Gly205Ser + Ser210Glu + Leu211Asn + Thr214Asn |
| Ala194Pro + Gly196Ser + Asn198Glu + Gly205Ser + Thr207Pro + Ser210Glu |
| Gly196Ser + Val197His + Asn198Asp + Gln200Ser + Thr207Gln + Ser210Asp |
| Asn198Glu + Val199Met + Gly205Pro + Ala209His + Ser210Glu + Thr214Pro |
| Val197Ser + Asn198Glu + Pro204Ser + Thr207Ser + Ala209Pro + Leu211Asp |
| Pro195Ser + Gln200Asp + Thr202Asn + Tyr203Ser + Ala209Asp + Asn212Ser |
| Gln200Asp + Pro204Ser + Gly205Pro + Tyr208His + Ala209Asp + Leu211Asn |
| Pro204Glu + Ser206Asp + Tyr208Ile + Leu211Gly + Asn212Gln + Thr214Asn |
| Gly196Ser + Asn198Ser + Val199Ala + Pro204Asp + Ser206Glu + Tyr208Ser |
| Pro195Asn + Pro204Asp + Ser206Asp + Tyr208Ser + Leu211Ser + Asn212Gln |

TABLE 28-continued

Loop 6 - Sextuple Mutation Variants

Ala194Gly + Asn198Glu + Gln200Ser + Thr207Gly + Ala209Asn + Asn212Glu
Asn198Glu + Gly205Gln + Ala209Pro + Leu211Cys + Asn212Asp + Gly213Pro
Ala194Thr + Val197Thr + Asn198Gln + Pro204Gly + Gly205Asp + Thr207Asp
Ala194Asn + Gly196Pro + Pro204Asp + Thr207Asp + Tyr208Cys + Gly213Asn
Ala194Thr + Pro195Gln + Gln200Ser + Pro204Glu + Thr207Asp + Gly213Pro
Val197Pro + Asn198Glu + Gln200Asp + Leu211Ala + Asn212Ser + Gly213Pro
Asn198Asp + Gln200Glu + Tyr203Val + Leu211Thr + Asn212Ser + Gly213Pro
Pro195Gln + Asn198Asp + Val199Gln + Gln200Glu + Pro204Asn + Ala209Pro
Ala194Gly + Gly196Asn + Asn198Asp + Gln200Asp + Thr207Gly + Asn212Ser
Gln200Asp + Thr202Asn + Tyr203Ala + Thr207Gln + Leu211Gln + Thr214Pro
Val197Asp + Val199His + Tyr203Val + Tyr208His + Leu211Asp + Gly213Pro
Pro195Asn + Val197Gln + Val199Gln + Thr207Asp + Ala209Glu + Gly213Ser
Asn198Gln + Gln200Asn + Tyr203Ala + Thr207Asp + Tyr208Val + Ala209Asp
Val197Ala + Asn198Gln + Pro204Ser + Tyr208Thr + Ser210Glu + Asn212Glu
Gly196Asn + Gln200Asn + Pro204Gln + Ser210Asp + Asn212Glu + Thr214Pro
Pro195Gln + Val199Pro + Ser210Asp + Asn212Glu + Gly213Asn + Thr214Gly
Pro195Gly + Gln200Ser + Thr207Pro + Tyr208Gln + Ser210Glu + Asn212Glu
Pro195Gly + Val199Cys + Thr202Asn + Tyr208His + Ser210Glu + Asn212Asp
Val199His + Thr202Gly + Pro204Gln + Ala209Thr + Ser210Asp + Asn212Asp
Asn198Gln + Thr202Pro + Ala209Ser + Ser210Glu + Asn212Glu + Gly213Pro
Ala194Ser + Val199Gln + Tyr208Gly + Ser210Asp + Leu211Gln + Asn212Asp
Ala194Asn + Val199Gly + Gly205Ser + Ala209His + Ser210Glu + Asn212Glu
Ala194Ser + Thr202Asn + Pro204Gly + Tyr208Glu + Ser210Glu + Gly213Gln
Pro195Gln + Val199Asn + Thr207Gly + Tyr208Asp + Ser210Asp + Leu211Ile
Pro195Gln + Gln200Asn + Tyr203Gln + Tyr208Glu + Ser210Glu + Asn212Gln
Ala194His + Tyr203Asn + Tyr208Asp + Ser210Asp + Leu211His + Thr214Ser
Gly196Asn + Val197Gln + Thr202Asn + Tyr208Glu + Ala209Asn + Ser210Glu
Ala194Asn + Gln200Ser + Tyr203Met + Ser206Glu + Tyr208Glu + Leu211Val
Asn198Ser + Pro204Gly + Ser206Glu + Tyr208Asp + Asn212Gln + Thr214Gly
Ala194Pro + Gln200Asn + Thr202Pro + Tyr203Met + Asn212Asp + Thr214Asp
Pro195Ser + Asn198Glu + Gln200Ser + Thr202Asn + Gly205Pro + Gly213Asp
Pro195Ser + Asn198Glu + Val199Ala + Ala209Glu + Leu211Asn + Thr214Gly
Pro195Gly + Asn198Glu + Gln200Asn + Thr202Pro + Tyr203Ile + Ala209Glu
Val197Ser + Asn198Asp + Tyr203Pro + Tyr208Met + Ala209Asp + Leu211Gln
Pro195Gln + Asn198Asp + Gln200Ser + Tyr208Met + Ala209Asp + Leu211Met
Gly196Asn + Val197Asp + Val199Gln + Gln200Glu + Gly205Asn + Gly213Pro
Gln200Glu + Thr202Gln + Tyr203Met + Ala209Asn + Leu211Ala + Asn212Asp
Ala194Pro + Gly196Pro + Gln200Asp + Thr202Asn + Tyr208Ser + Asn212Glu
Val197Gly + Val199Ser + Gln200Glu + Tyr203Gly + Asn212Glu + Gly213Pro
Pro204Asp + Thr207Gln + Tyr208Leu + Ala209Asp + Asn212Ser + Thr214Asn
Ala194Ser + Pro195Gln + Thr202Ser + Pro204Asp + Ala209Asp + Thr214Asn
Pro195Asn + Thr202Ser + Tyr203Leu + Tyr208Asp + Ala209His + Leu211Asp
Ala194Asn + Gly196Pro + Ser206Glu + Tyr208His + Ala209Asp + Thr214Gly
Pro204Gln + Gly205Asn + Ser206Glu + Thr207Gly + Ala209Asp + Leu211Cys
Val197Gln + Thr202Gln + Pro204Gly + Ser206Asp + Ala209Asp + Thr214Ser
Ala194Gly + Val197Gln + Asn198Gln + Tyr203Val + Ser206Asp + Ala209Asp
Gly196Ser + Val197Asn + Gln200Asp + Thr202Pro + Thr207Asp + Asn212Gln
Ala194Gly + Gly196Ser + Ser210Asp + Leu211Ser + Asn212Gln + Gly213Glu
Val197Thr + Tyr203His + Thr207Gln + Tyr208Pro + Ser210Asp + Gly213Asp
Asn198Ser + Val199Cys + Tyr203Val + Gly205Ser + Ser210Asp + Gly213Asp
Val197His + Val199Asn + Pro204Gln + Ser210Asp + Asn212Ser + Gly213Asp
Gly196Ser + Val197Ala + Gln200Asn + Thr202Pro + Ser210Glu + Gly213Glu
Asn198Glu + Tyr203Gly + Gly205Gln + Thr207Pro + Tyr208Val + Thr214Glu
Ala194Gly + Gly196Asn + Asn198Asp + Tyr203Leu + Tyr208His + Thr214Glu
Pro195Gly + Asn198Glu + Val199Cys + Ala209Gln + Asn212Gln + Thr214Asp
Asn198Asp + Val199Asn + Thr202Asn + Pro204Gln + Asn212Gln + Thr214Asp
Val199Pro + Gln200Asp + Tyr203Asn + Leu211Pro + Gly213Glu + Thr214Asn
Pro195Ser + Gly196Pro + Val199Ala + Gln200Asp + Asn212Gln + Gly213Asp
Ala194Thr + Pro195Gly + Gly196Pro + Gln200Glu + Gly205Asn + Gly213Glu
Val199His + Gln200Glu + Pro204Ser + Leu211His + Gly213Glu + Thr214Gln
Asn198Asp + Gln200Ser + Gly205Ser + Tyr208Asp + Leu211Ala + Asn212Ser
Ala194Ser + Asn198Asp + Thr202Ser + Tyr208Asp + Ala209Pro + Gly213Gln
Gln200Asn + Tyr203Pro + Pro204Glu + Gly205Pro + Ser210Asp + Leu211Pro
Val197Thr + Tyr203Pro + Pro204Asp + Ala209Gly + Ser210Asp + Thr214Asn
Gly196Asn + Pro204Glu + Ser210Glu + Leu211Pro + Asn212Ser + Thr214Gly

TABLE 29

Loop 6 - Heptuple Mutation Variants

Pro195Ser + Asn198Ser + Val199Met + Ser206Glu + Thr208Ser + Gly213Asn + Thr214Gln
Ala194Gln + Ala209Ser + Asn212Asp
Val197Asp + Gln200Asn + Thr202Pro + Gly205Gln + Thr207Gly + Tyr208Met + Leu211Val
Ala194Ser + Pro195Gly + Asn198Ser + Thr202Pro + Ser206Glu + Try208Ala + Thr214Gln
Ala194Pro + Pro195Asn + Thr202Gly + Tyr203Thr + Ser206Glu + Leu211Ser + Thr214Pro
Gly196Gln + Val197Thr + Gln200Asn + Tyr203Cys + Gly205Ser + Ser210Glu + Leu211Val
Ala194His + Val199Ser + Thr202Gly + Thr207Asn + Leu211Met + Gly213Glu + Thr214Pro
Val199Gly + Tyr203Cys + Pro204Gly + Thr207Asn + Ala209His + Asn212Asp + Gly213Asn

TABLE 29-continued

| Loop 6 - Heptuple Mutation Variants |
| --- |
| Ala194Gln + Gly196Pro + Tyr203Ser + Pro204Ser + Tyr208Ser + Leu211Glu + Thr214Pro |
| Gly196Gln + Gly205Asn + Thr207Asp + Tyr208Met + Asn212Gln + Gly213Ser + Thr214Pro |
| Gly196Gln + Val199Cys + Ser206Glu + Thr207Pro + Ala209Pro + Leu211Ile + Gly213Ser |
| Thr202Pro + Tyr203Val + Pro204Asn + Ser206Asp + Asn212Ser + Gly213Ser + Thr214Gly |
| Ala194Thr + Pro195Asn + Gly196Pro + Gln200Asn + Pro204Ser + Asn212Glu + Gly213Gln |
| Asn198Gln + Gln200Ser + Pro204Gln + Gly205Asn + Thr207Glu + Asn212Ser + Gly213Ser |
| Ala194Ser + Gly196Ser + Asn198Ser + Tyr203Gly + Gly205Pro + Ser206Glu + Gly213Pro |
| Ala194Thr + Gly196Gln + Val197Pro + Thr202Gln + Pro204Ser + Ala209Gly + Asn212Glu |
| Pro195Gln + Gly196Pro + Asn198Gln + Pro204Ser + Gly205Glu + Tyr208Gln + Gly213Asn |
| Val199Thr + Tyr203Gln + Pro204Gln + Gly205Asn + Thr207Glu + Leu211Thr + Thr214Gln |
| Val197Thr + Asn198Glu + Thr202Gly + Gly205Pro + Thr207Pro + Tyr208Met + Gly213Gln |
| Pro195Gly + Gly196Ser + Thr202Gly + Tyr203Gln + Pro204Gln + Tyr208Pro + Thr214Gln |
| Pro195Asn + Asn198Asp + Gln200Ser + Pro204Gly + Gly205Gln + Tyr208Gly + Ala209Asn |
| Pro195Asn + Val199His + Pro204Asn + Ala209Pro + Leu211Thr + Asn212Ser + Thr214Pro |
| Asn198Gln + Val199Thr + Gln200Asp + Pro204Asn + Leu211Val + Asn212Ser + Gly213Gln |
| Pro195Ser + Gly196Ser + Val197Met + Val199Gly + Gly205Pro + Ser210Glu + Asn212Gln |
| Ala194Thr + Pro195Gln + Asn198Gln + Thr202Asn + Thr207Asp + Tyr208Thr + Gly213Ser |
| Pro195Gln + Gly196Asn + Gly205Glu + Thr207Pro + Tyr208Asn + Ala209His + Asn212Ser |
| Asn198Gln + Thr202Pro + Thr207Pro + Leu211Pro + Asn212Glu + Gly213Asn + Thr214Ser |
| Ala194Pro + Val197Met + Pro204Ser + Thr207Gln + Tyr208Asn + Ala209Gln + Thr214Gly |
| Ala194Asn + Val197Cys + Pro204Asn + Tyr208Thr + Ala209Pro + Ser210Glu + Leu211Ser |
| Gly196Asn + Val197Gly + Tyr203Pro + Gly205Asp + Leu211Ala + Gly213Asn + Thr214Ser |
| Ala194Thr + Pro195Asn + Tyr203Pro + Gly205Ser + Ser210Glu + Leu211Ala + Gly213Pro |
| Ala194His + Gly196Asn + Val197Met + Asn198Ser + Ser206Asp + Leu211Asn + Asn212Ser |
| Ala194Thr + Gly196Ser + Val199Ser + Thr202Asn + Ala209Pro + Leu211Pro + Gly213Gln |
| Gly196Gln + Val199His + Thr202Pro + Tyr203Thr + Pro204Asp + Gly205Ser + Ala209Asn |
| Val197Cys + Val199Gly + Thr202Gln + Tyr203His + Gly205Glu + Tyr208Ile + Thr214Gln |
| Ala194Gly + Val197Cys + Asn198Asp + Gln200Ser + Tyr203Leu + Ala209Gln + Asn212Gln |
| Ala194Gly + Tyr203Cys + Gly205Gln + Ser206Glu + Tyr208Met + Leu211Cys + Thr214Gly |
| Gly196Ser + Val199Gln + Thr202Ser + Tyr203His + Pro204Gln + Tyr208Leu + Gly213Pro |
| Asn198Gln + Thr202Asn + Tyr203Ala + Pro204Glu + Tyr208Gly + Ala209Gln + Thr214Gln |
| Ala194Asn + Pro195Gln + Pro204Gly + Ser206Glu + Thr207Ser + Tyr208Ala + Asn212Ser |
| Ala194Pro + Pro195Gln + Val197Ser + Asn198Ser + Gln200Glu + Thr202Ser + Gly205Ser |
| Pro195Ser + Gly196Ser + Val199Gly + Thr202Gly + Pro204Glu + Leu211Ala + Thr214Asn |
| Ala194Thr + Gly196Pro + Asn198Gln + Ser + Pro204Asn + Tyr208Gly + Ser210Asp + Thr214Asn |
| Ala194Pro + Val199Asn + Thr202Gln + Pro204Gln + Gly205Asp + Thr207Ser + Ala209Pro |
| Ala194Pro + Pro195Gly + Val197Cys + Val199Gln + Tyr203Cys + Tyr208His + Gly213Glu |
| Val197Asp + Val199Ser + Gly205Pro + Thr207Gly + Leu211Thr + Asn212Gln + Gly213Ser |

TABLE 29-continued

| Loop 6 - Heptuple Mutation Variants |
| --- |
| Ala194Pro + Pro195Ser + Gln200Asn + Thr202Pro + Tyr208His + Gly213Asp + Thr214Gly |
| Ala194Thr + Val197Asn + Val199Pro + Gln200Asp + Thr202Ser + Thr207Asn + Tyr208Leu |
| Pro195Ser + Gly196Gln + Val197Ala + Thr202Gln + Tyr203Gly + Tyr208Cys + Gly213Asn |
| Ala194Gln + Val199Gln + Thr202Gly + Pro204Asn + Gly205Glu + Ala209His + Leu211His |
| Pro195Asn + Val199Thr + Tyr203Gly + Gly205Gln + Ser206Asp + Asn212Ser + Gly213Pro |
| Ala194Gln + Pro195Ser + Gly196Gln + Thr202Gln + Ala209His + Asn212Ser + Thr214Glu |
| Gly196Pro + Val197Cys + Tyr203Pro + Gly205Ser + Ser206Asp + Leu211Ile + Thr214Gly |
| Gly196Asn + Val197Gly + Val199His + Thr202Ser + Ala209His + Asn212Glu + Thr214Gln |
| Gly196Gln + Gln200Ser + Thr202Gln + Gly205Gln + Ala209Ser + Gly213Asp + Thr214Glu |
| Val199Gly + Gln200Asn + Thr202Gln + Gly205Ser + Ala209Glu + Ser210Asp + Leu211Asn |
| Val199Pro + Gln200Asn + Tyr203Val + Ala209Asp + Ser210Asp + Leu211Ser + Gly213Pro |
| Ala194Gly + Tyr203Val + Gly205Asn + Thr207Gly + Ala209Glu + Ser210Asp + Leu211Pro |
| Pro195Gln + Thr202Gly + Tyr203Val + Ala209Glu + Ser210Glu + Gly213Ser + Thr214Gln |
| Pro195Asn + Val197Ser + Tyr208Thr + Asl209Glu + Ser210Asp + Asn212Ser + Thr214Gln |
| Ala194Asn + Gly196Ser + Val199Gly + Thr202Pro + Tyr203Leu + Asn212Glu + Gly213Asp |
| Val197Cys + Asn198Ser + Gln200Ser + Thr202Asn + Thr207Gln + Asn212Asp + Gly213Asp |
| Gly196Pro + Thr202Asn + Pro204Asp + Gly205Glu + Ala209His + Leu211His + Gly213Ser |
| Pro195Gly + Gly196Gln + Tyr203Thr + Thr207Asn + Ser210Asp + Leu211Asp + Asn212Ser |
| Ala194Gly + Gly196Pro + Thr202Gln + Tyr203Val + Gly205Ser + Ser210Asp + Leu211Asp |
| Ala194His + Val199Cys + Tyr203Ala + Tyr208Gly + Ser210Asp + Leu211Asp + Gly213Pro |
| Ala194His + Gly196Ser + Val197Cys + Val199Ser + Gly205Glu + Ser206Glu + Tyr208Ser |
| Ala194His + Gly196Ser + Val197Thr + Val199Cys + Gly205Asp + Ser206Glu + Thr214Gln |
| Thr202Asn + Tyr203Thr + Gly205Glu + Ser206Asp + Ala209Gln + Leu211Thr + Thr214Gly |
| Ala194Pro + Val197Met + Asn198Ser + Val199Asn + Thr202Ser + Ser206Asp + Thr207Glu |
| Pro195Asn + Val199Met + Thr202Gly + Ser206Glu + Thr207Asp + Tyr208Thr + Asn212Ser |
| Pro195Gly + Gly196Asn + Val199Gln + Tyr203His + Ser206Glu + Thr207Asp + Asn212Gln |
| Pro195Asn + Val199Ala + Gly205Pro + Ser206Glu + Thr207Asp + Tyr208Gly + Asn212Ser |
| Pro195Asn + Gly196Ser + Val197Ala + Pro204Ser + Ser206Glu + Thr207Asp + Asn212Gln |
| Pro195Asn + Val197Thr + Ser206Asp + Thr207Asp + Leu211Thr + Gly213Ser + Thr214Ser |
| Ala194Thr + Val197Cys + Asn198Ser + Thr207Asp + Tyr208Asp + Asn212Ser + Gly213Asn |
| Ala194Thr + Gln200Asp + Thr202Gln + Ala209His + Ser210Asp + Leu211Gly + Thr214Gly |
| Pro195Gln + Gln200Asp + Tyr203Ala + Gly205Asn + Tyr208Ser + Ser210Asp + Gly213Asn |
| Ala194Thr + Val199Pro + Gln200Glu + Thr207Gly + Ser210Glu + Leu211Ser + Gly213Asn |
| Val197Ser + Gln200Glu + Tyr203Leu + Pro204Asn + Ala209Gly + Ser210Asp + Leu211Asn |
| Gly196Gln + Asn198Gln + Val199Pro + Gln200Asp + Thr202Gly + Pro204Gly + Ser210Asp |
| Asn198Gln + Val199Cys + Gln200Glu + Gly205Gln + Ser210Asp + Gly213Ser + Thr214Gly |
| Asn198Gln + Gln200Glu + Gly205Pro + Thr207Ser + Ala209Asn + Ser210Glu + Thr214Asn |
| Gln200Glu + Thr202Asn + Thr207Ser + Tyr208Pro + Ser210Glu + Gly213Gln + Thr214Gly |
| Ala194Pro + Pro195Ser + Gly196Asn + Val197Asp + Val199Thr + Pro204Gly + Asn212Glu |

TABLE 29-continued

| Loop 6 - Heptuple Mutation Variants |
|---|
| Gly196Asn + Asn198Glu + Tyr203Gly + Pro204Gln + Ser210Asp + Leu211Val + Asn212Ser |
| Gly196Pro + Val197Gly + Asn198Asp + Thr202Pro + Tyr203Val + Thr207Asn + Ser210Glu |
| Pro195Asn + Gly196Pro + Asn198Asp + Thr202Ser + Pro204Gln + Ser210Asp + Gly213Gln |
| Pro195Ser + Val197Pro + Asn198Glu + Val199Met + Thr207Ser + Ser210Asp + Thr214Gln |
| Ala194Ser + Gly196Asn + Val197Met + Asn198Asp + Val199Thr + Tyr208Met + Leu211Glu |
| Asn198Asp + Val199Gln + Pro204Ser + Leu211Asp + Asn212Ser + Gly213Pro + Thr214Asn |
| Pro195Gln + Asn198Asp + Thr202Pro + Gly205Gln + Tyr208Met + Leu211Glu + Gly213Asn |
| Gly196Pro + Gln200Asp + Thr202Ser + Tyr203Thr + Tyr208His + Ala209Glu + Leu211Ile |
| Ala194Thr + Gln200Asn + Thr202Pro + Pro204Asp + Ser206Glu + Thr207Asn + Ala209Ser |
| Gly196Pro + Pro204Asp + Gly205Ser + Ser206Asp + Tyr208Gly + Gly213Gln + Thr214Gly |
| Pro195Gln + Val197Gln + Gln200Ser + Pro204Glu + Ser206Asp + Ala209Gly + Thr214Gln |
| Ala194Thr + Pro195Gly + Val197Pro + Pro204Asp + Ser206Glu + Leu211Val + Gly213Ser |
| Pro195Asn + Gly196Ser + Pro204Glu + Ser206Asp + Thr207Gly + Tyr208Val + Ala209Thr |
| Pro195Asn + Gly196Pro + Val197Gln + Asn198Asp + Tyr203Gln + Tyr208Asn + Asn212Asp |
| Gly196Gln + Val197Thr + Asn198Asp + Val199Gly + Thr202Pro + Tyr208Asn + Asn212Glu |
| Pro195Asn + Asn198Asp + Val199Asn + Thr202Gln + Ala209Pro + Asn212Asp + Gly213Gln |
| Ala194Gly + Val197Met + Asn198Asp + Gln200Glu + Thr202Asn + Pro204Asn + Tyr208Asn |
| Pro195Ser + Val197Gln + Asn198Glu + Val199Cys + Gln200Asp + Gly205Ser + Ala209Pro |
| Pro195Gln + Gly196Pro + Asn198Glu + Val199Ser + Gln200Asp + Gly205Ser + Thr214Asn |
| Ala194Gln + Pro195Ser + Asn198Glu + Gln200Asp + Thr207Gln + Tyr208Leu + Asn212Gln |
| Ala194Pro + Pro195Asn + Gln200Glu + Pro204Gln + Thr207Gln + Tyr208Asp + Gly213Gln |
| Val199Thr + Gln200Asp + Tyr208Glu + Ala209Thr + Leu211Ser + Asn212Ser + Gly213Asn |
| Gly196Pro + Val197Glu + Asn198Gln + Val199Met + Tyr208Met + Gly213Asp + Thr214Asn |
| Pro195Gly + Val197Glu + Val199Thr + Gln200Ser + Gly205Asn + Ala209Gly + Leu211Glu |
| Val197Met + Val199Cys + Gly205Pro + Tyr208Ile + Leu211Asp + Asn212Ser + Gly213Asp |
| Pro195Gln + Asn198Ser + Val199Gln + Pro204Ser + Ser210Asp + Leu211Cys + Asn212Glu |
| Pro195Ser + Gly196Pro + Asn198Gln + Pro204Gln + Ala209Thr + Ser210Glu + Asn212Glu |
| Ala194Gly + Asn198Gln + Val199Gln + Thr207Ser + Ser210Asp + Leu211Gly + Asn212Asp |
| Aal194Gln + Val197Gly + Thr202Ser + Pro204Ser + Ser210Glu + Asn212Glu + Gly213Ser |
| Ala194Asn + Asn198Ser + Thr202Pro + Ser210Glu + Leu211Cys + Asn212Asp + Gly213Ser |
| Pro195Gly + Val197Thr + Thr202Asn + Gly205Ser + Ser210Asp + Asn212Glu + Gly213Ser |
| Pro195Gln + Gly205Gln + Ala209Gln + Ser210Asp + Leu211Asn + Asn212Glu + Thr214Gln |
| Val199His + Pro204Asn + Tyr208Ile + Ala209Thr + Ser210Glu + Leu211Gln + Asn212Asp |
| Val197Asn + Asn198Gln + Tyr203Pro + Pro204Asn + Ser210Glu + Asn212Glu + Thr214Gln |
| Ala194Pro + Gly196Ser + Gln200Ser + Gly205Gln + Tyr208Gly + Ser210Glu + Asn212Glu |
| Pro195Ser + Val197Gly + Asn198Gln + Val199Gln + Gln200Ser + Ser210Glu + Asn212Asp |
| Asn198Gln + Gln200Asn + Thr207Gly + Tyr208Glu + Ser210Glu + Asn212Ser + Thr214Asn |
| Pro195Gly + Thr202Ser + Tyr208Glu + Ala209Asn + Ser210Glu + Asn212Gln + Thr214Asn |

TABLE 29-continued

| Loop 6 - Heptuple Mutation Variants |
|---|
| Val199Thr + Thr202Ser + Gly205Pro + Ser206Glu + Tyr208Glu + Leu211His + Asn212Ser |
| Ala194Gln + Gly196Pro + Asn198Gln + Tyr203Ile + Ser206Asp + Tyr208Asp + Gly213Gln |
| Ala194Ser + Pro195Ser + Thr202Ser + Gly205Gln + Ser206Asp + Tyr208Asp + Asn212Gln |
| Pro195Gly + Val197His + Tyr203Gln + Thr207Pro + Asn212Asp + Gly213Ser + Thr214Asp |
| Pro195Gly + Val197Met + Thr202Asn + Tyr208Met + Leu211Thr + Asn212Glu + Thr214Asp |
| Val197Ser + Asn198Gln + Thr202Ser + Pro204Glu + Thr207Ser + Tyr208Asp + Ala209Ser |
| Ala194Pro + Val199Asn + Pro204Asp + Tyr208Glu + Leu211Glu + Asn212Gln + Gly213Ser |
| Pro195Gln + Val197Glu + Val199Gly + Gln200Ser + Thr207Ser + Ser210Glu + Leu211Asn |
| Pro195Ser + Val197Asp + Val199Cys + Pro204Gly + Thr208Ser + Ser210Glu + Asn212Ser |
| Ala194Gln + Val197Asp + Asn198Ser + Thr202Asn + Thr207Asn + Ser210Glu + Leu211His |
| Val197Asp + Gln200Asn + Tyr203Thr + Tyr208Val + Ser210Asp + Asn212Ser + Thr214Ser |
| Ala194Pro + Val197Asp + Gln200Ser + Thr202Gly + Leu211Cys + Gly213Asn + Thr214Glu |
| Pro195Ser + Val197Glu + Asn198Gln + Tyr208Ile + Ala209His + Leu211Val + Thr214Glu |
| Pro195Gly + Val197Asp + Gln200Ser + Thr202Pro + Ala209Thr + Gly213Gln + Thr214Asp |
| Pro195Asn + Gly196Pro + Asn198Asp + Pro204Asn + Gly205Asn + Ala209Asn + Gly213Asp |
| Ala194Pro + Asn198Asp + Val199Gln + Gln200Ser + Thr207Pro + Ala209Asp + Gly213Asn |
| Val197Asp + Val199His + Gln200Glu + Thr202Pro + Tyr203Ile + Thr207Gly + Thr214Gly |
| Val197Glu + Gln200Asp + Tyr203Ile + Pro204Gln + Ala209Gly + Leu211Ile + Thr214Pro |
| Pro195Asn + Gly196Ser + Val199Met + Gln200Asp + Tyr203Ala + Asn212Asp + Gly213Asn |
| Ala194Thr + Gly196Gln + Gln200Glu + Tyr203Val + Tyr208Ala + Leu211Ala + Asn212Glu |
| Val197Asn + Asn198Gln + Pro204Asp + Tyr208Met + Ala209Glu + Asn212Ser + Gly213Asn |
| Pro195Asn + Thr202Gly + Tyr203Asn + Pro204Glu + Gly205Asn + Thr207Ser + Ala209Glu |
| Ala194Pro + Gly196Pro + Tyr203Ala + Thr207Gln + Leu211Glu + Gly213Pro + Thr214Glu |
| Asn198Gln + Val199Thr + Thr202Pro + Pro204Gln + Ala209Thr + Leu211Glu + Thr214Asp |
| Ala194His + Val199Cys + Gln200Glu + Tyr203Ile + Gly205Asn + Thr207Glu + Tyr208Met |
| Val199Pro + Gln200Asp + Pro204Gln + Gly205Asn + Thr207Asp + Tyr208Cys + Thr214Pro |
| Ala194His + Pro195Gln + Gly196Gln + Val199His + Gln200Glu + Thr207Glu + Asn212Ser |
| Ala194Gly + Asn198Gln + Gln200Asn + Tyr203Leu + Ser210Asp + Leu211Gly + Gly213Glu |
| Asn198Gln + Gln200Asn + Thr202Ser + Ser210Asp + Leu211Ser + Gly213Glu + Thr214Asn |
| Pro195Asn + Val197Met + Tyr203Gly + Gly205Pro + Tyr208His + Ser210Asp + Gly213Asp |
| Pro195Ser + Gln200Asn + Thr207Pro + Ser210Glu + Leu211Met + Gly213Glu + Thr214Gln |
| Val197Gln + Val199Ser + Thr202Asn + Tyr208Gly + Ala209Gly + Ser210Glu + Gly213Asp |
| Gln200Asn + Pro204Gln + Thr207Glu + Ala209Ser + Ser210Asp + Leu211Thr + Gly213Asn |
| Ala194Gln + Thr202Gly + Tyr203Asn + Thr207Asp + Ser210Asp + Leu211Cys + Gly213Pro |
| Pro195Gln + Val199Gln + Gly205Gln + Thr207Glu + Tyr208Ile + Ser210Asp + Thr214Gly |
| Pro195Gly + Val197His + Val199Met + Tyr203Thr + Thr207Glu + Ser210Asp + Asn212Gln |
| Ala194Gln + Pro195Gln + Asn198Ser + Val199Gln + Pro204Gln + Thr207Glu + Ser210Glu |
| Val197Pro + Asn198Glu + Val199Thr + Pro204Asn + Leu211Cys + Asn212Ser + Thr214Asp |
| Ala194Ser + Val199Thr + Gln200Glu + Tyr203Cys + Tyr208Gly + Leu211Gly + Gly213Glu |

TABLE 29-continued

| Loop 6 - Heptuple Mutation Variants |
|---|
| Val199Pro + Gln200Asp + Tyr203Asn + Pro204Gly + Leu211Pro + Gly213Glu + Thr214Asn |
| Ala194Gln + Asn198Glu + Thr207Ser + Tyr208Glu + Asn212Gln + Gly213Gln + Thr214Gln |
| Pro195Gln + Asn198Asp + Gln200Ser + Gly205Ser + Tyr208Asp + Leu211Ala + Asn212Ser |
| Gly196Pro + Val197Asp + Asn198Gln + Val199Ala + Pro204Gln + Ala209Asp + Gly213Asn |
| Pro195Ser + Asn198Gln + Val199Gly + Pro204Glu + Ala209Gly + Ser210Asp + Asn212Gln |
| Pro195Ser + Gln200Ser + Pro204Glu + Thr207Pro + Ala209Gln + Ser210Asp + Asn212Gln |
| Ala194His + Gly196Ser + Val197Gly + Val199Asn + Gln200Glu + Pro204Glu + Ala209Thr |
| Gly196Pro + Asn198Ser + Pro204Asn + Tyr208Gly + Ala209Asp + Leu211Thr + Gly213Asp |
| Gly196Pro + Val199Thr + Gln200Asp + Thr202Asn + Tyr203Asn + Ser206Glu + Ala209Ser |
| Pro195Ser + Gly196Pro + Val199Pro + Gln200Glu + Pro204Gln + Ser206Asp + Leu211Ala |
| Pro195Ser + Gln200Asp + Thr202Gln + Pro204Gln + Ser206Glu + Tyr208Gly + Ala209Gly |
| Gly196Asn + Val199Ser + Gln200Glu + Thr202Pro + Ala209Thr + Leu211Cys + Thr214Asp |
| Val197Asn + Gln200Glu + Tyr203Gln + Gly205Pro + Ala209Thr + Leu211Val + Thr214Glu |
| Pro195Gly + Tyr203Gly + Ser206Glu + Tyr208Gly + Ala209Gln + Ser210Glu + Leu211Ile |
| Gly196Asn + Val197His + Val199Ala + Pro204Asn + Ser206Asp + Ser210Asp + Leu211Thr |
| Ala194Gln + Val197Ser + Val199Pro + Ser206Asp + Ser210Glu + Leu211Pro + Thr214Gly |
| Ala194His + Gln200Ser + Thr202Asn + Ser206Glu + Tyr208Cys + Ser210Asp + Asn212Ser |
| Val197Thr + Thr202Ser + Pro204Gly + Gly205Asn + Ser206Asp + Ser210Glu + Leu211Pro |

TABLE 30

| Loop 6 - Octuple Mutation Variants |
|---|
| Pro195Ser + Val197Ser + Asn198Ser + Val199Gly + Tyr203Thr + Thr207Asn + Tyr208Met + Asn212Glu |
| Pro195Gln + Gly196Gln + Val199Gln + Tyr203Gln + Tyr208Met + Ala209Gly + Leu211Val + Gly213Asp |
| Pro195Gln + Asn198Gln + Val199His + Pro204Gly + Ser206Glu + Thr207Gln + Tyr208Ser + Leu211Gln |
| Ala194Thr + Val197Met + Val199His + Thr202Ser + Tyr203Ile + Thr207Gln + Tyr208Pro + Leu211Gly |
| Pro195Gln + Val197Asn + Val199Cys + Tyr203Met + Pro204Asn + Gly205Glu + Thr207Pro + Tyr208Ser |
| Gly196Ser + Gln200Asn + Pro204Asp + Gly205Ser + Thr107Pro + Tyr208Met + Gly213Gln + Thr214Ser |
| Val197Gln + Gln200Asn + Tyr203His + Pro204Asp + Gly205Ser + Tyr208Thr + Ala208Gln + Leu211Pro |
| Pro195Gly + Gly196Ser + Val197Pro + Val199Ser + Thr202Asn + Ala209Glu + Leu211Ser + Gly213Pro |
| Ala194His + Gly196Ser + Val197Asn + Asn198Ser + Tyr203Leu + Pro204Asn + Thr207Ser + Ala209Thr |
| Ala194Pro + Gly196Pro + Val199Met + Gln200Asp + Thr202Asn + Thr207Asn + Ala209Pro + Gly213Pro |
| Pro195Asn + Gly196Pro + Val199Thr + Thr202Gln + Thr207Gly + Tyr208Ser + Ser210Asp + Asn212Ser |
| Ala194Thr + Pro195Asn + Gly196Gln + Thr202Pro + Pro204Ser + Gly205Pro + Tyr208Gln + Leu211Asp |
| Ala194Gly + Pro195Ser + Val197Ala + Thr202Gly + Tyr203Gly + Pro204Gln + Gly205Ser + Leu211Glu |
| Pro195Asn + Val197Glu + Val199Thr + Gln200Asn + Thr202Pro + Tyr203Ile + Pro204Ser + Leu211Cys |
| Ala194His + Pro195Gln + Val199Cys + Gln200Asp + Tyr203Ala + Thr207Ser + Gly213Gln + Thr214Pro |

TABLE 30-continued

| Loop 6 - Octuple Mutation Variants |
|---|
| Ala194Gln + Gly196Gln + Val199His + Thr202Pro + Tyr203Thr + Pro204Asp + Gly205Ser + Ala209Asn |
| Pro195Ser + Gly196Ser + Gln200Asn + Tyr203His + Thr207Pro + Leu211Met + Gly213Glu + Thr214Gln |
| Val197Cys + Asn198Ser + Val199Ala + Gln200Asp + Tyr203His + Leu211Asn + Asn212Gln + Gly213Asn |
| Ala194Gln + Gly196Pro + Asn198Gln + Val199His + Tyr203Val + Thr207Ser + Ala209Ser + Leu211Asn |
| Pro195Gly + Gly196Ser + Val197Pro + Thr207Gly + Leu211Thr + Asn212Ser + Gly213Asn + Thr214Glu |
| Val197Asn + Thr202Gly + Tyr203Ala + Gly205Gln + Tyr208Ile + Ala209Thr + Ser210Asp + Leu211Gly |
| Ala194Asn + Asn198Gln + Val199Ser + Thr202Gly + Tyr203Ile + Ala209Thr + Ser210Asp + Thr214Ser |
| Pro195Ser + Gly196Asn + Val197Asn + Asn198Ser + Thr202Asn + Tyr203Cys + Tyr208Asn + Leu211Thr |
| Ala194Gly + Pro195Ser + Gly196Gln + Val199Ala + Thr202Pro + Thr207Ser + Asn212Ser + Thr214Asp |
| Val197Cys + Val199Pro + Thr202Pro + Tyr203Ser + Ser206Glu + Thr207Gln + Ala209Gly + Thr214Gly |
| Ala194Gly + Pro195Gln + Gly196Gln + Asn198Ser + Val199Met + Ser206Glu + Tyr208Ala + Leu211Ala |
| Ala194Gly + Gly196Ser + Tyr203His + Pro204Asn + Ser206Asp + Tyr208Ile + Leu211Gln + Asn212Ser |
| Gly196Pro + Gln200Ser + Tyr203Gln + Pro204Ser + Gly205Ser + Tyr208Cys + Leu211Met + Gly213Gln |
| Ala194Asn + Tyr203Asn + Gly205Glu + Thr207Gln + Ala209Thr + Leu211His + Gly213Pro + Thr214Gln |
| Ala194Ser + Pro195Asn + Gly196Asn + Val199Ser + Pro204Ser + Gly205Asn + Ala209Asp + Thr214Gln |
| Pro195Asn + Gly196Gln + Thr202Pro + Gly205Ser + Ser206Glu + Tyr208Ser + Ala209Pro + Gly213Gln |
| Ala194Thr + Pro195Gly + Val197Asp + Asn198Gln + Gly205Ser + Tyr208Val + Asn212Gln + Gly213Ser |
| Pro195Gly + Asn198Ser + Tyr203Thr + Pro204Asn + Tyr208Pro + Ala209Thr + Asn212Ser + Gly213Ser |
| Ala194Thr + Pro195Ser + Gly196Asn + Val197Met + Gln200Ser + Thr202Asn + Tyr203His + Tyr208Gln |
| Ala194His + Asn198Ser + Tyr203Gln + Pro204Gln + Ala209Pro + Leu211Asp + Asn212Glu + Gly213Asn |
| Ala194Asn + Pro195Ser + Val197Gly + Pro204Gly + Gly205Asn + Ala209Asp + Ser210Asp + Thr214Gln |
| Gly196Gln + Val197Pro + Gln200Asn + Thr202Asn + Gly205Gln + Ala209Glu + Ser210Asp + Thr214Pro |
| Val197Ser + Val199Ala + Thr202Ser + Tyr203Pro + Gly205Asn + Tyr208Ile + Ala209Asp + Ser210Glu |
| Asn198Ser + Val199Met + Gln200Ser + Pro204Ser + Tyr208Ala + Ala209Glu + Ser210Asp + Leu211Gly |
| Ala194Gly + Val197Asn + Asn198Ser + Gln200Ser + Tyr203Thr + Ala209Asp + Ser210Asp + Thr214Pro |
| Ala194His + Pro195Ser + Asn198Ser + Tyr203Cys + Thr207Ser + Ala209Asp + Ser210Glu + Gly213Ser |
| Pro195Ser + Val199Asn + Gln200Ser + Pro204Ser + Thr207Gly + Ala209Asp + Ser210Asp + Asn212Ser |
| Ala194Gln + Gly196Pro + Val197Asp + Asn198Glu + Val199Ser + Gly205Gln + Ala209Gly + Asn212Ser |
| Pro195Gln + Val197Asp + Asn198Glu + Val199Ala + Gln200Ser + Thr202Ser + Thr207Gly + Tyr208Ala |
| Pro195Ser + Gly196Pro + Gln200Asn + Thr202Asn + Tyr203Met + Thr207Gly + Asp212Asp + Gly213Asp |
| Gly196Asn + Thr202Pro + Pro204Gly + Thr207Pro + Leu211Cys + Asn212Glu + Gly213Glu + Thr214Pro |
| Gly196Asn + Asn198Gln + Gln200Ser + Thr202Pro + Tyr203Cys + Pro204Asn + Asn212Asp + Gly213Glu |
| Asn198Ser + Val199Gly + Tyr203Ala + Pro204Asp + Gly205Glu + Tyr208Met + Ala209Ser + Leu211Pro |
| Val197Cys + Val199Asn + Thr202Gln + Pro204Asp + Gly205Asp + Ala209Gln + Leu211Gln + Asn212Ser |
| Pro195Asn + Val199Thr + Thr202Gly + Ala209His + Ser210Glu + Leu211Asp + Asn212Ser + Gly213Asn |
| Gly196Asn + Val199His + Tyr203Ala + Gly205Asp + Ser206Asp + Thr207Gln + Tyr208Gln + Leu211Asn |
| Ala194Gly + Gly196Gln + Val197Ala + Gln200Asn + Tyr203Ser + Gly205Asp + Ser206Asp + Tyr208Ala |
| Ala194Gln + Val197Gln + Pro204Asn + Gly205Asp + Ser206Glu + Tyr208Ala + Ala209His + Gly213Asn |
| Pro195Ser + Gly196Asn + Val197Thr + Gln200Asn + Pro204Ser + Gly205Glu + Ser206Glu + Tyr208Gly |

TABLE 30-continued

Loop 6 - Octuple Mutation Variants

Val197Gly + Asn198Gln + Val199Met + Gln200Asn + Tyr203His + Ser206Asp + Thr207Glu + Thr214Pro
Ala194Gln + Pro195Gly + Gly196Pro + Thr202Pro + Ser206Asp + Thr207Asp + Tyr208Val + Ala209His
Ala194Thr + Pro195Ser + Val197Gln + Asn198Gln + Thr202Ser + Pro204Asn + Ser206Glu + Thr207Asp
Ala194Gln + Val199Met + Thr202Ser + Tyr203Gly + Gly205Gln + Ser206Asp + Thr207Glu + Gly213Ser
Ala194Gly + Pro195Asn + Gly196Gln + Tyr203Ala + Ser206Asp + Thr207Glu + Ala209Thr + Asp212Gln
Gly196Ser + Gln200Ser + Tyr203Leu + Pro204Ser + Ser206Glu + Thr207Glu + Ala209Ser + Gly213Ser
Ala194Ser + Pro195Asn + Thr202Gln + Ser206Glu + Thr207Glu + Tyr208Gly + Asn212Ser + Thr214Gly
Ala194His + Pro195Gln + Val197Ala + Thr202Asn + Tyr203Pro + Gly204Pro + Tyr208Asp + Ala209Asp
Ala194Gln + Pro195Gln + Val197Asn + Gln200Asp + Ala209Gly + Ser210Asp + Leu211Ala + Thr214Asn
Ala194Pro + Val199Met + Gln200Glu + Thr202Gly + Pro204Gln + Gly205Asn + Tyr208Gln + Ser210Asp
Gly196Pro + Val197Cys + Val199Asn + Gln200Glu + Gly205Pro + Tyr208Val + Ser210Glu + Thr214Pro
Ala194Thr + Pro195Gly + Gly196Gln + Val197Asp + Val199His + Gln200Ser + Thr202Ser + Asn212Asp
Asn198Asp + Val199Pro + Gly205Asn + Thr207Gly + Tyr208Pro + Ser210Asp + Leu211Gly + Gly213Gln
Ala194Gln + Gly196Pro + Asn198Glu + Tyr203Gln + Thr207Gln + Tyr208Pro + Ala209Pro + Ser210Glu
Ala194Pro + Asn198Asp + Val199His + Gly205Asn + Ser210Glu + Leu211Asn + Asn212Ser + Thr214Pro
Asn198Glu + Val199Pro + Tyr203Asn + Thr207Pro + Ala209Asn + Ser210Glu + Asn212Ser + Gly213Gln
Ala194Gly + Pro195Asn + Asn198Asp + Tyr203Ala + Gly205Gln + Thr207Ser + Ser210Glu + Leu211Val
Ala194Thr + Asn198Asp + Thr202Gly + Pro204Ser + Gly205Ser + Thr207Asn + Ala209Pro + Ser210Glu
Ala194Gln + Asn198Asp + Tyr203Ala + Thr207Gln + Tyr208Pro + Ser210Glu + Leu211Pro + Asn212Ser
Ala194Thr + Pro195Ser + Asn198Asp + Tyr203Cys + Pro204Asn + Thr207Gln + Tyr208Gln + Ser210Glu
Pro195Ser + Asn198Asp + Val199Ser + Gln200Ser + Pro204Ser + Ser210Glu + Leu211Gly + Asn212Ser
Ala194Gln + Pro195Ser + Gly196Pro + Gln200Glu + Pro204Asn + Gly205Pro + Ala209Glu + Leu211Cys
Val199His + Gln200Ser + Pro204Asp + Gly205Ser + Ser206Asp + Tyr208Gly + Gly213Gln + Thr214Gly
Gly196Asn + Asn198Ser + Thr202Ser + Pro204Asp + Gly205Ser + Ser206Asp + Thr207Ser + Tyr208Val
Val197Ala + Gln200Asn + Pro204Glu + Gly205Ser + Ser206Glu + Tyr208Val + Leu211Ser + Asn212Ser
Pro195Asn + Val197Thr + Thr202Ser + Tyr203Ile + Pro204Asp + Ser206Asp + Thr207Gln + Ala209Gln
Pro195Gly + Val197Asn + Val199Ser + Gln200Asn + Tyr203Asn + Pro204Glu + Ser206Glu + Leu211Met
Gly196Ser + Asn198Ser + Val199Met + Gln200Asp + Pro204Glu + Ser206Asp + Leu211Val + Thr214Gln
Ala194Gln + Gly196Asn + Asn198Asp + Gln200Ser + Thr202Asn + Pro204Asn + Asn212Glu + Thr214Asp
Pro195Gly + Asn198Glu + Val199Asn + Gln200Ser + Thr202Gly + Thr207Asn + Ala209Thr + Asn212Asp
Pro195Asn + Gly196Ser + Asn198Glu + Thr207Ser + Tyr208Ser + Ala209Pro + Asn212Asp + Thr214Asn
Ala194Pro + Val197Ser + Asn198Glu + Gln200Asn + Tyr203Cys + Thr207Pro + Tyr208Thr + Asn212Asp
Pro195Gly + Gly196Ser + Thr202Asn + Pro204Asn + Gly205Glu + Thr207Asp + Tyr208Thr + Asn212Ser
Val197Gln + Val199Asn + Thr202Pro + Gly205Glu + Thr207Glu + Tyr208Ala + Leu211Ser + Gly213Asn
Ala194Ser + Pro195Ser + Val197Gly + Pro204Asp + Gly205Ser + Thr207Glu + Tyr208Val + Leu211Gly
Ala194Gln + Pro195Gly + Gly196Asn + Val197Cys + Asn198Gln + Pro204Glu + Thr207Asp + Gly213Gln
Pro195Gly + Asn198Asp + Gln200Glu + Gly213Gln + Tyr203Thr + Gly205Asn + Leu211Cys + Asn212Ser + Gly213Gln
Ala194Gly + Pro195Asn + Asn198Glu + Gln200Glu + Thr202Gln + Gly205Ser + Thr207Pro + Gly213Gln
Pro195Gly + Asn198Glu + Val199Gln + Thr202Gly + Pro204Gln + Thr207Pro + Leu211Cys
Pro195Asn + Gly196Gln + Asn198Glu + Gln200Asp + Thr202Gly + Tyr208Gln + Leu211Ser + Thr214Ser
Val197Asn + Asn198Ser + Gln200Glu + Thr202Asn + Tyr203Cys + Pro204Ser + Gly205Pro + Tyr208Glu
Ala194His + Val199His + Tyr203Asn + Tyr208His + Ala209Glu + Leu211Asp + Ala209Pro + Gly213Asp
Gly196Gln + Val197Ser + Gln200Glu + Tyr203Val + Thr207Pro + Ala209Thr + Leu211Glu + Asn212Ser
Pro195Gln + Val199Gly + Gln200Asp + Pro204Asn + Gly205Asn + Tyr208Ile + Ala209Pro + Leu211Glu
Pro195Gln + Asn198Ser + Val199Asn + Gln200Asp + Gly205Pro + Tyr208Ser + Leu211Glu + Thr214Asn
Ala194His + Pro195Ser + Val197Glu + Val199Cys + Thr202Pro + Leu211Glu + Asn212Gln + Thr214Asn
Ala194Ser + Pro195Gln + Asn198Ser + Gln200Asn + Gly205Gln + Leu211Asp + Asn212Gln + Gly213Glu
Gly196Gln + Val199Gln + Tyr203Gly + Gly205Asn + Ala209His + Leu211Asp + Asn212gln + Gly213Asp
Asn198Gln + Gln200Ser + Tyr204Leu + Gly205Asn + Thr207Glu + Ala209Asp + Leu211Ser + Gly213Asn
Ala194Ser + Pro195Ser + Val199Gln + Gln200Ser + Gly205Gln + Ser210Asp + Asn212Glu + Thr214Asn
Pro195Asn + Tyr203Cys + Pro204Gln + Tyr208Asn + Ala209His + Ser210Asp + Asn212Asp + Thr214Gly
Gly196Asn + Val199Ser + Thr202Gln + Pro204Ser + Thr207Gly + Ser210Glu + Leu211Thr + Asn212Asp
Gly196Gln + Val197Cys + Asn198Ser + Pro204Gln + Thr207Asn + Ala209Gln + Ser210Asp + Asn212Asp
Pro195Gly + Gly196Pro + Val197Cys + Asn198Ser + Gln200Asn + Tyr208His + Ser210Asp + Asn212Glu
Pro195Gln + Asn198Ser + Val199Gly + Thr202Pro + Thr207Ser + Tyr208Ile + Ser210Asp + Asn212Asp
Ala194Asn + Val197Met + Val199Thr + Ala209Asn + Ser210Asp + Leu211Val + Asn212Glu + Gly213Gln
Ala194Gln + Pro195Asn + Val199Asn + Tyr203Ser + Thr207Asn + Ser210Asp + Leu211Gly + Asn212Asp
Val199Cys + Gln200Ser + Thr202Asn + Gly205Asn + Thr207Gly + Tyr208Asn + Ser210Glu + Asn212Asp
Ala194Thr + Val199Cys + Gln200Ser + Gly205Ser + Ser206Glu + Tyr208Asp + Leu211Ala + Gly213Asn
Ala194Pro + Val197Pro + Gln200Ser + Ser206Asp + Thr207Pro + Tyr208Asp + Ala209Pro + Thr214Gly
Gly196Gln + Asn198Ser + Val199Met + Thr202Ser + Pro204Asn + Ser206Glu + Tyr208Glu + Asn212Gln
Pro195Asn + Gly196Asn + Val199Ala + Gln200Asn + Ser206Asp + Thr207Asn + Tyr208Asp + Ala209Ser
Gly196Asn + Tyr203Ala + Pro204Ser + Ser206Asp + Tyr208Asp + Ala209Ser + Asn212Ser + Thr214Gln
Val197Gly + Asn198Ser + Tyr203Asn + Pro204Gly + Gly205Ser + Thr207Pro + Asn212Asp + Thr214Asp
Ala194Gln + Val197Asp + Asn198Gln + Tyr203His + Ser210Glu + Leu211Ala + Gly213Ser + Thr214Asn
Ala194Pro + Val197Glu + Val199His + Gln200Ser + Tyr203His + Pro204Asn + Tyr208Thr + Thr214Glu
Gly196Asn + Asn198Asp + Val199Gln + Gln200Ser + Thr202Ser + Pro204Ser + Leu211Cys + Gly213Glu
Asn198Asp + Tyr203Met + Pro204Gly + Thr207Asn + Tyr208Gln + Ala209Glu + Asn212Ser + Thr214Ser
Asn198Glu + Val199Gly + Thr202Gly + Thr207Gln + Tyr208Cys + Ala209Asp + Leu211Thr + Asn212Gln
Ala194His + Val197Asp + Asn198Gln + Gln200Glu + Thr202Asn + Tyr208Pro + Leu211Ser + Asn212Ser
Pro195Gly + Gln200Asp + Tyr203Gly + Gly205Asn + Leu211Ser + Asn212Glu + Gly213Gln + Thr214Glu
Ala194Asn + Gly196Ser + Val199Pro + Gln200Glu + Thr207Gly + Tyr208Asn + Ala209Thr + Asn212Glu
Ala194Thr + Val199Asn + Gln200Glu + Tyr203Gln + Pro204Gly + Ala209His + Asn212Glu + Thr214Ser
Ala194Asn + Gly196Pro + Val197Ser + Asn198Gln + Tyr203Pro + Pro204Asp + Tyr208Asn + Ala209Asp
Pro195Ser + Val199Cys + Gln200Ser + Pro204Glu + Gly205Ser + Tyr208Ala + Ala209Glu + Asn212Gln
Asn198Asp + Val199His + Thr202Gly + Pro204Glu + Gly205Pro + Tyr208Ala + Ala209Glu + Asn212Gln
Gly196Ser + Asn198Ser + Val199Gly + Gln200Ser + Gly205Ser + Tyr208Asp + Leu211Asp + Thr214Ser
Pro195Gln + Gln196Asn + Val197Gly + Gln200Asn + Pro204Asn + Thr207Gly + Ala209Asp + Asn212Glu

TABLE 30-continued

Loop 6 - Octuple Mutation Variants

Ala194Ser + Gln200Ser + Gly205Ser + Ala209Asp + Leu211Gly + Asn212Asp + Gly213Gln + Thr214Asn
Ala194Gln + Pro195Gln + Gly196Pro + Tyr203Leu + Pro204Ser + Ser206Asp + Ala209Glu + Leu211Pro
Thr202Asn + Tyr203Ala + Pro204Ser + Ser206Asp + Tyr208Cys + Ala209Gly + Leu211Cys + Asn212Ser
Gly196Ser + Val199His + Gln200Asn + Gly205Asn + Ser206Glu + Ala209Asp + Leu211His + Asn212Ser
Ala194Asn + Val197Ala + Gln200Ser + Ser206Glu + Thr207Pro + Ala209Glu + Asn212Gln + Gly213Asn
Pro195Gln + Val197Met + Val199Thr + Gln200Ser + Tyr203Ala + Ala209Ser + Ser210Glu + Gly213Glu
Asn198Ser + Val199Asn + Ala209Pro + Ser210Glu + Leu211Gly + Asn212Ser + Gly213Asp + Thr214Gly
Ala194Gly + Asn198Gln + Tyr203Ala + Gly205Asp + Tyr208Gln + Ala209Asp + Leu211Ala + Asn212Gln
Ala194Gly + Gly196Gln + Thr202Gln + Tyr203Thr + Thr207Asp + Tyr208Thr + Ser210Glu + Asn212Ser
Ala194Pro + Val197Thr + Tyr203Pro + Pro204Ser + Thr207Asp + Ser210Asp + Leu211Pro + Thr214Ser
Pro195Asn + Val199Ala + Thr202Ser + Gly205Gln + Thr207Asp + Ala209His + Ser210Glu + Gly213Asn
Pro195Gly + Gly196Ser + Val197Pro + Pro204Gly + Thr207Glu + Tyr208Gln + Ala209His + Ser210Asp
Ala194Asn + Pro195Asn + Asn198Ser + Val199His + Thr207Asp + Tyr208Val + Ala209Pro + Ser210Glu
Ala194Gly + Gly196Ser + Asn198Asp + Thr207Asn + Ala209Gln + Leu211Pro + Gly213Gln + Thr214Asp
Ala194Gly + Pro195Ser + Val197His + Asn198Asp + Gln200Asn + Pro204Ser + Asn212Ser + Thr214Asp
Val199Asn + Gln200Glu + Pro204Gly + Gly205Asp + Tyr208Ser + Leu211Ala + Asn212Ser + Gly213Glu
Ala194Gln + Pro195Ser + Gly196Asn + Asn198Gln + Gln200Glu + Tyr203Cys + Leu211Ser + Gly213Glu
Ala194Ser + Gly196Asn + Val197Thr + Asn198Gln + Gln200Glu + Thr207Asn + Tyr208His + Gly213Asp
Ala194Gln + Val197Gln + Asn198Asp + Gln200Asn + Gly205Gln + Tyr208Asp + Leu211Gly + Thr214Ser
Ala194Ser + Asn198Ser + Thr202Pro + Pro204Asp + Gly205Gln + Thr207Asn + Ser210Asp + Asn212Ser
Pro195Gln + Gly196Asn + Pro204Glu + Gly205Asn + Thr207Asn + Tyr208Ser + Ala209Pro + Ser210Asp
Ala194Thr + Gly196Pro + Val199Pro + Gln200Asn + Pro204Glu + Ala209Thr + Ser210Asp + Leu211Ala
Ala194Ser + Gly196Gln + Val199Thr + Pro204Glu + Tyr208Ile + Ala209Gln + Ser210Asp + Thr214Gly
Ala194His + Val197Ser + Val199Ser + Gln200Ser + Pro204Glu + Thr207Gly + Ala209Pro + Ser210Asp
Ala194Gln + Val197Ala + Asn198Ser + Pro204Asp + Tyr208Cys + Ala209Gly + Ser210Asp + Asn212Ser
Gly196Ser + Val197Thr + Asn198Ser + Gln200Glu + Thr202Pro + Pro204Glu + Ala209Thr + Gly213Ser
Pro195Asn + Val197Pro + Val199Gly + Gln200Asp + Pro204Glu + Thr207Gly + Leu211Thr + Gly213Ser
Ala194Gln + Val197Asn + Gln200Ser + Thr202Gln + Thr207Glu + Ala209Gly + Leu211Glu + Gly213Asn
Ala194Ser + Gly196Ser + Val197Ser + Asn198Gln + Gly205Gln + Ser210Glu + Asn212Ser + Thr214Asp
Gly196Ser + Val199Cys + Gln200Ser + Thr207Pro + Tyr208Pro + Ala209Gly + Ser210Asp + Thr214Gly
Val197Cys + Val199Gly + Tyr203Gly + Tyr208Met + Ala209Ser + Ser210Glu + Leu211Ala + Thr214Glu
Ala194Pro + Pro195Ser + Gly196Ser + Val199Thr + Thr202Gly + Ser210Asp + Asn212Gln + Thr214Glu
Ala194Asn + Gly196Asn + Gln200Ser + Pro204Asn + Gly205Ser + Ala209Ser + Ser210Asp + Thr214Asp
Ala194His + Val197Cys + Tyr208Ile + Ser210Glu + Leu211Gly + Asn212Ser + Gly213Asn + Thr214Asp
Gly196Gln + Gln200Asn + Thr202Pro + Tyr203Cys + Gly205Gln + Tyr208Ser + Ser210Glu + Thr214Asp
Asn198Gln + Val199Pro + Gln200Glu + Thr202Pro + Pro204Ser + Ser206Glu + Tyr208Gln + Thr214Asn
Pro195Gly + Gln200Asp + Tyr203Val + Ser206Asp + Tyr208Thr + Leu211Gly + Asn212Gln + Gly213Asn
Gly196Gln + Gln200Glu + Thr202Gln + Tyr203Val + Ser206Glu + Tyr208Val + Ala209Asn + Leu211Gly
Pro195Gly + Gln200Glu + Thr202Pro + Gly205Ser + Ser206Glu + Ala109Gln + Leu211His + Asn212Gln
Asn198Gln + Gln200Glu + Thr204Gly + Gly205Gln + Ser206Asp + Tyr208Met + Asn212Ser + Thr214Asn
Ala194Pro + Pro195Gln + Gly196Ser + Val197His + Gln200Glu + Gly205Ser + Ser206Glu + Leu211Ser
Ala194Gln + Gln200Asp + Tyr203Gln + Pro204Asn + Ser206Glu + Tyr208Ile + Ala209Gly + Gly213Asn
Ala194Gln + Pro195Gln + Val197His + Gln200Glu + Pro204Ser + Ser206Asp + Tyr208Gln + Ala209Asn
Pro195Gln + Val197His + Val199Asn + Gln200Asp + Thr202Pro + Ser206Glu + Leu211Thr + Thr214Pro
Pro195Gly + Asn198Gln + Val199Cys + Gln200Asp + Thr202Gly + Ser206Glu + Tyr208Cys + Gly213Ser
Ala194Gly + Pro195Asn + Gly196Asn + Pro204Asp + Thr207Ser + Leu211Glu + Asn212Gln + Thr214Asn

TABLE 31

Loop 6 - Nonuple Mutation Variants

Ala194Gly + Pro195Ser + Val197Cys + Val199Asn + Gln200Asp + Tyr203Pro + Pro204Ser + Gly205Ser + Leu211Gln
Ala194Pro + Gln200Asn + Thr202Asn + Tyr203Asn + Pro204Ser + Tyr208Asn + Ala209Asn + Ser210Asp + Thr214Gln
Pro195Gly + Val199Ala + Gln200Ser + Thr202Gly + Gly205Pro + Ser206Glu + Ala209His + Leu211Ala + Gly213Asn
Pro195Gln + Gly196Gln + Val197Thr + Val199His + Thr202Gln + Tyr203Gly + Pro204Gly + Gly205Glu + Gly213Gln
Pro195Gly + Val197Gly + Val199Asn + Pro204Asn + Ser206Asp + Thr207Ser + Tyr208Gln + Ala209Gly + Thr214Asn
Ala194Thr + Val197Asn + Val199Pro + Gln200Asp + Thr202Ser + Tyr203Asn + Thr207Asn + Tyr208Leu + Ala209Gly
Pro195Asn + Gly196Asn + Asn198Gln + Tyr203Gln + Thr207Ser + Ala209Thr + Leu211Ala + Asn212Asp + Thr214Asn
Ala194Gln + Pro195Gly + Gly196Pro + Val197Gly + Gln200Asp + Thr202Ser + Pro204Gly + Tyr208Thr + Thr214Gln
Gly196Asn + Val199Gly + Tyr203Ser + Pro204Ser + Tyr208Gln + Ala209His + Asn212Ser + Gly213Asp + Thr214Gln
Val197His + Gln200Ser + Thr202Asn + Pro204Ser + Thr207Pro + Tyr208Gly + Ala209His + Ser210Glu + Leu211Ala
Pro195Ser + Val197His + Gln200Glu + Thr202Gln + Pro204Ser + Tyr208Val + Ala209His + Leu211Thr + Thr214Pro
Pro195Gly + Gly196Pro + Val199Thr + Thr202Pro + Tyr203Ile + Thr207Gly + Ala209Pro + Ser210Asp + Asn212Gln
Ala194Gly + Pro195His + Val197Asp + Tyr203Cys + Tyr208Val + Ala209Gln + Leu211Gly + Asn212Gln + Gly213Gln
Gly196Asn + Asn198Gln + Thr202Gly + Thr207Asp + Tyr208Gly + Ala209Ser + Leu211Thr + Asn212Ser + Thr214Pro
Ala194Pro + Gly196Asn + Val197Met + Gln200Glu + Tyr203Gln + Gly205Asn + Tyr208Asn + Ala209Thr + Thr214Gln
Ala194Pro + Gly196Gln + Val197Asn + Gly205Ser + Ser206Asp + Thr207Asn + Ala209Ser + Leu211Cys + Thr214Pro
Gly196Gln + Val197Thr + Gln200Ser + Tyr203Asn + Pro204Asn + Gly205Pro + Tyr208Ser + Ser210Glu + Asn212Ser
Ala194Thr + Pro195Ser + Gly196Pro + Val197Cys + Gln200Glu + Pro204Ser + Gly205Asn + Ala209His + Leu211Pro
Pro195Gln + Gly196Asn + Asn198Gln + Val199Gln + Gln200Asp + Pro204Asn + Ser206Asp + Thr207Ser + Tyr208Ser
Ala194His + Val197Asn + Tyr203Gly + Pro204Gln + Thr207Gly + Ala209Gln + Leu211His + Asn212Gln + Gly213Gln
Ala194Ser + Pro195Gln + Val197Met + Val199His + Thr207Pro + Tyr208Ala + Asn212Gln + Gly213Glu + Thr214Asn
Gly196Pro + Val197His + Asn198Gln + Gln200Glu + Tyr203Ser + Gly205Pro + Thr207Ser + Leu211Thr + Gly213Asn
Gly196Ser + Val197Asn + Val199Thr + Thr202Gly + Tyr203Asn + Pro204Asn + Ala209Gln + Leu211Pro + Thr214Asp
Ala194Thr + Pro195Ser + Val197Asn + Tyr203Met + Tyr208Ala + Ala109Ser + Asn212Gln + Gly213Asp + Thr214Asp
Ala194Asn + Gly196Gln + Val197Thr + Val199Ala + Gly205Asp + Ala209Pro + Leu211Asn + Gly213Glu + Thr214Asp
Pro195Asn + Val199Met + Gln200Asn + Thr202Asn + Tyr203Cys + Ala209Ser + Leu211Gln + Gly213Asp + Thr214Glu
Pro195Asn + Val197Met + Asn198Ser + Val199Asn + Gln200Asn + Tyr208Gln + Leu211His + Gly213Glu + Thr214Asp
Val197His + Val199Ala + Gln200Ser + Pro204Ser + Ala209Glu + Ser210Glu + Asn212Gln + Gly213Pro + Thr214Ser

TABLE 31-continued

| Loop 6 - Nonuple Mutation Variants |
|---|
| Gly196Gln + Val197Asn + Asn198Gln + Thr202Gly + Gly205Gln + Ala209Asp + Ser210Glu + Leu211Met + Thr214Gly |
| Val197Cys + Asn198Ser + Val199Gln + Tyr203Gly + Pro204Gln + Ala209Glu + Ser210Glu + Gly213Pro + Thr214Gly |
| Pro195Asn + Val199His + Gln200Ser + Pro204Gln + Gly205Gln + Ala209Glu + Ser210Asp + Leu211Gln + Asn212Gln |
| Val197Asp + Asn198Glu + Val199Met + Thr202Gln + Pro204Ser + Gly205Gln + Thr207Gln + Tyr208His + Asn212Ser |
| Ala194Thr + Val197Glu + Asn198Asp + Val199His + Tyr203Asn + Tyr208His + Ala209Ser + Gly213Ser + Thr214Asn |
| Val197Cys + Asn198Ser + Val199Pro + Gln200Ser + Tyr203Ala + Tyr208Asn + Asn212Asp + Gly213Glu + Thr214Ser |
| Gly196Asn + Val197Met + Asn198Ser + Thr202Gly + Pro204Gln + Ala209Ser + Leu211His + Asn212Asp + Gly213Asp |
| Ala194Thr + Pro195Ser + Gln200Asn + Thr202Asn + Tyr203Gln + Tyr208Ser + Leu211Ala + Asn212Asp + Gly213Asp |
| Pro195Gly + Asn198Ser + Val199Pro + Gly205Asp + Ser206Asp + Thr207Pro + Tyr208Ala + Asn212Ser + Gly213Ser |
| Pro195Gln + Asn198Ser + Gln200Asn + Thr202Ser + Tyr203Met + Gly205Asp + Ser206Glu + Thr207Pro + Thr214Ser |
| Gly196Ser + Val199Thr + Gln200Asn + Tyr203Ala + Gly205Asp + Ser206Asp + Tyr208Leu + Ala209Thr + Gly213Pro |
| Ala194Pro + Gly196Ser + Val197Asn + Val199His + Gln200Asn + Gly205Glu + Ser206Glu + Asn212Gln + Thr214Gln |
| Ala194Thr + Val199Ser + Thr202Asn + Gly205Glu + Ser206Asp + Ala209Pro + Leu211Pro + Asn212Gln + Gly213Gln |
| Asn198Ser + Thr202Ser + Tyr203Ser + Pro204Gly + Gly205Asn + Ser206Asp + Thr207Glu + Ala209Pro + Thr214Ser |
| Pro195Asn + Gly196Asn + Val197Pro + Val199Ser + Thr202Ser + Ser206Glu + Thr207Glu + Leu211Ile + Gly213Ser |
| Thr202Ser + Tyr203Thr + Thr207Asp + Tyr208Glu + Ala209Pro + Leu211Val + Asn212Ser + Gly213Ser + Thr214Asn |
| Val199Pro + Gln200Ser + Thr202Ser + Thr207Asp + Tyr208Asp + Ala209Gly + Leu211Met + Asn212Ser + Thr214Pro |
| Ala194Gln + Pro195Gly + Val197Ala + Gln200Glu + Tyr203Thr + Gly205Ser + Ala209Pro + Ser210Asp + Thr214Asn |
| Ala194Pro + Pro195Ser + Val199Met + Gln200Glu + Thr202Gly + Pro204Gln + Gly205Asn + Tyr208Gln + Ser210Asp |
| Ala194Gln + Val199Pro + Gln200Asp + Pro204Gly + Gly205Gln + Thr207Pro + Tyr208Asn + Ala209Gln + Ser210Asp |
| Ala194Pro + Gly196Pro + Asn198Gln + Gln200Asp + Pro204Gly + Gly205Asn + Tyr208Ile + Ser210Asp + Asn212Ser |
| Pro195Ser + Asn198Ser + Val199Ala + Gln200Glu + Tyr203Thr + Gly205Gln + Tyr208Met + Ser210Glu + Gly213Pro |
| Pro195Asn + Asn198Ser + Gln200Asp + Thr202Gln + Tyr203Ala + Gly205Pro + Ser210Asp + Leu211Ser + Gly213Ser |
| Pro195Asn + Gly196Asn + Val197Ala + Asn198Ser + Gln200Asp + Tyr203Gln + Pro204Asp + Ala209Ser + Ser210Asp |
| Pro195Ser + Val197Pro + Asn198Gln + Val199Pro + Gln200Glu + Thr202Gln + Thr207Asn + Ala209His + Ser210Glu |
| Pro195Ser + Gly196Asn + Asn198Gln + Gln200Glu + Thr202Ser + Pro204Gly + Thr207Asn + Ser210Glu + Thr214Asn |
| Ala194Ser + Pro195Ser + Val197His + Val199Thr + Gln200Glu + Gly205Gln + Thr207Gly + Ser210Glu + Gly214Pro |
| Pro195Asn + Val197Asp + Asn198Ser + Val199Asn + Thr207Pro + Tyr208Ala + Leu211Val + Asn212Glu + Gly213Ser |
| Pro195Asn + Gly196Asn + Val197Gln + Asn198Glu + Val199Thr + Tyr203Asn + Thr207Pro + Ser210Glu + Gly213Gln |
| Val197Cys + Asn198Asp + Val199Ser + Tyr203Gln + Gly205Ser + Thr207Ser + Tyr208Leu + Ser210Asp + Leu211Gly |
| Ala194Pro + Gly196Gln + Val197Gly + Asn198Glu + Gln200Ser + Tyr203Thr + Pro204Ser + Ala209His + Ser210Glu |
| Gly196Ser + Val197His + Asn198Glu + Thr202Pro + Tyr203Ile + Thr207Asn + Tyr208Val + Ser210Glu + Thr214Ser |
| Gly196Asn + Val197Thr + Asn198Asp + Val199Ala + Pro204Asn + Ser210Asp + Leu211Val + Gly213Gln + Thr214Pro |
| Gly196Ser + Asn198Glu + Thr202Asn + Gly205Ser + Thr207Gln + Tyr208Ile + Ser210Glu + Leu211Ser + Asp212Ser |
| Ala194Asn + Gly196Pro + Asn198Asp + Thr202Gly + Tyr208Ser + Ala209Pro + Ser210Glu + Leu211Ala + Thr214Asn |
| Ala194His + Asn198Glu + Val199Gly + Gln200Asn + Gly205Asn + Ser210Glu + Leu211His + Asn212Gln + Thr214Ser |
| Ala194Gly + Asn198Glu + Gln200Asn + Thr202Pro + Tyr203Cys + Thr207Gln + Tyr208Met + Ser210Asp + Asn212Gln |
| Pro195Gly + Gly196Gln + Asn198Glu + Gln200Ser + Pro204Gln + Tyr208Leu + Ala209Thr + Ser210Glu + Leu211Ile |
| Ala194Pro + Pro195Gln + Val197His + Asn198Glu + Thr202Gln + Gly205Pro + Thr207Asn + Tyr208Val + Leu211Asp |

TABLE 31-continued

| Loop 6 - Nonuple Mutation Variants |
|---|
| Pro195Gln + Asn198Glu + Thr202Ser + Tyr203Gly + Pro204Ser + Thr207Gln + Ala209Pro + Leu211Asp + Gly213Asn |
| Val199Asn + Gln200Asp + Thr202Gln + Tyr203Gly + Pro204Asn + Thr207Gln + Tyr208Ala + Ala209Glu + Asn212Ser |
| Gly196Pro + Val197Thr + Pro204Asp + Ser206Glu + Ala209Gln + Leu211Gln + Asn212Ser + Gly213Ser + Thr214Pro |
| Gly196Pro + Asn198Ser + Val199Thr + Pro204Glu + Ser206Asp + Thr207Gln + Ala209Gly + Asn212Ser + Thr214Gly |
| Ala194Asn + Val197Gly + Gln200Ser + Thr202Ser + Pro204Asp + Ser206Asp + Tyr208Gln + Ala209Gln + Leu211Gly |
| Ala194Pro + Thr202Gln + Tyr203Asp + Pro204Asp + Ser206Glu + Tyr208Gly + Ala209Ser + Gly213Pro + Thr214Pro |
| Ala194Asn + Pro195Gln + Val197Thr + Asn198Ser + Pro204Asp + Gly204Ser + Ser206Asp + Asn212Ser + Thr214Asn |
| Pro195Gly + Gln200Ser + Thr202Gln + Tyr203Pro + Pro204Asp + Gly205Asn + Ser206Glu + Thr207Asn + Leu211His |
| Ala194His + Gly196Asn + Val197Met + Asn198Ser + Pro204Asp + Ser206Asp + Leu211Asn + Asn212Ser + Thr214Gln |
| Asn198Gln + Val199Cys + Gln200Ser + Thr202Gln + Pro204Asp + Gly205Gln + Ser206Asp + Tyr208Leu + Thr214Pro |
| Ala194His + Pro195Ser + Gly196Pro + Asn198Gln + Pro204Glu + Ser206Asp + Thr207Pro + Tyr208His + Ala209Asn |
| Ala194Ser + Asn198Asp + Gln200Ser + Thr202Gly + Thr207Pro + Tyr208Asn + Ala209Gln + Leu211Ser + Asn212Glu |
| Gly196Asn + Asn198Gln + Gln200Asn + Tyr203Thr + Pro204Ser + Gly205Asp + Thr207Glu + Ala209Ser + Thr214Asn |
| Val197His + Asn198Gln + Val199Met + Gln200Ser + Pro204Glu + Gly205Ser + Thr207Glu + Tyr208Val + Thr214Gly |
| Val197Asn + Asn198Asp + Val199Ala + Gln200Glu + Tyr203Cys + Pro204Gly + Gly205Asn + Thr207Gln + Gly213Asn |
| Pro195Asn + Gly196Gln + Asn198Asp + Val199Pro + Gln200Glu + Tyr203Val + Gly205Asp + Tyr208Cys + Ala209Pro |
| Pro195Gly + Gly196Pro + Val197Asp + Thr202Ser + Pro204Gln + Thr207Gly + Tyr208Ile + Asn212Gln + Gly213Glu |
| Ala194Pro + Val197Glu + Tyr203His + Gly205Pro + Thr207Gly + Ala209Asn + Leu211His + Gly213Asp + Thr214Gly |
| Pro195Gln + Val197Glu + Asn198Gln + Val199Ala + Pro204Ser + Gly205Gln + Ala209Ser + Gly213Glu + Thr214Ser |
| Pro195Asn + Val197Asp + Asn198Gln + Val199Ser + Gln200Ser + Thr207Ser + Tyr208Ile + Asn212Ser + Gly213Asp |
| Gly196Pro + Val197Gln + Asn198Gln + Val199Asn + Pro204Gly + Thr207Pro + Leu211His + Gly213Asp + Thr214Asn |
| Ala194Ser + Asn198Gln + Thr202Pro + Tyr203Met + Pro204Ser + Thr207Gln + Ala209Asp + Leu211Glu + Thr214Gln |
| Gly196Pro + Val197Pro + Thr202Asn + Tyr203Cys + Tyr208Gln + Ser210Asp + Asn212Asp + Gly213Pro + Thr214Ser |
| Pro195Gln + Tyr203Thr + Gly205Gln + Ala209Gln + Ser210Asp + Leu211Asn + Asn212Glu + Gly213Asn + Thr214Gln |
| Ala194Gly + Pro195Ser + Val197His + Thr202Gln + Pro204Gly + Ser210Asp + Leu211His + Asn212Glu + Thr214Gly |
| Pro195Asn + Gly196Asn + Val197Asn + Thr202Ser + Tyr203Val + Gly205Ser + Ser210Asp + Asn212Glu + Gly213Pro |
| Gln200Ser + Thr202Gly + Tyr203Leu + Thr207Pro + Tyr208Pro + Ser210Asp + Leu211Pro + Asn212Glu + Thr214Gly |
| Ala194Gln + Gly196Ser + Val197Cys + Val199Met + Tyr203Leu + Ala209Thr + Ser210Asp + Asn212Glu + Thr214Ser |
| Val197Met + Val199Ala + Gln200Asn + Tyr203Thr + Thr207Gln + Tyr208Glu + Ser210Glu + Asn212Ser + Thr214Gly |
| Gly196Ser + Val197Ala + Val199Ser + Thr202Gly + Tyr203Cys + Gly205Asn + Ser206Glu + Tyr208Asp + Leu211Ile |
| Ala194Gly + Pro195Ser + Val199His + Thr202Asn + Gly205Gln + Ser206Asp + Tyr208Glu + Asn212Ser + Thr214Pro |
| Gly196Pro + Val199Gln + Thr202Ser + Gly205Pro + Ser206Asp + Thr207Gln + Tyr208Glu + Leu211His + Asn212Ser |
| Val197His + Asn198Ser + Gly205Ser + Thr207Pro + Tyr208Val + Leu211Val + Asn212Glu + Gly213Ser + Thr214Glu |
| Pro195Ser + Gly196Pro + Val199Thr + Tyr203Ser + Tyr208Gly + Ala209Asn + Asn212Glu + Gly213Ser + Thr214Glu |
| Pro195Asn + Asn198Gln + Gln200Asn + Thr202Asn + Thr207Asn + Tyr208Gln + Asn212Glu + Gly213Ser + Thr214Glu |
| Ala194Asn + Val199Ser + Thr202Gly + Pro204Asn + Gly205Ser + Ala209Asn + Leu211Asn + Asn212Asp + Thr214Glu |
| Ala194Ser + Gly196Gln + Pro204Asp + Gly205Pro + Thr207Pro + Tyr208Glu + Leu211Ile + Gly213Asn + Thr214Ser |
| Pro195Ser + Val197Asp + Asn198Gln + Gln200Asn + Tyr203Pro + Gly205Asn + Ser210Asp + Asn212Ser + Thr214Asn |
| Ala194His + Gly196Ser + Val197Asp + Asn198Ser + Gln200Asn + Thr202Ser + Gly205Gln + Ser210Glu + Asn212Ser |

TABLE 31-continued

| Loop 6 - Nonuple Mutation Variants |
|---|
| Ala194Thr + Val197Glu + Thr202Gln + Pro204Gln + Tyr208Gly + Ala209Thr + Ser210Glu + Asn212Ser + Thr214Gln |
| Gly196Ser + Val197Asp + Val199Pro + Tyr203Cys + Pro204Ser + Thr207Asn + Tyr208Asn + Ser210Asp + Asn212Ser |
| Ala194Pro + Pro195Ser + Gly196Gln + Val197Asp + Val199Met + Gln200Asn + Leu211Met + Gly213Pro + Thr214Asp |
| Pro195Asn + Gly196Gln + Asn198Gln + Val199Ala + Gln200Ser + Tyr203Pro + Gly205Glu + Thr207Asn + Tyr208Asp |
| Gly196Pro + Asn198Ser + Val199Asn + Thr202Gly + Pro204Gln + Gly205Asp + Thr207Gln + Tyr208Asp + Thr214Asn |
| Val197Ser + Asn198Glu + Gln200Asn + Tyr203Gln + Pro204Asn + Gly205Pro + Thr207Gly + Ala209Thr + Gly213Glu |
| Ala194Thr + Gly196Gln + Val197His + Asn198Asp + Val199Ser + Tyr203Pro + Tyr208Cys + Gly213Asp + Thr214Pro |
| Asn198Asp + Gln200Ser + Tyr203Gln + Pro204Ser + Gly205Asn + Thr207Asn + Ala209Glu + Leu211Gln + Asn212Ser |
| Pro195Gly + Gly196Asn + Asn198Glu + Thr202Gln + Tyr203Ala + Pro204Ser + Thr207Pro + Ala209Glu + Gly213Gln |
| Ala194Pro + Asn198Glu + Val199Thr + Pro204Gly + Thr207Gly + Tyr208Ile + Ala209Asp + Leu211Met + Asn212Ser |
| Ala194Ser + Val197Glu + Val199Thr + Gln200Asp + Tyr203Gly + Gly205Ser + Tyr208His + Ala209Thr + Asn212Ser |
| Gly196Gln + Val197Glu + Val199Pro + Gln200Asp + Gly205Gln + Thr207Ser + Ala209Thr + Leu211Pro + Thr214Gly |
| Val197Gly + Gln200Glu + Thr202Gly + Tyr203Leu + Gly205Gln + Thr207Gly + Tyr208Leu + Ala209Asn + Asn212Asp |
| Pro195Ser + Gly196Asn + Asn198Ser + Val199His + Gln200Glu + Tyr203Pro + Ala209Ser + Asn212Asp + Thr214Asn |
| Asn198Ser + Val199Met + Gln200Glu + Thr202Ser + Tyr203Ile + Gly205Pro + Ala209Pro + Asn212Glu + Gly213Gln |
| Gly196Pro + Val197Ser + Val199Pro + Gln200Glu + Ala209Gly + Leu211Gln + Asn212Asp + Gly213Pro + Thr214Asn |
| Ala194Gln + Gly196Ser + Val197Pro + Thr202Pro + Pro204Asp + Tyr208Gly + Ala209Glu + Gly213Asn + Thr214Pro |
| Ala194Pro + Val197Ser + Val199His + Gln200Asn + Pro204Gly + Ser206Glu + Thr207Asn + Tyr208Leu + Ala209Glu |
| Gly196Asn + Thr202Asn + Pro204Asn + Gly205Pro + Ser206Glu + Tyr208Asn + Ala209Asp + Leu211Met + Thr214Gln |
| Pro195Gly + Asn198Gln + Val199Ser + Gln200Ser + Tyr203Thr + Gly205Pro + Ser206Glu + Ala209Glu + Thr214Asn |
| Ala194Thr + Val197Ala + Thr202Ser + Tyr203Pro + Gly205Asn + Ser206Glu + Ala209Glu + Leu211Gln + Thr214Asn |
| Pro195Ser + Val197Ala + Thr202Asn + Pro204Gly + Ser206Asp + Thr207Asn + Ala209Glu + Asn212Ser + Thr214Ser |
| Ala194Thr + Val199Asn + Thr202Pro + Tyr203Ile + Pro204Asn + Ser206Asp + Thr207Asn + Ala209Glu + Thr214Asn |
| Ala194Ser + Pro195Asn + Val197Gly + Val199Gly + Gln200Glu + Thr202Gln + Pro204Asn + Thr207Asp + Leu211Gln |
| Ala194Gly + Val197His + Gln200Ser + Pro204Asn + Thr207Ser + Ser210Glu + Leu211Gly + Gly213Glu + Thr214Asn |
| Ala194Gln + Gly196Gln + Val197Met + Val199His + Thr202Pro + Gly205Asn + Ala209Ser + Ser210Glu + Gly213Glu |
| Pro195Asn + Val197Thr + Val199Ala + Gln200Asn + Tyr203Asn + Thr207Gly + Ser210Asp + Asn212Gln + Gly213Glu |
| Ala194His + Val199Pro + Gln200Asn + Thr202Pro + Tyr203Asn + Gly205Glu + Ala209Glu + Asn212Gln + Thr214Asn |
| Gly196Pro + Asn198Gln + Gln200Asn + Tyr203Gln + Pro204Gln + Gly205Asp + Ala209Glu + Asn212Gln + Thr214Gln |
| Pro195Gln + Asn198Gln + Val199Ala + Gln200Asn + Thr207Glu + Tyr208Leu + Ala209Ser + Ser210Asp + Gly213Pro |
| Pro195Gly + Gly196Gln + Val199Ser + Gln200Asn + Pro20Ser + Gly205Ser + Thr207Glu + Ser210Glu + Thr214Pro |
| Gly196Gln + Gln200Ser + Thr202Gly + Tyr203Ile + Thr207Asp + Tyr208Ile + Ser210Asp + Leu211Asn + Asn212Ser |
| Ala194His + Gly196Gln + Val197Gly + Thr207Glu + Tyr208Val + Ala209Gln + Ser210Asp + Leu211His + Gly213Ser |
| Ala194Gln + Asn198Asp + Val199Ser + Gln200Ser + Tyr203Ile + Gly205Asn + Thr207Asn + Asn212Gln + Thr214Asp |
| Val197Pro + Asn198Glu + Val199Thr + Gln200Ser + Pro204Asn + Gly205Pro + Leu211Cys + Asn212Ser + Thr214Asp |
| Ala194Ser + Val199Thr + Gln200Glu + Tyr203Cys + Tyr208Gly + Ala209His + Leu211Gly + Asn212Ser + Gly213Glu |
| Gly196Gln + Asn198Gln + Val199Met + Gln200Asp + Pro204Gln + Tyr208Pro + Asn212Gln + Gly213Asp + Thr214Gln |
| Val197Asp + Val199Gln + Gln200Ser + Thr202Pro + Thr207Gln + Ala209Glu + Leu211Gly + Asn212Ser + Gly213Gln |
| Ala194Ser + Gly196Pro + Val197Glu + Asn198Ser + Val199Met + Pro204Gly + Thr207Gln + Ala209Glu + Gly213Gln |

TABLE 31-continued

| Loop 6 - Nonuple Mutation Variants |
|---|
| Val197Asp + Asn198Ser + Pro204Gln + Gly205Gln + Thr207Gly + Tyr208Met + Ala209Glu + Asn212Gln + Thr214Gln |
| Ala194Ser + Val197Glu + Asn198Gln + Tyr203Asn + Gly205Asn + Ala209Glu + Asn212Gln + Gly213Ser + Thr214Pro |
| Pro195Gly + Val197Ser + Asn198Ser + Tyr203Leu + Pro204Glu + Ser210Asp + Leu211Ser + Asn212Ser + Thr214Gln |
| Ala194Asn + Pro195Gln + Asn198Gln + Val199Asn + Gln200Asp + Pro204Asp + Thr207Pro + Ser210Glu + Gly213Gln |
| Ala194Pro + Val197Ser + Asn198Ser + Thr202Pro + Tyr203Val + Pro204Glu + Ser210Asp + Asn212Ser + Thr214Asn |
| Ala194Gln + Pro195Ser + Gly196Pro + Val199Ser + Pro204Asp + Tyr208Cys + Ala209Thr + Ser210Glu + Gly213Asn |
| Pro195Ser + Tyr203Pro + Pro204Asp + Gly205Pro + Thr207Gln + Ala209Gly + Ser210Asp + Leu211Asn + Thr214Asn |
| Gly196Ser + Asn198Ser + Thr202Pro + Pro204Asp + Tyr208Val + Ala209Gln + Ser210Asp + Leu211Asn + Asn212Gln |
| Gly196Ser + Val199Met + Tyr204Ala + Pro204Glu + Gly205Ser + Thr207Ser + Tyr208Leu + Ala209Gln + Ser210Asp |
| Pro195Gly + Val197Pro + Thr202Asn + Pro204Glu + Gly205Ser + Thr207Asn + Tyr208Pro + Ser210Glu + Asn212Ser |
| Ala194Asn + Gly196Ser + Asn198Ser + Val199Met + Gln200Asn + Thr202Gly + Thr207Gln + Ala209Asp + Gly213Asp |
| Ala194Gln + Pro195Gln + Thr202Ser + Pro204Asn + Ala209Thr + Ser210Glu + Leu211Asn + Gly213Gln + Thr214Glu |
| Gly196Gln + Val197Pro + Asn198Gln + Val199Gly + Ala209Pro + Ser210Asp + Leu211Cys + Asn212Ser + Thr214Glu |
| Ala194Asn + Pro195Gly + Asn198Gln + Val199His + Tyr203Pro + Thr207Gly + Tyr208Met + Ser210Asp + Thr214Asp |
| Ala194Pro + Pro195Ser + Gly196Asn + Thr202Gly + Pro204Ser + Ala209His + Ser210Glu + Leu211Ser + Thr214Asp |
| Ala194Thr + Gly196Pro + Asn198Ser + Thr207Asn + Tyr208Ile + Ser210Asp + Leu211Val + Gly213Gln + Thr214Glu |
| Ala194Gly + Pro195Ser + Asn198Ser + Thr202Ser + Gly205Ser + Ala209Gln + Ser210Asp + Asn212Ser + Thr214Asp |
| Ala194Ser + Pro195Gly + Gly196Ser + Val199Ala + Tyr203Gln + Pro204Gln + Thr207Ser + Ser210Glu + Thr214Glu |
| Gly196Ser + Gln200Asn + Thr202Pro + Tyr203Leu + Thr207Gln + Ser210Asp + Leu211Ala + Gly213Pro + Thr214Asp |
| Ala194Gln + Asn198Ser + Val199Thr + Gln200Ser + Tyr203Thr + Ala209Pro + Ser210Asp + Leu211Asn + Thr214Glu |
| Pro195Gln + Gly196Gln + Tyr203Cys + Pro204Ser + Gly205Pro + Tyr208His + Ala209Thr + Ser210Asp + Thr214Glu |
| Gly196Gln + Asn198Ser + Val199Thr + Gln200Ser + Thr202Ser + Thr207Ser + Ala209His + Ser210Glu + Thr214Glu |
| Pro195Asn + Gly196Pro + Asn198Gln + Tyr203Ala + Thr207Ser + Ala209Pro + Ser210Asp + Leu211Thr + Thr214Asp |
| Ala194Ser + Pro195Asn + Val199Pro + Pro204Asn + Gly205Gln + Thr207Gln + Ser210Glu + Gly213Ser + Thr214Asp |
| Gly196Ser + Val197Asn + Thr202Gln + Tyr203Ser + Pro204Ser + Gly205Ser + Ser210Glu + Leu211Cys + Thr214Asp |
| Val197Asn + Gln200Asp + Tyr203Cys + Pro204Asn + Gly205Asn + Ser206Asp + Thr207Ser + Tyr208Leu + Asn212Gln |
| Pro195Asn + Gln200Asp + Thr202Gln + Tyr203Gln + Pro204Ser + Ser206Glu + Thr207Pro + Asn212Ser + Gly213Gln |
| Ala194Gln + Pro195Gln + Gly196Asn + Val199Ser + Gln200Asp + Thr202Ser + Gly205Ser + Ser206Glu + Ala209Ser |
| Pro195Asn + Gly196Pro + Val197Cys + Val199Met + Gln200Asp + Ser206Glu + Thr207Ser + Ala209Gln + Leu211Val |
| Pro195Gly + Val199Pro + Gln200Asp + Thr202Ser + Tyr203Gly + Pro204Gln + Ser206Asp + Leu211Met + Asn212Ser |
| Gly196Pro + Val197Cys + Asn198Gln + Gln200Glu + Thr202Asn + Ser206Asp + Ala209Asn + Leu211Cys + Gly213Ser |
| Pro195Gln + Asn198Ser + Gln200Glu + Thr202Asn + Pro204Gly + Ser206Asp + Thr207Ser + Tyr208Ser + Asn212Gln |
| Gly196Asn + Asn198Ser + Val199Met + Gln200Asp + Thr202Ser + Tyr203His + Pro204Asn + Gly205Gln + Ser206Glu |
| Ala194Thr + Asn198Gln + Val199Ala + Gln200Asp + Thr202Asn + Ser206Glu + Thr207Ser + Tyr208His + Gly213Gln |
| Ala194Gln + Gly196Gln + Asn198Gln + Gln200Asp + Thr202Asn + Ser206Glu + Thr207Ser + Tyr208Thr + Gly213Gln |

TABLE 32

Loop 6 - Decuple Mutation Variants

Ala194Ser + Gly196Gln + Val197Ala + Asn198Gln + Thr202Pro + Pro204Ser + Gly205Ser + Thr207Pro + Leu211Val + Asn212Asp
Pro195Ser + Val197Gln + Val199His + Thr202Asn + Tyr203Pro + Gly205Gln + Ala209Thr + Ser210Glu + Asn212Ser + Thr214Gln
Ala194Gly + Asn198Ser + Val199Ala + Thr202Gln + Tyr203Leu + Pro204Gly + Gly205por + Ala209His + Gly213Ser + Thr214Asp
Ala194His + Gly196Gln + Thr202Gly + Tyr203Val + Gly205Asn + Thr207Gln + Tyr208Cys + Ala209Ser + Gly213Gln + Thr214Asn
Ala194Thr + Pro195Ser + Gly196Asn + Asn198Gln + Gln200Asn + Thr202Gly + Pro204Ser + Asn212Gln + Gly213Pro + Thr214Gly
Ala194Ser + Pro195Asn + Gly196Asn + Val199Thr + Thr202Gln + Pro204Asp + Thr207Asn + Tyr208Ser + Leu211Asp + Asn212Gln
Pro195Asn + Gly196Ser + Val197Gly + Asn198Ser + Thr202Gly + Gly205Pro + Thr207Pro + Tyr208Asp + Ala209Ser + Thr214Asn
Ala194His + Pro195Gln + Gly196Asn + Asn198Gln + Val199His + Pro204Ser + Gly205Asn + Thr207Ser + Tyr208Ser + Thr214Ser
Ala194Pro + Pro195Ser + Val197Asn + Val199Cys + Gln200Ser + Thr202Pro + Pro204Ser + Ser206Glu + Tyr208His + Leu211Ile
Ala194Thr + Val197Met + Asn198Asp + Val199Gly + Gln200Ser + Tyr203Gln + Pro204Asn + Thr207Gln + Ala209Pro + Leu211Ala
Ala194Pro + Pro195Gly + Val197Asn + Asn198Ser + Val199His + Tyr208His + Ala209Asp + Leu211Thr + Asn212Gln + Thr214Gln
Pro195Ser + Val199Met + Thr202Ser + Tyr203Ile + Gly205Gln + Ser206Asp + Tyr208His + Leu21Pro + Asn212Gln + Gly213Pro
Ala194Thr + Val197Ser + Val199Asn + Thr202Gln + Tyr203Met + Gly205Pro + Ser206Glu + Tyr208Ile + Ala209Asn + Gly213Ser
Ala194Thr + Val197Gln + Asn198Gln + Val199Gly + Thr202Ser + Pro204Ser + Gly205Pro + Thr207Asn + Ala209Pro + Thr214Asn
Ala194His + Pro195Asn + Gly195Asn + Val199Thr + Gln200Asn + Thr202Asn + Tyr203Ala + Gly205Asp + Thr207Gly + Thr214Pro
Ala194Ser + Pro195Gly + Gly196Ser + Val197Pro + Asn198Gln + Val199Thr + Thr202Pro + Tyr203Met + Pro204Gln + Gly205Gln
Ala194Thr + Pro195Gln + Val197Asp + Gln200Ser + Thr202Pro + Pro204Ser + Gly205Gln + Thr207Gly + Tyr208His + Ala209Gly
Ala194Pro + Pro195Ser + Asn198Ser + Val199Gln + Gln200Asp + Thr202Gln + Tyr203Asn + Pro204Gly + Leu211Val + Thr214Pro
Pro195Ser + Gly198Gln + Val199Pro + Gln200Asn + Tyr203Gln + Thr207Asp + Ala209His + Leu211His + As TABLE 32-continued Loop 6 - Decuple Mutation Variants Gly205Ser + Thr207Asp + Leu211His + Asn212Ser + Thr214Ser
Ala194Asn + Pro195Ser + Val197Ser + Asn198Gln + Thr202Asn + Pro204Asp + Thr207Glu + Leu211His + Asn212Ser + Gly213Ser
Ala194Thr + Pro195Ser + Val197Gln + Asn198Glu + Val199Met + Gln200Asp + Pro204Gly + Gly205Ser + Ala209Asn + Thr214Asn
Pro195Gln + Gly196Pro + Val197Met + Asn198Asp + Val199Ala + Gln200Glu + Thr202Pro + Tyr203Ile + Tyr208Cys + Leu21Thr
Ala194Gln + Gly196Asn + Asn198Glu + Val199Ala + Gln200Asp + Thr202Ser + Tyr203Cys + Thr207Asn + Tyr208Met + Gly213Asn
Ala194Thr + Val197Pro + Val199His + Gln200Asp + Thr202Gln + Tyr203Met + Gly205Ser + Thr207Asn + Tyr208Asp + Asn212Ser
Pro195Asn + Val197Asp + Asn198Gln + Val199Gly + Gln200Ser + Thr207Ser + Tyr208Ile + Ala209Asn + Asn212Ser + Gly213Asp
Pro195Asn + Val197Pro + Asn198Gln + Gln200Glu + Gly205Gln + Tyr208Gly + Ala209Gly + Leu211Glu + Asn212Ser + Thr214Ser
Ala194Thr + Gly196Ser + Asn198Ser + Gln200Asp + Thr202Gly + Tyr203Met + Gly205Gln + Tyr208Ala + Leu211Asp + Thr214Asn
Pro195Ser + Asn198Ser + Val199Thr + Thr202Asn + Gly205Asn + Thr207Ser + Ala209Gly + Leu211Glu + Asn212Gln + Gly213Asp
Pro195Gln + Gly196Gln + Asn198Ser + Thr202Pro + Pro204Asn + Thr207Asp + Tyr208Gly + Ala209Asp + Leu211Ile + Asn212Ser
Ala194Gly + Pro195Gly + Asn198Ser + Gln200Asn + Thr202Asn + Tyr203Ala + Tyr208Val + Ser210Glu + Asn212Asp + Thr214Gly
Ala194Gln + Pro195Gln + Asn198Gln + Gln200Asn + Thr202Gly + Tyr203Leu + Gly205Gln + Ala209Gln + Ser210Glu + Asn212Glu
Pro195Gln + Val197Gly + Val199Gly + Thr202Asn + Gly205Pro + Thr207Asn + Ala209Asn + Ser210Glu + Leu211Met + Asn212Glu
Ala194Thr + Pro195Gly + Gly196Pro + Asn198Ser + Thr207Pro + Tyr208Cys + Ala209Ser + Ser210Glu + Leu211Ser + Asn212Asp
Ala194His + Pro195Ser + Gly196Gln + Val197Ala + Val199Asn + Tyr203Gln + Thr207Asn + Tyr208His + Ser210Asp + Asn212Glu
Ala194Gln + Pro195Asn + Gly196Ser + Val197Met + Pro204Ser + Gly205Pro + Thr207Ser + Tyr208Ala + Ser210Glu + Asn212Glu
Ala194Ser + Val199Thr + Thr202Ser + Tyr203Ala + Pro204Asn + Gly205Pro + Ser210Asp + Leu211Ala + Asn212Asp + Thr214Pro
Pro195Asn + Thr202Gln + Pro204Ser + Thr207Gly + Tyr208Glu + Ala209Asn + Ser210Glu + Leu211Asn + Asn212Gln + Gly213Asn
Gly196Asn + Val197Thr + Val199Thr + Pro204Asn + Thr207Gln + Tyr208Asp + Ser210Asp + Leu211Thr + Asn212Gln + Thr214Asn
Ala194Asn + Pro195Asn + Val199Cys + Gln200Asn + Pro204Gln + Thr207Ser + Tyr208Glu + Ser210Asp + Leu211Asn + Asn212Gln
Ala194Thr + Gly196Pro + Val199His + Gln200Ser + Gly205Asn + Ser206Glu + Tyr208Glu + Ala209Thr + Leu211Met + Thr214Ser
Ala194Ser + Pro195Gln + Asn198Gln + Val199His + Pro204Asn + Gly205Gln + Ser206Glu + Tyr208Asp + Ala209Thr + Gly213Asn
Gly196Gln + Val197Met + Val199Ser + Gln200Ser + Thr202Asn + Pro204Asn + Tyr208Thr + Ala209Gln + Asn212Glu + Thr214Asp
Val197Ala + Asn198Ser + Gln200Ser + Thr202Gly + Pro204Gln + Thr207Gln + Tyr208Gln + Ala209His + Asn212Glu + Thr214Asp
Ala194Pro + Gly196Ser + Val197Asp + Val199Asn + Thr202Asn + Tyr203Val + Thr207Gln + Ala209Asn + Ser210Glu + Asn212Gln
Pro195Ser + Val197Glu + Asn198Gln + Val199Gln + Tyr203Leu + Tyr208Val + Ala209Asn + Asn212Gln + Gly213Pro + Thr214Glu
Pro195Gln + Gly196Pro + Val197Asn + Asn198Glu + Gln200Ser + Pro204Asn + Gly205Asn + Leu211Cys + Asn212Gln + Gly213Asp
Pro195Gln + Gly196Pro + Val197Thr + Asn198Asp + Thr202Pro + Tyr203Gln + Thr207Gly + Ala209Glu + Gly214Ser + Thr214Ser
Ala194Ser + Pro195Gln + Val197Pro + Asn198Asp + Val199Ala + Tyr203Thr + Pro204Gln + Ala209Asp + Leu211Val + Asn212Ser
Pro195Gly + Val197Glu + Asn198Gln + Gln200Asp + Tyr203His + Pro204Ser + Thr207Gly + Tyr208His + Gly213Pro + Thr214Gly
Pro195Gly + Gly196Pro + Val199Thr + Gln200Glu + Tyr203Met + Pro204Gln + Gly205Pro + Tyr208Ser + Asn212Asp + Gly213Pro
Gly196Pro + Val197Ser + Val199Pro + Gln200Glu + Thr207Gly + Ala209Gly + Leu211Gln + Asn212Asp + Gly213Pro + Thr214Asn
Ala194His + Pro195Gln + Gly196Asn + Val197Ser + Gln200Glu + Tyr203Ala + Pro204Asn + Gly205Ser + Thr207Pro + Asn212Glu
Ala194Ser + Pro195Asn + Gly196Pro + Asn198Ser + Val199Thr + Tyr208Ile + Leu211Glu + Asn212Gln + Gly213Ser + Thr214Glu
Ala194Pro + Pro195Asn + Asn198Ser + Val199Met + Tyr203Met + Gly205Pro + Thr207Pro + Tyr208Ser + Leu211Glu + Thr214Glu
Ala194His + Pro195Gln + Gly196Gln + Val199Pro + Tyr203His + Thr207Asn + Ala209Asp + Leu211Ala + Asn212Glu + Thr214Asn
Ala194His + Gly196Gln + Thr202Ser + Tyr203Gly + Pro204Gly + Gly205Ser + Ser206Asp + Thr207Gln + Ala209Asp + Thr214Pro
Pro195Gln + Thr202Ser + Pro204Gln + Gly205Pro + Ser206Asp + Tyr208Met + Ala209Glu + Asn212Gln + Gly213Pro + Thr214Ser
Gly196Gln + Val197Pro + Thr202Asn + Tyr203Gly + Gly205Pro +
Ser206Glu + Thr207Ser + Ala209Glu + Leu211Gln + Asn212Ser
Ala194Asn + Pro195Ser + Gly196Pro + Val199Ala + Thr202Gln + Pro204Gln + Ser206Asp + Ala209Glu + Leu211His + Asn212Ser
Gly196Ser + Asn198Ser + Val199Ser + Gln200Asn + Tyr203Asn + Gly205Gln + Ser206Glu + Ala209Glu + Leu211Ser + Gly213Gln
Ala194Thr + Val197Cys + Val199Asn + Pro204Gly + Ser204Asp + Thr207Gly + Tyr208Gly + Ala209Glu + Leu211Ile + Thr214Gln
Ala194Gly + Pro195Ser + Gln200Ser + Thr202Gly + Tyr203Leu + Pro204Gly + Gly205Pro + Ser206Asp + Ala209Asp + Thr214Gly
Pro195Ser + Gly196Pro + Val199His + Gln200Asp + Thr202Pro + Gly205Pro + Thr207Asp + Ala209Thr + Asn212Gln + Gly213Gln
Ala194Gln + Gly196Asn + Asn198Gln + Val199Pro + Gln200Asp + Thr202Gly + Tyr203Thr + Gly205Pro + Thr207Asp + Ala209Gln
Pro195Asn + Val197Thr + Val199Ala + Gln200Asn + Tyr203Asn + Gly205Pro + Thr207Gly + Ser210Asp + Asn212Gln + Gly213Glu
Ala194Asn + Pro195Gln + Val197Asn + Val199Asn + Pro204Gly + Thr207Pro + Ser210Asp + Asn212Ser + Gly213Glu + Thr214Pro
Ala194Gln + Pro195Asn + Val197Gly + Tyr203Met + Pro204Ser + Tyr208Gln + Ala209Asn + Ser210Glu + Asn212Ser + Gly213Glu
Ala194His + Gly196Ser + Tyr203Asn + Pro204Gly + Gly205Pro + Ala209Ser + Ser210Glu + Leu211Pro + Asn212Ser + Gly213Asp
Gly196Pro + Gln200Asn + Thr202Asn + Tyr203His + Gly205Asp + Tyr208Ile + Ala209Glu + Leu211Met + Gly213Pro + Thr214Pro
Val197His + Val199Asn + Gln200Asn + Thr202Ser + Tyr203Ser + Gly205Glu + Tyr208Ser + Ala209Asp + Gly213Pro + Thr214Pro
Ala194Asn + Val197Pro + Gln200Ser + Thr202Gln + Tyr203Met + Gly205Gln + Thr207Asp + Ser210Asp + Leu211Ser + Asn212Ser
Ala194Thr + Asn198Ser + Tyr203Asn + Gly205Pro + Thr207Asp + Ala209Gln + Ser210Glu + Leu211Val + Asn212Ser + Thr214Ser
Asn198Gln + Val199Pro + Gln200Asn + Thr202Gln + Tyr203Asn + Thr207Asp + Ala209Pro + Ser210Glu + Asn212Ser + Gly213Asn
Ala194Ser + Pro195Asn + Asn198Gln + Val199Ala + Gln200Asp + Tyr203His + Ala209Thr + Leu211Ser + Gly213Asp + Thr214Ser
Ala194Pro + Pro195Asn + Gly196Pro + Val197Ser + Gln200Asp + Tyr208Cys + Leu211Gln + Asn212Ser + Gly213Asp + Thr214Gly
Ala194Gln + Pro195Ser + Gly196Gln + Asn198Asp + Gln200Ser + Thr202Ser + Tyr208Asp + Ala209Thr + Leu211His + Thr214Asn
Ala194Asn + Pro195Gln + Val197Thr + Asn198Asp + Pro204Asn + Thr207Ser + Tyr208Asp + Leu211Ile + Gly214Gln + Thr214Gln
Ala194Gln + Pro195Asn + Val199Asn + Tyr203Ser + Pro204Asp + Thr207Asn + Ser210Asp + Leu211Gly + Asn212Ser + Gly213Ser
Ala194Asn + Pro195Asn + Thr202Gly + Pro204Asp + Tyr208Ile + Ala209Gly + Ser210Asp + Leu211Val + Asn212Gln + Thr214Ser
Ala194Asn + Gly196Ser + Asn198Ser + Val199Pro + Tyr203His + Pro204Glu + Gly205Gln + Tyr208Met + Ala209Thr + Ser210Glu
Ala194Thr + Asn198Ser + Val199Thr + Thr202Asn + Pro204Glu + Gly205Asn + Thr207Gln + Ala209His + Ser210Glu + Thr214Gly
Ala194His + Pro195Gln + Asn198Ser + Val199Gly + Tyr203Gly + Pro204Asp + Thr207Gly + Ser210Glu + Asn212Gln + Gly213Ser
Pro195Asn + Tyr203Ser + Pro204Glu + Gly205Pro + Tyr208His + Ala209Gly + Ser210Glu + Leu211Pro + Gly213Pro + Thr214Asp
Gly196Asn + Asn198Ser + Gln200Ser + Thr202Gly + Pro204Asp + Gly205Asn + Ala209Thr + Ser210Glu + Gly213Pro + Thr214Ser
Gln200Ser + Thr202Gln + Tyr203Met + Pro204Asp + Gly205Pro + Tyr208Cys + Ala209Gly + Ser210Asp + Leu211Thr + Gly213Gln
Ala194Pro + Gly196Asn + Ser210Asp + Tyr203Ser + Pro204Glu + Thr207Gly + Ala209Asn + Ser210Asp + Leu211Val + Thr214Ser
Val199His + Gln200Ser + Thr202Ser + Pro204Asp + Gly205Asn + Tyr208Pro + Ser210Asp + Leu211Pro + Gly213Pro + Thr214Pro
Ala194Ser + Pro195Asn + Gly196Ser + Val197Ser + Asn198Gln + Val199Ser + Pro204Glu + Tyr208Leu + Ser210Asp + Leu211Ser
Ala194His + Gly196Pro + Val199Gly + Gln200Asp + Pro204Glu + Tyr208Gln + Ala209Gly + Leu211Ser + Asn212Ser + Thr214Asn
Ala194Gln + Val197Pro + Val199Asn + Gln200Asp + Thr202Gln + Pro204Asp + Gly205Asn + Tyr208His + Ala209Asn + geu211Ile
Pro195Ser + Val197Met + Asn198Ser + Gln200Asp + Thr202Gly + Tyr203Gln + Pro204Glu + Thr207Pro + Asn212Ser + Thr214Gly
Pro195Ser + Val197Met + Gln200Ser + Pro204Gln + Thr207Ser + Ala209Glu + Leu211Ala + Asn212Gln + Gly213Glu + Thr214Gly
Pro195Gln + Gly196Pro + Asn198Ser + Val199Gly + Tyr203Asn + Gly205Asn + Thr207Pro + Ala209Glu + Leu211Val + Gly213Asp
Ala194Asn + Pro195Gln + Asn198Ser + Val199Ser + Gly205Asn + Thr207Gln + Ala209Ser + Leu211Glu + Asn212Gln + Thr214Ser
Ala194Ser + Asn198Ser + Gln200Ser + Thr202Gly + Tyr203Leu + Thr207Gly + Ala209His + Ser210Glu + Asn212Ser + Thr214Asp
Gly196Ser + Gln200Asn + Thr202Pro + Tyr203Leu + Pro204Asn + Thr207Gln + Ser210Asp + Leu211Ala + Gly213Pro + Thr214Asp
Gly196Ser + Asn198Gln + Tyr203Gly + Pro204Gln + Gly205Pro +

TABLE 32-continued

Loop 6 - Decuple Mutation Variants

Thr207Pro + Tyr208His + Ser210Glu + Gly213Gln + Thr214Asp
Val197Thr + Val199Thr + Gln200Ser + Thr202Ser + Gly205Asn + Thr207Pro + Tyr208Cys + Ser210Glu + Gly213Ser + Thr214Asp
Gly196Gln + Val197Thr + Gln200Asp + Thr202Asn + Tyr203His + Ser206Glu + Thr207Ser + Tyr208Pro + Leu211Pro + Asn212Gln
Val197Met + Val199Gln + Gln200Glu + Thr202Gln + Pro204Gln + Gly205Asn + Ser206Asp + Thr207Gln + Leu211Val + Thr214Ser
Ala194Thr + Pro195Gly + Gly196Asn + Val197Ser + Gln200Glu + Thr202Pro + Gly205Pro + Ser206Glu + Leu211Met + Asn212Ser
Pro195Ser + Gly196Gln + Val199Cys + Gln200Glu + Ser206Glu + Tyr208Thr + Leu211Gln + Asn212Gln + Gly213Pro + Thr214Asn
Gly196Gln + Val197Gly + Asn198Gln + Gln200Glu + Gly205Asn + Ser206Glu + Thr207Pro + Ala209Asn + Asn212Gln + Gly213Ser
Pro195Gln + Val197Gly + Gln200Glu + Thr202Gln + Tyr203Val + Gly205Gln + Ser206Asp + Tyr208Met + Ala209Pro + Thr214Gly
Ala194Ser + Pro195Asn + Val197Thr + Val199Thr + Gln200Glu + Thr202Pro + Tyr203Ser + Gly205Pro + Ser206Glu + Thr214Gly
Pro195Ser + Gln200Gln + Thr202Gln + Tyr203Gly + Gly205Pro + Ser206Asp + Thr207Gly + Ala209His + Leu211His + Thr214Gly
Ala194Asn + Pro195Gly + Gly196Asn + Val197Cys + Val199Asn + Gln200Glu + Tyr203Pro + Pro204Gln + Ser206Asp + Leu211Ala
Ala194Thr + Pro195Asn + Gly196Gln + Val197Asn + Gln200Glu + Thr202Ser + Ser206Glu + Ala109His + Leu211Ala + Thr214Ser
Val199Gly + Gln200Glu + Thr202Gln + Pro204Asn + Gly205Pro + Ser206Asp + Thr207Ser + Ala209Gly + Leu211Cys + Asn212Ser
Ala194Thr + Val197Ser + Val199Gln + Gln200Asp + Thr202Gln + Pro204Gln + Ser206Asn + Ala209Gly + Leu211His + Gly213Gln
Ala194Gly + Gly196Asn + Asn198Gln + Gln200Glu + Gly205Pro + Ser206Asp + Ala209His + Leu211Pro + Gly213Gln + Thr214Gly
Gly196Ser + Val199Ser + Thr202Ser + Pro204Asp + Thr207Asn + Tyr208Leu + Leu211Glu + Asn212Glu + Gly213Ser + Thr214Pro
Ala194Pro + Pro195Asn + Val197Pro + Thr202Pro + Tyr203Thr + Thr207Gln + Tyr208Glu + Asn212Glu + Gly213Ser + Thr214Ser
Gly196Asn + Gln200Ser + Gly205Pro + Thr207Gln + Tyr208Asp + Ala209Ser + Leu211Ser + Asn212Glu + Gly213Pro + Thr214Pro
Ala194Gly + Val199Pro + Gln200Asp + Thr202Pro + Tyr203Cys + Pro204Gly + Ala209Gln + Leu211Cys + Asn212Gln + Thr214Asp
Gly196Ser + Val197Gly + Gln200Asp + Tyr203Cys + Pro204Ser + Thr207Gln + Leu211Ala + Asn212Gln + Gly213Ser + Thr214Asp
Ala194Pro + Val197Thr + Thr202Gln + Tyr203Met + Pro204Asn + Ser206Asp + Tyr208His + Ala209His + Ser210Asp + Thr214Asn
Gly196Asn + Val197Cys + Thr202Asn + Tyr203Met + Gly205Pro + Ser206Asp + Thr207Gly + Ala209Pro + Ser210Asp + Gly213Gln
Ala194Thr + Val197Ser + Val199His + Thr202Gln + Tyr203Ser + Ser206Asp + Thr207Ser + Ser210Asp + Gly213Pro + Thr214Pro
Ala194Thr + Pro195Ser + Gly196Asn + Val197Pro + Asn198Gln + Thr202Gln + Ser206Glu + Ser210Glu + Asn212Ser + Thr214Gly
Pro195Asn + Gly196Ser + Val197Ser + Asn198Gln + Thr202Asn + Tyr203Met + Ser206Glu + Ser210Asp + Asn212Gln + Thr214Gln

TABLE 33

Multi-loop Double Mutation Variants

Leu94Gly + Gln200Glu
Gln57Ser + Asn60Ser
Val93Gln + Gly213Asp
Tyr102Cys + Thr207Gly
Ser154Glu + Asn198Gln
Leu241Ile + Asn198Gln
Ala209Gly + Ser210Glu
Gln57Asp + Leu94Gly
Leu94Ala + Ser154Glu
Ser101Asp + Leu211Thr
Ala131Glu + Gly196Gln
Ser128Glu + Pro204Asn
Ser103Asp + Pro129Asn
Gly157Asn + Thr207Ser
Gly98Glu + Gly155Gln
Gln200Asp + Ala209Pro
Asn60Glu + Asn198Gln
Leu94Ile + Ser99Asp
Leu124Ile + Ser210Asp
Ser126Glu + Thr202Ser
Val93Ala + Pro127Asp
Gly157Pro + Ser210Asp
Val197Gly + Thr207Asp
Gln184Glu + Ala194Thr
Ser97Glu + Tyr203Asn
Gly100Pro + Thr207Asp
Ser210Asp + Leu211Met
Tyr161Asn + Thr207Asp
Leu124Ser + Pro127Asn
Gly61Ser + Thr207Pro
Gly98Glu + Gln200Ser
Gln200Asn + Asn212Glu
Asp58Glu + Ile105Cys
Gly61Pro + Ala209Thr
Leu124Asp + Pro204Asn
Gln57Glu + Asn198Ser
Gln185Ser + Asn212Asp
Phe183His + Val197Glu
Asn60Glu + Gln200Ser
Gly59Asn + Gly61Glu
Gly155Asp + Ile159Cys
Gly63Gln + Leu211Gly
Thr64Pro + Tyr161Asp
Leu94Gln + Pro127Gly
Thr207Gly + Gly213Glu
Gln185Asp + Tyr203Ser
Gly63Asn + Ala209Asn
Tyr208Met + Gly213Asn
Ser210Glu + Leu211Asn
Tyr102Ala + Pro129Asn
Gly125Asp + Leu211Gly
Ser130Asp + Thr207Ser
Ser128Glu + Leu211His
Gly155Gln + Leu211His
Gln57Asn + Gln200Asp
Ser103Asp + Gly157Gln
Gly125Ser + Thr207Gly
Ile105Pro + Val197Glu
Pro204Asp + Ala209Gln
Tyr161Asp + Thr207Asn
Asn198Ser + Ser210Asp
Gln95Ser + Gln200Asp
Gly59Gln + Ala156Glu
Gly98Gln + Tyr102Cys
Ala181His + Thr207Glu
Ser154Glu + Pro204Ser
Gly205Asn + Thr207Gln
Ser210Glu + Leu211Pro
Leu94Gln + Ser210Glu
Ala209Asp + Leu211Pro
Asn60Glu + Leu211His
Ala96Asn + Thr214Gly
Asn60Glu + Ala194Gly
Ser103Asp + Ala181His
Gly125Glu + Ala209Asn
Ser158Asp + Asn198Ser
Gly155Ser + Asn198Ser
Ser104Asp + Gly152Asn
Ser182Asp + Leu211Cys
Val93Ser + Gly125Glu
Asn198Glu + Leu211Ser
Gly100Ser + Ser103Asp
Ala181Gln + Gly213Gln
Thr64Gly + Ser126Asp
Ile159Cys + Gln200Asp
Thr207Glu + Leu211Asn
Ser104Glu + Pro204Gly
Ser130Asp + Pro204Asn
Pro129Gln + Gln185Asn
Asn60Glu + Gly157Ser
Gly125Pro + Val197Met
Asn60Glu + Ile105Cys
Pro127Gln + Val197Thr
Ser101Asp + Leu211Ala
Gln57Ser + Ser99Glu
Phe183Pro + Asn198Glu
Asn198Glu + Thr202Pro
Val197Gln + Leu211His

TABLE 33-continued

| Multi-loop Double Mutation Variants |
|---|
| Gly61Ser + Gln200Ser |
| Gly61Asp + Asn198Gln |
| Gly61Glu + Phe183Ser |
| Thr207Asn + Asn212Glu |
| Tyr203Thr + Tyr208Gly |
| Asn198Ser + Leu211Cys |
| Asn153Asp + Leu211Ser |
| Gln57Asn + Gly213Pro |
| Thr64Ser + Ser210Asp |
| Pro204Asp + Leu211Ile |
| Gln57Asp + Gly61Pro |
| Gly155Gln + Ser210Asp |
| Ala156Gly + Thr207Asn |
| Gly61Gln + Ala181Thr |
| Ile159Cys + Asn198Gln |
| Pro129Gly + Leu211Glu |
| Asn198Glu + Thr207Ser |
| Gly98Ser + Ser128Asp |
| Ala131Asn + Val193Ser |
| Gln185Ser + Gln200Asn |
| Ser210Asp + Leu211His |
| Gly125Glu + Ala156Gln |
| Ser97Asp + Gly125Gln |
| Asn60Gln + Gly155Pro |
| Ser126Glu + Thr207Ser |
| Phe183Met + Thr207Pro |
| Ser154Glu + Phe183Ile |
| Val93Gln + Ser210Asp |
| Val93Gln + Tyr208His |
| Asn60Ser + Asn198Glu |
| Gly152Gln + Gln200Asp |
| Pro127Asn + Gly152Asn |
| Gly155Gln + Thr214Asn |
| Ala96Ser + Tyr208His |
| Tyr161Thr + Ser210Asp |
| Gly100Pro + Pro204Gln |
| Gln57Asp + Ala194Asn |
| Asn60Gln + Thr202Asn |
| Gly157Pro + Gly213Asn |
| Val93Thr + Leu211Ala |
| Ser103Glu + Leu211Thr |
| Ser101Asp + Leu124Ile |
| Leu94Glu + Pro204Gln |
| Gln200Glu + Ala209His |
| Ser101Glu + Gly152Gln |
| Asn198Asp + Gly205Pro |
| Gly61Ser + Gln200Asn |
| Ser158Asp + Val197Asn |
| Gly61Glu + Phe183Ile |
| Asp58Glu + Tyr203Ser |
| Gly213Ser + Thr214Gly |
| Gln57Asp + Asn198Gln |
| Tyr102Leu + Ser158Glu |
| Ala96Gln + Leu211Asn |
| Val93Asp + Thr202Asn |
| Leu94Ser + Asn198Asp |
| Gly196Ser + Asn212Asp |
| Gly155Asn + Gly157Asp |
| Val93Asn + Ser130Asp |
| Leu94Ile + Ser210Asp |
| Val197Ala + Ser210Asp |
| Ser104Asp + Gly205Pro |
| Asn153Asp + Ala181Gly |
| Gln200Asn + Leu211Glu |
| Leu94Asn + Ser210Glu |
| Gln185Asp + Val197Gln |
| Tyr102Ser + Thr207Asp |
| Gly61Glu + Gly95Asn |
| Gly61Asp + Pro129Gln |
| Ser99Asp + Thr207Ser |
| Ser126Glu + Gly152Gln |
| Val197His + Ser206Glu |
| Gly61Asn + Gly155Glu |
| Gly155Asn + Asn198Glu |
| Ala209Asn + Ser210Glu |
| Ser128Asp + Thr207Gly |
| Ala209Thr + Ser210Asp |

TABLE 33-continued

| Multi-loop Double Mutation Variants |
|---|
| Gln185Asn + Gly213Pro |
| Ser126Glu + Leu211Gly |
| Ser97Asp + Gly205Ser |
| Leu94Thr + Leu124Thr |
| Asn60Gln + Leu211Gly |
| Pro129Asp + Gly155Pro |
| Asp58Glu + Gly157Ser |
| Thr202Pro + Thr207Glu |
| Ala156Ser + Tyr208Asp |
| Gly98Glu + Tyr161Gln |
| Ile105Cys + Gln200Asn |
| Gln200Glu + Pro204Gly |
| Gly98Pro + Ala131Asn |
| Gly59Asp + Thr207Gln |
| Tyr102Gln + Ala209Gln |
| Gly98Glu + Ile105His |
| Ser101Asp + Pro129Gln |
| Pro127Asp + Gly213Asn |
| Ser104Glu + Asn198Gln |
| Gln57Ser + Gln200Asn |
| Val197Cys + Gln200Ser |
| Val93Ala + Ala156Glu |
| Gln200Asn + Gly205Glu |
| Leu94Ala + Thr207Asn |
| Ala131Thr + Gln200Ser |
| Leu94Glu + Tyr161Thr |
| Gln200Asn + Ser210Asp |
| Gln57Asp + Thr207Asn |
| Ser99Glu + Ala156Pro |
| Leu124Ile + Asn198Ser |
| Tyr161Gly + Thr207Gln |
| Ile105Cys + Thr214Asp |
| Ile159His + Ser206Asp |
| Gly63Gln + Gly125Asn |
| Asn198Asp + Gly205Ser |
| Ser104Glu + Leu124Gln |
| Ala209Pro + Ser210Glu |
| Tyr161Val + Asn198Asp |
| Pro129Ser + Gln200Asp |
| Ser97Asp + Tyr203Ser |
| Ser103Asp + Phe183Thr |
| Tyr161Gly + Val197Ala |
| Asn198Gln + Pro204Glu |
| Leu211Gly + Asn212Glu |
| Ser206Glu + Leu211Thr |
| Gly152Pro + Val197Ser |
| Ile105Ala + Ala156Gln |
| Gly63Asn + Tyr102Pro |
| Ser182Glu + Val197Asn |
| Thr64Glu + Ala96Gln |
| Asn60Gln + Ser206Glu |
| Asn60Gln + Ser128Asp |
| Ser101Asp + Ile159Pro |
| Gly100Ser + Thr207Ser |
| Gly63Asn + Gly205Ser |
| Ala181Glu + Thr207Asn |
| Gly125Ser + Tyr161Ser |
| Gln200Glu + Leu211Ala |
| Ser101Asp + Tyr102Leu |
| Ser126Glu + Thr207Pro |
| Gly59Asp + Tyr102Thr |
| Gly100Gln + Tyr102Met |
| Gly59Ser + Asn198Asp |
| Asn60Ser + Leu94Cys |
| Pro127Glu + Gly205Pro |
| Gln57Glu + Ala156Asn |
| Ala131Asn + Thr207Asp |
| Ala131Asp + Thr202Ser |
| Leu124His + Ala131Asn |
| Gly152Glu + Leu211His |
| Ser101Glu + Ala181Thr |
| Asp58Glu + Gly205Ser |
| Gly61Asn + Gln200Asp |
| Pro129Gly + Val197Asp |
| Thr64Gln + Asn198Ser |
| Val93Ala + Ser154Glu |
| Ser130Glu + Tyr161Val |

TABLE 33-continued

Multi-loop Double Mutation Variants

Phe183Asp + Leu211Thr
Ser206Glu + Asn212Gln
Gly63Ser + Ala131Glu
Pro127Asn + Gln200Asp
Ser130Asp + Phe183Thr
Ala181Thr + Pro195Ser
Gly95Ser + Ala156Glu
Tyr161Gln + Tyr208Ile
Gln57Asp + Leu211Cys
Asn153Gln + Gly213Asn
Val93Thr + Leu124Ser
Ser101Glu + Asn212Gln
Gly157Ser + Asn198Glu
Gly152Ser + Ser182Glu
Tyr161Gln + Gly213Ser
Pro195Gly + Gln200Asn
Asn60Asp + Leu211Pro
Pro195Ser + Tyr208Glu
Gln200Asp + Leu211Asn
Leu124Val + Thr207Pro
Thr64Pro + Ser126Glu
Thr64Ser + Tyr203Val
Ser97Glu + Asn198Ser
Gly152Gln + Leu211Pro
Asn198Asp + Leu211Asn
Val93Glu + Gly125Gln
Gly98Asn + Gln200Asp
Gln200Asn + Thr207Asp
Asn198Ser + Gln200Glu
Tyr102Leu + Asn198Gln
Leu124Cys + Asn153Ser
Asn198Asp + Leu211Pro
Ser126Glu + Tyr208Met
Ala96Asn + Gly100Ser
Ser99Glu + Leu211Cys
Ser97Asp + Leu211Ala
Ser182Glu + Leu211His
Ile159Cys + Leu211Glu
Gly152Asn + Ser210Asp
Val197Ala + Gln200Glu
Asn60Ser + Ser158Glu
Ser104Glu + Tyr208Asn
Pro204Asp + Leu211Gly
Asp58Glu + Val197Gly
Ser182Glu + Tyr208Ser
Ser103Asp + Ala194Ser
Ala156Gln + Thr207Asp
Asn198Ser + Thr207Ser
Gln57Asp + Thr207Ser
Gly152Glu + Thr207Gly
Ala131Ser + Ile159Asn
Pro127Asn + Gly152Glu
Gln200Asn + Gly213Glu
Leu124Asp + Leu211Ala
Gly98Glu + Gly125Asn
Ile159Gly + Thr207Asn
Pro127Gln + Asn153Asp
Ser103Glu + Phe183Tyr
Ser160Glu + Pro204Ser
Gly157Ser + Tyr161His
Ala156Pro + Ser158Glu
Gly100Glu + Pro127Asn
Gln57Asn + Asn60Glu
Gly125Ser + Ser210Glu
Gly125Pro + Ser128Asp
Gly125Glu + Val197Gly
Val193Met + Asn198Ser
Ser160Glu + Gly213Asn
Ser206Glu + Ala209His
Ser97Glu + Gly213Ser
Gly100Asp + Leu211Gly
Pro129Gln + Thr207Gly
Gly95Gln + Ser210Asp
Gln185Ser + Pro204Glu
Pro129Glu + Ala156Ser
Ser126Asp + Asn212Ser
Gly59Ser + Ile159Ala

TABLE 33-continued

Multi-loop Double Mutation Variants

Ala96Asn + Ser99Glu
Ser104Asp + Ile159Val
Gly63Asn + Ser210Glu
Phe183Pro + Ser210Glu
Ala96Asp + Tyr208Ile
Gly98Asp + Thr207Gln
Val93Gln + Gly125Glu
Ile159Glu + Thr207Gln
Leu94Ile + Leu211Val
Gly157Asp + Leu211His
Gly61Asp + Leu211Cys
Gln57Asn + Gly157Asn
Gly100Glu + Val197Ser
Gln200Glu + Pro204Asn
Ala131Gly + Leu211His
Ser206Asp + Leu211Asn
Asn153Asp + Ile159Leu
Gly152Ser + Asn198Glu
Leu94Met + Ser130Glu
Gln57Glu + Asn198Gln
Ser182Glu + Leu211Thr
Val199Ala + Ser210Glu
Thr207Gly + Ser210Glu
Thr64Gly + Gly98Asp
Gly61Gln + Ser99Asp
Gly155Glu + Leu211Ser
Leu124Ser + Thr207Asp
Val93Ser + Asn198Gln
Ser99Asp + Gly125Asn
Gln57Asn + Asn198Glu
Ser99Glu + Ile159Met

TABLE 34

Multi-loop Triple Mutation Variants

Gln57Ser + Leu94Gly + Gln200Glu
Asn60Ser + Val93Gln + Gly213Asp
Tyr102Cys + Asn198Gln + Thr207Gly
Leu124Ile + Ser154Glu + Asn198Gln
Leu94Gly + Ala209Gly + Ser210Glu
Gly155Asp + Ala209Gln + Asn212Gln
Pro129Asn + Gly157Asn + Thr207Ser
Asn198Gln + Gln200Asp + Ala209Pro
Val93Ala + Pro127Asp + Thr202Ser
Tyr161Asn + Thr207Asp + Leu211Met
Gly61Ser + Pro127Asn + Thr207Pro
Gly61Pro + Leu124Asp + Pro204Asn
Gln57Glu + Gln185Ser + Asn198Ser
Gly59Asn + Asn60Glu + Gln200Ser
Gly63Gln + Gln200Asp + Leu211Gly
Tyr203Ser + Thr207Gly + Gly213Glu
Gly63Asn + Gln185Asp + Ala209Asn
Pro129Asn + Ser210Glu + Leu211Asn
Tyr102Ala + Gly125Glu + Leu211Gly
Gln57Asn + Gly155Gln + Leu211His
Ile105Pro + Gly125Ser + Thr207Gly
Asn198Ser + Thr207Asn + Ser210Asp
Gly59Gln + Gly95Ser + Ala156Glu
Tyr102Cys + Ser210Glu + Leu211Asn
Gly205Asn + Thr207Gln + Ser210Glu
Leu94Gln + Ala209Asp + Leu211Pro
Asn60Glu + Leu211His + Thr214Gly
Asn60Glu + Ala181His + Ala194Gly
Ser104Asp + Gly155Ser + Asn198Ser
Gly152Asn + Ser182Asp + Leu211Cys
Gly100Ser + Ser103Asp + Leu211Ser
Thr64Gly + Ser126Asp + Ile159Cys
Ser130Asp + Ala181Asn + Pro204Gly
Pro129Gln + Gly157Ser + Gln185Asn
Asn60Glu + Gly125Pro + Val197Met
Ile105Cys + Pro127Gln + Val197Thr
Gln57Ser + Ser99Glu + Phe183Pro
Gly61Ser + Val197Gln + Leu211His

TABLE 34-continued

Multi-loop Triple Mutation Variants

Gly61Asp + Asn198Gln + Gln200Ser
Tyr203Thr + Thr207Asn + Tyr208Gly
Asn153Asp + Asn198Ser + Leu211Ser
Gln57Asn + Ser210Asp + Gly213Pro
Thr64Ser + Pro204Asp + Leu211Ile
Ser101Asp + Ala156Gly + Thr207Asn
Ile159Cys + Ala181Thr + Asn198Gln
Gly98Ser + Asn198Glu + Thr207Ser
Ser128Asp + Ala131Asn + Val193Ser
Gln185Ser + Gln200Asn + Leu211His
Ser126Glu + Phe183Met + Thr207Ser
Ser154Glu + Phe183Ile + Thr207Pro
Val93Gln + Tyr208His + Ser210Asp
Val93His + Pro127Asn + Gly152Gln
Gly155Gln + Gly213Glu + Thr214Asn
Gly100Pro + Tyr161Thr + Ser210Asp
Gln57Asp + Ala194Asn + Pro204Gln
Gly157Pro + Thr202Asn + Gly213Asn
Thr64Gln + Val93Thr + Leu211Ala
Gly61Ser + Gln200Asn + Gly205Pro
Ser158Asp + Phe183Ile + Val197Asn
Asn198Asp + Gly213Ser + Thr214Gly
Gly152Ser + Gly155Ser + Ser206Asp
Gly152Gln + Gln185Ser + Val197Gln
Leu94Ile + Val197Ala + Ser210Asp
Ala181Gly + Gln200Asn + Leu211Glu
Leu94Asn + Val197Gln + Ser210Glu
Gly61Asp + Pro129Gln + Thr207Ser
Gln57Asn + Gly61Asn + Gly155Glu
Gly61Pro + Ser128Asp + Ala209Thr
Thr207Gly + Ala209Thr + Ser210Asp
Ser128Asp + Gln185Asn + Gly213Pro
Leu94Thr + Leu124Thr + Gly205Ser
Asn60Gln + Gly155Pro + Leu211Gly
Asp58Glu + Gly157Ser + Thr202Pro
Gly98Glu + Ile105Cys + Gln200Asn
Gly98Pro + Gln200Glu + Pro204Gly
Gly59Asp + Ala131Asn + Thr207Gln
Gly98Glu + Tyr102Gln + Ala209Gln
Ser101Asp + Ile105His + Pro129Gln
Pro127Asp + Asn198Gln + Gly213Asn
Ile159Gly + Val197Gly + Asn198Gln
Gln57Ser + Gly155Glu + Gln200Asn
Val197Cys + Asn198Glu + Gln200Ser
Leu94Ala + Gln200Asn + Gly205Glu
Ala131Thr + Gln200Ser + Thr207Asn
Leu124Ile + Ala156Pro + Asn198Ser
Val93Glu + Tyr161Gly + Thr207Gln
Gly63Gln + Gly125Asn + Ala209Glu
Tyr161Gly + Val197Ala + Asn198Gln
Ser158Asp + Asn198Ser + Leu211Gly
Ile105Ala + Gly152Pro + Val197Ser
Gly63Asn + Tyr102Pro + Ala156Gln
Ala96Gln + Ser182Glu + Val197Asn
Asn60Gln + Ser101Asp + Ile159Pro
Gly100Ser + Gly205Ser + Thr207Ser
Tyr161Ser + Ala181Glu + Thr207Asn
Gly125Ser + Gln200Glu + Leu211Ala
Gly59Asp + Tyr102Thr + Thr207Pro
Gly59Ser + Gly100Gln + Tyr102Met
Asn60Ser + Leu94Cys + Asn198Asp
Pro127Glu + Ala156Asn + Gly205Pro
Asp58Glu + Ala181Thr + Gly205Ser
Thr64Gln + Val93Ala + Asn198Ser
Phe183Asp + Leu211Thr + Asn212Gln
Pro127Asn + Ser130Asp + Phe183Thr
Tyr161Gln + Tyr208Ile + Leu211Cys
Leu124Ser + Asn153Gln + Gly213Asn
Val93Thr + Ser101Glu + Asn212Gln
Tyr161Gln + Gln200Asn + Gly213Ser
Gln200Asp + Thr207Pro + Leu211Asn
Thr64Pro + Leu124Val + Ser126Glu
Thr64Ser + Ser97Glu + Asn198Ser
Gly152Gln + Ser210Asp + Leu211Pro
Val93Pro + Asn198Ser + Gln200Glu
Thr64Gln + Tyr102Leu + Asn153Ser
Ala96Asn + Gly100Ser + Tyr208Met
Ile159Cys + Ser182Glu + Leu211His
Asn60Ser + Ser158Glu + Tyr208Asn
Ser103Asp + Ala194Ser + Tyr208Ser
Ala156Gln + Asn198Ser + Thr207Asp
Ala131Ser + Gly152Glu + Ile159Asn
Pro127Asn + Gln200Asn + Gly213Glu
Gly98Glu + Gly125Asn + Leu211Ala
Ile159Gly + Thr207Asn + Ser210Glu
Ser103Glu + Phe183Tyr + Pro204Ser
Gly157Ser + Ser160Glu + Tyr161His
Gln57Asn + Gly100Glu + Pro127Asn
Gly125Pro + Val197Gly + Ser210Glu
Val193Met + Asn198Ser + Gly213Asn
Gly95Gln + Pro129Gln + Thr207Gly
Gly59Ser + Ser126Asp + Asn212Ser
Gly63Asn + Ile159Val + Ser210Glu
Phe183Pro + Tyr208Ile + Ser210Glu
Leu94Ile + Ile159Glu + Thr207Gln
Gln57Asn + Gly157Asn + Leu211Cys
Ala131Gly + Pro204Asn + Leu211His
Ile159Leu + Ser206Asp + Leu211Asn
Leu94Met + Gly152Ser + Asn198Glu
Ser182Glu + Val199Ala + Leu211Thr
Leu124Ser + Thr207Asp + Leu211Ser
Val93Ser + Gly125Asn + Asn198Gln
Tyr102Pro + Ala156Ser + Phe183His
Gly98Gln + Ser128Glu + Ile159Cys
Ser104Asp + Ile105Pro + Tyr161Thr
Tyr102Pro + Ile105Thr + Ala181Glu
Thr64Ser + Ile105Glu + Gln200Asn
Ser104Asp + Gln200Ser + Thr214Pro
Thr64Pro + Ala156Glu + Thr202Gly
Gly63Gln + Gly100Asp + Leu211His
Asn60Ser + Gly98Asp + Leu211Thr
Tyr161Gly + Val197Cys + Ser206Glu
Thr207Gln + Tyr208Gln + Ser210Glu
Gly98Ser + Ile105Leu + Ser210Glu
Thr64Gly + Pro195Ser + Thr214Ser
Val93Met + Ser154Asp + Leu211Met
Leu124Ser + Asn198Ser + Leu211Asp
Thr64Gly + Ala156Ser + Gly157Pro
Gly59Ser + Gln200Asn + Gly213Glu
Gly61Asn + Leu124Ile + Ala181Pro
Ala96His + Gln185Asp + Leu211Ala
Ser101Asp + Asn198Ser + Thr214Ser
Leu94Met + Asn153Asp + Pro195Gln
Pro127Gln + Gly152Asp + Val193His
Ser97Asp + Ile105Thr + Thr207Gln
Gly61Pro + Ser160Glu + Thr207Gln
Leu124Val + Pro204Gly + Leu211Ile
Ser99Asp + Asn198Gln + Gln200Ser
Ser101Glu + Ala181Asn + Ala209Pro
Gly61Asn + Ala96Thr + Gly98Ser
Val93Pro + Asn198Asp + Thr107Gln
Thr64Pro + Ala96Pro + Gly155Glu
Thr64Gly + Ala181Thr + Thr214Pro
Thr64Pro + Leu94Cys + Tyr208Met
Gln57Asn + Leu94Gln + Thr214Asn
Leu94Gln + Tyr161Pro + Thr207Gly
Val93His + Gln185Asn + Thr207Pro
Gly125Pro + Asn198Glu + Gln200Ser
Asn153Ser + Ile159Cys + Ser160Asp
Thr64Gly + Gln200Glu + Leu211Cys
Leu94Val + Pro195Gln + Leu211Asp
Gly59Pro + Gly100Ser + Thr207Pro
Tyr102Cys + Gly157Gln + Thr207Pro
Ser99Asp + Leu124Ser + Thr214Asn
Gly59Gln + Gln200Asp + Thr207Ser
Ala96His + Ala181Asp + Leu211Cys
Val93Met + Ala181His + Thr207Ser
Pro129Gln + Asn198Ser + Thr207Ser
Asp58Glu + Gly95Ser + Ala194Gly
Ser160Glu + Thr207Gln + Thr214Gly
Thr64Asn + Phe183Asp + Thr207Asn
Ser158Asp + Phe183Ile + Val197His
Gly95Pro + Asn153Ser + Gln200Glu
Gly157Asp + Pro204Gly + Thr207Ser

TABLE 34-continued

Multi-loop Triple Mutation Variants

Val197Pro + Asn198Gln + Thr207Gln
Gly61Pro + Leu94Glu + Tyr161Ile
Pro129Gln + Gly155Pro + Ser210Glu
Val93Met + Ser182Asp + Gln200Ser
Pro127Ser + Leu211Met + Gly213Ser
Ala96His + Ser160Asp + Tyr208Gly
Gly98Pro + Pro129Ser + Pro204Asp
Gly59Ser + Gly63Pro + Pro129Asp
Gly100Pro + Leu124Pro + Thr207Asn
Ser103Asp + Ile159Ala + Thr202Gln
Gly59Asn + Ser130Glu + Leu211Thr
Ala96Gly + Ala131Asn + Gly155Pro
Asn153Ser + Gln200Asn + Ser210Glu
Asn153Glu + Thr207Pro + Leu211Ala
Pro127Asn + Val197His + Thr207Asp
Gly100Asp + Ala131Gln + Tyr208Thr
Gly125Pro + Phe183Pro + Asn198Glu
Asn60Ser + Ile105Thr + Thr207Glu
Thr64Ser + Pro127Asp + Ala131Thr
Ser99Asp + Leu124Asn + Phe183Pro
Thr64Gln + Ser101Asp + Leu211Ser
Pro195Gln + Val197Gly + Leu211Ser
Gly100Asn + Tyr102Gly + Thr207Pro
Asn198Ser + Gln200Asp + Leu211Pro
Tyr102Met + Ser182Glu + Leu211Ala
Gly61Asn + Gln200Asn + Gly213Asn
Ser99Asp + Gly152Pro + Gly157Ser
Leu124Ser + Tyr161Met + Gln200Glu
Tyr102Met + Leu211Glu + Thr214Ser
Asp58Glu + Gly98Asn + Tyr161Asn
Ile159Ser + Gln200Asn + Tyr208Asn
Thr64Asn + Ala156Gly + Leu211Asp
Gln200Asn + Ser210Glu + Leu211Thr
Asn60Asp + Gly155Pro + Val197Asn
Ala156Gln + Asn198Glu + Gly205Gln
Gln57Asp + Gln200Ser + Tyr208Thr
Leu124Ile + Ala209Glu + Ser210Asp
Gly59Glu + Asn60Asp + Leu211Ala
Ala131Gly + Gly152Asp + Asn153Glu
Tyr203Val + Ser210Glu + Leu211Glu
Gly152Asn + Ser210Asp + Leu211Glu
Phe183Val + Ser210Asp + Leu211Asp
Tyr102Leu + Ser210Asp + Leu211Glu
Gln200Asn + Thr207Glu + Tyr208Glu
Ala156Ser + Thr207Glu + Tyr208Asp
Pro129Asp + Ser130Asp + Asn198Ser
Asn198Ser + Gln200Asp + Ser210Asp
Leu124Cys + Gln200Glu + Ser210Glu
Thr64Gly + Gln200Asp + Ser210Asp
Gly61Asn + Gln200Asp + Ser210Glu
Phe183His + Val197Glu + Asn212Asp
Ala96Gly + Ser101Glu + Ser103Glu
Ser126Glu + Ser128Glu + Asn198Ser
Gly61Pro + Ser154Asp + Ala156Glu
Val93Asp + Ser104Asp + Leu211Ala
Ala96Ser + Gly125Asp + Tyr161Asp
Ser97Asp + Ser99Glu + Leu211Cys
Ser97Asp + Ser99Glu + Asn153Gln
Ala96Pro + Gly152Asp + Ser154Asp
Gly98Asn + Asn198Asp + Gln200Asp
Asn60Ser + Asn198Glu + Gln200Asp
Pro129Ser + Asn198Asp + Gln200Asp
Gln57Glu + Gly59Glu + Leu211Gln
Ser128Asp + Ser130Glu + Ala209His
Ser158Asp + Ser160Glu + Gln185Asp
Pro127Gln + Ser210Glu + Asn212Asp
Ser210Glu + Leu211Asn + Asn212Asp
Val197Asp + Gln200Glu + Ser210Asp
Phe183Glu + Tyr208Val + Gly213Asp
Pro127Glu + Gly152Glu + Tyr161Asp
Leu94Glu + Ser101Asp + Leu124Ile
Leu94Glu + Ser101Asp + Gln200Asn
Pro127Gln + Asn153Glu + Ala156Glu
Asp58Glu + Gly61Gln + Gly95Asp
Pro129Gly + Val197Asp + Ser210Glu
Asp58Glu + Gly61Glu + Gly95Glu
Val197Glu + Ser210Asp + Gly213Asp

Ser154Glu + Ser182Glu + Pro204Ser
Ser101Glu + Gly125Glu + Ser126Glu
Ser99Asp + Ser104Asp + Ile105Leu
Ser128Glu + Ala131Glu + Gly196Gln
Gly61Glu + Ser97Asp + Ala131His
Ser97Asp + Gly100Asp + Ser104Glu
Asp58Glu + Pro204Asn + Gly205Asp
Gln185Glu + Leu211Cys + Gly213Asp
Gln200Asp + Thr207Glu + Leu211Asn
Gly125Ser + Gln200Asp + Thr207Glu
Gln200Glu + Thr207Asp + Leu211Cys
Asp58Glu + Val93Gly + Ser97Glu
Asp58Glu + Ser97Glu + Tyr203Asn
Gly61Glu + Gly95Asn + Thr207Asp
Ala96Pro + Thr207Asp + Ser210Asp
Pro204Asn + Thr207Glu + Ser210Asp
Gly100Pro + Thr207Asp + Ser210Asp
Gly61Asp + Thr207Asp + Ser210Asp
Asp58Glu + Thr64Asp + Ser97Glu
Asn153Asp + Gly157Glu + Ala181Glu
Ser130Asp + Ser160Asp + Gly205Gln
Tyr102Asp + Ser128Asp + Ser160Asp
Gln57Asp + Ser206Asp + Thr207Glu
Ser99Asp + Ser126Glu + Gly152Gln
Ala181His + Asn198Glu + Thr214Glu
Gln57Asn + Thr64Glu + Gln200Glu
Thr64Asp + Leu124Thr + Gln200Asp
Gly98Asp + Gly125Glu + Thr207Gln
Asn198Glu + Gln200Glu + Pro204Glu
Asp58Glu + Gly59Asp + Gln200Asp
Leu124Asp + Val197Asp + Asn198Asp
Pro129Glu + Asn212Asp + Gly213Glu
Ser158Asp + Ser210Asp + Leu211Glu
Ser101Glu + Tyr102Glu + Gln200Asp
Ser103Asp + Ser104Asp + Asn198Asp
Asn60Glu + Ser103Glu + Ser104Glu
Ser182Asp + Gln200Asp + Ser210Asp
Gly157Glu + Gln200Glu + Ser210Asp
Gln57Asp + Gln200Asp + Ser210Glu
Ser99Glu + Gln200Asp + Ser210Asp
Ser182Glu + Asn198Asp + Gln200Glu
Gln57Ser + Gln200Asp + Gly213Asp
Ser99Glu + Ser103Asp + Ile159Met
Ser99Asp + Ser103Asp + Gly213Gln
Gly155Glu + Gln185Glu + Asn198Glu
Gly155Asp + Gln185Glu + Ser210Asp
Gln57Asp + Thr64Glu + Ser210Glu
Thr207Glu + Leu211Glu + Gly213Asp
Ser126Asp + Ser160Asp + Ser210Asp
Ser130Glu + Asn198Asp + Ser210Asp
Ser126Asp + Asn198Asp + Ser210Glu
Ser101Asp + Asn198Glu + Leu211Glu
Gly155Glu + Asn198Asp + Leu211Glu
Asp58Glu + Asn60Glu + Ser103Asp
Ser99Glu + Ser104Glu + Ser126Glu
Gly59Asp + Gly61Gln + Ser99Asp
Asn60Glu + Ser158Glu + Gln185Glu
Gly100Glu + Ser104Asp + Ser210Glu
Gly100Asp + Ser104Asp + Ser182Glu
Ser128Glu + Ser130Asp + Asn198Glu
Ser154Glu + Gln200Asp + Leu211Glu
Ser103Asp + Gln200Glu + Leu211Asp
Ser103Glu + Gln200Glu + Leu211Asp
Ser126Asp + Ala156Glu + Ser182Asp
Ser158Asp + Ser160Glu + Val197Glu
Ser158Asp + Ser160Asp + Val197Glu
Val93Gln + Gly125Glu + Ser158Glu
Gln57Asp + Leu124Asp + Ser126Asp
Asn60Asp + Ser210Glu + Asn212Glu
Gly157Asp + Ser210Glu + Asn212Asp
Ser99Glu + Ser101Glu + Ser210Glu
Asp58Glu + Asn198Glu + Pro204Glu
Tyr102Asp + Ser130Glu + Ser182Asp
Asn60Asp + Gly95Glu + Ser128Asp
Leu94Glu + Ser97Asp + Ser206Glu
Gln57Asp + Ser126Glu + Gly152Asp
Leu94Glu + Ser101Glu + Leu211Asp

TABLE 34-continued

Multi-loop Triple Mutation Variants

Gly59Glu + Ser97Glu + Ser182Glu
Gly100Asp + Ser103Glu + Ser206Asp
Asn60Glu + Gln185Glu + Thr214Glu
Asn60Glu + Ser130Glu + Pro204Asp
Asn60Asp + Asn198Asp + Pro204Asp
Ser99Asp + Ser182Glu + Gln185Asp
Pro204Asp + Ser210Glu + Leu211Gly
Tyr161Val + Pro204Glu + Ser210Glu
Ser101Glu + Asn198Asp + Gly213Glu
Leu124Asp + Ser154Glu + Val193Ser
Ser99Glu + Ala181Glu + Asn212Asp
Ala96Asp + Gly100Asp + Ser154Glu
Gly61Asp + Ser99Asp + Ser210Glu
Asp58Glu + Thr207Glu + Ser210Asp

TABLE 35

Multi-loop Quadruple Mutation Variants

Gln57Ser + Asn60Ser + Leu94Gly + Gln200Glu
Val93Gln + Tyr102Cys + Thr207Gly + Gly213Asp
Ile105Val + Leu124Ile + Ser154Glu + Asn198Gln
Leu94Gly + Ser103Glu + Gln200Asn + Ala209Gly
Ala156His + Gln200Ser + Thr207Pro + Leu211Thr
Pro129Asn + Gly155Asp + Ala209Gln + Asn212Gln
Leu124Pro + Ala194Asn + Asn198Glu + Gln200Asn
Gly61Ser + Asn198Gln + Gln200Ser + Leu211His
Tyr203Thr + Thr207Asn + Tyr208Gly + Asn212Glu
Gln57Asn + Asn153Asp + Leu211Ser + Gly213Pro
Ala131Asn + Gln185Ser + Val193Ser + Gln200Asn
Ala181Gly + Ala194Pro + Asn198Ser + Asn212Asp
Ser101Asp + Leu124Val + Pro195Gln + Thr207Pro
Gly95Asp + Asn198Gln + Gln200Asn + Thr207Ser
Ala96Gln + Tyr102Pro + Ser182Glu + Val197Asn
Asn60Gln + Gly100Ser + Ser101Asp + Ile159Pro
Gly63Asn + Asn153Asp + Gly205Ser + Thr207Ser
Ser126Glu + Ala131Pro + Asn153Glu + Phe183Thr
Asn153Gln + Gly205Pro + Ser210Glu + Gly213Pro
Ile159Glu + Ala194Ser + Pro204Gly + Leu211Ile
Asp58Glu + Val93Glu + Ala194Pro + Gln200Ser
Gly95Asp + Ile105Gln + Phe183Cys + Asn198Gln
Gly59Pro + Gly98Asn + Leu211Val + Thr214Asp
Gly61Pro + Val93Pro + Pro129Asn + Gly213Pro
Gln57Asn + Ala156Pro + Ala181Pro + Phe183Gly
Gly95Gln + Gly152Asp + Phe183Met + Asn198Gln
Gly59Ser + Gly95Asn + Pro127Gln + Ser210Glu
Val197Cys + Asn198Gln + Thr207Glu + Leu211Cys
Pro129Asn + Ser154Asp + Phe183Pro + Leu211Cys
Gly59Gln + Gly100Glu + Ala131Gly + Ala181Gln
Gly61Glu + Tyr161Leu + Pro204Ser + Gly213Pro
Asp58Glu + Ile159Met + Tyr161Gln + Gly213Asn
Ile105Pro + Leu124Asn + Ile159Ser + Asn198Asp
Tyr102Pro + Ala156Ser + Phe183His + Pro204Asp
Tyr102Pro + Ile105Pro + Gln200Asn + Pro204Glu
Thr64Ser + Ile105Glu + Gln200Ser + Thr214Pro
Gly63Gln + Gly100Asp + Asn198Ser + Leu211His
Asn60Asp + Ile105Leu + Gly152Gln + Ala209Gln
Gly152Gln + Gln185Asn + Gly205Ser + Leu211Ala
Gln57Ser + Gly100Pro + Pro127Gly + Asn198Glu
Leu94Cys + Pro127Gly + Val197Gly + Asn198Ser
Leu94Thr + Tyr102Cys + Leu124Cys + Tyr208Ser
Ala96Ser + Ala181Asn + Pro204Ser + Tyr208Ile
Leu124Val + Asn198Gln + Pro204Gly + Leu211Ile
Gly61Asn + Ala96Thr + Gly98Ser + Ser210Asp
Thr64Pro + Ala96Pro + Gly155Glu + Leu211Cys
Gly157Asp + Val197Pro + Asn198Gln + Pro204Gly
Pro129Gln + Gly155Pro + Val197His + Ser210Glu
Val93Met + Ser182Asp + Gln200Ser + Gly213Ser
Leu94Glu + Pro127Ser + Gln200Asn + Leu211Met
Ala96His + Gly98Pro + Pro129Ser + Pro204Asp
Ser97Asp + Gly100Pro + Leu124Pro + Thr207Asn
Gly59Asn + Thr207Pro + Ser210Glu + Leu211Thr
Ala96Gly + Ala131Asn + Gly155Pro + Ser210Glu
Asn153Ser + Val197Thr + Gln200Asn + Ser210Glu

TABLE 35-continued

Multi-loop Quadruple Mutation Variants

Asn60Ser + Ile105Thr + Ser182Glu + Thr207Ser
Gly98Asn + Tyr161Asn + Gln200Asn + Tyr208Asn
Leu94Gly + Ser99Glu + Leu124Ser + Ala181Pro
Ser104Glu + Ala131Pro + Leu211Ser + Gly213Ser
Tyr102Asp + Asn198Ser + Thr207Gln + Leu211Asn
Gly98Pro + Ser206Glu + Leu211Gly + Gly213Pro
Ala131Asn + Ala181Thr + Tyr208Gln + Ser210Asp
Gly155Gln + Tyr161Cys + Gln185Ser + Ala209Gln
Thr64Asn + Val93Asn + Ser126Glu + Gln200Asn
Ala131Pro + Phe183Ala + Thr207Asp + Thr214Gln
Ser97Glu + Leu124Pro + Ala131Ser + Pro204Gly
Gly59Asp + Tyr161His + Thr207Gly + Leu211Met
Gly95Pro + Gly98Pro + Ser101Glu + Leu211Cys
Gly59Ser + Thr64Gly + Leu124Ile + Gly125Glu
Thr64Pro + Ser101Glu + Tyr161Gly + Gln200Asn
Gly100Glu + Pro195Ser + Val197Ser + Thr207Asn
Ser160Glu + Tyr161Gln + Pro204Ser + Leu211Gln
Leu124Met + Tyr161Leu + Ser182Glu + Leu211His
Ile105Thr + Pro127Asn + Gly157Asn + Tyr161Pro
Gln185Asn + Thr207Gln + Asn212Ser + Thr214Gln
Val93Gln + Leu94Ser + Gly98Glu + Thr214Gly
Asn153Gln + Ser154Glu + Ala181Asn + Leu211Val
Gly125Asn + Ser154Asp + Val197Ser + Leu211Val
Ile159Asn + Gln185Glu + Val197Met + Asn212Gln
Ala96Pro + Gly196Gln + Val197Ala + Asn198Gln
Ala131Glu + Gly152Gln + Ala194Ser + Leu211Ile
Phe183Ser + Asn198Asp + Gln200Ser + Thr207Pro
Gly95Gln + Gly100Ser + Ser130Glu + Thr207Gln
Leu124Cys + Gly152Ser + Tyr161Met + Thr207Gln
Leu94Met + Leu124Met + Leu211Ala + Asn212Ser
Gly61Asn + Ala96Ser + Gly125Pro + Gln200Asp
Ile159Gln + Val197Glu + Gln200Asn + Tyr208His
Tyr161Asn + Ser182Glu + Ala209Ser + Asn212Ser
Gln57Asn + Gly152Ser + Phe183Glu + Gln185Asn
Asn198Gln + Thr207Glu + Ala209Gly + Gly213Pro
Val197Glu + Tyr208Gly + Ala209Pro + Leu211Pro
Ala131His + Gly205Gln + Tyr208Asp + Leu211Gln
Gly61Asn + Val93Cys + Gly98Gln + Leu211Gly
Leu124Ala + Val197Gln + Ser210Glu + Asn212Ser
Pro127Gln + Ile159Leu + Ser160Glu + Ala209Ser
Asp58Glu + Gly59Gln + Gly205Gln + Leu211Cys
Asp58Glu + Phe183Tyr + Asn198Ser + Thr207Gln
Pro204Gly + Ser206Asp + Thr207Gln + Leu211His
Gln57Asp + Gly98Ser + Ile105Gln + Tyr208Met
Ser103Glu + Gly155Ser + Ala209His + Leu211Thr
Ser104Glu + Ala181Asn + Asn198Gln + Leu211Thr
Gln185Asn + Val197Cys + Gly205Asp + Leu211Cys
Gly59Gln + Tyr102Glu + Pro127Gly + Ala209Thr
Ala131Thr + Asn153Ser + Val193Gln + Val197Asp
Ala131Ser + Asn153Ser + Phe183Tyr + Ala194Ser
Pro129Gln + Ala181Pro + Ala209His + Leu211Ala
Pro127Gly + Gly196Asn + Ser210Glu + Leu211Met
Leu94Ile + Gly100Asp + Asn198Asp + Tyr208Leu
Asn153Ser + Gly155Pro + Gly205Asp + Leu211Ser
Gly63Asn + Gly152Pro + Asn198Gln + Thr207Glu
Gly152Ser + Ser160Glu + Tyr161His + Leu211Met
Pro129Asn + Asn153Gln + Gly155Gln + Ser210Asp
Gln57Ser + Thr64Gln + Val197Asn + Gln200Asp
Ser126Asp + Asn153Gln + Pro204Gln + Leu211Gln
Gly61Gln + Ala96Gln + Phe183Leu + Leu211Thr
Gly63Asn + Ala156Asn + Asn198Ser + Ser210Glu
Gly59Asp + Gly205Pro + Thr207Gln + Leu211Asn
Gly98Ser + Leu124Pro + Ile159Thr + Val197Glu
Gly205Pro + Ala209Gln + Ser210Glu + Leu211Pro
Pro129Ser + Thr207Gly + Ser210Glu + Leu211Asn
Gln57Asp + Ala131Gln + Leu211Met + Asn212Gln
Thr64Asn + Tyr161Ile + Phe183Asn + Ser210Asp
Gly155Gln + Pro204Ser + Ala209His + Leu211Asp
Gly100Gln + Gly157Pro + Ile159Leu + Ser160Asp
Gly98Pro + Ser103Asp + Ala131Gly + Leu211Asn
Gln57Ser + Gly61Pro + Ile159Gln + Leu211Asn
Gly155Ser + Gln185Asp + Val199Met + Thr207Gly
Asp58Glu + Ala96Gly + Phe183Thr + Thr207Gly
Val93Ala + Ser126Glu + Ala131Thr + Thr207Pro
Thr64Gln + Gly98Pro + Val197Thr + Gln200Glu
Gly152Glu + Asn153Gln + Gly155Pro + Gly213Pro
Ser154Glu + Asn198Ser + Gln200Ser + Leu211Ser

TABLE 35-continued

Multi-loop Quadruple Mutation Variants

Ile105Thr + Ile159Thr + Phe183Val + Leu211Asp
Leu124Pro + Ser128Glu + Ile159Met + Leu211Pro
Gln57Asp + Asp58Glu + Leu211Thr + Thr214Ser
Gly59Asp + Asn60Asp + Val197Pro + Val199Ala
Ala96Thr + Leu124Cys + Val197Asp + Asn198Glu
Thr64Asn + Ala156Gly + Ser210Asp + Leu211Asp
Leu124Ser + Gln200Asn + Gly205Asp + Ser206Glu
Gly63Pro + Ala156Gly + Gly157Asp + Ile159Gln
Thr64Gly + Gly100Glu + Ser101Glu + Leu211Asn
Gly61Asn + Asn153Gln + Gln200Asp + Ser210Asp
Leu124Ser + Gln200Glu + Ser210Glu + Leu211Gln
Val197Gln + Gln200Glu + Thr207Ser + Ser210Glu
Ala209Glu + Ser210Glu + Leu211Glu + Gly213Ser
Thr207Pro + Ser210Glu + Leu211Asp + Asn212Glu
Ser101Asp + Ser104Asp + Asn198Gln + Leu211Ser
Thr64Asn + Ala96Asp + Gly98Asp + Gly213Asn
Asn198Glu + Gln200Asn + Ser210Asp + Leu211Thr
Tyr161Val + Asn198Glu + Ser210Glu + Gly213Asn
Val93Pro + Asn198Glu + Gln200Ser + Ser210Glu
Val193Pro + Asn198Asp + Thr207Ser + Ser210Asp
Gln185Ser + Asn198Asp + Gln200Asp + Ser210Glu
Gly95Ser + Gly98Asp + Asn198Asp + Leu211Asp
Val93His + Ala96His + Gln200Glu + Ala209Asp
Leu94Cys + Ile159Leu + Gln200Asp + Ala209Glu
Gln57Asn + Gly61Asp + Thr64Asp + Leu94Val
Ala156Gln + Asn198Glu + Gly205Gln + Asn212Asp
Tyr102Asp + Ser104Asp + Phe183Gln + Val197His
Ala96Ser + Asn153Ser + Gly155Asp + Ser182Asp
Ala96Asn + Asn153Glu + Gln185Glu + Thr214Gly
Asp58Glu + Gly61Glu + Asn153Ser + Leu211Cys
Pro129Ser + Asn198Asp + Gln200Asp + Leu211Pro
Gly125Ser + Asn198Asp + Gln200Glu + Leu211Ala
Asn198Asp + Gln200Asp + Thr207Pro + Leu211Pro
Gly98Pro + Asn198Asp + Gln200Glu + Tyr203Ser
Asn198Glu + Gln200Glu + Tyr203Leu + Thr214Asn
Gly100Asp + Tyr102Asp + Asn153Ser + Tyr208Leu
Thr64Gln + Thr207Asn + Ser210Glu + Asn212Glu
Pro127Gln + Ile159Cys + Ser210Glu + Asn212Asp
Val93Ala + Ser99Asp + Ser101Glu + Ile105Asn
Gly100Gln + Gly155Gln + Asn212Asp + Thr214Asp
Gly95Ser + Tyr102Leu + Pro129Glu + Ser160Asp
Gly5Ser + Pro129Asp + Ser160Asp + Leu211Pro
Thr64Pro + Ala96Thr + Asn153Glu + Ser182Asp
Asp58Glu + Gly61Gln + Gly95Asp + Ala181Thr
Gly63Pro + Ser99Asp + Ser101Glu + Ser103Glu
Asn153Gln + Val197Asp + Leu211Glu + Thr214Glu
Gly152Ser + Ala181Pro + Asn198Asp + Gly213Asp
Ser154Glu + Gly155Pro + Ser160Asp + Asn198Gln
Gly152Asn + Ser154Glu + Ser158Glu + Leu211Asn
Asn60Glu + Leu94Asp + Tyr208Ala + Gly213Pro
Thr64Asp + Gln200Asp + Ser210Asp + Gly213Pro
Ser103Asp + Ser130Glu + Ile159Ala + Thr202Gln
Ser103Glu + Ser130Glu + Asn198Gln + Pro204Asn
Thr207Pro + Ser210Asp + Leu211Glu + Thr214Glu
Ser210Glu + Leu211Met + Gly213Glu + Thr214Glu
Gly125Ser + Gln200Asp + Ser206Glu + Thr207Glu
Ala9Pro + Gly125Asp + Ser154Asp + Ala156Asp
Ser99Asp + Ser104Asp + Ile105Met + Gln200Ser
Gly59Gln + Ser128Asp + Ser154Glu + Ser160Asp
Asp58Glu + Gly98Asp + Leu124Ser + Tyr161Met
Gln185Glu + Asn198Ser + Leu211Cys + Gly213Asp
Gly61Gln + Gly98Pro + Gln200Asp + Thr207Glu
Gly100Gln + Gln200Glu + Tyr203Pro + Thr207Glu
Val197Pro + Gln200Asp + Thr207Asp + Ala209Gln
Asp58Glu + Val93Gly + Ser97Glu + Tyr161Ile
Asp58Glu + Ser97Asp + Gln200Ser + Tyr208Thr
Gly152Asp + Gly157Glu + Val199Ser + Thr207Ser
Val197Gln + Pro204Ser + Thr207Asp + Ser210Asp
Gly125Asn + Pro129Asn + Thr207Glu + Ser210Glu
Ser101Asp + Ser128Asp + Pro129Glu + Gly152Ser
Leu94Ala + Asn198Glu + Gln200Asp + Thr214Glu
Ala96Ser + Ile105Glu + Ser126Glu + Ser160Asp
Ser130Asp + Ser158Glu + Ser160Asp + Asn198Gln
Leu124Asp + Phe183Glu + Tyr208Val + Gly213Asp
Ser101Asp + Ser126Glu + Ala156Gly + Thr207Asn
Asp58Glu + Asn60Asp + Gly100Asp + Ala181Gln
Asp58Glu + Gly205Ser + Thr207Asp + Tyr208Glu

Thr64Gln + Leu94Glu + Ser97Asp + Gly125Asp
Ser158Glu + Ile159Asp + Leu211Val + Gly213Glu
Gln57Asp + Thr64Asp + Leu124Thr + Gln200Asp
Gly61Glu + Gln200Ser + Gly205Glu + Ser210Glu
Asp58Glu + Ile105Gly + Leu211Asp + Asn212Glu
Gln57Asp + Asp58Glu + Gln200Glu + Pro204Ser
Gln57Asp + Asp58Glu + Ala96His + Ser160Glu
Gly157Asp + Gln200Ser + Ala209Glu + Ser210Glu
Gly59Glu + Asn60Asp + Gly95Asn + Gln185Ser
Ser101Asp + Tyr102His + Val197Glu + Asn198Glu
Gly152Asp + Asn153Glu + Ser210Asp + Leu211Met
Gly59Asp + Tyr102Ile + Ser210Asp + Leu211Asp
Ser101Glu + Tyr102Asp + Gln200Glu + Leu211Asn
Gly59Asn + Ser130Glu + Gly205Asp + Ser206Asp
Ser128Asp + Tyr161Gly + Ser206Asp + Thr207Glu
Asn60Gln + Ser97Glu + Ser182Asp + Phe183Asp
Gly98Glu + Ser99Asp + Ser160Glu + Thr207Gln
Gly98Asp + Thr202Gln + Thr207Glu + Tyr208Asp
Ser154Glu + Tyr161Leu + Ser210Glu + Asn212Glu
Asn60Asp + Ile105Ser + Gln200Asp + Ser210Glu
Ala131Asp + Gln200Glu + Ser210Asp + Leu211Pro
Gln57Asp + Gln200Glu + Ser210Asp + Gly213Pro
Pro129Gln + Ser160Glu + Gln200Asp + Ser210Glu
Pro129Asp + Asn198Gln + Gln200Asp + Ser210Glu
Gly59Glu + Thr64Gly + Gln200Glu + Ser210Glu
Asn60Glu + Ala96Glu + Asn198Gln + Ser210Glu
Asn60Asp + Ala96Asp + Ser130Glu + Ala156Pro
Gln57Ser + Ile159Ser + Gln200Asp + Gly213Glu
Gly155Asp + Gln185Glu + Asn198Glu + Tyr203His
Ser104Glu + Leu124Asp + Gln185Ser + Val197Gly
Gly59Gln + Ser101Glu + Ser103Asp + Asn198Asp
Asn60Gln + Ser126Asp + Ser128Asp + Ser210Glu
Ser126Glu + Ser128Asp + Gly155Asn + Asn212Glu
Ser103Asp + Asn198Glu + Ser210Glu + Thr214Gln
Ser160Glu + Asn198Glu + Ser210Asp + Leu211Ser
Asp58Glu + Asn198Asp + Thr207Pro + Ser210Asp
Gly98Asn + Ser103Glu + Asn198Glu + Ser210Glu
Ser128Asp + Gly155Pro + Asn198Asp + Ser210Asp
Gly152Glu + Asn198Asp + Thr207Asn + Ser210Asp
Ser101Asp + Pro129Gly + Asn198Asp + Leu211Glu
Asn198Glu + Tyr208Asp + Gly213Ser + Thr214Ser
Ser97Glu + Gly152Glu + Ser154Asp + Gln185Ser
Thr64Asp + Ser210Asp + Leu211Val + Gly213Gln
Thr64Glu + Gly205Ser + Ser210Asp + Leu211Asn
Leu94Thr + Ser126Glu + Pro204Glu + Thr207Asp
Gly100Gln + Tyr102Asp + Pro204Asp + Thr207Asp
Ser101Glu + Asn198Glu + Gln200Glu + Leu211Ala
Thr64Asp + Ser99Glu + Pro204Glu + Thr207Asn
Gly155Pro + Ser182Asp + Gln200Asp + Leu211Glu
Gly100Asn + Ser160Glu + Gln200Glu + Leu211Glu
Asp58Glu + Val93Asn + Ser206Glu + Leu211Met
Ala131Pro + Asn153Glu + Ser182Asp + Asn198Glu
Asp58Glu + Ala96Glu + Pro127Ser + Gly157Glu
Leu94Asp + Tyr102Leu + Thr207Glu + Ala209Glu
Ala96Gln + Ser158Asp + Ser160Glu + Val197Gly
Gly100Asp + Ser126Glu + Ser154Asp + Ile159Gly
Tyr102Asn + Gln200Glu + Thr207Glu + Gly213Asp
Val93Glu + Pro127Ser + Ser210Asp + Asn212Asp
Ile105Asp + Ala131Glu + Ala156Gln + Thr202Pro
Gln57Ser + Ser126Glu + Gly152Asp + Ser210Glu
Ser126Glu + Gly152Glu + Asn198Glu + Thr207Asn
Leu94Glu + Ser101Asp + Tyr102Leu + Thr207Glu
Leu94Asp + Ser101Asp + Ser154Asp + Gly213Asn
Asn60Asp + Thr64Glu + Ser103Glu + Thr214Asn
Asp58Glu + Val197Asp + Ser210Glu + Leu211Pro
Ser160Asp + Phe183Tyr + Val197Asp + Ser210Asp
Pro129Glu + Val197Glu + Ser210Glu + Leu211His
Ser126Glu + Ser130Glu + Ser182Glu + Gln200Ser
Ser126Asp + Ser130Glu + Asn198Asp + Leu211His
Thr64Ser + Pro204Asp + Ser210Asp + Leu211Ile
Ser97Asp + Gly100Glu + Gly152Pro + Asn198Glu
Ser97Asp + Gly100Glu + Gln200Glu + Tyr208Gly
Asp58Glu + Gly59Pro + Ser154Asp + Gly157Asp
Gly155Gln + Ala181Glu + Gln185Asp + Ser210Asp
Gly125Glu + Asn153Asp + Gln200Asp + Tyr208Pro
Gln57Ser + Ser101Asp + Ser154Asp + Ser160Asp
Ser104Asp + Asn198Glu + Ala209Asp + Leu211Met

TABLE 35-continued

Multi-loop Quadruple Mutation Variants

Leu124Ile + Gly125Pro + Pro129Glu + Ser158Glu
Ser154Glu + Ser158Asp + Gly205Pro + Thr207Glu
Gly152Glu + Ser158Asp + Gln200Asp + Thr207Pro
Ala131Asp + Gly152Asp + Ser158Asp + Val197Thr
Ser103Glu + Gln200Glu + Thr207Pro + Asn212Asp
Ser130Glu + Gln200Glu + Thr202Ser + Asn212Glu
Asn60Glu + Leu94Glu + Ile105Leu + Ser130Glu
Ser99Glu + Pro127Asp + Pro129Ser + Ser154Glu
Asn153Glu + Ile159Gly + Leu211Glu + Gly213Asn
Ala156Asp + Ser160Glu + Gly205Gln + Leu211Asp
Ser104Asp + Ser130Asp + Gly155Pro + Gly157Asn
Gly98Asp + Ser101Asp + Ser128Asp + Ala181Gln
Asn60Asp + Tyr102Gly + Gln200Glu + Thr207Asp
Gly59Pro + Ala131Asp + Ser154Asp + Thr214Asp
Ser103Glu + Ala131Asp + Asn198Glu + Asn212Gln
Asn60Asp + Gly98Asn + Ser103Glu + Ser130Asp
Ser160Asp + Phe183Ser + Ser210Glu + Thr214Asp
Asp58Glu + Ser99Asp + Val197Pro + Pro204Asn
Asp58Glu + Gly98Glu + Gly155Gln + Leu211Asp
Thr64Glu + Leu94Glu + Gln185Ser + Ser210Asp
Asn60Asp + Ser99Glu + Ala181Glu + Val197Asn
Ser128Glu + Ser206Asp + Ala209Glu + Asn212Gln
Gly100Asp + Gln185Glu + Leu211Ser + Gly213Glu
Ser126Glu + Ser154Glu + Asn198Gln + Gly205Glu
Gly125Glu + Val197Thr + Gln200Glu + Thr207Asp
Asn60Glu + Ile195Pro + Ile159Val + Leu211Ile
Pro129Asn + Gln200Glu + Pro204Asp + Thr207Gln
Asn198Ser + Gln200Asp + Tyr293Ile + Pro204Glu
Gly98Ser + Ser193Glu + Ala131Glu + Ser210Asp
Ser103Glu + Ala131Asp + Tyr161His + Ser219Glu
Gly61Glu + Gly125Pro + Ser126Glu + Thr207Glu
Gly152Asp + Gly157Asp + Pro204Asp + Ala209Thr
Pro127Asp + Asn153Glu + Pro294Ser + Ser206Asp
Gln57Asp + Gln299Ser + Thr207Glu + Ser210Glu
Ser154Asp + Thr297Glu + Ser219Glu + Thr214Gln
Ser130Glu + Pro294Asn + Thr297Glu + Ser210Asp
Asp58Glu + Val93Ala + Ser101Glu + Ser139Asp
Gly125Glu + Ser139Asp + Gln299Asp + Leu211Thr
Leu94Glu + Ser182Asp + Thr297Gln + Asn212Glu
Ser97Glu + Ile159Asp + Phe183Ile + Thr214Asp
Gly95Glu + Ser103Asp + Pro129Asn + Ala131Pro
Asn69Gln + Gly61Glu + Ser130Asp + Ser210Asp
Ser101Glu + Ser126Asp + Ala299Glu + Asn212Ser
Ser101Glu + Ser126Asp + Tyr161Leu + Gly295Glu
Asn60Ser + Gly98Asp + Ser126Glu + Leu211Thr
Val93Glu + Ser97Glu + Pro129Ser + Gln299Glu
Thr64Asn + Gln299Asn + Thr207Asp + Leu211Asp
Gly98Glu + Ser104Asp + Ser126Asp + Phe183Gly
Gly125Asp + Gly157Asp + Thr297Gln + Gly213Glu
Leu94Asp + Ser128Asp + Gly152Asp + Leu211Met
Ser158Glu + Ser182Glu + Thr297Gly + Tyr298Cys
Gln200Asn + Pro204Gln + Ser210Glu + Thr214Glu
Thr64Glu + Ala131Asp + Ser210Asp + Leu211Ala
Asp58Glu + Gly59Pro + Gly199Pro + Thr207Asp
Asn198Gln + Gln209Glu + Ser296Glu + Tyr208His
Gly95Pro + Ser126Asp + Ala131Glu + Gln290Glu
Ser97Glu + Ser101Glu + Gln200Asp + Pro204Asn
Ser97Asp + Ser101Asp + Gly125Gln + Ser210Asp
Ala131Gly + Ser154Asp + Tyr161Glu + Ser210Asp
Ser126Glu + Pro204Asp + Thr207Gly + Ser210Asp
Gly98Glu + Ser104Asp + Val197Glu + Asn198Ser
Ser104Asp + Ser139Glu + Ala156Thr + Thr207Asp
Ser104Asp + Ser130Asp + Ala131Thr + Thr207Asp
Pro127Ser + Ser158Asp + Gln200Ser + Thr214Glu
Asn60Asp + Tyr102Ser + Val197Asn + Thr297Asp
Ser101Asp + Pro127Ser + Ala131Glu + Ala156Glu
Asp58Glu + Ser99Asp + Gln299Glu + Tyr298Ser
Asp58Glu + Ser99Asp + Leu124His + Asn198Glu
Gly61Glu + Thr64Ser + Val93Asp + Tyr208Gly
Asn60Glu + Gln185Ser + Asn198Ser + Ser296Asp
Gly61Pro + Ser158Asp + Ala181Glu + Leu211Asp
Tyr161Glu + Gln209Glu + Tyr293His + Pro294Glu
Gly61Glu + Gly157Asp + Leu211Met + Asn212Asp
Gly59Ser + Gly98Glu + Tyr102Glu + Ser158Asp

TABLE 36

Multi-loop Quintuple Mutation Variants

Val93Gln + Tyr102Cys + Ser154Glu + Asn198Gln + Thr207Gly
Leu94Gly + Leu124Ile + Asn198Gln + Ala209Gly + Ser210Glu
Leu124Asp + Ala156His + Gln200Ser + Thr207Pro + Leu211Thr
Pro129Asn + Gly155Asp + Gly157Asn + Thr207Ser + Asn212Gln
Gly61Ser + Gly98Glu + Pro127Asn + Gln200Ser + Thr207Pro
Ala156Gln + Gln185Ser + Gln200Asn + Ser210Asp + Leu211His
Gly63Asn + Tyr102Pro + Ala156Gln + Ser182Glu + Val197Asn
Ala96Pro + Ile105Pro + Thr207Ser + Leu211Ile + Thr214Pro
Val93Asn + Val197Gly + Asn198Gln + Ser210Asp + Leu211Ser
Val93Pro + Leu94Ile + Ile159Asn + Gln200Ser + Thr207Ser
Gly61Pro + Gly95Pro + Ser154Glu + Ala181His + Gly213Pro
Gly157Ser + Ser182Glu + Pro195Gln + Thr207Pro + Leu211Ser
Ser97Glu + Tyr102Met + Asn198Ser + Ala209Gln + Leu211Ala
Leu124His + Ala131His + Gly157Pro + Asn198Asp + Thr202Ser
Gly95Asp + Ala181Pro + Gln200Asn + Leu211Ala + Gly213Gln
Leu94Ile + Gly95Asn + Ser158Glu + Leu211Met + Gly213Ser
Gly98Asn + Gly125Pro + Pro127Gly + Tyr161Ile + Tyr208Met
Ala96Ser + Ser154Glu + Tyr161Gly + Gly196Gln + Val197Gln
Leu94Ser + Gly95Asn + Pro127Asn + Val197Ser + Thr214Asn
Asp58Glu + Val93Gln + Leu94Met + Gln200Asn + Thr207Gln
Gly95Asp + Gly155Ser + Val197Thr + Thr207Gly + Leu211Pro
Gly98Ser + Ala131Glu + Val197Gln + Gln200Ser + Pro204Gly
Gln57Asn + Val93Thr + Tyr102Ser + Leu124Pro + Ser126Asp
Ser101Asp + Tyr102Cys + Leu124Val + Phe183Gly + Val199Asn
Asp58Glu + Thr64Gln + Ile105Pro + Gly125Gln + Asn198Ser
Gly155Glu + Tyr161Val + Pro204Gly + Thr207Pro + Leu211Ile
Gly100Gln + Ser182Asp + Phe183Asn + Asn198Ser + Thr207Gln
Gly98Glu + Pro129Gly + Gly155Pro + Thr207Gly + Thr214Gly
Leu94Met + Gly100Ser + Gly196Gln + Gln200Asn + Asn212Asp
Ser104Glu + Gly152Gln + Asn153Gln + Ala194Gln + Asn212Ser
Pro129Gln + Val197Thr + Tyr208Ile + Ser210Glu + Thr214Ser
Val93Gly + Ala96Asn + Pro129Gln + Ser160Asp + Pro204Gly
Pro127Gln + Ala131Asn + Gly196Ser + Val197Thr + Ser206Glu
Pro127Ser + Ser128Asp + Ala156His + Ala194Gln + Leu211Ala
Gly95Gln + Pro127Gly + Val197Gly + Gly205Asn + Ser210Glu
Ala131His + Pro204Gly + Thr207Asn + Leu211Thr + Gly213Asn
Leu94Gly + Tyr102Gln + Phe183Val + Thr207Ser + Leu211Asp
Gly61Asn + Ile105Met + Gly125Ser + Val193Gly + Asn198Glu
Gly59Pro + Ala96Gly + Ser101Asp + Tyr208His + Leu211His
Tyr102Val + Gln200Asp + Pro204Ser + Leu211Ile + Thr214Pro
Val93Thr + Ser104Glu + Pro195Ser + Val199Pro + Leu211Val
Ile159Asn + Tyr161Ala + Phe183Leu + Ser210Glu + Thr214Gly
Gly59Asn + Pro127Ser + Ile159Ala + Gln200Asn + Leu211Met
Gln57Glu + Val93His + Gly125Gln + Ala131Thr + Ala156Asn
Ser126Asp + Gly157Ser + Asn198Gln + Gln200Ser + Thr207Ser
Gly125Asn + Pro129Ser + Phe183Asp + Thr207Gly + Leu211Gly
Asn60Asp + Leu94Met + Tyr102Pro + Gly152Asn + Thr207Gln
Ile105Leu + Gly152Pro + Ser158Glu + Asn198Ser + Thr214Gly
Ala96Asn + Ala131Thr + Gly157Asn + Thr207Gly + Ser210Glu
Val93Gln + Leu124Met + Ala181Gln + Asn198Glu + Gln200Ser
Pro127Ser + Ile159Thr + Pro195Gly + Asn198Ser + Gln200Glu
Ala96Asn + Val197His + Asn198Ser + Gln200Asn + Asn212Asp
Asp58Glu + Leu94Ala + Leu124Pro + Ala156Gly + Leu211Gln
Ile105Thr + Gly157Pro + Phe183Pro + Val197Asp + Tyr208Val
Gly95Glu + Gly100Gln + Tyr102Gly + Tyr161His + Tyr208Cys
Thr64Gly + Val93Asp + Gly95Pro + Gly100Pro + Asn198Gln
Gln57Asn + Asn60Gln + Ser101Glu + Gly155Ser + Pro204Ser
Gly125Ser + Gln185Asn + Asn198Gln + Ser206Glu + Ala209His
Gly98Ser + Pro129Asn + Val197Glu + Gln200Asn + Tyr208Asn
Gly98Asp + Asn153Gln + Gln200Asn + Pro204Ser + Leu211Ser
Ala96Thr + Ala181Thr + Val197Asn + Gln200Asn + Thr207Pro
Gly95Gln + Pro129Asn + Tyr161Ala + Gln185Asp + Thr207Asn
Gly95Asn + Gly152Gln + Ser160Glu + Ala194Asn + Tyr208His
Gln57Asp + Phe183Leu + Thr207Ser + Ala209Gln + Leu211Met
Ile105His + Gly125Asp + Gly152Asn + Pro204Asn + Tyr208Leu
Gln57Asn + Leu94Glu + Ala96Gln + Pro127Gly + Leu211Pro
Asn153Ser + Tyr161Met + Ala181Gln + Asn198Ser + Ser210Asp
Gly95Asn + Gly98Glu + Pro129Asn + Ala209Pro + Thr214Pro
Gly61Asn + Asn198Ser + Ala209Glu + Leu211Ser + Gly213Pro
Ser99Asp + Pro127Asn + Pro195Asn + Tyr208His + Leu211Cys
Asn60Gln + Thr64Asn + Gly100Asn + Ile105Leu + Pro127Asn
Pro127Gln + Ala194Gln + Gln200Asn + Thr207Ser + Leu211Cys
Thr64Gly + Leu94Gly + Val197Asn + Gln200Ser + Ala209Pro
Gly59Gln + Leu94Ser + Ala96Ser + Leu211Thr + Thr214Glu
Pro129Gly + Ala194Asn + Gln200Ser + Leu211Gln + Asn212Asp
Ala131Gly + Asn153Glu + Thr207Asn + Leu211Thr + Gly213Gln
Gly59Pro + Thr64Asn + Asn198Gln + Ala209Glu + Ser210Asp

TABLE 36-continued

Multi-loop Quintuple Mutation Variants

Gly155Asn + Ser160Asp + Tyr161Glu + Asn198Ser + Leu211Ser
Ser126Glu + Pro127Glu + Gln200Ser + Thr207Ser + Leu211Pro
Ala131Gly + Ala209Thr + Ser210Asp + Leu211Glu + Thr214Gly
Gly61Asn + Ile159Ser + Ser206Glu + Thr207Asp + Leu211Ala
Gly98Glu + Ser99Glu + Tyr161Leu + Phe183Asn + Asn198Gln
Gln57Ser + Val93Asn + Gly155Asn + Gln200Glu + Ser210Glu
Thr64Asn + Gly95Glu + Ala96Asp + Gly98Asp + Gln200Ser
Ile105Ser + Ser210Glu + Leu211Asp + Asn212Asp + Gly213Ser
Ala96Asn + Gly100Ser + Ile105Cys + Asn198Asp + Ser210Glu
Ala96Gln + Gly98Asn + Asn198Asp + Pro204Asn + Ser210Asp
Gly98Gln + Asn198Glu + Gln200Glu + Tyr208Asn + Ser210Asp
Ile105Pro + Leu124Asn + Ile159Ser + Asn198Asp + Leu211Asp
Leu94Gln + Tyr161Pro + Asn198Glu + Thr207Gly + Leu211Gln
Tyr161Gly + Val197Ala + Asn198Gln + Pro204Glu + Ser206Asp
Leu124Ala + Asn198Asp + Tyr208Gly + Ser210Glu + Asn212Asp
Gln185Asn + Asn198Asp + Gln200Glu + Thr207Gln + Leu211Asp
Pro127Gly + Tyr161Ala + Pro204Glu + Thr207Asp + Thr214Ser
Gln57Asn + Leu124Ser + Val197Glu + Asn198Glu + Gln200Glu
Asp58Glu + Ala96Asp + Val197Ala + Gly205Ser + Thr207Gly
Ser158Asp + Ser160Asp + Pro195Ser + Thr207Ser + Leu211Met
Asp58Glu + Asn60Glu + Thr64Glu + Gly157Asn + Leu211Ala
Leu124Glu + Ser126Asp + Ile159Met + Phe183Val + Val193His
Leu94Ile + Pro127Glu + Pro129Asp + Ser130Asp + Tyr203His
Leu94Cys + Ser99Asp + Ser101Glu + Asn198Gln + Asn212Gln
Gly61Asn + Ser128Glu + Ser160Glu + Ala181Asn + Thr207Gln
Tyr161Met + Val197Asp + Gln200Asp + Ser210Glu + Asn212Gln
Val93Ala + Gly125Pro + Ser154Glu + Gly157Asp + Ser158Asp
Leu94Glu + Ser101Asp + Phe183Ala + Gln200Asn + Leu211Met
Leu94Asp + Ser103Glu + Ser104Asp + Asn198Ser + Tyr208Gly
Gly125Asp + Asn153Glu + Ser160Glu + Tyr161Asn + Asn198Ser
Leu94Asn + Pro127Asn + Ser154Asp + Gln185Glu + Thr214Asp
Gly61Gln + Thr64Asn + Asn198Glu + Ser210Asp + Gly213Asp
Leu124Gln + Asn198Glu + Gln200Asp + Thr207Gly + Tyr208Glu
Leu94Glu + Leu124Asp + Pro129Asn + Ala156Ser + Thr207Gly
Gly98Asn + Ala156Pro + Asn198Asp + Gln200Asn + Gly213Asp
Gly95Glu + Gly98Gln + Ser99Glu + Tyr102Cys + Ser104Glu
Gly125Asn + Gln200Asp + Thr207Glu + Ser210Asp + Leu211His
Gly59Asp + Ser97Asp + Ser99Asp + Ala131Pro + Pro204Gly
Gln57Ser + Tyr102Gln + Asn198Asp + Ala209Glu + Leu211Ser
Asn153Asp + Ile159Asp + Tyr161His + Phe183His + Gly213Pro
Gly100Ser + Gly155Asp + Ile159Glu + Val197Met + Thr207Pro
Pro127Ser + Gln200Asp + Thr207Gly + Ser210Asp + Gly213Glu
Ala96Thr + Ser126Glu + Gly152Glu + Ser158Glu + Thr207Asn
Leu94Ala + Gly95Asp + Ser97Asp + Ser101Asp + Thr202Gly
Gly152Ser + Gly205Ser + Thr207Glu + Ser210Glu + Leu211Asp
Tyr161Pro + Pro195Ser + Thr207Asp + Ser210Glu + Leu211Asp
Asp58Glu + Ser97Glu + Ser99Asp + Gln185Asn + Gly196Ser
Thr64Gly + Ser101Glu + Ile105Glu + Ser126Asp + Tyr161Leu
Thr64Gly + Ser99Asp + Ile105Glu + Gly205Pro + Leu211Ala
Asn153Glu + Ala194Thr + Asn198Glu + Tyr208Ile + Gly213Glu
Gly152Gln + Gln200Asn + Ser206Glu + Ala209Asp + Ser210Glu
Ser103Glu + Gly125Pro + Ala131Glu + Tyr161Cys + Leu211Thr
Gly100Ser + Gln200Asn + Thr207Glu + Ser210Asp + Leu211Gln
Gly100Pro + Asn198Asp + Gln200Glu + Gly205Gln + Thr207Glu
Ala96Asp + Ser99Glu + Ser104Asp + Val197Met + Gly213Ser
Gly98Asp + Gly100Pro + Ser101Asp + Gly125Ser + Ala156Ser
Gly98Asp + Gly125Asp + Ser160Glu + Tyr161Ile + Thr214Gly
Gly61Glu + Gly155Gln + Asn198Gln + Ser206Glu + Tyr208His
Asp58Glu + Asn60Glu + Leu124Asn + Ser206Asp + Thr207Asn
Gly61Asp + Thr202Pro + Thr207Gln + Ser210Glu + Leu211Pro
Gly61Glu + Tyr102His + Phe183His + Gln185Asn + Ser210Asp
Ser99Asp + Ser126Asp + Pro129Asp + Gly152Ser + Leu211His
Leu94Ile + Gly125Glu + Ser128Asp + Pro129Glu + Ser154Asp
Asn198Asp + Gln200Ser + Gly205Pro + Gly213Ser + Thr214Asp
Gly61Asn + Ser182Asp + Val93Gln + Asn198Asp + Ser210Glu
Gly61Glu + Leu940ys + Gln200Ser + Gly205Glu + Ser210Glu
Asp58Glu + Phe183Ser + Pro204Glu + Thr207Ser + Ser210Glu
Leu94Met + Ala156Asp + Tyr161Cys + Asn212Glu + Thr214Glu
Asp58Glu + Leu124Pro + Ile159Thr + Leu211Asp + Asn212Glu
Gln57Glu + Leu94Thr + Val197Ser + Ala209Glu + Ser210Asp
Ser104Glu + Pro129Ser + Ala156Gly + Ala209Glu + Ser210Glu
Asn153Asp + Ser154Glu + Asn198Asp + Thr207Glu + Leu211Gln
Gly59Asp + Asn60Glu + Ser101Glu + Tyr102His + Thr207Asn
Gly61Gln + Ser104Asp + Ile105Asp + Asn153Ser + Thr207Asp
Ser97Glu + Val197Gln + Asn198Gln + Asn212Asp + Gly213Asp
Tyr102Val + Ser154Glu + Gly205Glu + Ser206Asp + Leu211Cys
Asn153Glu + Tyr161Thr + Pro195Gly + Ser206Asp + Thr207Glu
Gly59Gln + Thr64Pro + Gly98Glu + Ser130Asp + Ala131Glu
Gly125Pro + Gly152Asn + Ser158Glu + Ile159Glu + Ser210Glu
Ser97Asp + Gly98Asp + Ile105Val + Leu124Thr + Gln200Asp
Gly100Glu + Ser101Asp + Ser160Asp + Val197Ala + Leu211Gln
Ser103Asp + Ser104Asp + Ala181Ser + Asn198Asp + Tyr208Ile
Ser99Glu + Gly100Glu + Gly125Asn + Ser182Asp + Thr207Gly
Leu94Gly + Gly100Asp + Ala131Gly + Gln200Glu + Ser210Asp
Ser97Glu + Ala131Gln + Gln200Asp + Thr207Gly + Ser210Glu
Gly125Asn + Ser130Glu + Phe183Asn + Gln200Asp + Ser210Glu
Gly95Gln + Tyr102Leu + Pro127Glu + Gln200Asp + Ser210Asp
Gly125Glu + Gly155Asn + Gln200Glu + Ser210Asp + Thr214Gly
Gln57Ser + Asp58Glu + Gln200Asp + Thr207Gly + Ser210Glu
Pro127Asp + Tyr161Cys + Gln185Asn + Gln200Asp + Ser210Asp
Gly100Glu + Gln200Asp + Thr207Pro + Ser210Asp + Leu211Ala
Gly59Pro + Ser160Asp + Asn198Gln + Gln200Asp + Ser210Glu
Thr64Glu + Ile105Cys + Leu124Ser + Val197Glu + Ser210Asp
Gln57Glu + Val93Glu + Gly95Ser + Ser103Glu + Asn198Gln
Asn60Glu + Ala96Asp + Tyr102Glu + Gln200Ser + Thr207Gly
Gln57Ser + Asn60Ser + Leu94Gly + Gln200Glu + Gly213Asp
Asn198Asp + Pro204Gln + Ser206Glu + Ser210Glu + Leu211Thr
Val93Glu + Ser126Glu + Ser160Asp + Val197Gln + Leu211Ser
Gly98Asp + Ser126Glu + Pro129Asp + Ala181Ser + Gly213Ser
Ala96Glu + Gly98Glu + Ser103Asp + Pro127Ser + Ile159Pro
Gly63Gln + Ser128Glu + Gly155Ser + Asn198Glu + Ser210Glu
Gln57Asp + Ala96Thr + Gln185Asn + Asn198Asp + Ser210Asp
Asn60Gln + Gly95Asp + Asn198Glu + Gln200Asn + Ser210Asp
Ser104Asp + Ile105Met + Asn198Asp + Ser210Asp + Leu211Asn
Tyr102Glu + Asn198Asp + Gln200Asn + Ser210Asp + Leu211Val
Gln57Asp + Gly125Ser + Asn198Asp + Gly205Asn + Ser210Asp
Tyr102Leu + Gln185Glu + Asn198Glu + Gln200Ser + Ser210Glu
Gly59Asp + Tyr102Ile + Asn198Glu + Ser210Asp + Thr214Ser
Val93Thr + Leu124Val + Ile159Glu + Asn198Asp + Ser210Glu
Ser101Asp + Pro129Gly + Asn198Asp + Thr207Ser + Leu211Glu
Gly152Gln + Gly155Gln + Asn198Asp + Gly205Asp + Leu211Asp
Gly59Gln + Thr64Ser + Ala156Asp + Ser158Glu + Gly205Glu
Pro127Glu + Asn198Ser + Pro204Glu + Ser206Asp + Thr207Pro
Asp58Glu + Ile159Gly + Asn198Asp + Leu211Ile + Asn212Glu
Ser130Asp + Ile159Gly + Asn198Glu + Leu211Met + Asn212Glu
Asp58Glu + Asn60Glu + Ile159Met + Tyr161Gln + Gln200Asp
Ser97Asp + Ser103Asp + Ile105Glu + Val197Cys + Leu211Val
Ser103Glu + Ile105Glu + Asn153Ser + Gln200Ser + Ser210Asp
Ala96Pro + Gly152Asp + Ser160Asp + Thr207Glu + Leu211Gln
Gly95Asp + Ser99Glu + Ile105Gly + Gly157Pro + Leu211Glu
Ser97Asp + Ser99Glu + Val197Glu + Asn198Ser + Thr214Gly
Gln57Asn + Ser97Glu + Ser99Glu + Asn153Glu + Val193His
Thr64Glu + Ala131Asn + Tyr208Leu + Ser210Asp + Gly213Ser
Gln57Glu + Ala156Pro + Ser158Asp + Gln185Glu + Thr207Gln
Ser97Asp + Pro129Asn + Ser158Glu + Gln185Glu + Leu211Ser
Ala96Thr + Ala156His + Ser158Glu + Gln185Asp + Leu211Asp
Leu94Ala + Ser101Asp + Ser126Glu + Ala131Gln + Ser154Asp
Gly157Glu + Ile159Leu + Gln200Asn + Pro204Asp + Thr207Glu
Leu94Thr + Ser126Glu + Pro204Glu + Thr207Asp + Gly213Asn
Gly100Gln + Ser154Glu + Asn198Glu + Gln200Asp + Leu211Ser
Gln57Glu + Asn198Glu + Gln200Glu + Tyr203Val + Gly213Pro
Ile105Met + Ser158Glu + Ile159Ser + Asn198Glu + Gln200Asp
Ser104Asp + Ala181Gln + Asn198Glu + Gln200Asp + Thr207Gly
Gly100Asn + Gly152Pro + Ser182Asp + Gln200Asp + Gly213Asp
Tyr102Met + Ser128Glu + Ser130Asp + Asn198Asp + Leu211Met
Ser128Glu + Ser130Glu + Ala131Thr + Asn198Glu + Asn212Gln
Val93Thr + Leu124Glu + Ile159Asn + Gln200Asp + Leu211Asp
Gly157Ser + Ser182Asp + Gln200Glu + Thr207Pro + Leu211Glu
Ser130Glu + Gln200Asp + Gly205Gln + Thr207Gln + Leu211Glu
Gln57Asn + Gly59Asn + Asn60Glu + Gly98Glu + Ser130Asp
Gly61Asp + Tyr102Pro + Ser206Glu + Thr207Asn + Ser210Glu
Thr64Asn + Ser97Asp + Pro129Asn + Val197Asp + Leu211Glu
Ser99Glu + Ala181Thr + Val197Glu + Ala209Asn + Leu211Asp
Gly59Asp + Val93Ser + Asn153Ser + Val197Glu + Leu211Asp
Ser101Glu + Asn153Ser + Tyr208Met + Leu211Glu + Gly213Asp
Gly157Asp + Gln185Asn + Thr207Glu + Ala209Asn + Asn212Gln
Gly100Gln + Gly125Ser + Phe183Asp + Ser210Asp + Thr214Glu
Asn198Gln + Ser206Glu + Thr207Pro + Ser210Asp + Asn212Asp
Ala181Thr + Gln200Glu + Thr207Asp + Leu211Ala + Gly213Glu
Asn60Asp + Gly98Pro + Ser126Asp + Pro129Glu + Gln200Ser
Asp58Glu + Ile159Pro + Ser210Glu + Asn212Asp + Thr214Gln
Asp58Glu + Gly125Ser + Ala131Ser + Ser210Asp + Asn212Glu
Gly59Ser + Ser101Glu + Ala131His + Ser210Glu + Asn212Glu
Asn60Gln + Val93Ala + Ser103Glu + Ser210Glu + Asn212Glu

TABLE 36-continued

Multi-loop Quintuple Mutation Variants

Ser158Glu + Asn198Ser + Tyr208Glu + Ser210Asp + Leu211Ser
Ala96Ser + Ser160Asp + Asn198Glu + Asn212Ser + Thr214Glu
Leu94Asn + Gly98Asp + Gly100Glu + Pro127Glu + Val197Met
Asn60Ser + Gly98Asp + Gly100Asp + Tyr102Asn + Gln200Glu
Leu94Ser + Ala96Thr + Ile105Asp + Tyr161Glu + Leu211Ile
Gly95Ser + Ser99Asp + Ser101Asp + Leu211Met + Gly213Glu
Gly61Glu + Gly125Ser + Ser128Glu + Ser160Asp + Ala181Pro
Ser182Glu + Val193Met + Asn198Glu + Gly205Gln + Ala209Asp
Leu94Glu + Gly100Asn + Ser104Asp + Ile105Val + Ser206Glu
Thr64Asp + Ser126Asp + Gly152Asp + Pro204Gly + Leu211Asn
Gly59Asp + Val93Glu + Leu94Pro + Ile105Met + Leu211Ser
Pro129Glu + Ser160Asp + Gln200Ser + Gly205Gln + Ser210Glu
Ile159Val + Ser160Glu + Phe183Glu + Pro204Gln + Ala209Asn
Leu94Asp + Val197Asp + Thr207Gly + Ser210Asp + Leu211Met
Leu124Glu + Phe183Pro + Val197Glu + Tyr208Leu + Ser210Glu
Leu94Met + Leu124Asp + Asn153Asp + Tyr161Ala + Leu211Glu
Gly98Asp + Gly152Glu + Ala156Asp + Tyr208Met + Asn212Ser
Val93Asp + Gly98Gln + Ser126Asp + Ser130Glu + Ala209Pro
Asp58Glu + Tyr102Ala + Ser126Asp + Ser130Glu + Ile159Asn
Ser126Asp + Ser130Glu + Val197Gly + Leu211Glu + Asn212Ser
Ser104Glu + Ile105Pro + Asn198Asp + Leu211His + Gly213Asp
Ser97Asp + Gly100Glu + Gly152Pro + Tyr161Glu + Ala181Gln
Ser128Glu + Ala131Glu + Ser154Glu + Asn198Gln + Ala209His
Ser99Asp + Pro129Ser + Ser154Glu + Ser160Asp + Pro204Gln
Asp58Glu + Ile105Cys + Leu124Ser + Ser154Glu + Ser158Glu
Ala131Asp + Val197Glu + Gln200Glu + Thr207Pro + Thr214Gly
Ser99Asp + Val197Asp + Asn198Gln + Gln200Glu + Thr207Gly
Ser101Glu + Val197Asp + Gln200Glu + Pro204Gly + Thr207Ser
Ala131Asp + Val197Asp + Asn198Gln + Gln200Glu + Ala209Asn
Gly95Pro + Gly98Asp + Leu124Glu + Thr207Asn + Asn212Glu
Gln57Glu + Asn60Glu + Val93Thr + Gly95Asn + Ser182Asp
Asn60Asp + Ile105Gln + Ala131Thr + Thr207Ser + Ala209Glu
Ser103Glu + Gln200Glu + Thr207Pro + Ala209Gln + Asn212Asp
Gly61Pro + Leu94Glu + Gln200Asp + Leu211Asn + Asn212Glu
Gly59Pro + Val93Glu + Gln200Asp + Leu211Val + Asn212Asp
Ser97Glu + Gly157Ser + Ala181Pro + Gln200Glu + Asn212Glu
Val93Thr + Gly98Gln + Tyr102Glu + Ala131Glu + Ser210Asp
Gly61Glu + Ser104Asp + Phe183Ala + Thr207Gly + Ala209Glu
Ala156Asp + Ser160Asp + Ala181Gly + Asn198Ser + Gln200Asp
Gln57Glu + Gly61Asp + Asn153Gln + Asn198Asp + Gly205Ser
Gly100Glu + Ile105Ser + Leu124Glu + Val197Met + Ser210Asp
Tyr102Glu + Ser126Glu + Val193Pro + Pro204Asn + Ser210Asp
Gly59Pro + Ala131Asp + Asn153Ser + Ser154Asp + Thr214Asp
Ser103Glu + Ser130Glu + Gln200Ser + Gly205Glu + Thr214Gly
Asp58Glu + Ala156Pro + Gly157Asp + Ser160Asp + Gln200Ser
Thr64Glu + Leu94Asp + Ala96Gln + Gln185Ser + Ser210Asp
Ser130Asp + Gly157Glu + Phe183Asp + Asn198Gln + Leu211Met
Asp58Glu + Pro129Glu + Ala156His + Pro204Ser + Gly205Glu
Ser126Glu + Ile159Leu + Ala209Asp + Leu211Ala + Asn212Glu
Gly59Asp + Ser126Asp + Ser154Glu + Phe183Leu + Leu211Val
Gly155Asn + Gly157Asp + Gln200Glu + Thr207Glu + Leu211Asn
Gly59Glu + Gly95Pro + Ala181His + Gln200Glu + Thr207Asp
Gln57Glu + Pro127Gly + Gly152Ser + Gln200Asp + Thr207Asp
Ala96Glu + Asn198Ser + Gln200Glu + Thr207Glu + Thr214Ser
Thr64Asp + Leu124Ser + Pro129Asp + Tyr161Asn + Thr207Asp
Ser97Asp + Tyr161Gly + Ser210Glu + Leu211Pro + Gly213Asp
Pro127Ser + Pro129Asn + Gly157Asp + Ser210Asp + Gly213Glu
Tyr102Cys + Ser130Asp + Pro204Gln + Ser210Glu + Gly213Asp
Ser99Glu + Ala156Ser + Ala209Thr + Ser210Asp + Gly213Asp
Gly196Pro + Gln200Asp + Pro204Asp + Thr207Gln + Leu211Asn
Asp58Glu + Ser97Glu + Ser104Asp + Pro129Gly + Tyr161Thr
Asp58Glu + Leu94Ser + Ser97Asp + Gly98Pro + Gln200Asp
Gly61Glu + Ser101Asp + Thr207Asp + Leu211Ile + Thr214Ser
Gly61Asp + Ser101Glu + Tyr102Val + Thr207Glu + Thr214Ser
Gly61Asp + Asn153Gln + Ile159Gly + Asn198Asp + Thr207Glu
Gly61Glu + Ile159Ser + Val197Met + Asn198Glu + Thr207Asp
Thr64Gln + Gly100Glu + Gln200Asn + Thr207Glu + Ser210Asp
Ser126Glu + Gly155Pro + Tyr161Thr + Thr207Glu + Ser210Asp
Tyr102Glu + Gly125Gln + Ala181Pro + Thr207Asp + Ser210Glu
Gly100Glu + Gly205Ser + Thr207Glu + Ser210Glu + Asn212Gln
Gly59Ser + Gly95Glu + Thr207Glu + Ser210Asp + Leu211Val
Tyr161Asp + Asn198Ser + Thr207Glu + Ser210Glu + Gly213Pro
Pro129Gln + Ser130Glu + Asn198Glu + Thr207Asp + Ser210Glu
Gln57Asp + Phe183Gly + Pro204Gln + Thr207Glu + Ser210Asp
Asn60Gln + Gly157Glu + Pro204Gly + Thr207Asp + Ser210Asp
Pro129Asp + Gly152Pro + Thr207Asp + Ser210Glu + Leu211Asn
Gly61Glu + Ser99Asp + Gly155Asn + Pro195Gln + Gln200Asn

Gly98Glu + Ser101Glu + Ala181Gly + Gln185Glu + Thr207Pro
Gly59Pro + Thr64Asp + Pro129Gln + Ala181Glu + Asn198Asp
Gly98Asp + Tyr161Met + Ala181Glu + Asn198Asp + Leu211Val
Ile159Glu + Val197Thr + Tyr208Gln + Ala209Glu + Thr214Asp
Ser126Glu + Gly1s7Glu + Ser182Glu + Asn198Gln + Leu211Val
Gly61Asp + Ser128Glu + Ser206Asp + Tyr208Gly + Leu211Met
Gly98Pro + Ser130Glu + Ser160Glu + Thr207Gly + Ser210Asp
Gln57Asp + Gly125Gln + Ser130Asp + Asn153Ser + Ser160Asp
Tyr161Met + Gln200Glu + Ser206Glu + Ala209His + Gly213Asp
Gly61Asp + Ala156Glu + Gly205Asn + Thr207Gln + Ser210Glu
Ile105Glu + Ser130Asp + Gln200Asn + Gly205Glu + Thr207Asn
Gln57Ser + Asn60Asp + Gln200Asp + Gly205Glu + Thr207Ser
Ser101Glu + Ser126Glu + Val197Asp + Thr207Gly + Leu211Cys
Ser101Asp + Ser126Asp + Gly152Ser + Asn198Glu + Gln200Asn
Gln57Asp + Gly125Asp + Gly205Asp + Thr207Ser + Tyr208Thr
Leu94Met + Ser128Asp + Ser158Glu + Asn198Gln + Ser210Asp
Gly59Asp + Gly95Pro + Ala194Gln + Asn198Asp + Thr214Asp
Gln57Glu + Gly61Asn + Gly98Asp + Gly100Pro + Val193Cys
Thr64Gln + Val93Glu + Ser97Glu + Pro129Ser + Gln200Glu
Gln57Glu + Thr64Asn + Val93Asp + Gln200Glu + Thr207Asn
Gly100Asp + Gly125Ser + Ser126Glu + Gly196Gln + Val197Glu
Val93Met + Gly100Asp + Ser126Glu + Tyr161Ala + Asn198Asp
Gly100Glu + Ser126Asp + Ala181His + Val197Cys + Gln200Glu
Asn60Gln + Ser99Asp + Ser103Glu + Ser210Asp + Leu211Ala
Gln57Ser + Ser99Glu + Ser103Glu + Gln200Asp + Thr207Asn
Gly63Ser + Ala96Ser + Ser210Glu + Leu211Pro + Thr214Asp
Pro129Gly + Val197Gln + Ser210Glu + Leu211His + Thr214Asp
Pro127Asp + Gly155Glu + Tyr161Ser + Thr207Ser + Ser210Glu
Asp58Glu + Val93His + Gly155Pro + Gln200Asn + Thr207Glu
Thr64Asn + Asn198Ser + Gln200Glu + Ser206Glu + Thr214Gln
Gly59Pro + Gly61Glu + Ser154Asp + Gln200Asp + Thr214Asn
Ser126Asp + Pro129Ser + Ala156Asp + Ser210Asp + Leu211Ala
Ser103Glu + Ile159Leu + Pro204Glu + Gly205Asn + Ser210Asp
Ala131Thr + Asn153Glu + Tyr203Asn + Pro204Glu + Ser210Asp
Gly157Asn + Ser160Glu + Pro204Glu + Gly205Ser + Ser210Glu
Gly95Gln + Gly98Pro + Gly152Glu + Gly157Pro + Val197Asp
Gln57Glu + Leu94Pro + Gly125Ser + Asn153Glu + Leu211Glu
Gly59Ser + Ser104Asp + Ser130Glu + Ser210Glu + Leu211Ser
Ser104Glu + Ser130Asp + Gly155Asn + Leu211Gly + Gly213Asp
Ser104Glu + Ser130Glu + Asn198Asp + Gln200Asn + Thr207Gln
Ser158Glu + Thr202Ser + Thr207Pro + Leu211Thr + Thr214Asp
Gly59Glu + Leu94Val + Ser101Asp + Ala131Glu + Tyr161Met
Asp58Glu + Ser99Glu + Tyr102Asn + Ala209Asn + Ser210Glu
Ser101Asp + Phe183Ser + Gln200Asp + Pro204Glu + Thr214Gln
Gly61Asp + Gly98Asn + Ser99Glu + Ile105Ser + Val197Glu
Asn60Ser + Gly125Pro + Ala156Asp + Tyr161Asp + Ser210Asp
Gly59Pro + Ser128Glu + Ser154Asp + Thr207Glu + Leu211Ile
Ser103Asp + Ala156Gly + Ser182Glu + Asn198Glu + Tyr203His
Val93Ala + Gly125Pro + Ser160Glu + Thr207Asp + Leu211Glu
Ser97Asp + Gly152Pro + Thr207Glu + Leu211Glu + Gly213Gln
Gln57Glu + Ser103Asp + Pro129Glu + Ala181Gly + Thr207Pro
Ser158Asp + Tyr161Pro + Ser182Asp + Thr207Gln + Ser210Asp

TABLE 37

Multi-loop Sextuple Mutation Variants

Tyr102Cys + Ile105Val + Leu124Ile + Ser154Glu + Asn198Gln + Thr207Gly
Ser160Glu + Tyr203Cys + Thr207Pro + Leu211Met + Asn212Gln + Gly213Gln
Val93Ser + Ser103Glu + Gly125Ser + Gln185Asn + Ala194Gln + Asn198Gln
Gly100Ser + Ile105Met + Gly157pro + Gln200Asn + Thr207Asn + Leu211Val
Thr64Glu + Leu94Asn + Val197Cys + Thr202Gln + Thr207Gln + Leu211Val
Gly152Pro + Gly157Gln + Ala181Asp + Asn198Gln + Gln200Asn + Thr207Asn
Gly95Gln + Ala96Asn + Leu124Thr + Asn153Ser + Ser154Glu + Val197His
Val93Met + Pro127Ser + Gly155Pro + Ser182Asp + Gln200Ser + Gly213Ser

TABLE 37-continued

Multi-loop Sextuple Mutation Variants

Gly61Pro + Gly95Pro + Ser154Glu + Ala181His + Leu211Asn + Gly213Pro
Tyr161Thr + Pro195Asn + Gln200Asn + Thr207Gly + Tyr208Leu + Leu211Pro
Leu94Pro + Ala96Ser + Pro127Asp + Ile159Ala + Thr207Pro + Gly213Gln
Gly100Asn + Ile105Gln + Gly125Gln + Pro129Gly + Gln185Glu + Thr207Gln
Gly98Glu + Pro129Gly + Gly155Pro + Thr207Gly + Ala209His + Thr214Gly
Ile105Gln + Gly152Asp + Phe183His + Ala194Gln + Gly205Ser + Asn212Gln
Ala194Gln + Asn198Ser + Gln200Asn + Ser206Asp + Leu211His + Thr214Gln
Ser99Glu + Pro129Asn + Ala131Pro + Gln185Asn + Thr207Pro + Leu211Val
Leu94Val + Gly98Gln + Leu124Gly + Val197Glu + Gln200Asn + Thr207Gly
Gln57Ser + Gly98Asn + Tyr102Asp + Tyr161Asn + Gln200Ser + Thr207Gln
Asn60Gln + Gly61Ser + Tyr102Cys + Gly152Asp + Val199Ser + Pro204Asn
Tyr102Thr + Gly155Glu + Ala156Asn + Tyr161Pro + Gln200Asn + Leu211Thr
Tyr102Glu + Gly157Pro + Phe183His + Asn198Gln + Thr207Pro + Leu211Cys
Leu124Cys + Pro127Asn + Tyr208Met + Ser210Asp + Leu211His + Gly213Gln
Gly98Ser + Leu124Ala + Ser126Asp + Ala181Asn + Ala209Gly + Gly213Gln
Ala96His + Tyr102Ser + Ile105Ser + Gly157Ser + Ile159Gln + Leu211Asp
Thr64Pro + Ala96Pro + Ser97Asp + Pro127Ser + Gly205Asn + Leu211Ser
Val93Gly + Gly98Ser + Tyr102Asn + Val197Met + Thr207Gln + Ser210Asp
Asn60Gln + Ala96Gln + Asn153Glu + Thr202Gln + Gly205Asn + Leu211Met
Gly59Asn + Leu94Val + Pro127Ser + Ile159Ala + Gln200Asn + Leu211Met
Ile105Gln + Gly157Gln + Val193Asn + Val197Asp + Thr207Pro + Tyr208Cys
Asn60Gln + Gly63Gln + Ile105Glu + Asn198Gln + Leu211Ile + Thr214Gly
Gly61Gln + Gly125Glu + Tyr161Gly + Gly205Gln + Thr207Ser + Ala209Gln
Gly98Ser + Ala156Gln + Tyr161Ala + Ser182Glu + Gln200Ser + Thr207Gln
Gly61Pro + Val93Ala + Leu124Gly + Ala131Thr + Val197Glu + Asn198Gln
Val93Asp + Ala96Asn + Val197His + Asn198Ser + Val199Ser + Thr207Gln
Tyr102Ile + Ile159Asp + Ala181Asn + Gln200Ser + Pro204Gln + Leu211His
Gly100Pro + Pro129Ser + Gln200Ser + Thr207Pro + Ala209Glu + Ser210Glu
Val197Pro + Asn198Gln + Gln200Glu + Pro204Gly + Thr207Gln + Ser210Asp
Ala96Gln + Leu124Met + Ile159Ser + Gln200Glu + Pro204Gly + Ser210Asp
Asn60Gln + Ile159Thr + Asn198Ser + Gln200Glu + Ser210Glu + Leu211Asp
Gly61Ser + Val197Gln + Asn198Glu + Gln200Ser + Ser210Asp + Leu211His
Gly100Asn + Ala181Pro + Asn198Asp + Thr207Ser + Ser210Glu + Gly213Gln
Gly98Asn + Pro129Ser + Asn198Asp + Gln200Asp + Ser210Glu + Leu211Pro
Gly63Ser + Leu94Gln + Ile159Ala + Gly205Glu + Thr207Glu + Thr214Asn
Asp58Glu + Gly61Glu + Gly98Asn + Asn153Ser + Tyr161Asn + Leu211Cys
Leu124Ser + Ile159Thr + Asn198Glu + Gln200Glu + Pro204Gly + Thr207Gln
Gly61Gln + Gly95Asn + Ala194Gly + Asn198Asp + Gln200Asp + Leu211Val
Gln57Ser + Tyr102Gln + Asn198Glu + Ala209Glu + Ser210Glu + Leu211Ser
Gly59Gln + Gly125Pro + Ser154Glu + Gly155Asp + Tyr161Ala + Ser182Asp
Gln57Glu + Gly59Asp + Thr64Gln + Tyr208Pro + Ala209Gln + Leu211Asn
Asn60Asp + Gly61Gln + Gly95Glu + Gly98Glu + Asn153Ser + Ile159Leu
Ile105Thr + Gly152Ser + Ser158Asp + Ser160Asp + Thr207Gly + Leu211Ala
Gly61Gln + Thr64Asn + Asn198Glu + Ser210Asp + Leu211Asp + Gly213Asp
Leu94Pro + Ala96Gly + Thr207Ser + Ser210Asp + Leu211Cys + Asn212Glu
Gly98Glu + Gly100Asp + Ala181Pro + Tyr203Val + Pro204Asn + Thr207Ser
Asp58Glu + Gly157Ser + Gln185Asn + Val197Gln + Pro204Glu + Asn212Gln
Gly61Asn + Leu124Thr + Ser128Glu + Ser160Glu + Ala181Asn + Thr207Gln
Ile105Leu + Leu124Ser + Gly125Asp + Gly152Glu + Asn153Glu + Gly213Glu
Leu124Gln + Asn198Glu + Gln200Asp + Thr207Gly + Tyr208Glu + Leu211Asp
Leu94Ile + Gly152Ser + Gly155Glu + Ser158Asp + Ala181Gly + Val197His
Asp58Glu + Tyr161Gly + Val197Ala + Asn198Gln + Pro204Glu + Ser206Asp
Gln57Ser + Ile159Ser + Asn198Asp + Gln200Asn + Tyr208Asn + Gly213Glu
Gly152Ser + Phe183Ala + Asn198Glu + Val199Ser + Leu211Cys + Gly213Glu
Leu94Ile + Ser154Asp + Ile159Glu + Asn198Ser + Gln200Asn + Leu211Met
Ala96Pro + Ser154Asp + Ala156His + Gly157Asn + Ser158Glu + Pro204Ser
Gln57Asp + Gly59Pro + Asn60Asp + Gly95Pro + Thr207Ser + Ala209Gln
Thr64Ser + Gly152Gln + Ala181His + Gln200Glu + Leu211His + Asn212Glu
Gln57Asn + Gly98Gln + Gln200Asp + Leu211Cys + Asn212Asp + Gly213Ser
Ala96Asn + Gly100Asp + Leu124Asp + Val197Gly + Thr207Pro + Gly213Ser
Ala96Ser + Ser154Asp + Phe183Gln + Thr207Ser + Leu211Thr + Gly213Asp
Gly95Asp + Gly98Pro + Ser99Asp + Gly100Ser + Tyr102Glu + Ser103Glu
Gln57Asp + Asp58Glu + Thr64Asp + Ser97Glu + Gln200Ser + Tyr208Thr
Gly125Asp + Ser130Asp + Asn153Glu + Ala156Thr + Ser160Glu + Asn198Ser
Gly59Asn + Leu124Thr + Ile159Met + Ala209Asp + Leu211Cys + Asn212Asp
Gly95Gln + Gly100Asn + Ile105Met + Ala181Gln + Gln200Glu + Thr207Glu
Ile105Met + Ser126Asp + Asn153Glu + Gly205Gln + Thr207Pro + Leu211Met
Pro129Gly + Ala131His + Val197Thr + Thr207Asn + Ser210Glu + Gly213Glu
Gly98Asp + Gly152Glu + Asn153Glu + Ser154Asp + Val197Ser + Gln200Asn
Asp58Glu + Gly61Pro + Val93Gly + Ser97Glu + Pro129Asn + Tyr161Ile
Ser130Asp + Gly152Ser + Val197Gly + Asn198Glu + Ser210Glu + Leu211Asp
Tyr102Val + Gly155Asn + Ser182Asp + Val197Asp + Gln200Asp + Ser210Asp
Thr64Gly + Ser128Glu + Gln200Glu + Thr207Ser + Ser210Asp + Leu211Asp
Gln57Glu + Tyr102Ser + Thr207Pro + Ser210Asp + Leu211Asp + Asn212Asp
Pro127Asn + Gly152Glu + Ile159Asn + Asn198Asp + Gln200Asn + Gly213Glu
Asn153Ser + Gly155Ser + Ile159Thr + Asn198Asp + Ser210Glu + Thr214Asp

TABLE 37-continued

Multi-loop Sextuple Mutation Variants

Val93Thr + Ser154Asp + Ser158Glu + Ser182Glu + Asn198Ser + Thr207Ser
Ser101Asp + Gly155Pro + Asn198Glu + Gln200Glu + Ala209Asn + Ser210Asp
Ser99Glu + Ser126A3p + Pro127Asp + Ile159Ser + Gln200Ser + Leu211Met
Pro129Asn + Asn153Asp + Ser158Asp + Gln200Ser + Pro204Ser + Gly205Ser
Val197Cys + Gly205Asp + Thr207Asp + Ser210Asp + Leu211Ile + Asn212Ser
Gly61Asn + Asn198Asp + Gln200Glu + Thr207Glu + Tyr208Cys + Leu211His
Asn60Asp + Pro127Gln + Asn153Glu + Ser154Glu + Ala156Glu + Thr207Pro
Ser99Glu + Asn153Asp + Ser154Asp + Ala156Glu + Gln185Asn + Pro195Ser
Thr64Asn + Ala156Asn + Val197Asp + Gln200Glu + Leu211Pro + Thr214Glu
Ser126Asp + Pro127Gln + Ser128Asp + Ser160Asp + Gln200Glu + Thr214Ser
Asn153Asp + Gln185Glu + Asn198Ser + Gln200Glu + Leu211Cys + Gly213Asp
Ile105Gln + Leu124Glu + Gly125Glu + Ser160Asp + Ala194Gln + Pro204Glu
Asp58Glu + Leu94Pro + Ser154Glu + Gly155Asp + Ser182Asp + Asn198Gln
Ser99Glu + Val197Glu + Thr207Gly + Ala209Asn + Ser210Glu + Leu211Asp
Gln57Asn + Gly125Glu + Asn153Glu + Gln200Asn + Leu211Ser + Asn212Asp
Leu94Ser + Gly125Gln + Ser126Glu + Val197Asp + Ser210Asp + Asn212Glu
Thr64Glu + Ile159His + Asn198Glu + Gln200Asp + Leu211Cys + Thr214Gly
Gly98Asp + Gly152Glu + Gly155Glu + Ala156Asp + Tyr208Met + Asn212Ser
Gly98Pro + Ser104Glu + Asn198Glu + Gln200Asp + Gly205Gln + Asn212Asp
Asp58Glu + Thr64Glu + Ala96Ser + Tyr102His + Gln200Glu + Leu211Gly
Leu94Ala + Gly100Gln + Phe183Asp + Val193Gln + Val197Asp + Gln200Glu
Asn60Gln + Thr64Gly + Gly125Glu + Ser154Glu + Gly157Asp + Thr207Gly
Val93Met + Gly100Asp + Ser126Glu + Pro129Asp + Ala181Asn + Thr214Ser
Gly125Asn + Ser182Glu + Phe183Tyr + Gln185Asp + Asn198Asp + Asn212Glu
Leu94Gln + Gly125Asp + Ser128Glu + Pro129Glu + Asn198Gln + Ser210Glu
Gly59Gln + Thr64Asp + Asn198Gln + Gln200Asn + Ser210Asp + Asn212Asp
Gly59Gln + Gly125Glu + Asn198Asp + Gln200Asp + Leu211Ile + Gly213Asp
Thr64Asn + Gly125Asp + Asn153Asp + Gln185Glu + Thr207Ser + Leu211Asp
Asp58Glu + Gly95Glu + Gly98Glu + Gln185Asn + Pro204Ser + Ser210Asp
Gln57Glu + Gly59Glu + Thr64Asp + Gly152Ser + Ala156Glu + Leu211Ser
Asn60Ser + Ala156Gln + Asn198Glu + Gly205Gln + Thr207Asp + Leu211Asp
Leu94Ala + Ser101Asp + Ser154Glu + Ser158Asp + Ser160Asp + Leu211Thr
Asp58Glu + Gln200Glu + Thr207Glu + Ser210Glu + Leu211Thr + Gly213Pro
Gly61Gln + Gly152Asp + Gln200Glu + Ser210Asp + Leu211Gly + Thr214Asp
Asn60Glu + Tyr102Ile + Gln200Glu + Thr207Asp + Ser210Asp + Asn212Ser
Gly59Ser + Val93Asp + Ile159Asp + Ser160Glu + Thr207Asn + Gly213Ser
Thr64Asn + Ser104Asp + Ile105Cys + Ala156Gly + Ser210Asp + Leu211Asp
Gln57Asn + Gly98Asp + Gly100Gln + Ser206Glu + Thr207Glu + Tyr208Met
Gln57Asn + Ser158Asp + Ile159Glu + Phe183Met + Asn198Asp + Thr207Asn
Gly95Asp + Ala96Gly + Ala131Gln + Thr207Glu + Tyr208Glu + Leu211Thr
Ser103Asp + Ser104Asp + Gln200Asn + Leu211Asn + Asn212Asp + Gly213Asp
Gly61Gln + Gly98Glu + Gly155Asp + Phe183Asp + Thr207Gln + Leu211Pro
Leu94Ser + Gly95Ser + Ser97Glu + Gly98Glu + Ala131Glu + Asn212Ser
Thr64Asn + Tyr102Ile + Ser103Asp + Ser104Asp + Ala181Asn + Tyr208Asp
Thr64Gly + Tyr102Asp + Gln200Glu + Thr207Asn + Tyr208Gln + Ser210Glu
Ser99Glu + Tyr102His + Ile159Ala + Gln200Asp + Thr207Gln + Ser210Glu
Thr64Glu + Leu124Cys + Val197Glu + Gln200Asn + Ser210Asp + Leu211Gly
Thr64Gly + Ser154Asp + Ala181Asn + Gln200Glu + Thr207Glu + Ser210Asp
Tyr102Ala + Ala181Asn + Ser182Glu + Gln200Asp + Thr207Asp + Ser210Asp
Gly125Pro + Gly152Asn + Ser158Glu + Ile159Glu + Asn198Asp + Ser210Glu
Gln57Ser + Asn60Ser + Val93Gln + Leu94Gly + Gln200Glu + Gly213Asp
Gly61Glu + Thr64Ser + Val93Asp + Asn198Ser + Pro204Glu + Tyr208Gly
Ser101Asp + Ser103Glu + Leu124Met + Gly155Ser + Ser210Asp + Leu211Gln
Ser99Glu + Pro127Asp + Pro129Ser + Ser154Glu + Ser158Glu + Thr207Ser
Gly61Glu + Ser101Glu + Ser104Glu + Ile159Leu + Gly196Asn + Asn198Gln
Gly59Asp + Asn60Glu + Ser99Glu + Val197Thr + Thr207Asp + Gly213Gln
Gly61Asn + Ala96Glu + Gly98Glu + Leu124Gln + Pro127Ser + Gly152Glu
Gly125Ser + Phe183Asp + Gln185Glu + Ala209Glu + Ser210Asp + Leu211His
Ser130Asp + Ile159Gly + Asn198Glu + Thr207Gln + Ser210Asp + Leu211Met
Pro127Gly + Ser130Asp + Tyr161Thr + Asn198Glu + Ser210Glu + Thr214Gln
Gly98Pro + Tyr102Glu + Phe183Met + Asn198Asp + Gln200Asn + Ser210Asp
Ser99Glu + Pro127Ser + Gly155Pro + Val197Cys + Asn198Glu + Leu211Glu
Leu94Ser + Ser101Glu + Ile105Glu + Pro195Gln + Val197Glu + Asn198Glu
Pro127Glu + Asn198Ser + Pro204Glu + Gly205Ser + Ser206Asp + Thr207Pro
Gln57Ser + Asn60Asp + Gln185Asn + AsnI98Glu + Leu211Thr + Asn212Asp
Asp58Glu + Asn60Asp + Tyr102Ala + Ile159Ser + Ser160Glu + Gly205Pro
Ala96Gly + Ala181Asp + Asn198Asp + Thr207Glu + Ala209His + Ser210Glu
Gln57Asn + Asn60Glu + Gly95Glu + Gly100Glu + Gly125Ser + Ser210Glu
Asp58Glu + Phe183Ser + Pro204Glu + Thr207Ser + Ser210Glu + Asn212Glu
Leu94Asp + Pro129Glu + Ala156Ser + Tyr161Asp + Gln185Ser + Asn212Ser
Gly95Glu + Ser99Asp + Ala156His + Val197Glu + Asn198Gln + Thr207Asn
Thr64Glu + Pro127Asn + Ala156Glu + Ala209Asp + Ser210Asp + Leu211Asn
Gly59Ser + Gly63Pro + Pro129Ser + Gly157Glu + Gln185Asp + Ser210Glu
Gln57Ser + Gly59Asp + Leu94Glu + Gly125Asp + Ser160Glu + Gln185Asn
Ile105Gln + Ser126Glu + Ser128Asp + Leu211Glu + Gly213Asp + Thr214Gly
Pro127Ser + Ser182Glu + Gln185Glu + Asn198Asp + Thr207Pro + Ser210Glu

TABLE 37-continued

| Multi-loop Sextuple Mutation Variants |
|---|
| Ala96Asn + Ala131Pro + Ala181Asp + Thr207Asp + Ser210Asp + Leu211Asp |
| Asp58Glu + Gly59Pro + Ser126Asp + Gly152Asp + Ser158Glu + Leu211Ile |
| Gly155Asp + Ser182Asp + Val197Gly + Gln200Asp + Thr202Asn + Leu211Glu |
| Ser126Asp + Ile159Ser + Asn198Ser + Gln200Ser + Pro204Glu + Thr207Asp |
| Asn60Ser + Gly63Asn + Gln185Glu + Pro495Ser + Asn198Asp + Gln200Glu |
| Gly59Ser + Ile105Asp + Ala181Asn + Asn198Asp + Gln200Asp + Leu211Thr |
| Leu94Glu + Ser99Asp + Gly100Gln + Ser103Asp + Gln200Glu + Tyr208Met |
| Asp58Glu + Leu94Asp + Ser99Glu + Gly100Pro + Gly157Asp + Tyr203Val |
| Asp58Glu + Thr64Gln + Gly98Glu + Ser99Asp + Pro129Glu + Gly155Ser |
| Val93Gln + Ser101Asp + Ile105Asp + Asn198Asp + Gly205Ser + Leu211Asn |
| Ser99Glu + Ile105Ala + Ser210Glu + Leu211His + Asn212Glu + Thr214Asp |
| Val93Ala + Leu124His + Ala131Gly + Gly157Asp + Val197Asp + Gly213Asp |
| Ile105His + Gly152Ser + Ala156Asn + Ser158Glu + Val197Asp + Gly213Asp |
| Gly61Asp + Leu94Thr + Val197Met + Asn198Gln + Gln200Glu + Gly205Glu |
| Tyr102Pro + Ser128Asp + Ser130Glu + Ala131Thr + Gln200Asp + Leu211Asp |
| Gly98Ser + Ser126Asp + Ser128Glu + Gly152Gln + Ser158Asp + Gly205Glu |
| Ser130Asp + Phe183Ile + Thr207Gly + Tyr208Asp + Ser210Glu + Asn212Asp |
| Asp58Glu + Leu94Thr + Gly100Gln + Tyr102His + Ser206Asp + Thr214Pro |
| Asp58Glu + Thr64Glu + Ser126Glu + Pro129Ser + Ala181Gly + Asn198Gln |
| Asn60Ser + Leu94Asp + Ala96Glu + Ala181Glu + Gln185Asn + Thr207Gly |
| Pro127Asp + Pro129Glu + Ala181Gln + Pro195Ser + Ser206Asp + Thr214Gln |
| Gly152Gln + Ala156Asp + Thr207Asp + Ala209Glu + Leu211Pro + Gly213Pro |
| Ser103Glu + Gly157Ser + Ser158Glu + Ser160Glu + Tyr161His + Pro204Ser |
| Leu94Asp + Gly95Gln + Gly98Asp + Ser126Glu + Ser154Asp + Thr207Ser |
| Ser97Glu + Ile105Glu + Leu124Asp + Phe183Gly + Thr207Gly + Leu211Gln |
| Gly100Glu + Pro129Ser + Ala181Ser + Tyr161Val + Ser210Asp + Asn212Glu |
| Gly59Ser + Ser101Glu + Ile105Gln + Ala131His + Ser210Glu + Asn212Glu |
| Gln57Asn + Pro127Gln + Ala156Asp + Ile159Asp + Pro195Gly + Ser206Asp |
| Val93His + Gly100Glu + Ser126Asp + Ser128Glu + Gln185Asp + Pro204Gly |
| Gly95Ser + Ser99Asp + Ser101Asp + Val197Asn + Leu211Met + Gly213Glu |
| Gln57Ser + Gly61Glu + Ala96Glu + Asn153Asp + Gly213Pro + Thr214Glu |
| Gln57Ser + Ala156Asp + Ser160Asp + Val197Gly + Leu211Asp + Gly213Asp |
| Gly98Pro + Ser104Asp + Ala181Glu + Ser182Glu + Asn198Glu + Asn212Gln |
| Ile105Glu + Leu124Thr + Val197Ser + Pro204Glu + Thr207Asp + Ser210Asp |
| Asn60Ser + Gly61Pro + Ser160Asp + Gln185Asp + Gln200Asn + Ser210Glu |
| Gly61Ser + Leu94Asp + Ser104Asp + Leu124Asn + Asn198Ser + Gly213Asp |
| Asn60Glu + Val93Met + Gly95Asp + Gly98Asn + Asn198Glu + Leu211Cys |
| Gly95Ser + Gly98Asp + Ser99Glu + Ser126Glu + Ser182Glu + Thr207Gly |

TABLE 37-continued

| Multi-loop Sextuple Mutation Variants |
|---|
| Asp58Glu + Gly98Asp + Leu124Cys + Gln200Asp + Ser210Asp + Asn212Ser |
| Leu94Glu + Ser97Asp + Ser158Glu + Val197Thr + Tyr208Ser + Leu211Ser |
| Ser101Glu + Ile105Glu + Ser154Glu + Gly157Glu + Asn198Ser + Leu211Ala |
| Gly63Ser + Gly98Glu + Gly100Pro + Gly152Asp + Gln200Asn + Gly213Asp |
| Leu94Glu + Ser101Asp + Phe183Ala + Gln200Asn + Ser206Glu + Leu211Met |
| Gln57Glu + Asp58Glu + Leu124Pro + Asn198Ser + Ser206Asp + Gly213Asp |
| Gly125Glu + Ala131His + Gly205Asp + Ala209Glu + Ser210Glu + Thr214Ser |
| Gly59Ser + Gly100Glu + Ser103Asp + Asn198Ser + Tyr208Leu + Ser210Glu |
| Asp58Glu + Asn60Asp + Gly155Asp + Val197Asn + Thr207Ser + Thr214Asp |
| Ser99Asp + Ser128Glu + Pro129Asp + Gly152Glu + Gln200Asn + Thr207Asn |
| Pro127Gln + Asn153Glu + Ser182Asp + Val197Cys + Ser210Glu + Leu211Pro |
| Ser104Glu + Leu124Pro + Asn153Glu + Ala156Thr + Ile159Leu + Ser182Glu |
| Thr64Asn + Tyr102Cys + Ser128Asp + Ser158Asp + Phe183Glu + Asn198Ser |
| Ala96Gln + Tyr161Asn + Gln185Asn + Val197Glu + Gly205Glu + Ser210Asp |
| Gly98Ser + Ser101Glu + Pro127Gly + Gln200Asp + Leu211Asp + Thr214Glu |
| Gly59Gln + Thr64Glu + Gly95Ser + Gly155Glu + Ser158Asp + Val197Cys |
| Tyr102Val + Ser103Glu + Asn198Asp + Gln200Glu + Thr207Glu + Ala209Asn |
| Asn60Glu + Gly98Gln + Asn153Glu + Ser210Asp + Leu211Ala + Gly213Glu |
| Asp58Glu + Gly61Glu + Ser101Glu + Leu124Asn + Pro129Gly + Ser130Asp |
| Ser126Glu + Ser130Asp + Ala131Thr + Gln200Asn + Thr202Gln + Pro204Asp |
| Gly63Gln + Ser97Glu + Ser126Asp + Ser130Asp + Asn198Ser + Gln200Ser |
| Val93Gln + Leu94Cys + Ser97Glu + Ser101Glu + Asn212Gln + Gly213Ser |
| Asp58Glu + Gly95Glu + Ser154Asp + Ser158Asp + Thr207Pro + Tyr208Val |
| Asn60Gln + Thr64Ser + Pro129Asn + Pro204Asp + Ser210Asp + Leu211Ile |
| Ser99Asp + Ile159Gln + Val197Gly + Asn198Glu + Leu211Val + Gly213Asp |
| Ser97Glu + Gly100Glu + Gly152Glu + Gly155Gln + Ala181Ser + Ala209His |
| Asp58Glu + Ala96Glu + Ser126Glu + Asn153Asp + Phe183Leu + Gly205Asn |
| Gly98Asp + Pro127Glu + Gly152Pro + Ser158Glu + Gly205Pro + Leu211Gln |
| Ser154Glu + Gly157Asp + Ile159Asn + Asn198Glu + Gln200Asn + Tyr203Asn |
| Gly63Ser + Phe183Glu + Thr207Glu + Ser210Glu + Leu211Pro + Thr214Asp |
| Gly100Glu + Asn153Ser + Ser154Asp + Ser160Glu + Asn198Ser + Gly213Glu |
| Gln57Glu + Ala96His + Gly98Pro + Ser160Asp + Pro204Asp + Tyr208Gly |
| Gly59Asp + Gly95Pro + Ala194Gln + Asn198Asp + Gln200Asp + Thr214Asp |
| Gly95Glu + Val197Glu + Asn198Gln + Gln200Glu + Thr207Gln + Leu211Ala |
| Gly98Asp + Ser128Asp + Gly155Pro + Ser158Asp + Gln185Glu + Gln200Ser |
| Gly98Glu + Leu124Asp + Gly125Asn + Ile159Gly + Val197Asp + Leu211Ala |
| Thr64Asp + Gly152Asn + Ser160Glu + Gln185Asn + Thr207Asp + Ser210Asp |
| Thr64Asp + Gly155Asp + Ala156Ser + Val197Ser + Asn198Glu + Leu211Asp |

TABLE 37-continued

Multi-loop Sextuple Mutation Variants

Gln57Asn + Thr64Pro + Ile105Glu + Ser126Glu + Ser160Asp + Ser206Glu
Gly98Asn + Gly157Asp + Phe188Glu + Val197Asn + Ser206Asp + Thr214Glu
Ser97Asp + Ser126Glu + Ser128Asp + Pro129Asn + Ala156Asp + Leu211Gln
Gln57Glu + Leu124?ro + Phe183Asn + Val197Glu + Gly205Glu + Gly213Glu
Ser126Asp + Ser158Glu + Gln200Asp + Thr207Pro + Leu211Glu + Asn212Ser
Gly98Ser + Gly100Pro + Pro129Glu + Gly157Glu + Ser158Glu + Asn198Asp
Gly61Asp + Gln185Asp + Asn198Gln + Gln200Asp + Thr207Asp + Leu211Ser
Asp58Glu + Asn198Gln + Gln200Glu + Thr207Glu + Leu211Ala + Asn212Glu
Gly59Asp + Ser97Glu + Pro129Asn + Gly152Pro + Ser182Glu + Thr214Asp
Gly59Glu + Thr64Glu + Pro127Gln + Pro129Asn + Ala131Gly + Asn153Glu
Pro127Glu + Ser130Asp + Ser154Glu + Ile159Cys + Ser210Glu + Leu211Ser
Asp58Glu + Val93Asn + Ser97Asp + Gly100Glu + Gly152Pro + Asn198Glu
Gly125Glu + Gly155Asp + Gly157Asn + Gln200Glu + Gly205Asn + Ser210Asp
Ala96Ser + Ser103Glu + Leu124Asp + Gln200Glu + Ser210Glu + Leu211Cys
Ser101Asp + Pro129Asp + Gly155Asn + Ala181Glu + Ser182Asp + Gly205Pro
Asp58Glu + Gly61Glu + Ala96His + Asn153Asp + Val197Gln + Gln200Glu
Asn60A3p + Ser99Glu + Gly155Pro + Ala181Glu + Val197Asn + Asn212Asp
Asn60Gln + Gly98Asn + Ser130Asp + Ala181Asp + Ala209Asp + Asn212Asp
Gly61Asp + Ala131Asp + Val197Ala + Asn198Asp + Gln200Asp + Thr214Asn
Thr64Asp + Ser99Asp + Ser101Glu + Ala181Gln + Gln200Ser + Ser210Glu
Leu124Ser + Tyr161Glu + Ser182Asp + Val197Glu + Thr207Gln + Leu211Asn
Gly95Glu + Gly98Asp + Ser103Asp + Ala181Gln + Thr207Gln + Asn212Asp
Asn60Glu + Ser97Glu + Ser101Glu + Leu124Ala + Pro127Glu + Val197Gln
Val93Asp + Ala96Glu + Ala131Asp + Gly152Gln + Gly196Ser + Val197His
Val93Gly + Ala131Asp + Ile159Gly + Ser182Glu + Asn198Gln + Gly213Asp
Ser130Asp + Ser182Asp + Gln185Ser + Val197Asn + Asn198Glu + Ser210Asp
Ile159Thr + Ser182Asp + Gln200Asp + Gly205Asp + Thr207Asn + Asn212Glu
Val93Thr + Ser104Glu + Pro127Ser + Ser128Asp + Ser130Glu + Asn153Glu
Asn60Glu + Leu94Asp + Gln200Ser + Gly205Asp + Ser210Asp + Leu211Gln
Gly95Asp + Ser101Asp + Ser130Glu + Asn198Asp + Gln200Ser + Leu211Ala
Ser104Asp + Ser154Glu + Thr207Asn + Ala209Asp + Ser210Glu + Leu211Asn
Asp58Glu + Gly59Asp + Ile105Leu + Ser126Asp + Phe183Asn + Ser210Asp
Gly59Glu + Asn60Asp + Gly95Asn + Pro129Glu + Gly152Ser + Gln185Glu
Gly59Asp + Ser160Glu + Gly196Ser + Gly205Ser + Ser210Asp + Leu211Asp
Asn60Glu + Ser99Asp + Gly157Glu + Phe183Leu + Val197Asn + Thr207Gln
Ser99Glu + Asn198Asp + Ser206Glu + Thr207Asp + Tyr208Asn + Leu211His
Gly98Glu + Ser99Asp + Ala131Pro + Asn153Glu + Tyr161Pro + Tyr208Glu
Ser97Glu + Gly98Glu + Ser182Asp + Thr207Gln + Ser210Asp + Gly213Ser
Ser97Asp + Gly98Asp + Ile105Val + Pro129Gly + Gln200Asp + Gly205Glu
Asp58Glu + Ser103Asp + Ser104Asp + Phe183Gly + Val197Pro + Asn198Asp
Asn60Ser + Ser99Glu + Gly100Asp + Pro129Gly + Gly205Asp + Ser210Glu
Ser99Glu + Ser154Asp + Tyr161Cys + Val197Ser + Gln200Asp + Ser210Asp
Ser101Glu + Gly155Asp + Gln185Ser + Asn198Gln + Gln200Asp + Ser210Glu
Gly59Asp + Tyr102Asn + Ser158Asp + Gln200Asp + Tyr208Val + Ser210Glu
Gly59Asp + Ala156Gln + Ile159Asp + Phe183Gly + Gln200Asp + Ser210Asp
Pro127Ser + Ser160Asp + Ser182Asp + Val197Gln + Gln200Glu + Ser210Asp
Gln57Asn + Val93Asp + Pro127Glu + Asn198Gln + Gln200Glu + Ser210Glu
Leu94Glu + Pro129Gln + Ser154Asp + Val197His + Gln200Asp + Ser210Glu
Ala96Ser + Gly98Gln + Ser126Asp + Ser154Asp + Val197Thr + Thr207Asp
Gln57Ser + Ser104Asp + Gly125Asp + Ser160Glu + Gly205Pro + Ser210Glu
Leu94Gln + Ser99Asp + Gly155Pro + Val193Asn + Gln200Asp + Thr207Asp
Gly95Glu + Gln200Glu + Thr202Ser + Thr207Asp + Leu211Gln + Thr214Gln
Thr64Gln + Ala96Thr + Ser104Asp + Gln200Asp + Thr207Asp + Thr214Pro
Thr64Glu + Tyr102Cys + Ala156Ser + Phe183Glu + Pro195Gln + Thr207Glu
Gly98Glu + Val197His + Thr207Gln + Ala209Ser + Ser210Asp + Gly213Asp
Gly95Ser + Gly157Asp + Phe183Glu + Thr207Asp + Ala209Gln + Ser210Asp
Asp58Glu + Val93Asp + Ser128Glu + Ala131Glu + Gly196Gln + Pro204Asn
Gln57Ser + Pro127Glu + Gln185Asn + Asn198Asp + Gln200Glu + Ser206Glu
Val93Glu + Gly152Asn + Thr207Glu + Ser210Asp + Leu211Ser + Gly213Glu
Thr64G4y + Ser99Glu + Ser103Glu + Pro127Asn + Gly152Glu + Ser158Glu
Gly157Asn + Ser158Glu + Asn198Asp + Ser206Asp + Thr207Gln + Ser210Asp
Ala96Asp + Ser126Glu + Ser160Glu + Tyr161Leu + Ser210Glu + Gly213Ser
Asp58Glu + Ala96Ser + Ser101Asp + Ser104Glu + Ala209Gln + Ser210Asp
Gly61Asp + Thr64Gln + Val93oys + Ile105Ser + Leu211Val + Asn212Glu
Gly61Glu + Phe183Ser + Tyr203Thr + Thr207Asn + Tyr208Gly + Asn212Glu
Ser97Glu + Ile105Cys + Pro127Ser + Ser160Asp + Asn198Glu + Ser210Asp
Leu94Asp + Ser130Glu + Asn198Asp + Pro204Asn + Thr207Gln + Ser210Asp
Ile105Asp + Leu124Pro + Ile159Leu + Asn198Glu + Ser206Asp + Leu211Glu
Tyr102Gly + Ala131Ser + Ser182Glu + Phe183Pro + Thr207Glu + Ser210Asp
Asn60Gln + Gly61Glu + Ser97Asp + Gly125Glu + Tyr208Pro + Ser210Asp
Gly98Gln + Ser160Glu + Ala181Thr + Asn198Asp + Ser206Asp + Asn212Glu
Leu124Ala + Ser128Glu + Asn153Gln + Gly205Asp + Thr207Glu + Asn212Glu
Gly59Glu + Gly100Pro + Ser103Glu + Ile105Glu + Val197Gly + Ser210Glu
Asn60Glu + Ser97Glu + Pro127Asp + Val193Met + Thr207Asp + Ala209Asn
Thr64Gln + Ala96Asn + Ser101Glu + Ser130Asp + Asn198Ser + Leu211Asp
Gly61Pro + Leu94Glu + Ser103Asp + Ile159Pro + Leu211Asn + Asn212Glu

TABLE 37-continued

Multi-loop Sextuple Mutation Variants

Val93Cys + Leu94Asp + Gly100Ser + Ser103Glu + Ser206Asp + Tyr208Gly
Ser130Asp + Gly152Glu + Ser154Glu + Gly157Ser + Ala181Pro + Asn198Glu
Gly59Glu + Ser130Asp + Ser154Asp + Gln185Asp + Thr207Gly + Leu211Pro
Gln57Glu + Leu94Ala + Ser101Asp + Ser126Glu + Ala131Gln + Ser154Asp
Ser103Asp + Ile105Met + Gly125Asn + Ser160Asp + Val197Ser + Thr214Asp
Asp58Glu + Val93Asp + Gly125Ser + Gly152Ser + Val193His + Gln200Glu
Asp58Glu + Gly98Asp + Leu124Ser + Gly125Glu + Tyr161Met + Gln200Glu
Gly61Asp + Leu94Ile + Asn153Asp + Ser158Asp + Val197Ala + Ser210Glu
Asn60Ser + Val93Ser + Ser103Glu + Ser160Glu + Asn198Asp + Gln200Asp
Asn60Gln + Ser97Asp + Ser128Asp + Asn198Glu + Gln200Asp + Ala209Gly
Val93Ser + Tyr102Asn + Ser104Asp + Gly152Asp + Asn198Glu + Gln200Glu
Gly59Asp + Ile105Met + Ser158Glu + Ile159Ser + Asn198Glu + Gln200Asp
Gly59Glu + Ser101Glu + Ile159Cys + Asn198Glu + Val199Gln + Gln200Asp
Gly61Asp + Pro127Asp + Gln185Asp + Asn198Ser + Gln200Ser + Ser210Asp
Gly100Glu + Ser104Glu + Ser182Glu + Thr207Gly + Tyr208Met + Ser210Glu
Thr64Gly + Gly157Asp + Ser182Glu + Val197Gln + Asn198Ser + Ser210Asp
Ser128Glu + Ser130Asp + Tyr161Val + Asn198Glu + Ser206Glu + Gly213Asn
Gly59Gln + Thr64Asp + Ser99Glu + Asn198Asp + Pro204Glu + Thr207Asn
Gly95Glu + Ser126Asp + Gln185Ser + Val197Cys + Gln200Glu + Leu211Glu
Gly98Pro + Ser99Glu + Ser158Asp + Gln200Asp + Ala209Ser + Leu211Asp
Ser101Glu + Pro129Glu + Asn153Ser + Ser160Asp + Thr207Glu + Leu211Cys
Asn60Glu + Gly98Asp + Pro127Asp + Ala131Gln + Ala181Asp + Asn198Ser
Asp58Glu + Ser126Asp + Gly157Asn + Thr207Ser + Leu211Asp + Gly213Asp
Ser104Asp + Leu124Gly + Asn153Asp + Ser182Glu + Asn198Glu + Thr207Asn
Gly95Ser + Ser103Glu + Pro129Glu + Ser160Asp + Gln200Asp + Leu211Pro
Gly59Glu + Gly125Asp + Pro127Glu + Ala131His + Ala209Asp + Leu211Ile
Pro127Glu + Gly157Asn + Pro204Gly + Thr207Asp + Ala209Asp + Thr214Asp
Gln57Glu + Leu94Glu + Ser103Asp + Gly152Asp + Gly205Ser + Leu211Ala
Ala96Glu + Ser103Asp + Gly152Gln + Ser158Glu + Ser160Asp + Thr214Asn
Gly61Glu + Tyr102His + Asn153Asp + Phe183His + Gln185Asn + Ser210Asp
Ser97Asp + Ser126Asp + Pro129Glu + Val197His + Asn198Asp + Gln200Asn
Asn60Glu + Ala96Pro + Ile105Asp + Leu124Ala + Ser130Glu + Ile159Ser
Gln57Glu + Pro127Gly + Ser128Glu + Ala131Ser + Ser210Asp + Asn212Glu
Ala96Glu + Tyr102Asp + Ser128Glu + Ala156Pro + Tyr161Val + Leu211Thr
Gln57Ser + Asp58Glu + Ser99Asp + Gln200Glu + Tyr208Ser + Asn212Glu
Gly59Asp + Leu94Met + Ile105Ala + Gly152Glu + Ser182Glu + Gln185Ser
Asn60Glu + Ala156Gly + Val197Asp + Asn198Ser + Gln200Glu + Ser206Asp
Gly100Ser + Ser101Asp + Gly125Gln + Ser126Asp + Pro127Asn + Asn198Glu

TABLE 37-continued

Multi-loop Sextuple Mutation Variants

Ala96Glu + Ser99Asp + Ser160Asp + Ala181Gly + Gly205Ser + Ser210Asp
Leu124Asp + Gly125Pro + Ser130Glu + Ser154Asp + Gly205Gln + Ala209Thr
Ser101Glu + Gly152Glu + Gly155Glu + Asn198Gln + Gln200Asp + Asn212Ser
Gly95Asn + Ser103Asp + Gly152Glu + Gly155Asp + Tyr208Val + Ser210Glu
Ser99Glu + Gly100Ser + Gly125Asn + Gly152Asp + Gly155Asp + Gly205Asp
Ala96Glu + Ser160Asp + Tyr161Met + Phe183Leu + Gln185Asp + Gly205Asp
Leu94Glu + Ser104Asp + Gly157Glu + Asn198Gln + Thr207Asn + Ala209Asp
Thr64Gln + Ser101Glu + Ile105Pro + Gly125Ser + Pro129Glu + Thr214Asn
Gly98Asp + Tyr102Gln + Gly125Asn + Ser12GGlu + Ser158Glu + Asn198Glu
Leu94Asp + Tyr161Ile + Ala181Gly + Phe183Asp + Gln200Glu + Thr214Asp

TABLE 38

Preferred Subtilisin 309 Variants

Single Mutation

Thr207Glu
Ser210Glu
Ser210Asp
Ser210Gly
Val197Glu

Double Mutation

Gln200Glu + Ser210Glu
Val199Leu + Ser210Glu
Val199Leu + Ser210Asp
Pro204Ala + Ala209Thr
Thr207Glu + Ser210Glu
Tyr208phe + Leu211Asn
Ala194Glu + Ser210Glu
Gln200Glu + Tyr211Asn
Gln206Glu + Thr207Glu Triple Mutation Gln200Pro + Gly205Ala + Ser210Glu
Thr207Glu + Ser210Glu + leu211Asn
Val199Ile + Pro204Asn + Thr207Glu
Gln200Glu + Ser210Glu + Leu211Asp
Gln200Glu + Thr207Glu + Leu211Glu
Gln200Glu + Thr207Glu + Ser210Glu Quadruple Mutation Pro204Ala + Thr207Glu + Ser210Glu + Leu211Asn
Gln206Glu + Thr207Glu + Ser210Glu + Leu211Gly Quintuple Mutation Val197Leu + Pro204Ala + Thr207Glu + Ser210Glu + Leu217Asp
Asn198Glu + Gln200Glu + Thr207Glu + Ser210Glu + Leu211Asp

II. Cleaning Compositions

In another embodiment of the present invention, an effective amount of one or more enzyme variants of the present invention are included in compositions useful for cleaning a variety of surfaces in need of proteinaceous stain removal. Such cleaning compositions include detergent compositions for cleaning hard surfaces, unlimited in form (e.g., liquid and granular); detergent compositions for cleaning fabrics, unlimited in form (e.g., granular, liquid and bar formulations); dishwashing compositions (unlimited in form); oral cleaning compositions, unlimited in form (e.g., dentifrice, toothpaste and mouthwash formulations); denture cleaning compositions, unlimited in form (e.g., liquid, tablet); and contact lens cleaning compositions, unlimited in form (e.g., liquid, tablet). As used herein, "effective amount of enzyme variant" refers to the quantity of enzyme variant necessary to achieve the enzymatic activity necessary in the specific cleaning composition. Such effective amounts are readily ascertained by one of ordinary skill in the art and is based on many factors, such as the particular enzyme variant used, the cleaning application, the specific composition of the cleaning composition, and whether a liquid or dry (e.g., granular, bar) composition is required, and the like. Preferably the cleaning compositions of the present invention comprise from about 0.0001% to about 10% of one or more enzyme variants of the present invention, more preferably from about 0.001% to about 1%, more preferably still from about 0.01% to about 0.1%. Several examples of various cleaning compositions wherein the enzyme variants of the present invention may be employed are discussed in further detail below. All parts, percentages and ratios used herein are by weight unless otherwise specified.

As used herein, "non-fabric cleaning compositions" include hard surface cleaning compositions, dishwashing compositions, oral cleaning compositions, denture cleaning compositions and contact lens cleaning compositions.

A. Cleaning Compositions for Hard Surfaces, Dishes and Fabrics

The enzymes of the present invention can be used in any detergent composition where high sudsing and good insoluble substrate removal are desired. Thus the enzyme variants of the present invention can be used with various conventional ingredients to provide fully-formulated hard-surface cleaners, dishwashing compositions, fabric laundering compositions and the like. Such compositions can be in the form of liquids, granules, bars and the like. Such compositions can be formulated as modern "concentrated" detergents which contain as much as 30%–60% by weight of surfactants.

The cleaning compositions herein can optionally, and preferably, contain various anionic, nonionic, zwitterionic, etc., surfactants. Such surfactants are typically present at levels of from about 5% to about 35% of the compositions.

Nonlimiting examples of surfactants useful herein include the conventional $C_{11}$–$C_{18}$ alkyl benzene sulfonates and primary and random alkyl sulfates, the $C_{10}$–$C_{18}$ secondary (2,3) alkyl sulfates of the formulas $CH_3(CH_2)x(CHOSO_3^-M^+)CH_3$ and $CH_3(CH_2)y(CHOSO_3^-M^+)CH_2CH_3$ wherein x and (y+1) are integers of at least about 7, preferably at least about 9, and M is a water-solubilizingh cation, especially sodium, the $C_{10}$–$C_{18}$ alkyl alkoxy sulfates (especially EO 1–5 ethoxy sulfates), $C_{10}$–$C_{18}$ alkyl alkoxy carboxylates (especially the EO 1–5 ethoxycarboxylates), the $C_{10}$–$C_{18}$ alkyl polyglycosides, and their corresponding sulfated polyglycosides, $C_{12}$–$C_{18}$ alpha-sulfonated fatty acid esters, $C_{12}$–$C_{18}$ alkyl and alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like. The alkyl alkoxy sulfates (AES) and alkyl alkoxy carboxylates (AEC) are preferred herein. (Use of such surfactants in combination with the aforesaid amine oxide and/or betaine or sultaine surfactants is also preferred, depending on the desires of the formulator.) Other conventional useful surfactants are listed in standard texts. Particularly useful surfactants include the $C_{10}$–$C_{18}$ N-methyl glucamides disclosed in U.S. Pat. No. 5,194,639, Connor et al., issued Mar. 16, 1993, incorporated herein by reference.

A wide variety of other ingredients useful in detergent cleaning compositions can be included in the compositions herein, including other active ingredients, carriers, hydrotropes, processing aids, dyes or pigments, solvents for liquid formulations, etc. If an additional increment or sudsing is desired, suds boosters such as the $C_{10}$–$C_{16}$ alkolamides can be incorporated into the compositions, typically at about 1% to about 10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, from about 0.1% to about 2%, to provide additionally sudsing.

The liquid detergent compositions herein can contain water and other solvents as carriers. Low molecular weight primary or secondary alcohols exemplified by methanol, ethanol, propanol, and isopropanol are suitable. Monohydric alcohols are preferred for solubilizing surfactants, but polyols such as those containing from about 2 to about 6 carbon atoms and from about 2 to about 6 hydroxy groups (e.g., 1,3-propanediol, ethylene glycol, glycerine, and 1,2-propanediol) can also be used. The compositions may contain from about 5% to about 90%, typically from about 10% to about 50% of such carriers.

The detergent compositions herein will preferably be formulated such that during use in aqueous cleaning operations, the wash water will have a pH between about 6.8 and about 11.0. Finished products thus are typically formulated at this range. Techniques for controlling pH at recommended usage levels include the use of buffers, alkalis, acids, etc., and are well known to those skilled in the art.

When formulating the hard surface cleaning compositions and fabric cleaning compositions of the present invention, the formulator may wish to employ various builders at levels from about 5% to about 50% by weight. Typical builders include the 1–10 micron zeolites, polycarboxylates such as citrate and oxydisuccinates, layered silicates, phosphates, and the like. Other conventional builders are listed in standard formularies.

Likewise, the formulator may wish to employ various additional enzymes, such as cellulases, lipases, amylases and proteases in such compositions, typically at levels of from about 0.001% to about 1% by weight. Various detersive and fabric care enzymes are well-known in the laundry detergent art.

Various bleaching compounds, such as the percarbonates, perborates and the like, can be used in such compositions, typically at levels from about 1% to about 15% by weight. If desired, such compositions can also contain bleach activators such as tetraacetyl ethylenediamine, nonanoyloxybenzene sulfonate, and the like, which are also known in the art. Usage levels typically range from about 1% to about 10% by weight.

Various soil release agents, especially of the anionic oligoester type, various chelating agents, especially the aminophosphonates and ethylenediaminedisuccinates, various clay soil removal agents, especially ethoxylated tetraethylene pentamine, various dispersing agents, especially polyacrylates and polyasparatates, various brighteners, especially anionic brighteners, various suds suppressors, especially silicones and secondary alcohols, various fabric softeners, especially smectitie clays, and the like can all be used in such compositions at levels ranging from about 1% to about 35% by weight. Standard formularies and published patents contain multiple, detailed descriptions of such conventional materials.

Enzyme stabilizers may also be used in the cleaning compositions of the present invention. Such enzyme stabilizers include propylene glycol (preferably from about 1% to about 10%), sodium formate (preferably from about 0.1% to about 1%) and calcium formate (preferably from about 0.1% to about 1%).

1. Hard surface cleaning compositions

As used herein "hard surface cleaning composition" refers to liquid and granular detergent compositions for cleaning hard surfaces such as floors, walls, bathroom tiles, and the like. Hard surface cleaning compositions of the present invention comprise an effective amount of one or more enzyme variants of the present invention, preferably from about 0.001% to about 10%, more preferably from about 0.01% to about 5%, more preferably still from about 0.05% to about 1% by weight of active enzyme of the composition. In addition to comprising one or more enzyme variants of the present invention, such hard surface cleaning compositions typically comprise a surfactant and a water-soluble sequestering builder. In certain specialized products such as spray window cleaners, however, the surfactants are sometimes not used since they may produce a filmy/streaky residue on the glass surface.

The surfactant component, when present, may comprise as little as 0.1% of the compositions herein, but typically the compositions will contain from about 0.25% to about 10%, more preferably from about 1% to about 5% of surfactant.

Typically the compositions will contain from about 0.5% to about 50% of a detergency builder, preferably from about 1% to about 10%. Preferably the pH should be in the range of about 8 to 12. Conventional pH adjustment agents such as sodium hydroxide, sodium carbonate or hydrochloric acid can be used if adjustment is necessary.

Solvents may be included in the compositions. Useful solvents include, but are not limited to, glycol ethers such as diethyleneglycol monohexyl ether, diethyleneglycol monobutyl ether, ethyleneglycol monobutyl ether, ethyleneglycol monohexyl ether, propyleneglycol monobutyl ether, dipropylenegycol monobutyl ether, and diols such as 2,2,4-trimethyl-1,3-pentanediol and 2-ethyl-1,3-hexanediol. When used, such solvents are typically present at levels of from about 0.5% to about 15%, preferably from about 3% to about 11%.

Additionally, highly volatile solvents such as isopropanol or ethanol can be used in the present compositions to facilitate faster evaporation of the composition from surfaces when the surface is not rinsed after "full strength" application of the composition to the surface. When used, volatile solvents are typically present at levels of from about 2% to about 12% in the compositions.

The hard surface cleaning composition embodiment of the present invention is illustrated by the following examples.

EXAMPLES 7–12

Liquid Hard Surface Cleaning Compositions

| Component | Example No. | | | | | |
|---|---|---|---|---|---|---|
| | 7 | 8 | 9 | 10 | 11 | 12 |
| Thr207Glu | 0.05 | 0.50 | 0.02 | 0.03 | 0.10 | 0.03 |
| Val199Leu + Ser210Asp | — | — | — | — | 0.20 | 0.02 |

-continued

Liquid Hard Surface Cleaning Compositions

| Component | Example No. | | | | | |
|---|---|---|---|---|---|---|
| | 7 | 8 | 9 | 10 | 11 | 12 |
| Na$_2$DIDA* EDTA** | — | — | 2.90 | 2.90 | — | — |
| Na Citrate | — | — | — | — | 2.90 | 2.90 |
| NaC$_{12}$ Alkyl-benzene sulfonate | 1.95 | — | 1.95 | — | 1.95 | — |
| NaC$_{12}$ Alkylsulfate | — | 2.20 | — | 2.20 | — | 2.20 |
| NaC$_{12}$(ethoxy)*** sulfate | — | 2.20 | — | 2.20 | — | 2.20 |
| C$_{12}$ Dimethylamine oxide | — | 0.50 | — | 0.50 | — | 0.50 |
| Na Cumene sulfonate | 1.30 | — | 1.30 | — | 1.30 | — |
| Hexyl Carbitol*** | 6.30 | 6.30 | 6.30 | 6.30 | 6.30 | 6.30 |
| Water**** | balance to 100% | | | | | |

*Disodium N-diethyleneglycol-N,N-iminodiacetate
**Na$_4$ ethylenediamine diacetic acid
***Diethyleneglycol monohexyl ether
****All formulas adjusted to pH 7

In Examples 7–10, the subtilisin 309 variants recited in Tables 3–38, among others, are substituted for Thr207Glu, with substantially similar results.

In Examples 11–12, any combination of the subtilisin 309 variants recited in Tables 3–38, among others, are substituted for Val199Leu+Ser210Asp, with substantially similar results.

EXAMPLES 13–18

Spray Compositions for Cleaning Hard Surfaces and Removing Household Mildew

| Component | Example No. | | | | | |
|---|---|---|---|---|---|---|
| | 13 | 14 | 15 | 16 | 17 | 18 |
| Gln200Glu + Thr207Glu | 0.50 | 0.05 | 0.60 | 0.30 | 0.20 | 0.30 |
| Ser210Glu | — | — | — | — | 0.30 | 0.10 |
| Sodium octyl sulfate | 2.00 | 2.00 | 2.00 | 2.00 | 2.00 | 2.00 |
| Sodium dodecyl sulfate | 4.00 | 4.00 | 4.00 | 4.00 | 4.00 | 4.00 |
| Sodium hydroxide | 0.80 | 0.80 | 0.80 | 0.80 | 0.80 | 0.80 |
| Silicate (Na) | 0.04 | 0.04 | 0.04 | 0.04 | 0.04 | 0.04 |
| Perfume | 0.35 | 0.35 | 0.35 | 0.35 | 0.35 | 0.35 |
| Water | balance to 100% | | | | | |

Product pH is about 7.

In Examples 13–16, the subtilisin 309 variants recited in Tables 3–38, among others, are substituted for Gln200Glu+Thr207Glu, with substantially similar results.

In Examples 17–18, any combination of the subtilisin 309 variants recited in Tables 3–38, among others, are substituted for Gln200Glu+Thr207Glu and Ser210Glu, with substantially similar results.

2. Dishwashing Compositions

In another embodiment of the present invention, dishwashing compositions comprise one or more enzyme variants of the present invention. As used herein, "dishwashing composition" refers to all forms for compositions for cleaning dishes, including but not limited to, granular and liquid forms. The dishwashing composition embodiment of the present invention is illustrated by the following examples.

EXAMPLES 19–24

Dishwashing Composition

| Component | Example No. | | | | | |
|---|---|---|---|---|---|---|
| | 19 | 20 | 21 | 22 | 23 | 24 |
| Gln200Pro + Gly205Ala + Ser210Asp | 0.05 | 0.50 | 0.02 | 0.40 | 0.10 | 0.03 |
| Val199Leu + Ser210Asp | — | — | — | — | 0.40 | 0.02 |
| $C_{12}$–$C_{14}$N-methyl-glucamide | 0.90 | 0.90 | 0.90 | 0.90 | 0.90 | 0.90 |
| $C_{12}$ ethoxy(1)sulfate | 12.00 | 12.00 | 12.00 | 12.00 | 12.00 | 12.00 |
| 2-methyl undecanoic acid | 4.50 | 4.50 | 4.50 | 4.50 | 4.50 | 4.50 |
| $C_{12}$ ethoxy(2)carboxylate | 4.50 | 4.50 | 4.50 | 4.50 | 4.50 | 4.50 |
| $C_{12}$ alcohol ethoxylate (4) | 3.00 | 3.00 | 3.00 | 3.00 | 3.00 | 3.00 |
| $C_{12}$ amine oxide | 3.00 | 3.00 | 3.00 | 3.00 | 3.00 | 3.00 |
| Sodium cumene sulfonate | 2.00 | 2.00 | 2.00 | 2.00 | 2.00 | 2.00 |
| Ethanol | 4.00 | 4.00 | 4.00 | 4.00 | 4.00 | 4.00 |
| $Mg^{++}$ (as $MgCl_2$) | 0.20 | 0.20 | 0.20 | 0.20 | 0.20 | 0.20 |
| $Ca^{++}$ (as $MgCl_2$) | 0.40 | 0.40 | 0.40 | 0.40 | 0.40 | 0.40 |
| Water | balance to 100% | | | | | |

Product pH is adjusted to 7.

In Examples 19–22, the subtilisin 309 variants recited in Tables 3–38, among others, are substituted for Gln200Pro+Gly205Ala+Ser210Asp, with substantially similar results.

In Examples 23–24, any combination of the subtilisin 309 variants recited in Tables 3–38, among others, are substituted for Gln200Pro+Gly205Ala+Ser210Asp and Val199Leu+Ser210Asp, with substantially similar results.

3. Fabric cleaning compositions

In another embodiment of the present invention, fabric cleaning compositions comprise one or more enzyme variants of the present invention. As used herein, "fabric cleaning composition" refers to all forms for detergent compositions for cleaning fabrics, including but not limited to, granular, liquid and bar forms. Preferred fabric cleaning compositions are those in the liquid form.

a. Granular fabric cleaning compositions

The granular fabric cleaning compositions of the present invention contain an effective amount of one or more enzyme variants of the present invention, preferably from about 0.001% to about 10%, more preferably from about 0.005% to about 5%, more preferably from about 0.01% to about 1% by weight of active enzyme of the composition. In addition to one or more enzyme variants, the granular fabric cleaning compositions typically comprise at least one surfactant, one or more builders, and, in some cases, a bleaching agent.

The granular fabric cleaning composition embodiment of the present invention is illustrated by the following examples.

EXAMPLES 25–28

Granular Fabric Cleaning Composition

| Component | Example No. | | | |
|---|---|---|---|---|
| | 25 | 26 | 27 | 28 |
| Ser99Asp | 0.10 | 0.20 | 0.03 | 0.05 |
| Ser99Gly | — | — | 0.02 | 0.05 |
| $C_{13}$ linear alkyl benzene sulfonate | 22.00 | 22.00 | 22.00 | 22.00 |
| Phosphate (as sodium tripolyphosphates) | 23.00 | 23.00 | 23.00 | 23.00 |
| Sodium carbonate | 23.00 | 23.00 | 23.00 | 23.00 |
| Sodium silicate | 14.00 | 14.00 | 14.00 | 14.00 |
| Zeolite | 8.20 | 8.20 | 8.20 | 8.20 |
| Chelant (diethylaenetriamine-pentaacetic acid) | 0.40 | 0.40 | 0.40 | 0.40 |
| Sodium sulfate | 5.50 | 5.50 | 5.50 | 5.50 |
| Water | balance to 100% | | | |

In Examples 25–26, the subtilisin 309 variants recited in Tables 3–38, among others, are substituted for Ser99Asp, with substantially similar results.

In Examples 27–28, any combination of the subtilisin 309 variants recited in Tables 3–38, among others, are substituted for Ser99Asp and Ser99Gly, with substantially similar results.

EXAMPLES 29–32

Granular Fabric Cleaning Composition

| Component | Example No. | | | |
|---|---|---|---|---|
| | 29 | 30 | 31 | 32 |
| Gln200Glu + Thr207Glu + Ser210Glu | 0.10 | 0.20 | 0.03 | 0.05 |
| Asn74Asp + Pro204Ala + Thr207Glu | — | — | 0.02 | 0.05 |
| $C_{12}$ alkyl benzene sulfonate | 12.00 | 12.00 | 12.00 | 12.00 |
| Zeolite A (1-10 micrometer) | 26.00 | 26.00 | 26.00 | 26.00 |
| 2-butyl octanoic acid | 4.00 | 4.00 | 4.00 | 4.00 |
| $C_{12}$–$C_{14}$ secondary (2,3) alkyl sulfate, Na salt | 5.00 | 5.00 | 5.00 | 5.00 |
| Sodium citrate | 5.00 | 5.00 | 5.00 | 5.00 |
| Optical brightener | 0.10 | 0.10 | 0.10 | 0.10 |
| Sodium sulfate | 17.00 | 17.00 | 17.00 | 17.00 |
| Water and minors | balance to 100% | | | |

In Examples 29–30, the subtilisin 309 variants recited in Tables 3–38, among others, are substituted for Gln200Glu+Thr207Glu+Ser210Glu, with substantially similar results.

In Examples 31–32, any combination of the subtilisin 309 variants recited in Tables 3–38, among others, are substituted for Gln200Glu+Thr207Glu+Ser210Glu and Asn74Asp+Pro204Ala+Thr207Glu, with substantially similar results.

EXAMPLES 33–36

Granular Fabric Cleaning Composition

| Component | Example No. | | | |
|---|---|---|---|---|
| | 33 | 34 | 35 | 36 |
| Leu94Gly + Gln200Glu | 0.10 | 0.20 | 0.03 | 0.05 |
| Gln57Ser + Leu94Gly + Gln200Glu | — | — | 0.02 | 0.05 |
| $C_{13}$ linear alkyl benzene sulfonate | 22.00 | 22.00 | 22.00 | 22.00 |
| Phosphate (as sodium tripolyphosphates) | 23.00 | 23.00 | 23.00 | 23.00 |

-continued

Granular Fabric Cleaning Composition

| Component | Example No. 33 | 34 | 35 | 36 |
|---|---|---|---|---|
| Sodium carbonate | 23.00 | 23.00 | 23.00 | 23.00 |
| Sodium silicate | 14.00 | 14.00 | 14.00 | 14.00 |
| Zeolite | 8.20 | 8.20 | 8.20 | 8.20 |
| Chelant (diethylaenetriamine-pentaacetic acid) | 0.40 | 0.40 | 0.40 | 0.40 |
| Sodium sulfate | 5.50 | 5.50 | 5.50 | 5.50 |
| Water | balance to 100% | | | |

In Examples 33–34, the subtilisin 309 variants recited in Tables 3–38, among others, are substituted for Leu 94Gly+Gln200Glu, with substantially similar results.

In Examples 35–36, any combination of the subtilisin 309 variants recited in Tables 3–38, among others, are substituted for Leu 94Gly+Gln200Glu and Gln 57Ser+Leu 94Gly+Gln200Glu, with substantially similar results.

EXAMPLES 37–40

Granular Fabric Cleaning Composition

| Component | Example No. 37 | 38 | 39 | 40 |
|---|---|---|---|---|
| Asn74His + Gln57Ser + Asn60Ser + Leu94Gly + Gln200Glu | 0.10 | 0.20 | 0.03 | 0.05 |
| Val93Gln + Tyr102Cys + Ser154Glu + Asn198Gln + Thr207Gly | — | — | 0.02 | 0.05 |
| $C_{12}$ alkyl benzene sulfonate | 12.00 | 12.00 | 12.00 | 12.00 |
| Zeolite A (1-10 micrometer) | 26.00 | 26.00 | 26.00 | 26.00 |
| 2-butyl octanoic acid | 4.00 | 4.00 | 4.00 | 4.00 |
| $C_{12}$—$C_{14}$ secondary (2,3) alkyl sulfate, Na salt | 5.00 | 5.00 | 5.00 | 5.00 |
| Sodium citrate | 5.00 | 5.00 | 5.00 | 5.00 |
| Optical brightener | 0.10 | 0.10 | 0.10 | 0.10 |
| Sodium sulfate | 17.00 | 17.00 | 17.00 | 17.00 |
| Water and minors | balance to 100% | | | |

In Examples 37–38, the subtilisin 309 variants recited in Tables 3–38, among others, are substituted for Asn74His+Gln 57Ser+Asn 60Ser+Leu 94Gly+Gln200Glu, with substantially similar results.

In Examples 39–40, any combination of the subtilisin 309 variants recited in Tables 3–38, among others, are substituted for Asn74His+Gln 57Ser+Asn 60Ser+Leu 94Gln+Gly200Glu and Val 93Gln+Tyr102Cys+Ser154Glu+Asn198Gln+Thr207Gly, with substantially similar results.

EXAMPLES 41–42

Granular Fabric Cleaning Composition

| Component | Example No. 41 | 42 |
|---|---|---|
| Linear alkyl benzene sulphonate | 11.4 | 10.70 |
| Tallow alkyl sulphate | 1.8 | 2.40 |
| $C_{14-15}$ alkyl sulphate | 3.00 | 3.10 |

-continued

Granular Fabric Cleaning Composition

| Component | Example No. 41 | 42 |
|---|---|---|
| $C_{14-15}$ alcohol 7 times ethoxylated | 4.00 | 4.00 |
| Tallow alcohol 11 times ethoxylated | 1.80 | 1.80 |
| Dispersant | 0.07 | 0.1 |
| Silicone fluid | 0.80 | 0.80 |
| Trisodium citrate | 14.00 | 15.00 |
| Citric acid | 3.00 | 2.50 |
| Zeolite | 32.50 | 32.10 |
| Maleic acid acrylic acid copolymer | 5.00 | 5.00 |
| Diethylene triamine penta methylene phosphonic acid | 1.00 | 0.20 |
| Ser210Asp | 0.30 | 0.30 |
| Lipase | 0.36 | 0.40 |
| Amylase | 0.30 | 0.30 |
| Sodium silicate | 2.00 | 2.50 |
| Sodium sulphate | 3.50 | 5.20 |
| Polyvinyl pyrrolidone | 0.30 | 0.50 |
| Perborate | 0.5 | 1 |
| Phenol sulphonate | 0.1 | 0.2 |
| Peroxidase | 0.1 | 0.1 |
| Minors | Up to 100 | Up to 100 |

EXAMPLES 43–44

Granular Fabric Cleaning Composition

| Component | Example No. 43 | 44 |
|---|---|---|
| Sodium linear $C_{12}$ alkyl benzene-sulfonate | 6.5 | 8.0 |
| Sodium sulfate | 15.0 | 18.0 |
| Zeolite A | 26.0 | 22.0 |
| Sodium nitrilotriacetate | 5.0 | 5.0 |
| Polyvinyl pyrrolidone | 0.5 | 0.7 |
| Tetraacetylethylene diamine | 3.0 | 3.0 |
| Boric acid | 4.0 | — |
| Perborate | 0.5 | 1 |
| Phenol sulphonate | 0.1 | 0.2 |
| Val199Leu + Ser210Glu | 0.4 | 0.4 |
| Fillers (e.g., silicates; carbonates; perfumes; water) | Up to 100 | Up to 100 |

EXAMPLE 45

Compact Granular Fabric Cleaning Composition

| Component | Weight % |
|---|---|
| Alkyl Sulphate | 8.0 |
| Alkyl Ethoxy Sulphate | 2.0 |
| Mixture of $C_{25}$ and $C_{45}$ alcohol 3 and 7 times ethoxylated | 6.0 |
| Polyhydroxy fatty acid amide | 2.5 |
| Zeolite | 17.0 |
| Layered silicate/citrate | 16.0 |
| Carbonate | 7.0 |
| Maleic acid acrylic acid copolymer | 5.0 |
| Soil release polymer | 0.4 |
| Carboxymethyl cellulose | 0.4 |
| Poly(4-vinylpyridine)-N-oxide | 0.1 |
| Copolymer of vinylimidazole and vinylpyrrolidone | 0.1 |
| PEG2000 | 0.2 |
| Asn74Asp + Val197Glu + Gln200Glu + Ser210Glu | 0.5 |
| Lipase | 0.2 |

-continued

Compact Granular Fabric Cleaning Composition

| Component | Weight % |
|---|---|
| Cellulase | 0.2 |
| Tetracetylethylene diamine | 6.0 |
| Percarbonate | 22.0 |
| Ethylene diamine disuccinic acid | 0.3 |
| Suds suppressor | 3.5 |
| Disodium-4,4'-bis(2-morpholino-4-anilino-s-triazin-6-ylamino)stilbene-2,2'-disulphonate | 0.25 |
| Disodium-4,4'-bis(2-sulfostyril)biphenyl | 0.05 |
| Water, Perfume and Minors | Up to 100 |

EXAMPLE 46

Granular Fabric Cleaning Composition

| Component | Weight % |
|---|---|
| Linear alkyl benzene sulphonate | 7.6 |
| $C_{16}$–$C_{18}$ alkyl sulfate | 1.3 |
| $C_{14-15}$ alcohol 7 times ethoxylated | 4.0 |
| Coco-alkyl-dimethyl hydroxyethyl ammonium chloride | 1.4 |
| Dispersant | 0.07 |
| Silicond fluid | 0.8 |
| Trisodium citrate | 5.0 |
| Zeolite 4A | 15.0 |
| Maleic acid acrylic acid copolymer | 4.0 |
| Diethylene triamine penta methylene phosphonic acid | 0.4 |
| Perborate | 15.0 |
| Tetraacetylethylene diamine | 5.0 |
| Smectite clay | 10.0 |
| Poly (oxy ethylene) (MW 300,000) | 0.3 |
| Tyr208phe + Leu211Asn | 0.4 |
| Lipase | 0.2 |
| Amylase | 0.3 |
| Cellulase | 0.2 |
| Sodium silicate | 3.0 |
| Sodium carbonate | 10.0 |
| Carboxymethyl cellulose | 0.2 |
| Brighteners | 0.2 |
| Water, perfume and minors | Up to 100 |

EXAMPLE 47

Granular Fabric Cleaning Composition

| Component | Weight % |
|---|---|
| Linear alkyl benzene sulfonate | 6.92 |
| Tallow alkyl sulfate | 2.05 |
| $C_{14-15}$ alcohol 7 times ethoxylated | 4.4 |
| $C_{12-15}$ alkyl ethoxy sulfate - 3 times ethoxylated | 0.16 |
| Zeolite | 20.2 |
| Citrate | 5.5 |
| Carbonate | 15.4 |
| Silicate | 3.0 |
| Maleic acid acrylic acid copolymer | 4.0 |
| Carboxymethyl cellulase | 0.31 |
| Soil release polymer | 0.30 |
| Asn74His + Val197Glu + Pro204Ala + Ala209Thr + Ser210Glu | 0.2 |
| Lipase | 0.36 |
| Cellulase | 0.13 |
| Perborate tetrahydrate | 11.64 |
| Perborate monohydrate | 8.7 |
| Tetraacetylethylene diamine | 5.0 |
| Diethylene triamine penta methyl phosphonic acid | 0.38 |

-continued

Granular Fabric Cleaning Composition

| Component | Weight % |
|---|---|
| Magnesium sulfate | 0.40 |
| Brightener | 0.19 |
| Perfume, silicone, suds suppressors | 0.85 |
| Minors | Up to 100 | b. Liquid fabric cleaning compositions

Liquid fabric cleaning compositions of the present invention comprise an effective amount of one or more enzyme variants of the present invention, preferably from about 0.005% to about 5%, more preferably from about 0.01% to about 1%, by weight of active enzyme of the composition. Such liquid fabric cleaning compositions typically additionally comprise an anionic surfactant, a fatty acid, a water-soluble detergency builder and water.

The liquid fabric cleaning composition embodiment of the present invention is illustrated by the following examples.

EXAMPLES 48–52

Liquid Fabric Cleaning Compositions

| | Example No. | | | | |
|---|---|---|---|---|---|
| Component | 48 | 49 | 50 | 51 | 52 |
| Pro204Ala + Ala209Thr | 0.05 | 0.03 | 0.30 | 0.03 | 0.10 |
| Gln200Glu + Thr207Glu + Ser210Glu | — | — | — | 0.01 | 0.20 |
| $C_{12}$–$C_{14}$ alkyl sulfate, Na | 20.00 | 20.00 | 20.00 | 20.00 | 20.00 |
| 2-butyl octanoic acid | 5.00 | 5.00 | 5.00 | 5.00 | 5.00 |
| Sodium citrate | 1.00 | 1.00 | 1.00 | 1.00 | 1.00 |
| $C_{10}$ alcohol ethoxylate (3) | 13.00 | 13.00 | 13.00 | 13.00 | 13.00 |
| Monethanolamine | 2.50 | 2.50 | 2.50 | 2.50 | 2.50 |
| Water/propylene glycol/ethanol (100:1:1) | balance to 100% | | | | |

In Examples 48–50 the subtilisin 309 variants recited in Tables 3–38, among others, are substituted for Pro240Ala+Ala209Thr, with substantially similar results.

In Examples 51–52, any combination of the subtilisin 309 variants recited in Tables 3–38, among others, are substituted for Pro240Ala+Ala209Thr and Gln200Glu+Thr207Glu+Ser210Glu, with substantially similar results.

EXAMPLES 53–57

Liquid Fabric Cleaning Compositions

| | Example No. | | | | |
|---|---|---|---|---|---|
| Component | 53 | 54 | 55 | 56 | 57 |
| Tyr102Cys + Ile105Val + Leu124Ile + Ser154Glu + Asn198Gln + Thr207Gly | 0.05 | 0.03 | 0.30 | 0.03 | 0.10 |
| Asn74Asp + Ser97Asp + Gln57Ser + Asn60Ser | — | — | — | 0.01 | 0.20 |
| $C_{12}$–$C_{14}$ alkyl sulfate, Na | 20.00 | 20.00 | 20.00 | 20.00 | 20.00 |
| 2-butyl octanoic acid | 5.00 | 5.00 | 5.00 | 5.00 | 5.00 |
| Sodium citrate | 1.00 | 1.00 | 1.00 | 1.00 | 1.00 |
| $C_{10}$ alcohol ethoxylate (3) | 13.00 | 13.00 | 13.00 | 13.00 | 13.00 |

-continued

Liquid Fabric Cleaning Compositions

| Component | Example No. | | | | |
|---|---|---|---|---|---|
| | 53 | 54 | 55 | 56 | 57 |
| Monethanolamine | 2.50 | 2.50 | 2.50 | 2.50 | 2.50 |
| Water/propylene glycol/ethanol (100:1:1) | | balance to 100% | | | |

In Examples 53–55 the subtilisin 309 variants recited in Tables 3–38, among others, are substituted for Tyr102Cys+Ile105Val+Leu124Ile+Ser154Glu+Asn198Gln+Thr207Gly, with substantially similar results.

In Examples 56–57, any combination of the subtilisin 309 variants recited in Tables 212, among others, are substituted for Tyr102Cys+Ile105Val+Leu124Ile+Ser154Glu+Asn198Gln+Thr207Gly and Asn74Asp+Ser97Asp+Gln 57Ser+Asn 60Ser, with substantially similar results.

EXAMPLES 58–59

Granular Fabric Cleaning Composition

| Component | Example No. | |
|---|---|---|
| | 58 | 59 |
| $C_{12-14}$ alkenyl succinic acid | 3.0 | 8.0 |
| Citric acid monohydrate | 10.0 | 15.0 |
| Sodium $C_{12-15}$ alkyl sulphate | 8.0 | 8.0 |
| Sodium sulfate of $C_{12-15}$ alcohol 2 times ethoxylated | — | 3.0 |
| $C_{12-15}$ alcohol 7 times ethoxylated | — | 8.0 |
| $C_{12-15}$ alcohol 5 times ethoxylated | 8.0 | — |
| Diethylene triamine penta (methylene phosphonic acid) | 0.2 | — |
| Oleic acid | 1.8 | — |
| Ethanol | 4.0 | 4.0 |
| Propanediol | 2.0 | 2.0 |
| Asn74Asp + Ser210Glu | 0.2 | 0.2 |
| Polyviny pyrrolidone | 1.0 | 2.0 |
| Suds suppressor | 0.15 | 0.15 |
| NaOH | up to pH 7.5 | |
| Perborate | 0.5 | 1 |
| Phenol sulphonate | 0.1 | 0.2 |
| Peroxidase | 0.4 | 0.1 |
| Water and minors | up to 100 parts | |

In each of Examples 58 and 59 herein, the subtilisin 309 variants recited in Tables 3–38, among others, are substituted for Asn74Asp+Ser210Glu, with substantially similar results.

EXAMPLES 60–62

Liquid Fabric Cleaning Composition

| Component | Example No. | | |
|---|---|---|---|
| | 60 | 61 | 62 |
| Citric Acid | 7.10 | 3.00 | 3.00 |
| Fatty Acid | 2.00 | — | 2.00 |
| Ethanol | 1.93 | 3.20 | 3.20 |
| Boric Acid | 2.22 | 3.50 | 3.50 |
| Monoethanolamine | 0.71 | 1.09 | 1.09 |
| 1,2 Propanediol | 7.89 | 8.00 | 8.00 |

-continued

Liquid Fabric Cleaning Composition

| Component | Example No. | | |
|---|---|---|---|
| | 60 | 61 | 62 |
| NaCumene Sulfonate | 1.80 | 3.00 | 3.00 |
| NaFormate | 0.08 | 0.08 | 0.08 |
| NaOH | 6.70 | 3.80 | 3.80 |
| Silicon anti-foam agent | 1.16 | 1.18 | 1.18 |
| Ser210Glu | 0.0145 | — | — |
| Asn74Asp + Ser97Asp + Ser210Glu | — | 0.0145 | — |
| Gln200Glu + Ser210Glu | — | — | 0.0145 |
| Lipase | 0.200 | 0.200 | 0.200 |
| Cellulase | — | 7.50 | 7.50 |
| Soil release polymer | 0.29 | 0.15 | 0.15 |
| Anti-foaming agents | 0.06 | 0.085 | 0.085 |
| Brightener 36 | 0.095 | — | — |
| Brightener 3 | — | 0.05 | 0.05 |
| $C_{12}$ alkyl benzenesulfonic acid | 9.86 | — | — |
| $C_{12-15}$ alkyl polyethoxylate (2.5) sulfate | 13.80 | 18.00 | 18.00 |
| $C_{12}$ glucose amide | — | 5.00 | 5.00 |
| $C_{12-13}$ alkyl polyethoxylate (9) | 2.00 | 2.00 | 2.00 |
| Water, perfume and minors | balance to 100% | | | c. Bar fabric cleaning compositions

Bar fabric cleaning compositions of the present invention suitable for hand-washing soiled fabrics contain an effective amount of one or more enzyme variants of the present invention, preferably from about 0.001% to about 10%, more preferably from about 0.01% to about 1% by weight of the composition.

The bar fabric cleaning composition embodiment of the present invention is illustrated by the following examples.

EXAMPLES 63–66

Bar Fabric Cleaning Compositions

| Component | Example No. | | | |
|---|---|---|---|---|
| | 63 | 64 | 65 | 66 |
| Val196Glu | 0.3 | — | 0.1 | 0.02 |
| Tyr208Phe + Leu211Asn | — | — | 0.4 | 0.03 |
| $C_{12}$—$C_{16}$ alkyl sulfate, Na | 20.0 | 20.0 | 20.0 | 20.00 |
| $C_{12}$—$C_{14}$ N-methyl glucamide | 5.0 | 5.0 | 5.0 | 5.00 |
| $C_{11}$—$C_{13}$ alkyl benzene sulfonate, Na | 10.0 | 10.0 | 10.0 | 10.00 |
| Sodium carbonate | 25.0 | 25.0 | 25.0 | 25.00 |
| Sodium pyrophosphate | 7.0 | 7.0 | 7.0 | 7.00 |
| Sodium tripolyphosphate | 7.0 | 7.0 | 7.0 | 7.00 |
| Zeolite A (0.1–.10 $\mu$) | 5.0 | 5.0 | 5.0 | 5.00 |
| Carboxymethylcellulose | 0.2 | 0.2 | 0.2 | 0.20 |
| Polyacrylate (MW 1400) | 0.2 | 0.2 | 0.2 | 0.20 |
| Coconut monethanolamide | 5.0 | 5.0 | 5.0 | 5.00 |
| Brightener, perfume | 0.2 | 0.2 | 0.2 | 0.20 |
| $CaSO_4$ | 1.0 | 1.0 | 1.0 | 1.00 |
| $MgSO_4$ | 1.0 | 1.0 | 1.0 | 1.00 |
| Water | 4.0 | 4.0 | 4.0 | 4.00 |
| Filler* | balance to 100% | | | |

*Can be selected from convenient materials such as $CaCO_3$, talc, clay, silicates and the like.

In Examples 63–64 the subtilisin 309 variants recited in Tables 3–38, among others, are substituted for Val197Glu, with substantially similar results.

In Examples 65–66, any combination of the subtilisin 309 variants recited in Tables 3–38, among others, are substituted for Val197Glu and Tyr208Phe+Leu211Asn, with substantially similar results.

EXAMPLES 67–70

Bar Fabric Cleaning Compositions

| | Example No. | | | |
|---|---|---|---|---|
| Component | 67 | 68 | 69 | 70 |
| Asn60Ser + Val93Gln + Gly213Asp | 0.3 | — | 0.1 | 0.02 |
| Val93Gln + Tyr102Cys ° Thr207Gly + Gly213Asp | — | 0.3 | 0.4 | 0.03 |
| $C_{12}$–$C_{16}$ alkyl sulfate, Na | 20.0 | 20.0 | 20.0 | 20.00 |
| $C_{12}$–$C_{14}$ N-methyl glucamide | 5.0 | 5.0 | 5.0 | 5.00 |
| $C_{11}$–$C_{13}$ alkyl benzene sulfonate, Na | 10.0 | 10.0 | 10.0 | 10.00 |
| Sodium carbonate | 25.0 | 25.0 | 25.0 | 25.00 |
| Sodium pyrophosphate | 7.0 | 7.0 | 7.0 | 7.00 |
| Sodium tripolyphosphate | 7.0 | 7.0 | 7.0 | 7.00 |
| Zeolite A (0.1–.10 $\mu$) | 5.0 | 5.0 | 5.0 | 5.00 |
| Carboxymethylcellulose | 0.2 | 0.2 | 0.2 | 0.20 |
| Polyacrylate (MW 1400) | 0.2 | 0.2 | 0.2 | 0.20 |
| Coconut monethanolamide | 5.0 | 5.0 | 5.0 | 5.00 |
| Brightener, perfume | 0.2 | 0.2 | 0.2 | 0.20 |
| $CaSO_4$ | 1.0 | 1.0 | 1.0 | 1.00 |
| $MgSO_4$ | 1.0 | 1.0 | 1.0 | 1.00 |
| Water | 4.0 | 4.0 | 4.0 | 4.00 |
| Filler* | balance to 100% | | | |

*Can be selected from convenient materials such as $CaCO_3$, talc, clay, silicates and the like.

In Example 67, the subtilisin 309 variants recited in Tables 3–38, among others, are substituted for Asn60Ser+Val 93Gln+Gly213Asp, with substantially similar results.

In Example 68, the subtilisin 309 variants recited in Tables 3–38, among others, are substituted for Val 93Gln+Tyr102Cys+Thr207Gly+Gly213Asp, with substantially similar results.

In Examples 69–70, any combination of the subtilisin 309 variants recited in Tables 3–38, among others, are substituted for Asn 60Ser+Val 93Gln+Gly213Asp and Val 93Gln+Tyr102Cys+Thr207Gly+Gly213Asp, with substantially similar results.

B. Additional Cleaning Compositions

In addition to the hard surface cleaning, dishwashing and fabric cleaning compositions discussed above, one or more enzyme variants of the present invention may be incorporated into a variety of other cleaning compositions where hydrolysis of an insoluble substrate is desired. Such additional cleaning compositions include but are not limited to, oral cleaning compositions, denture cleaning compositions, and contact lens cleaning compositions.

1. Oral cleaning compositions

In another embodiment of the present invention, a pharmaceutically-acceptable amount of one or more enzyme variants of the present invention are included in compositions useful for removing proteinaceous stains from teeth or dentures. As used herein, "oral cleaning compositions" refers to dentifrices, toothpastes, toothgels, toothpowders, mouthwashes, mouth sprays, mouth gels, chewing gums, lozenges, sachets, tablets, biogels, prophylaxis pastes, dental treatment solutions, and the like. Preferably, the oral cleaning compositions comprise from about 0.0001% to about 20% of one or more enzyme variants of the present invention, more preferably from about 0.001% to about 10%, more preferably still from about 0.01% to about 5%, by weight of the composition, and a pharmaceutically-acceptable carrier. As used herein, "pharmaceutically-acceptable" means that drugs, medicaments or inert ingredients which the term describes are suitable for use in contact with the tissues of humans and lower animals without undue toxicity, incompatability, instability, irritation, allergic response, and the like, commensurate with a reasonable benefit/risk ratio.

Typically, the pharmaceutically-acceptable oral cleaning carrier components of the oral cleaning components of the oral cleaning compositions will generally comprise from about 50% to about 99.99%, preferably from about 65% to about 99.99%, more preferably from about 65% to about 99%, by weight of the composition.

The pharmaceutically-acceptable carrier components and optional components which may be included in the oral cleaning compositions of the present invention are well known to those skilled in the art. A wide variety of composition types, carrier components and optional components useful in the oral cleaning compositions are disclosed in U.S. Pat. No. 5,096,700, Seibel, issued Mar. 17, 1992; U.S. Pat. No. 5,028,414, Sampathkumar, issued Jul. 2, 1991; and U.S. Pat. No. 5,028,415, Benedict, Bush and Sunberg, issued Jul. 2, 1991; all of which are incorporated herein by reference.

The oral cleaning composition embodiment of the present invention is illustrated by the following examples.

EXAMPLES 71–74

Dentifrice Composition

| | Example No. | | | |
|---|---|---|---|---|
| Component | 71 | 72 | 73 | 74 |
| Val199Leu + Pro204Ala + Thr207Glu + Ser210Glu | 2.00 | 3.500 | 1.500 | 2.000 |
| Sorbitol (70% aqueous solution) | 35.000 | 35.000 | 35.000 | 35.000 |
| PEG-6* | 1.000 | 1.000 | 1.000 | 1.000 |
| Silica dental abrasive** | 20.000 | 20.000 | 20.000 | 20.000 |
| Sodium Fluoride | 0.243 | 0.243 | 0.243 | 0.243 |
| Titanium dioxide | 0.500 | 0.500 | 0.500 | 0.500 |
| Sodium saccharin | 0.286 | 0.286 | 0.286 | 0.286 |
| Sodium alkyl sulfate (27.9% aqueous solution) | 4.000 | 4.000 | 4.000 | 4.000 |
| Flavor | 1.040 | 1.040 | 1.040 | 1.040 |
| Carboxyvinyl Polymer*** | 0.300 | 0.300 | 0.300 | 0.300 |
| Carrageenan**** | 0.800 | 0.800 | 0.800 | 0.800 |
| Water | balance to 100% | | | |

*PEG-6 = Polyethylene glycol having a molecular weight of 600.
**Precipitated silica identified as Zeodent 119 offered by J. M. Huber.
***Carbopol offered by B. F. Goodrich Chemical Company.
****Iota Carrageenan offered by Hercules Chemical Company.

In Examples 71–74 the subtilisin 309 variants recited in Tables 3–38, among others, are substituted for Val199Leu+Pro240Ala+Thr207Glu+Ser210Glu, with substantially similar results.

EXAMPLES 75–78

Mouthwash Composition

| | Example No. | | | |
|---|---|---|---|---|
| Component | 75 | 76 | 77 | 78 |
| Ser210Asp | 3.00 | 7.50 | 1.00 | 5.00 |
| SDA 40 Alcohol | 8.00 | 8.00 | 8.00 | 8.00 |
| Flavor | 0.08 | 0.08 | 0.08 | 0.08 |
| Emulsifier | 0.08 | 0.08 | 0.08 | 0.08 |
| Sodium Fluoride | 0.05 | 0.05 | 0.05 | 0.05 |

-continued

Mouthwash Composition

| Component | Example No. | | | |
|---|---|---|---|---|
| | 75 | 76 | 77 | 78 |
| Glycerin | 10.00 | 10.00 | 10.00 | 10.00 |
| Sweetener | 0.02 | 0.02 | 0.02 | 0.02 |
| Benzoic acid | 0.05 | 0.05 | 0.05 | 0.05 |
| Sodium hydroxide | 0.20 | 0.20 | 0.20 | 0.20 |
| Dye | 0.04 | 0.04 | 0.04 | 0.04 |
| Water | balance to 100% | | | |

In Examples 75–78, the subtilisin 309 variants recited in Tables 3–38, among others, are substituted for Ser210Asp, with substantially similar results.

EXAMPLES 79–82

Lozenge Composition

| Component | Example No. | | | |
|---|---|---|---|---|
| | 79 | 80 | 81 | 82 |
| Tyr208Phe + Leu211Asn | 0.01 | 0.03 | 0.10 | 0.02 |
| Sorbitol | 17.50 | 17.50 | 17.50 | 17.50 |
| Mannitol | 17.50 | 17.50 | 17.50 | 17.50 |
| Starch | 13.60 | 13.60 | 13.60 | 13.60 |
| Sweetener | 1.20 | 1.20 | 1.20 | 1.20 |
| Flavor | 11.70 | 11.70 | 11.70 | 11.70 |
| Color | 0.10 | 0.10 | 0.10 | 0.10 |
| Corn Syrup | balance to 100% | | | |

In Examples 79–82, the subtilisin 309 variants reduced in Tables 3–38, among others, are substituted for Tyr208Phe+Leu211Asn, with substantially similar results.

EXAMPLES 83–86

Chewing Gum Composition

| Component | Example No. | | | |
|---|---|---|---|---|
| | 83 | 84 | 85 | 86 |
| Val199Met + Pro204Ala + Thr207Glu | 0.03 | 0.02 | 0.10 | 0.05 |
| Sorbitol crystals | 38.44 | 38.40 | 38.40 | 38.40 |
| Paloja-T gum base* | 20.00 | 20.00 | 20.00 | 20.00 |
| Sorbitol (70% aqueous solution) | 22.00 | 22.00 | 22.00 | 22.00 |
| Mannitol | 10.00 | 10.00 | 10.00 | 10.00 |
| Glycerine | 7.56 | 7.56 | 7.56 | 7.56 |
| Flavor | 1.00 | 1.00 | 1.00 | 1.00 |

*Supplied by L. A. Dreyfus Company.

In Examples 83–86, the subtilisin 309 variants recited in Tables 3–38, among others, are substituted for Val199Met+Pro204Ala+Thr207Glu, with substantially similar results.

2. Denture cleaning compositions

In another embodiment of the present invention, denture cleaning compositions for cleaning dentures outside of the oral cavity comprise one or more enzyme variants of the present invention. Such denture cleaning compositions comprise an effective amount of one or more of the enzyme variants, preferably from about 0.0001% to about 50% of one or more of the enzyme variants, more preferably from about 0.001% to about 35%, more preferably still from about 0.01% to about 20%, by weight of the composition, and a denture cleansing carrier. Various denture cleansing composition formats such as effervescent tablets and the like are well known in the art (see for example U.S. Pat. No. 5,055,305, Young, incorporated herein by reference), and are generally appropriate for incorporation of one or more of the enzyme variants for removing proteinaceous stains from dentures.

The denture cleaning composition embodiment of the present invention is illustrated by the following examples.

EXAMPLES 87–90

Two-layer Effervescent Denture Cleansing Tablet

| Component | Example No. | | | |
|---|---|---|---|---|
| | 87 | 88 | 89 | 90 |
| Acidic Layer | | | | |
| Ser210Glu | 1.0 | 1.5 | 0.01 | 0.05 |
| Tartaric acid | 24.0 | 24.0 | 24.0 | 24.0 |
| Sodium carbonate | 4.0 | 4.0 | 4.00 | 4.00 |
| Sulphamic acid | 10.0 | 10.0 | 10.00 | 10.00 |
| PEG 20,000 | 4.0 | 4.0 | 4.00 | 4.00 |
| Sodium bicarbonate | 24.5 | 24.5 | 24.50 | 24.50 |
| Potassium persulfate | 15.0 | 15.0 | 15.00 | 15.00 |
| Sodium acid pyrophosphate | 7.0 | 7.0 | 7.00 | 7.00 |
| Pyrogenic silica | 2.0 | 2.0 | 2.00 | 2.00 |
| TAED* | 7.0 | 7.0 | 7.00 | 7.00 |
| Ricinoleylsulfosuccinate | 0.5 | 0.5 | 0.50 | 0.50 |
| Flavor | 1.0 | 1.0 | 1.00 | 1.00 |
| Alkaline Layer | | | | |
| Sodium perborate monohydrate | 32.0 | 32.0 | 32.00 | 32.00 |
| Sodium bicarbonate | 19.0 | 19.0 | 19.00 | 19.00 |
| EDTA | 3.0 | 3.0 | 3.00 | 3.00 |
| Sodium tripolyphosphate | 12.0 | 12.0 | 12.00 | 12.00 |
| PEG 20,000 | 2.0 | 2.0 | 2.00 | 2.00 |
| Potassium persulfate | 26.0 | 26.0 | 26.00 | 26.00 |
| Sodium carbonate | 2.0 | 2.0 | 2.00 | 2.00 |
| Pyrogenic silica | 2.0 | 2.0 | 2.00 | 2.00 |
| Dye/flavor | 2.0 | 2.0 | 2.00 | 2.00 |

*Tetraacetylethylene diamine

In Examples 87–90, the subtilisin 309 variants recited in Tables 3–38, among others, are substituted for Ser210Glu, with substantially similar results.

3. Contact Lens Cleaning Compositions

In another embodiment of the present invention, contact lens cleaning compositions comprise one or more enzyme variants of the present invention. Such contact lens cleaning compositions comprise an effective amount of one or more of the enzyme variants, preferably from about 0.01% to about 50% of one or more of the enzyme variants, more preferably from about 0.01% to about 20%, more preferably still from about 1% to about 5%, by weight of the composition, and a contact lens cleaning carrier. Various contact lens cleaning composition formats such as tablets, liquids and the like are well known in the art (see for example U.S. Pat. No. 4,863,627, Davies, Maeken and Rees, issued Sep. 5, 1989; U.S. Pat. No. Re. 32,672, Huth, Lam and Kirai, issued May 24, 1988; U.S. Pat. No. 4,609,493,Schäfer, issued Sep. 2, 1986; U.S. Pat. No. 4,690,793, Ogunbiyi and Smith, issued Sep. 1, 1987; U.S. Pat. No. 4,614,549, Ogunbiyi, Riedhamme and Smith, issued Sep. 30, 1986; and U.S. Pat. No. 4,285,738, Ogata, issued Aug. 25, 1981; each of which are incorporated herein by reference), and are generally appropriate for incorporation of one or more enzyme variants of the present invention for removing proteinaceous stains from contact lens.

The contact lens cleaning composition embodiment of the present invention is illustrated by the following examples.

EXAMPLES 91–94

Enzymatic Contact Lens Cleaning Solution

| | Example No. | | | |
|---|---|---|---|---|
| Component | 91 | 92 | 93 | 94 |
| Val199Leu + Ser210Asp | 0.01 | 0.05 | 0.1 | 2.0 |
| Glucose | 50.00 | 50.0 | 50.0 | 50.0 |
| Nonionic surfactant (polyoxyethlene-polyoxypropylene copolymer) | 2.00 | 2.0 | 2.0 | 2.0 |
| Anionic surfactant (polyoxyethlene-alkylphenylether sodium sulfricester) | 1.00 | 1.0 | 1.0 | 1.0 |
| Sodium chloride | 1.00 | 1.0 | 1.0 | 1.0 |
| Borax | 0.30 | 0.3 | 0.3 | 0.3 |
| Water | balance to 100% | | | |

In Examples 91–94, the subtilisin 309 variants recited in Tables 3–38, among others, are substituted for Val199Leu+ Ser210Asp, with substantially similar results.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of the invention.

---

What is claimed is:

1. A subtilisin 309 variant having a modified amino acid sequence of subtilisin 309 wild-type amino acid sequence set forth in SEQ ID NO:1, wherein the modified amino acid sequence comprises a substitution at one or more of positions 194, 195, 196, 197, 199, 200, 201, 202, 203, 204, 205, 207, 208, 209, 211, or 214, wherein a. when a substitution occurs at position 194, the substituting amino acid is His, Thr, Pro, Gly, Gln, Asn, Ser, Asp or Glu;

b. when a substitution occurs at position 195, the substituting amino acid is Gly, Gln, Asn, Ser, Asp or Glu;

c. when a substitution occurs at position 196, the substituting amino acid is Pro, Gln, Asn, Ser, Asp or Glu;

d. when a substitution occurs at position 197, the substituting amino acid is Met, Cys, Ala, His, Pro, Gly, Gln or Ser;

e. when a substitution occurs at position 199, the substituting amino acid is Met, Cys, Ala, His, Pro, Gly, Gln, Asn or Ser;

f. when a substitution occurs at position 200, the substituting amino acid is Asn or Ser;

g. when a substitution occurs at position 201, the substituting amino acid is Asp or Glu;

h. when a substitution occurs at position 202, the substituting amino acid is Pro, Gly, Gln, Asn, Ser, Asp or Glu;

i. when a substitution occurs at position 203, the substituting amino acid is Ile, Met, Ala, His, Pro, Gln, Asn or Ser;

j. when a substitution occurs at position 204, the substituting amino acid is Gly, Gln, Asn or Ser;

k. when a substitution occurs at position 205, the substituting amino acid is Pro, Gln, Asn or Ser;

l. when a substitution occurs at position 207, the substituting amino acid is Pro, Gly, Gln, Asn or Ser; but when position 207 is substituted the variant is not a double mutation variant having a substitution at position 211; and wherein when the variant is a single mutation variant the substitution does not occur at position 207;

m. when a substitution occurs at position 208, the substituting amino acid is Leu, Ile, Met, Cys, Ala, His, Pro, Gly, Gln or Asn; but when position 208 is substituted the variant is not a double mutation variant having a substitution at position 211; and wherein when the variant is a single mutation variant the substitution does not occur at position 208;

n. when a substitution occurs at position 209, the substituting amino acid is His, Thr, Pro, Gly, Gln, Asn or Ser; but when position 209 is substituted the variant is not a double mutation variant having a substitution at position 211; and wherein when the variant is a single mutation variant the substitution does not occur at position 209;

o. when a substitution occurs at position 211, the substituting amino acid is Ile, Val, Met, Cys, Ala, His, Thr, Pro, Gly, Gln, Asn or Ser; wherein when the variant is a single mutation variant, the substitution does not occur at position 211; and p. when a substitution occurs at position 214, the substituting amino acid is Pro, Gly, Gln, Asn, Asp, Ser or Glu;

whereby the subtilisin 309 variant has decreased adsorption to, and increased hydrolysis of, an insoluble substrate as compared to wild-type subtilisin 309 and wherein single amino acid substitutions at sixth loop positions 207 to 209 and 211 are combined with at least one further amino acid substitution selected from positions 194, 195, 196, 197, 199, 200, 201, 202, 203, 204, 205 and 214.

2. The subtilisin 309 variant of claim 1 wherein a. when a substitution occurs at position 200, the substituting amino acid is Ser;

b. when a substitution occurs at position 205, the substituting amino acid is Pro, Gln, Asn or Ser;

c. when a substitution occurs at position 208, the substituting amino acid is Leu, Ile, Met, Cys, Ala, His, Pro, Gly, Gln or Asn; and d. when a substitution occurs at position 209, the substituting amino acid is Pro, Gln, Asn or Ser.

3. The subtilisin 309 variant of claim 2 wherein the modified amino acid sequence further comprises His or Asp substituted for Asn at position 74.

4. The subtilisin 309 variant of claim 2, wherein when a substitution occurs at one or more of positions 194, 195, 196, 197, 199, 201, 202, 203, 204, 205, 207, 208, 209, 211 or 214, the substituting amino acid is Asp or Glu; when a substitution occurs at position 203, the substituting amino acid for position 203 is Asp; and when a substitution occurs at position 207 the substituting amino acid for position 207 is Glu.

5. The subtilisin 309 variant of claim 2 wherein a substitution occurs at one or more of positions of 194, 195, 196, 197, 201, 202, 203, 204, 205 or 209.

6. The subtilisin 309 variant of claim 5 wherein the substitution occurs at one or more of positions 194, 195, 196, 197 or 201.

7. An isolated subtilisin 309 variant having a modified amino acid sequence of subtilisin 309 wild-type amino acid sequence set forth in SEQ ID NO:1, wherein the modified amino acid sequence comprises a substitution at two or more of positions 194, 195, 196, 197, 198, 199, 200, 201, 202, 203, 204, 205, 207, 208, 209, 211, 212 or 214, wherein a. when a substitution occurs at position 194, the substituting amino acid is His, Thr, Pro, Gly, Gln, Asn, Ser, Asp or Glu;

b. when a substitution occurs at position 195, the substituting amino acid is Gly, Gln, Asn, Ser, Asp or Glu;

c. when a substitution occurs at position 196, the substituting amino acid is Pro, Gln, Asn, Ser, Asp or Glu;

d. when a substitution occurs at position 197, the substituting amino acid is Met, Cys, Ala, His, Pro, Thr, Gly, Gln, Asn or Ser;

e. when a substitution occurs at position 198, the substituting amino acid is Glu, Gln, Asp or Ser;

f. when a substitution occurs at position 199, the substituting amino acid is Met, Cys, Ala, His, Pro, Gly, Gln, Asn or Ser;

g. when a substitution occurs at position 200, the substituting amino acid is Asn or Ser;

h. when a substitution occurs at position 201, the substituting amino acid is Asp or Glu;

i. when a substitution occurs at position 202, the substituting amino acid is Pro, Gly, Gln, Asn, Ser, Asp or Glu;

j. when a substitution occurs at position 203, the substituting amino acid is Leu, Ile, Val, Met, Cys, Ala, His, Thr, Pro, Gln, Asn, Ser or Glu;

k. when a substitution occurs at position 204, the substituting amino acid is Gly, Gln, Asn or Ser;

l. when a substitution occurs at position 205, the substituting amino acid Pro, Gln, Asn or Ser;

m. when a substitution occurs at position 207, the substituting amino acid Pro, Gly, Gln, Asn, Ser or Asp; but when position 207 is substituted the variant is not a double mutation variant having a substitution at position 211;

n. when a substitution occurs at position 208, the substituting amino acid Leu, Ile, Met, Cys, Thr, Ala, His, Pro, Gly, Gln or Asn; but when position 208 is substituted the variant is not a double mutation variant having a substitution at position 211;

o. when a substitution occurs at position 209, the substituting amino acid His, Thr, Pro, Gly, Gln, Asn or Ser; but when position 209 is substituted the variant is not a double mutation variant having a substitution at position 211;

p. when a substitution occurs at position 211, the substituting amino acid Ile, Val, Met, Cys, Ala, His, Thr, Pro, Gly, Gln, Asn, Ser, Glu;

q. when a substitution occurs at position 212, the substituting amino acid Gln, Ser or Asp; but when position 212 is substituted the variant is not a double mutation variant having a substitution at position 211; and r. when a substitution occurs at position 214, the substituting amino acid is Pro, Gly, Gln, Asn, Asp, Ser or Glu;

whereby the subtilisin 309 variant has decreased adsorption to, and increased hydrolysis of, an insoluble substrate as compared to wild-type subtilisin 309 and wherein single amino acid substitution at sixth loop positions 207 to 209 and 211 are combined with at least one further amino acid substitution selected from positions 194, 195, 196, 197, 198, 199, 200, 201, 202, 203, 204, 205, 212 and 214.

8. The subtilisin 309 variant of claim 7 comprising two amino acid substitutions, wherein the substitutions are Ala for Pro at position 204 and Thr for Ala at position 209.

9. The subtilisin 309 variant of claim 7 wherein a. when a substitution occurs at position 200, the substituting amino acid is Asn or Ser;

b. when a substitution occurs at position 204, the substituting amino acid is Gly, Gln, Asn or Ser;

c. when a substitution occurs at position 205, the substituting amino acid is Pro, Gln, Asn or Ser;

d. when a substitution occurs at position 208, the substituting amino acid is Leu Ile, Met, Cys, Ala, His, Pro, Gly, Gln or Asn; and e. when a substitution occurs at position 209, the substituting amino acid is Pro, Gln, Asn or Ser.

10. The subtilisin 309 variant of claim 9, wherein the modified amino acid sequence further comprises His or Asp substituted for Asn at position 74.

11. The subtilisin 309 variant of claim 7 wherein a substitution occurs at two or more of positions 194, 195, 196, 197, 201, 202, 203, 204, 205 or 209.

12. The subtilisin 309 variant of claim 11, wherein a substitution occurs at two or more of positions 194, 195, 196, 197 or 201.

13. A subtilisin 309 variant having a modified amino acid sequence of subtilisin 309 wild-type amino acid sequence set forth in SEQ ID NO:1, wherein the modified amino acid sequence comprises a substitution at three or more of positions 194, 195, 196, 197, 198, 199, 200, 201, 202, 203, 204, 205, 207, 208, 209, 211, 212 or 214 is substituted, wherein a. when a substitution occurs at position 194, the substituting amino acid is His, Thr, Pro, Gly, Gln, Asn, Ser, Asp or Glu;

b. when a substitution occurs at position 195, the substituting amino acid is Gly, Gln, Asn, Ser, Asp or Glu;

c. when a substitution occurs at position 196, the substituting amino acid is Pro, Gln, Asn, Ser. Asp or Glu;

d. when a substitution occurs at position 197, the substituting amino acid is Met, Cys, Ala, His, Pro, Thr, Gly, Gln, Asn or Ser;

e. when a substitution occurs at position 198, the substituting amino acid is Glu, Gln, Asp or Ser;

f. when a substitution occurs at position 199, the substituting amino acid is Met, Cys, Ala, His, Pro, Gly, Gln, Asn or Ser;

g. when a substitution occurs at position 200, the substituting amino acid is Asn or Ser;

h. when a substitution occurs at position 201, the substituting amino acid is Asp or Glu;

i. when a substitution occurs at position 202, the substituting amino acid is Pro, Gly, Gln, Asn, Ser, Asp or Glu;

j. when a substitution occurs at position 203, the substituting amino acid is Leu, Ile, Val, Met, Cys, Ala, His, Thr, Pro, Gln, Asn, Ser or Glu;

k. when a substitution occurs at position 204, the substituting amino acid is Gly, Gln, Asn or Ser;

l. when a substitution occurs at position 205, the substituting amino acid is Pro, Gln, Asn or Ser;

m. when a substitution occurs at position 207, the substituting amino acid is Pro, Gly, Gln, Asn, Ser or Asp;

n. when a substitution occurs at position 280, the substituting amino acid is Leu, Ile, Met, Cys, Thr, Ala, His, Pro, Gly, Gln or Asn;

o. when a substitution occurs at position 209, the substituting amino acid is His, Thr, Pro, Gly, Gln, Asn or Ser;

p. when a substitution occurs at position 211, the substituting amino acid is Ile, Val, Met, Cys, Ala, His, Thr, Pro, Gly, Gln, Asn, Ser or Glu;

q. when a substitution occurs at position 212, the substituting amino acid is Gln, Ser or Asp;

r. when a substitution occurs at position 214, the substituting amino acid is Pro, Gly, Gln, Asn, Asp. Ser or Glu;

whereby the 309 variant has decreased absorption to, and increased hydrolysis of, an insoluble substrate as compared to wild-type subtilisin 309.

14. The subtilisin 309 variant of claim 13 wherein
   a. when a substitution occurs at position 200, the substituting amino acid is Asn or Ser;
   b. when a substitution occurs at position 204, the substituting amino acid is Gly, Gln, Asn or Ser;
   c. when a substitution occurs at position 205, the substituting amino acid is Pro, Gln, Asn or Ser;
   d. when a substitution occurs at position 208, the substituting amino acid is Leu, Ile, Met, Cys, Ala, His, Pro, Gly, Gln or Asn; and
   e. when a substitution occurs at position 209, the substituting amino acid is Pro, Gln, Asn or Ser.

15. The subtilisin 309 variant of claim 14 wherein a substitution occurs at three or more of positions 194, 195, 196, 197, 201, 202, 203, 204, 205 or 209.

16. The subtilisin 39 variant of claim 14, wherein the modified amino acid sequence further comprises Asp or His substituted for Asn at position 74.

17. The subtilisin 309 variant of claim 15 wherein a substitution occurs at three or more of positions 194, 195, 196, 197 or 201.

18. The 309 variant of claim 13 wherein Glu is substituted for Gln at position 200.

19. A subtilisin 309 variant having a modified amino acid sequence of subtilisin 309 wild-type amino acid sequence set forth in SEQ ID NO:1, wherein the modified amino acid sequence comprises Glu substituted for Gln at position 200, Glu substituted for Thr at position 207, and Glu substituted for Ser at position 210.

20. An isolated subtilisin 309 variant having a modified amino acid sequence of subtilisin 309 wild-type amino acid sequence set forth in SEQ ID NO:1, the wild-type amino acid sequence comprising a first loop region, a second loop region, a third loop region, a fourth loop region, a fifth loop region, and a sixth loop region; wherein the modified amino acid sequence comprises a substitution at one position in one of the loop regions; wherein
   A. when the substitution occurs in the first loop region, the substitution occurs at one of positions 59, 60, 61, 63, or 64; wherein
      a. when a substitution occurs at position 59, the substituting amino acid is Asn, Gln, Pro or Ser;
      b. when a substitution occurs at position 60, the substituting amino acid is Gln or Ser;
      c. when a substitution occurs at position 61, the substituting amino acid is Asn, Asp, Gln, Glu, Pro or Ser;
      d. when a substitution occurs at position 63, the substituting amino acid is Asn, Asp, Gln, Glu, Pro or Ser; and
      e. when a substitution occurs at position 64, the substituting amino acid is Asn, Asp, Gln, Glu, Gly, Pro or Ser;
   B. when the substitution occurs in the third loop region, the substitution occurs at position 131; wherein the substituting amino acid is Asn, Gln, Gly, His, Pro, Ser or Thr;
   C. when the substitution occurs in the fifth loop region, the substitution occurs at one of positions 181, 184 or 185; wherein
      a. when a substitution occurs at position 181, the substituting amino acid is Asn, Asp, Gln, Glu, or Ser;
      b. when a substitution occurs at position 184, the substituting amino acid is Asp or Glu; and
      c. when a substitution occurs at position 185, the substituting amino acid is Asn or Ser; and
   D. when the substitution occurs in the sixth loop region, the substitution occurs at one of positions 194, 195, 196, 197, 199, 200, 201, 202, 203, 204, 205, or 214; wherein
      a. when a substitution occurs at position 194, the substituting amino acid is His, Thr, Pro, Gly, Gln, Asn, Ser, Asp or Glu;
      b. when a substitution occurs at position 195, the substituting amino acid is Gly, Gln, Asn, Ser, Asp or Glu;
      c. when a substitution occurs at position 196, the substituting amino acid is Pro, Gln, Asn, Ser, Asp or Glu;
      d. when a substitution occurs at position 197, the substituting amino acid is Met, Cys, Ala, His, Pro, Gly, Gln or Ser;
      e. when a substitution occurs at position 199, the substituting amino acid is Met, Cys, Ala, His, Pro, Gly, Gln, Asn or Ser;
      f. when a substitution occurs at position 200, the substituting amino acid is Asn or Ser;
      g. when a substitution occurs at position 201, the substituting amino acid is Asp or Glu;
      h. when a substitution occurs at position 202, the substituting amino acid is Pro, Gly, Gln, Asn, Ser, Asp or Glu;
      i. when a substitution occurs at position 203, the substituting amino acid is Ile, Met, Ala, His, Pro, Gln, Asn or Ser;
      j. when a substitution occurs at position 204, the substituting amino acid is Gly, Gln, Asn or Ser;
      k. when a substitution occurs at position 205, the substituting amino acid is Pro, Gln, Asn or Ser; and
      l. when a substitution occurs at position 214, the substituting amino acid is Pro, Gly, Gln, Asn, Asp, Ser or Glu;
   whereby the subtilisin 309 variant has decreased adsorption to, and increased hydrolysis of, an insoluble substrate as compared to wild-type subtilisin 309 and wherein an amino acid substitution at either of the subtilisin 309 variant positions 181 or 185 is combined with at least one further substitution at a corresponding subtilisin 309 variant position selected from the group consisting of: 59, 60, 61, 63, 64, 131, 181, 184, 185, 194, 195, 196, 197, 199, 200, 201, 202, 203, 204, 205, 214 and combinations thereof.

21. The subtilisin 309 variant of claim 20, wherein the substitution occurs in the sixth loop region.

22. The subtilisin 309 variant of claim 20, wherein the substitution occurs in the first loop region.

23. The subtilisin 309 variant of claim 20, wherein the substitution occurs in the second loop region.

24. The subtilisin 309 variant of claim 20, wherein the substitution occurs in the third loop region.

25. The subtilisin 309 variant of claim 20, wherein the substitution occurs in the fifth loop region.

26. An isolated subtilisin 309 variant having a modified amino acid sequence of subtilisin 309 wild-type amino acid sequence set forth in SEQ ID NO:1, the wild-type amino acid sequence comprising a first loop region, a second loop region, a third loop region, a fourth loop region, a fifth loop region, and a sixth loop region; wherein the modified amino acid sequence comprises a substitution at two or more positions in one or more of the loop regions; wherein
   A. when a substitution occurs in the first loop region, the substitution occurs at one or more of positions 57, 58, 59, 60, 61, 63, or 64; wherein a. when a substitution occurs at position 57, the substituting amino acid is Asn, Asp, Glu or Ser;
b. when a substitution occurs at position 58, the substituting amino acid is Glu;
c. when a substitution occurs at position 59, the substituting amino acid is Asn, Asp, Gln, Glu, Pro or Ser;
d. when a substitution occurs at position 60, the substituting amino acid is Asp, Gln, Glu or Ser;
e. when a substitution occurs at position 61, the substituting amino acid is Asn, Asp, Gln, Glu, Pro or Ser;
f. when a substitution occurs at position 63, the substituting amino acid is Asn, Asp, Gln, Glu, Pro or Ser; and
g. when a substitution occurs at position 64, the substituting amino acid is Asn, Asp, Gln, Glu, Gly, Pro or Ser;

B. when a substitution occurs in the second loop region, the substitution occurs at one or more of positions 93, 94, 95, 96, 97, 98, 99, 100, 101, 102, 103, 104 or 105; wherein
a. when a substitution occurs at position 93, the substituting amino acid is Ala, Asn, Asp, Cys, Gln, Glu, Gly, His, Met, Pro, Ser or Thr;
b. when a substitution occurs at position 94, the substituting amino acid is Ala, Asn, Asp, Cys, Gln, Glu, Gly, His, Ile, Met, Pro, Ser, Thr or Val;
c. when a substitution occurs at position 95, the substituting amino acid is Asn, Asp, Gln, Glu, Pro or Ser; provided that if position 96 or position 207 is substituted with Asp, and the variant is a double mutation variant, then position 95 is not substituted with Asp; and when position 95 is substituted the variant is not a double, triple, quadruple, quintuple, sextuple, or septuple mutation variant having substitutions at positions selected from the group consisting of 102, 153, 154, 160, 183, and 211;
d. when a substitution occurs at position 96, the substituting amino acid is Asn, Asp, Gln, Glu, Gly, His, Pro, Ser or Thr; provided that if position 207 is substituted with Asp, and the variant is a double mutation variant, then position 96 is not substituted with Asp; and when position 96 is substituted the variant is not a double, triple, quadruple, quintuple, or sextuple mutation variant having substitutions at positions selected from the group consisting of 102, 154, 160, 183, and 211;
e. when a substitution occurs at position 97, the substituting amino acid is Asp or Glu; but when position 97 is substituted the variant is not a double, triple, quadruple, quintuple, or sextuple mutation variant having substitutions at positions selected from the group consisting of 102, 154, 160, 183, and 211;
f. when a substitution occurs at position 98, the substituting amino acid is Asn, Asp, Gln, Glu, Pro or Ser; but when position 98 is substituted the variant is not a double, triple, quadruple, quintuple, or sextuple mutation variant having substitutions at positions selected from the group consisting of 102, 154, 160, 183, and 211;
g. when a substitution occurs at position 99, the substituting amino acid is Asp or Glu; but when position 99 is substituted the variant is not a double, triple, quadruple, quintuple, or sextuple mutation variant having substitutions at positions selected from the group consisting of 102, 154, 160, 183, and 211;
h. when a substitution occurs at position 100, the substituting amino acid is Asn, Asp, Gln, Glu, Pro or Ser; but when position 100 is substituted the variant is not a double, triple, quadruple, quintuple, or sextuple mutation variant having substitutions at positions selected from the group consisting of 102, 154, 160, 183, and 211;
i. when a substitution occurs at position 101, the substituting amino acid is Asp or Glu; but when position 101 is substituted the variant is not a double, triple, quadruple, quintuple, or sextuple mutation variant having substitutions at positions selected from the group consisting of 102, 154, 160, 183, and 211;
j. when a substitution occurs at position 102, the substituting amino acid is Ala, Asn, Asp, Cys, Gln, Glu, Gly, His, Met, Pro, Ser or Thr;
k. when a substitution occurs at position 103, the substituting amino acid is Asp or Glu;
l. when a substitution occurs at position 104, the substituting amino acid is Asp or Glu; and
m. when a substitution occurs at position 105, the substituting amino acid is Ala, Asn, Asp, Cys, Gln, Glu, Gly, His, Leu, Met, Pro, Ser, Thr or Val; but when position 105 is substituted the variant is not a double, triple, quadruple, quintuple, sextuple, or septuple mutation variant having substitutions at positions selected from the group consisting of 102, 153, 154, 160, 183, and 211;

C. when a substitution occurs in the third loop region, the substitution occurs at one or more of positions 124, 125, 126, 127, 128, 129, 130 or 131; wherein
a. when a substitution occurs at position 124, the substituting amino acid is Ala, Asn, Asp, Cys, Gln, Glu, Gly, His, Ile, Met, Pro, Ser. Thr or Val; but when position 124 is substituted the variant is not a double, triple, quadruple, quintuple, sextuple, or septuple mutation variant having substitutions at positions selected from the group consisting of 102, 153, 154, 160, 183, and 211;
b. when a substitution occurs at position 125, the substituting amino acid is Asn, Asp, Gln, Glu, Pro or Ser; but when position 125 is substituted the variant is not a double, triple, quadruple, quintuple, sextuple, or septuple mutation variant having substitutions at positions selected from the group consisting of 102, 153, 154, 160, 183, and 211;
c. when a substitution occurs at position 126, the substituting amino acid is Asp or Glu; but when position 126 is substituted the variant is not a double, triple, quadruple quintuple, sextuple, or septuple mutation variant having substitutions at positions selected from the group consisting of 102, 153, 154, 160, 183, and 211;
d. when a substitution occurs at position 127, the substituting amino acid is Asn, Asp, Gln, Glu, Gly or Ser; but when position 127 is substituted the variant is not a double, triple, quadruple, quintuple, sextuple, or septuple mutation variant having substitutions at positions selected from the group consisting of 102, 153, 154, 160, 183, and 211;
e. when a substitution occurs at position 128, the substituting amino acid is Asp or Glu;
f. when a substitution occurs at position 129, the substituting amino acid is Asn, Asp, Gln, Glu, Gly or Ser;
g. when a substitution occurs at position 130, the substituting amino acid is Asp or Glu; and h. when a substitution occurs at position 131, the substituting amino acid is Asn, Asp, Gln, Glu, Gly, His, Pro, Ser or Thr;

D. when a substitution occurs in the fourth loop region, the substitution occurs at one or more of positions 152, 153, 154, 155, 156, 157, 158, 159, 160 or 161; wherein
  a. when a substitution occurs at position 152, the substituting amino acid is Asn, Asp, Gln, Glu, Pro or Ser; but when position 152 is substituted the variant is not a double, triple, quadruple, quintuple, or sextuple mutation variant having substitutions at positions selected from the group consisting of 102, 154, 160, 183, and 211;
  b. when a substitution occurs at position 153, the substituting amino acid is Asp, Gln, Glu, Pro or Ser;
  c. when a substitution occurs at position 154, the substituting amino acid is Asp or Glu; but when position 154 is substituted the variant is not a double, triple, quadruple, or quintuple mutation variant having substitutions at positions selected from the group consisting of 102, 160, 183, and 211;
  d. when a substitution occurs at position 155, the substituting amino acid is Asn, Asp, Gln, Glu, Pro or Ser; but when position 155 is substituted the variant is not a double, triple, quadruple, quintuple, or sextuple mutation variant having substitutions at positions selected from the group consisting of 102, 154, 160, 183, and 211;
  e. when a substitution occurs at position 156, the substituting amino acid is Asn, Asp, Gln, Glu, Gly, His, Pro, Ser or Thr; but when position 156 is substituted the variant is not a double, triple, quadruple, quintuple, or sextuple mutation variant having substitutions at positions selected from the group consisting of 102, 154, 160, 183, and 211;
  f. when a substitution occurs at position 157, the substituting amino acid is Asn, Asp, Gln, Glu, Pro or Ser; but when position 157 is substituted the variant is not a double, triple, quadruple, quintuple, or sextuple mutation variant having substitutions at positions selected from the group consisting of 102, 154, 160, 183, and 211;
  g. when a substitution occurs at position 158, the substituting amino acid is Asp or Glu; but when position 158 is substituted the variant is not a double, triple, quadruple, quintuple, or sextuple mutation variant having substitutions at positions selected from the group consisting of 102, 154, 160, 183, and 211;
  h. when a substitution occurs at position 159, the substituting amino acid is Ala, Asn, Asp, Cys, Gln, Glu, Gly, His, Leu, Met, Pro, Ser, Thr or Val; wherein when position 159 is substituted with Leu, the variant is not a double mutation variant having a substitution at position 158 with Glu; and when position 159 is substituted the variant is not a double, triple, quadruple, quintuple, or sextuple mutation variant having substitutions at positions selected from the group consisting of 102, 154, 160, 183, and 211;
  i. when a substitution occurs at position 160, the substituting amino acid is Asp or Glu; but when position 160 is substituted the variant is not a double mutation variant having a substitution at position 60 with Asp or Glu; and
  j. when a substitution occurs at position 161, the substituting amino acid is Ala, Asn, Asp, Cys, Gln, Glu, Gly, His, Ile, Leu, Met, Pro, Ser, Thr or Val; but when position 161 is substituted the variant is not a double, triple, quadruple, quintuple, or sextuple mutation variant having substitutions at positions selected from the group consisting of 102, 154, 160, 183, and 211;

E. when a substitution occurs in the fifth loop region, the substitution occurs at one or more of positions 181, 182, 183, 184 or 185; wherein
  a. when a substitution occurs at position 181, the substituting amino acid is Asn, Asp, Gln, Glu, Gly, His, Pro, Ser or Thr;
  b. when a substitution occurs at position 182, the substituting amino acid is Asp or Glu;
  c. when a substitution occurs at position 183, the substituting amino acid is Ala, Asn, Asp, Cys, Gln, Glu, Gly, His, Ile, Leu, Met, Pro, Ser, Thr, Tyr or Val;
  d. when a substitution occurs at position 184, the substituting amino acid is Asp or Glu; and
  e. when a substitution occurs at position 185, the substituting amino acid is Asn, Asp, Glu or Ser; and F. when a substitution occurs in the sixth loop region, the substitution occurs at one or more of positions 193, 194, 195, 196, 197, 198, 199, 200, 201, 202, 203, 204, 205, 206, 207, 208, 209, 210, 211, 212, 213 or 214; wherein
  a. when a substitution occurs at position 193, the substituting amino acid is Met, Cys, Ala, His, Thr, Pro, Gly, Gln, Asn, Ser, Asp or Glu;
  b. when a substitution occurs at position 194, the substituting amino acid is His, Thr, Pro, Gly, Gln, Asn, Ser, Asp or Glu;
  c. when a substitution occurs at position 195, the substituting amino acid is Gly, Gln, Asn, Ser, Asp or Glu;
  d. when a substitution occurs at position 196, the substituting amino acid is Pro, Gln, Asn, Ser, Asp or Glu;
  e. when a substitution occurs at position 197, the substituting amino acid is Met, Cys, Ala, His, Thr, Pro, Gly, Gln, Asn, Ser, Asp or Glu;
  f. when a substitution occurs at position 198, the substituting amino acid is Glu, Gln, Asp or Ser;
  g. when a substitution occurs at position 199, the substituting amino acid is Met, Cys, Ala, His, Thr, Pro, Gly, Gln, Asn, Ser, Asp or Glu;
  h. when a substitution occurs at position 200, the substituting amino acid is Asn, Ser, Glu or Asp;
  i. when a substitution occurs at position 201, the substituting amino acid is Asp or Glu;
  j. when a substitution occurs at position 202, the substituting amino acid is Pro, Gly, Gln, Asn, Ser, Asp or Glu;
  k. when a substitution occurs at position 203, the substituting amino acid is Leu, Ile, Val, Met, Cys, Ala, His, Thr, Pro, Gly, Gln, Asn, Ser, Asp or Glu;
  l. when a substitution occurs at position 204, the substituting amino acid is Gly, Gln, Asn, Ser, Asp or Glu;
  m. when a substitution occurs at position 205, the substituting amino acid Pro, Gln, Asn, Ser, Asp or Glu;
  n. when a substitution occurs at position 206, the substituting amino acid Asp or Glu;
  o. when a substitution occurs at position 207, the substituting amino acid Pro, Gly, Gln, Asn, Ser, Asp or Glu; but when position 207 is substituted the variant is not a double triple, quadruple, quintuple, sextuple, or septuple mutation variant having a substitutions at positions selected from the group consisting of 102, 153, 154, 160, 183, and 211;
p. when a substitution occurs at position 208, the substituting amino acid Leu, Ile, Val, Met, Cys, Thr, Ala, His, Pro, Gly, Gln, Asn, Asp or Glu; but when position 208 is substituted the variant is not a double, triple, quadruple, quintuple, sextuple, or septuple mutation variant having substitutions at positions selected from the group consisting of 102, 153, 154, 160, 183, and 211;
q. when a substitution occurs at position 209, the substituting amino acid His, Thr, Pro, Gly, Asn, Ser, Asp or Glu; but when position 209 is substituted the variant is not a double, triple, quadruple, quintuple, sextuple, or septuple mutation variant having substitutions at positions selected from the group consisting of 102, 153, 154, 160, 183, and 211;
r. when a substitution occurs at position 210, the substituting amino acid Asp or Glu;
s. when a substitution occurs at position 211, the substituting amino acid Ile, Val, Met, Cys, Ala, His, Thr, Pro, Gly, Gln, Asn, Ser, Glu or Asp; wherein when position 211 is substituted with Glu, the variant is not a double mutation variant having a substitution of Asn at position 102;
t. when a substitution occurs at position 212, the substituting amino acid Gln, Ser, Asp, or Glu; wherein the variant is not a double mutation variant having substitutions at positions 211 and 212 and wherein when position 212 is substituted with Asp, the variant is not a double mutation variant having a substitution at position 160 with Asp;
u. when a substitution occurs at position 213, the substituting amino acid is Pro, Gln, Asn, Ser, Asp or Glu; and
v. when a substitution occurs at position 214, the substituting amino acid is Pro, Gly, Gln, Asn, Asp, Ser or Glu;
whereby the subtilisin 309 variant has decreased adsorption to, and increased hydrolysis of, an insoluble substrate as compared with wild-type subtilisin 309 wherein amino acid substitutions at positions 193 and 203 of the sixth loop region are combined with at least one further substitution at a corresponding subtilisin 309 variant position, selected from the group consisting of: 57, 58, 59, 60, 61, 63, 64, 93, 94, 95, 96, 97, 98, 99, 100, 101, 102, 103, 104, 105, 124, 125, 126, 127, 128, 129, 130, 131, 152, 153, 154, 155, 156, 157, 158, 159, 160, 161, 181, 182, 183, 184, 185, 193, 194, 195, 196, 197, 198, 199, 200, 201, 202, 203, 204, 205, 206, 207, 208, 209, 210, 211, 212, 213, 214 and combinations thereof.

27. The subtilisin 309 variant of claim 26, wherein two or more substitutions occur in the sixth loop region.

28. The subtilisin 309 variant of claim 26, wherein two or more substitutions occur in the first loop region.

29. The subtilisin 309 variant of claim 26, wherein two or more substitutions occur in the second loop region.

30. The subtilisin 309 variant of claim 26, wherein two more substitutions occur in the third loop region.

31. The subtilisin 309 variant of claim 26, wherein two or more substitutions occur in the fourth loop region.

32. The subtilisin 309 variant of claim 26, wherein two or more substitutions occur in the fifth loop region.

33. An isolated subtilisin 309 variant having a modified amino acid sequence of subtilisin 309 wild-type amino acid sequence set forth in SEQ ID NO:1, the wild-type amino acid sequence comprising a first loop region, a second loop region, a third loop region, a fourth loop region, a fifth loop region, and a sixth loop region; wherein the modified amino acid sequence comprises a substitution at two or more positions in one or more of the loop regions; wherein A. when the substitution occurs in the first loop region, the substitution occurs at one or more of positions 59, 60, 61, 63, or 64; wherein
  a. when a substitution occurs at position 59, the substituting amino acid is Asn, Gln, Pro or Ser;
  b. when a substitution occurs at position 60, the substituting amino acid is Gln or Ser;
  c. when a substitution occurs at position 61, the substituting amino acid is Asn, Asp, Gln, Glu, Pro or Ser;
  d. when a substitution occurs at position 63, the substituting amino acid is Asn, Asp, Gln, Glu, Pro or Ser; and
  e. when a substitution occurs at position 64, the substituting amino acid is Asn, Asp, Gln, Glu, Gly, Pro Ser;

B. when a substitution occurs in the second loop region, the substitution occurs at one or more of positions 93, 94, 95, 96, 97, 98, 99, 100, 101, 102, 103, 104 or 105; wherein
  a. when substitution occurs at position 93, the substituting amino acid is Ala, Asn, Asp, Cys, Gln, Glu, Gly, His, Met, Pro, Ser or Thr;
  b. when a substitution occurs at position 94, the substituting amino acid is Ala, Asn, Asp, Cys, Gln, Glu, Gly, His, Ile, Met, Pro, Ser, Thr or Val;
  c. when a substitution occurs at position 95, the substituting amino acid is Asn, Asp, Gln, Glu, Pro or Ser; provided that if position 96 or position 207 is substituted with Asp, and the variant is a double mutation variant, then position 95 is not substituted with Asp; and when position 95 is substituted the variant is not a double, triple, quadruple, quintuple, sextuple, or septuple mutation variant having substitution at position selected from the group consisting of 102, 153, 154, 160, 183, and 211;
  d. when a substitution occurs at position 96, the substituting amino acid is Asn, Asp, Gln, Glu, Gly, His, Pro, Ser or Thr; provided that if position 207 is substituted with Asp, and the variant is a double mutation variant, then position 96 is not substituted with Asp; and when position 96 is substituted the variant is not a double, triple, quadruple, quintuple, or sextuple mutation variant having a substitutions at positions selected from the group consisting of 102, 154, 160, 183, and 211;
  e. when a substitution occurs at position 97, the substituting amino acid is Asp or Glu; but when position 97 is substituted the variant is not a double, triple, quadruple, quintuple, or sextuple mutation variant having a substitutions at positions selected from the group consisting of 102, 154, 160, 183, and 211;
  f. when a substitution occurs at position 98, the substituting amino acid is Asn, Asp, Gln, Glu, Pro or Ser; but when position 98 is substituted the variant is not a double, triple, quadruple, quintuple, or sextuple mutation variant having a substitutions at positions selected from the group consisting of 102, 154, 160, 183, and 211;
  g. when a substitution occurs at position 99, the substituting amino acid is Asp or Glu; but when position 99 is substituted the variant is not a double, triple, quadruple, quintuple, or sextuple mutation variant having substitutions at positions selected from the group consisting of 102, 154, 160, 183, and 211;

h. when a substitution occurs at position 100, the substituting amino acid is Asn, Asp, Gln, Glu, Pro or Ser; but when position 100 is substituted the variant is not a double, triple, quadruple, quintuple, or sextuple mutation variant having substitutions at positions selected from the group consisting of 102, 154, 160, 183, and 211;

i. when a substitution occurs at position 101, the substituting amino acid is Asp or Glu; but when position 101 is substituted the variant is not a double, triple, quadruple, quintuple, or sextuple mutation variant having a substitutions at positions selected from the group consisting of 102, 154, 160, 183, and 211;

j. when a substitution occurs at position 102, the substituting amino acid is Ala, Asn, Asp, Cys, Gln, Glu, Gly, His, Met, Pro, Ser or Thr;

k. when a substitution occurs at position 103, the substituting amino acid is Asp or Glu;

i. when a substitution occurs at position 104, the substituting amino acid is Asp or Glu; and m. when a substitution occurs at position 105, the substituting amino acid is Ala, Asn, Asp, Cys, Gln, Glu, Glu, Gly, His, Leu, Met, Pro, Ser, Thr or Val; but when position 105 is substituted the variant is not a double, triple, quadruple, quintuple, sextuple, or septuple mutation variant having substitutions at positions selected from the group consisting of 102, 153, 154, 160, 183, and 211;

C. when a substitution occurs in the third loop region, the substitution occurs at one or more of positions 124, 125, 126, 127, 128, 129, 130 or 131; wherein a. when a substitution occurs at position 124, the substituting amino acid is Ala, Asn, Asp, Cys, Gln, Glu, Gly, His Ile, Met, Pro, Ser, Thr or Val; but when position 124 is substituted the variant is not a double, triple, quadruple, quintuple, sextuple, or septuple mutation variant having substitutions at positions selected from the group consisting of 102, 153, 154, 160, 183, and 211;

b. when a substitution occurs at position 125, the substituting amino acid is Asn, Asp, Gln, Glu, Pro or Ser; but when position 125 is substituted the variant is not a double, triple, quadruple, quintuple, sextuple, or septuple mutation variant having a substitutions at positions selected from the group consisting of 102, 153, 154, 160, 183, and 211;

c. when a substitution occurs at position 126, the substituting amino acid is Asp or Glu; but when position 126 is substituted the variant is not a double, triple, quadruple, quintuple, sextuple, or septuple mutation variant having a substitutions at positions selected from the group consisting of 102, 153, 154, 160, 183, and 211;

d. when a substitution occurs at position 127, the substituting amino acid is Asn, Asp, Gln, Glu, Gly or Ser; but when position 127 is substituted the variant is not a double, triple, quadruple, quintuple, sextuple, or septuple mutation variant having a substitutions at positions selected from the group consisting of 102, 153, 154, 160, 183, and 211;

e. when a substitution occurs at position 128, the substituting amino acid is Asp or Glu;

f. when a substitution occurs at position 129, the substituting amino acid is Asn, Asp, Gln, Glu, Gly or Ser;

g. when a substitution occurs at position 130, the substituting amino acid is Asp or Glu; and h. when a substitution occurs at position 131, the substituting amino acid is Asn, Asp, Gln, Glu, Gly, His, Pro, Ser or Thr;

D. when a substitution occurs in the fourth loop region, the substitution occurs at one or more of positions 152, 153, 154, 155, 156, 157, 158, 159, 160 or 161; wherein a. when a substitution occurs at position 152, the substituting amino acid is Asn, Asp, Gln, Glu, Pro or Ser; but when position 152 is substituted the variant is not a double, triple, quadruple, quintuple, or sextuple mutation variant having substitutions at positions selected from the group consisting of 102, 154, 160, 183, and 211;

b. when a substitution occurs at position 153, the substituting amino acid is Asp, Gln, Glu, Pro or Ser;

c. when a substitution occurs at position 154, the substituting amino acid is Asp or Glu; but when position 154 is substituted the variant is not a double, triple, quadruple, or quintuple mutation variant having substitutions at positions selected from the group consisting of 102, 160, 183, and 211;

d. when a substitution occurs at position 155, the substituting amino acid is Asn, Asp, Gln, Glu, Pro or Ser; but when position 155 is substituted the variant is not a double, triple, quadruple, quintuple, or sextuple mutation variant having a substitutions at positions selected from the group consisting of 102, 154, 160, 183, and 211;

e. when a substitution occurs at position 156, the substituting amino acid is Asn, Asp, Gln, Glu, Gly, His, Pro, Ser or Thr; but when positions 156 is substituted the variant is not a double, triple, quadruple, quintuple, or sextuple mutation variant having a substitutions at positions selected from the group consisting of 102, 154, 160, 183, and 211;

f. when a substitution occurs at position 157, the substituting amino acid is Asn, Asp, Gln, Glu, Pro or Ser; but when position 157 is substituted the variant is not a double, triple, quadruple, quintuple, or sextuple mutation variant having substitutions at positions selected from the group consisting of 102, 154, 160, 183, and 211;

g. when a substitution occurs at position 158, the substituting amino acid is Asp or Glu; but when position 158 is substituted the variant is not a double, triple, quadruple, quintuple, or sextuple mutation variant having substitutions at positions selected from the group consisting of 102, 154, 160, 183, and 211;

h. when a substitution occurs at position 159, the substituting amino acid is Ala, Asn, Asp, Cys, Gln, Glu, Gly, His, Leu, Met, Pro, Ser, Thr or Val; wherein when position 159 is substituted with Leu, the variant is not a double mutation variant having a substitution at position 158 with Glu; and when position 159 is substituted the variant is not a double, triple, quadruple, quintuple, or sextuple mutation variant having substitutions at positions selected from the group consisting of 102, 154, 160, 183, and 211;

i. when a substitution occurs at position 160, the substituting amino acid is Asp or Glu; and j. when a substitution occurs at position 161, the substituting amino acid is Ala, Asn, Asp, Cys, Gln, Glu, Gly, His, Ile, Leu, Met, Pro, Ser, Thr or Val; but when position 161 is substituted the variant is not a double, triple, quadruple, quintuple, or sextuple mutation variant having substitutions at positions selected from the group consisting of 102, 154, 160, 183, and 211;

E. when a substitution occurs in the fifth loop region, the substitution occurs at one or more of positions 181, 182, 183, 184 or 185; wherein
  a. when a substitution occurs at position 181, the substituting amino acid is Asn, Asp, Gln, Glu, Gly, His, Pro, Ser or Thr;
  b. when a substitution occurs at position 182, the substituting amino acid is Asp or Glu;
  c. when a substitution occurs at position 183, the substituting amino acid is Ala, Asn, Asp, Cys, Gln, Glu, Gly, His, Ile, Leu, Met, Pro, Ser, Thr, Tyr or Val;
  d. when a substitution occurs at position 184, the substituting amino acid is Asp or Glu; and
  e. when a substitution occurs at position 185, the substitution amino acid is Asn, Asp, Glu or Ser; and F. when a substitution occurs in the sixth loop region, the substitution occurs at one or more of positions 193, 194, 195, 196, 197, 198, 199, 200, 201, 202, 203, 204, 205, 206, 207, 208, 209, 210, 211, 212, 213 or 214; wherein
  a. when a substitution occurs at position 193, the substituting amino acid is Met, Cys, Ala, His, Thr, Pro, Gly, Gln, Asn, Ser, Asp or Glu;
  b. when a substitution occurs at position 194, the substituting amino acid is His, Thr, Pro, Gly, Gln, Asn, Ser, Asp or Glu;
  c. when a substitution occurs at position 195, the substituting amino acid is Gly, Gln, Asn, Ser, Asp or Glu;
  d. when a substitution occurs at position 196, the substituting amino acid is Pro, Gln, Asn, Ser, Asp or Glu;
  e. when a substitution occurs at position 197, the substituting amino acid is Met, Cys, Ala, His, Thr, Pro, Gly, Gln, Asn, Ser, Asp or Glu;
  f. when a substitution occurs at position 198, the substituting amino acid is Glu, Gln, Asp or Ser;
  g. when a substitution occurs at position 199, the substituting amino acid is Met, Cys, Ala, His, Thr, Pro, Gly, Gln, Asn, Ser, Asp or Glu;
  h. when a substitution occurs at position 200, the substituting amino acid is Asn, Ser, Glu or Asp;
  i. when a substitution occurs at position 201, the substituting amino acid is Asp or Glu;
  j. when a substitution occurs at position 202, the substituting amino acid is Pro, Gly, Gln, Asn, Ser, Asp or Glu;
  k. when a substitution occurs at position 203, the substituting amino acid is Leu, Ile, Val, Met, Cys, Ala, His, Thr, Pro, Gly, Gln, Asn, Ser, Asp or Glu;
  l. when a substitution occurs at position 204, the substituting amino acid is Gly, Gln, Asn, Ser, Asp or Glu;
  m. when a substitution occurs at position 205, the substituting amino acid Pro, Gln, Asn, Ser, Asp or Glu;
  n. when a substitution occurs at position 206, the substituting amino acid Asp or Glu;
  o. when a substitution occurs at position 207, the substituting amino acid Pro, Gly, Gln, Asn, Ser, Asp or Glu; but when position 207 is substituted the variant is not a double, triple, quadruple, quintuple, sextuple, or septuple mutation variant having a substitutions at positions selected from the group consisting of 102, 153, 154, 160, 183, and 211;
  p. when a substitution occurs at position 208, the substituting amino acid Leu, Ile, Val, Met, Cys, Thr, Ala, His, Pro, Gly, Gln, Asn, Asp or Glu; but when position 208 is substituted the variant is not a double, triple, quadruple, quintuple, sextuple, or septuple mutation variant having substitutions at positions selected from the group consisting of 102, 153, 154, 160, 183, and 211;
  q. when a substitution occurs at position 209, the substituting amino acid His, Thr, Pro, Gly, Gln, Asn, Ser, Asp or Glu; but when position 209 is substituted the variant is not a double triple, quadruple, quintuple, sextuple, or septuple mutation variant having a substitutions at positions selected from the group consisting of 102, 153, 154, 160, 183, and 211;
  r. when a substitution occurs at position 210, the substituting amino acid Asp or Glu;
  s. when a substitution occurs at position 211, the substituting amino acid Ile, Val, Met, Cys, Ala, His, Thr, Pro, Gly, Gln, Asn, Ser, Glu or Asp; but when position 211 is substituted with Glu, the variant is not a double mutation variant having a substitution of Glu at position 127 or a substitution of Asn at position 102;
  t. when a substitution occurs at position 212, the substituting amino acid Gln, Ser, Asp, or Glu; but when position 212 is substitution the variant is not a double mutation variant having a substitution at position 211; and wherein when position 212 is substituted with Asp, the variant is not a double mutation variant having a substitution at position 160 with Asp;
  u. when a substitution occurs at position 213, the substituting amino acid is Pro, Gln, Asn, Ser, Asp or Glu; and
  v. when a substitution occurs at position 214, the substituting amino acid is Pro, Gly, Gln, Asn, Asp, Ser or Glu;

whereby the subtilisin 309 variant has decreased adsorption to, and increased hydrolysis of, an insoluble substrate as compared to wild-type subtilisin 309.

34. The subtilisin 309 variant of claim 33, wherein two or more substitutions occur in the sixth loop region.

35. The subtilisin 309 variant of claim 33, wherein two or more substitutions occur in the first loop region.

36. The subtilisin 309 variant of claim 33, wherein two or more substitutions occur in the second loop region.

37. The subtilisin 309 variant of claim 33, wherein two or more substitutions occur in the third loop region.

38. The subtilisin 309 variant of claim 33, wherein two or more substitutions occur in the fourth loop region.

39. The subtilisin 309 variant of claim 33, wherein two or more substitutions occur in the fifth loop region.

40. An isolated subtilisin 309 variant having a modified amino acid sequence of subtilisin 309 wild-type amino acid sequence set forth in SEQ ID NO:1, the wild-type amino acid sequence comprising a first loop region, a second loop region, a third loop region, a fourth loop region, a fifth loop region, and a sixth loop region, wherein the modified amino acid sequence comprises a substitution at two or more positions in one or more of the loop regions; wherein
  A. when a substitution occurs in the first loop region, the substitution occurs at one or more of positions 57, 58, 59, 60, 61, 63, or 64; wherein
    a. when a substitution occurs at position 57, the substituting amino acid is Asn, Asp, Glu or Ser;

b. when a substitution occurs at position 58, the substituting amino acid is Glu;
c. when a substitution occurs at position 59, the substituting amino acid is Asn, Asp, Gln, Glu, Pro or Ser;
d. when a substitution occurs at position 60, the substituting amino acid is Asp, Gln, Glu or Ser;
e. when a substitution occurs at position 61, the substituting amino acid is Asn, Asp, Gln, Glu, Pro or Ser;
f. when a substitution occurs at position 63, the substituting amino acid is Asn, Asp, Gln, Glu, Pro or Ser; and
g. when a substitution occurs at position 64, the substituting amino acid is Asn, Asp, Gln, Glu, Gly, Pro or Ser;
B. when a substitution occurs in the second loop region, the substitution occurs at one or more of positions 93, 94, 95, 96, 98, 100, 102 or 105; wherein
a. when a substitution occurs at position 93, the substituting amino acid is Ala, Asn, Cys, Gln, Gly, His, Met, Pro, Ser or Thr;
b. when a substitution occurs at position 94, the substituting amino acid is Ala, Asn, Asp, Cys, Gln, Glu, Gly, His, Ile, Met, Pro, Ser, Thr or Val;
c. when a substitution occurs at position 95, the substituting amino acid is Gln or Ser; but when position 95 is substituted the variant is not a double, triple, quadruple, quintuple, sextuple, or septuple mutation variant having substitutions at positions selected from the group consisting of 102, 153, 154, 160, 183, and 211;
d. when a substitution occurs at position 96, the substituting amino acid is Asn, Gly, His, Ser or Thr; but when position 96 is substituted the variant is not a double, triple, quadruple, quintuple, or sextuple mutation variant having substitutions at positions selected from the group consisting of 102, 154, 160, 183, and 211;
e. when a substitution occurs at position 98, the substituting amino acid is Asn, Gln, Pro or Ser; but when position 98 is substituted the variant is not a double, triple, quadruple, quintuple, or sextuple mutation variant having substitutions at positions selected from the group consisting of 102, 154, 160, 183, and 211;
f. when a substitution occurs at position 100, the substituting amino acid is Asn, Asp, Gln, Glu, Pro or Ser; but when position 100 is substituted the variant is not a double, triple, quadruple, quintuple, or sextuple mutation variant having substitutions at positions selected from the group consisting of 102, 154, 160, 183, and 211;
g. when a substitution occurs at position 102, the substituting amino acid is Cys or Met; and
h. when a substitution occurs at position 105, the substituting amino acid is Ala, Asn, Cys, Gln, Gly, His, Leu, Met, Pro, Ser, Thr or Val; but when position 105 is substituted the variant is not a double, triple, quadruple, quintuple, sextuple, or septuple mutation variant having substitutions at positions selected from the group consisting of 102, 153, 154, 160, 183, and 211;
C. when a substitution occurs in the third loop region, the substitution occurs at one or more positions 124, 125, 126, 127, 128, 129, 130 or 131; wherein
a. when a substitution occurs at position 124, the substituting amino acid is Also, Asn, Asp, Cys, Gln, Glu, Gly, His, Ile, Met, Pro, Ser, Thr or Val; but when position 124 is substituted the variant is not a double, triple, quadruple, quintuple, sextuple, or septuple mutation variant having substitutions at positions selected from the group consisting of 102, 153, 154, 160, 183, and 211;
b. when a substitution occurs at position 125, the substituting amino acid is Asn, Asp, Gln, Glu, Pro or Ser; but when position 125 is substituted the variant is not a double, triple, quadruple, quintuple, sextuple, or septuple mutation variant having substitutions at positions selected from the group consisting of 102, 153, 154, 160, 183, and 211;
c. when a substitution occurs at position 126, the substituting amino acid is Asp or Glu; but when position 126 is substituted the variant is not a double, triple, quadruple, quintuple, sextuple, or septuple mutation variant having a substitutions at positions selected from the group consisting of 102, 153, 154, 160, 183, and 211;
d. when a substitution occurs at position 127, the substituting amino acid is Asn, Asp, Gln, Glu, Gly or Ser; but when position 127 is substituted the variant is not a double, triple, quadruple, quintuple, sextuple, or septuple mutation variant having substitutions at positions selected from the group consisting of 102, 153, 154, 160, 183, and 211;
e. when a substitution occurs at position 128, the substituting amino acid is Asp or Glu;
f. when a substitution occurs at position 129, the substituting amino acid is Asn, Asp, Gln, Glu, Gly or Ser;
g. when a substitution occurs at position 130, the substituting amino acid is Asp or Glu; and
h. when a substitution occurs at position 131, the substituting amino acid is Asn, Asp, Gln, Glu, Gly, His, Pro, Ser or Thr;
D. when a substitution occurs in the fourth loop region, the substitution occurs at one or more of positions 152, 153, 154, 155, 156, 157, 158, 159, 160 or 161; wherein
a. when a substitution occurs at position 152, the substituting amino acid is Asn, Asp, Gln, Glu, Pro or Ser; but when position 152 is substituted the variant is not a double, triple, quadruple, quintuple, or sextuple mutation variant having a substitutions at positions selected from the group consisting of 102, 154, 160, 183, and 211;
b. when a substitution occurs at position 153, the substituting amino acid is Asp, Gln, Glu, Pro or Ser;
c. when a substitution occurs at position 154, the substituting amino acid is Asp or Glu; but when position 154 is substituted the variant is not a double, triple, quadruple, or quintuple mutation variant having substitutions at positions selected from the group consisting of 102, 160, 183, and 211;
d. when a substitution occurs at position 155, the substituting amino acid is Asn, Asp, Gln, Glu, Pro or Ser; but when position 155 is substituted the variant is not a double, triple, quadruple, quintuple, or sextuple mutation variant having a substitutions at positions selected from the group consisting of 102, 154, 160, 183, and 211;
e. when a substitution occurs at position 156, the substituting amino acid is Asn, Asp, Gln, Glu, Gly, His, Pro, Ser or Thr; but when position 156 is substituted the variant is not a double, triple, quadruple, quintuple, or sextuple mutation variant having a substitutions at positions selected from the group consisting of 102, 154, 160, 183, and 211;

f. when a substitution occurs at position 157, the substituting amino acid is Asn, Asp, Gln, Glu, Pro or Ser; but when position 157 is substituted the variant is not a double, triple, quadruple, quintuple, or sextuple mutation variant having a substitutions at positions selected from the group consisting of 102, 154, 160, 183, and 211;

g. when a substitution occurs at position 158, the substituting amino acid is Asp or Glu; but when position 158 is substituted the variant is not a double, triple, quadruple, quintuple, or sextuple mutation variant having substitutions at positions selected from the group consisting of 102, 154, 160, 183, and 211;

h. when a substitution occurs at position 159, the substituting amino acid is Ala, Asn, Asp, Cys, Gln, Glu, Gly, His, Leu, Met, Pro, Ser, Thr or Val; but when position 159 is substituted with Leu, the variant is not a double mutation variant having a substitution at position 158 with Glu; and when position 159 is substituted the variant is not a double, triple, quadruple, quintuple, or sextuple mutation variant having a substitutions at positions selected from the group consisting of 102, 154, 160, 183, and 211;

i. when a substitution occurs at position 160, the substituting amino acid is Asp or Glu; but when position 160 is substituted the variant is not a double mutation variant having a substitution at position 60 with Asp or Glu; and j. when a substitution occurs at position 161, the substituting amino acid is Ala, Asn, Asp, Cys, Gln, Glu, Gly, His, Ile, Leu, Met, Pro, Ser, Thr or Val; but when position 161 is substituted the variant is not a double, triple, quadruple, quintuple, or sextuple, mutation variant having substitutions at positions selected from the group consisting of 102, 154, 160, 183, and 211;

E. when a substitution occurs in the fifth loop region, the substitution occurs at one or more of positions 181, 182, 183, 184 or 185; wherein a. when a substitution occurs at position 181, the substituting amino acid is Asn, Asp, Gln, Glu, Gly, His, Pro, Ser or Thr;

b. when a substitution occurs at position 182, the substituting amino acid is Asp or Glu;

c. when a substitution occurs at position 183, the substituting amino acid is Ala, Asn, Asp, Cys, Gln, Glu, Gly, His, Ile, Leu, Met, Pro, Ser, Thr, Tyr or Val;

d. when a substitution occurs at position 184, the substituting amino acid is Asp or Glu; and e. when a substitution occurs at position 185, the substituting amino acid is Asn, Asp, Glu or Ser; and F. when substitution occurs in the sixth loop region, the substitution occurs at one or more of positions 193, 194, 195, 196, 197, 198, 199, 200, 201, 202, 203, 204, 205, 206, 207, 208, 209, 210, 211, 212, 213 or 214; wherein a. when a substitution occurs at position 193, the substituting amino acid is Met, Cys, Ala, His, Thr, Pro, Gly, Gln, Asn, Ser, Asp or Glu;

b. when a substitution occurs at position 194, the substituting amino acid is His, Thr, Pro, Gly, Gln, Asn, Ser, Asp or Glu;

c. when a substitution occurs at position 195, the substituting amino acid is Gly, Gln, Asn, Ser, Asp or Glu;

d. when a substitution occurs at position 196, the substituting amino acid is Pro, Gln, Asn, Ser, Asp or Glu;

e. when a substitution occurs at position 197, the substituting amino acid is Met, Cys, Ala, His, Thr, Pro, Gly, Gln, Asn, Ser, Asp or Glu;

f. when a substitution occurs at position 198, the substituting amino acid is Glu, Gln, Asp or Ser;

g. when a substitution occurs at position 199, the substituting amino acid is Met, Cys, Ala, His, Thr, Pro, Gly, Gln, Asn, Ser, Asp or Glu;

h. when a substitution occurs at position 200, the substituting amino acid is Asn, Ser, Glu or Asp;

i. when a substitution occurs at position 201, the substituting amino acid is Asp or Glu;

j. when a substitution occurs at position 202, the substituting amino acid is Pro, Gly, Gln, Asn, Ser, Asp or Glu;

k. when a substitution occurs at position 203, the substituting amino acid is Leu, Ile, Val, Met, Cys, Ala, His, Thr, Pro, Gly, Gln, Asn, Ser, Asp or Glu;

l. when a substitution occurs at position 204, the substituting amino acid is Gly, Gln, Asn, Ser, Asp or Glu;

m. when a substitution occurs at position 205, the substituting amino acid Pro, Gln, Asn, Ser, Asp or Glu;

n. when a substitution occurs at position 206, the substituting amino acid Asp or Glu;

o. when a substitution occurs at position 207, the substituting amino acid Pro, Gly, Gln, Asn, Ser, Asp or Glu; but when position 207 is substituted the variant is not a double, triple, quadruple, quintuple, sextuple, or septuple mutation variant having substitutions at positions selected from the group consisting of 102, 153, 154, 160, 183, and 211;

p. when a substitution occurs at position 208, the substituting amino acid Leu, Ile, Val, Met, Cys, Thr, Ala, His, Pro, Gly, Gln, Asn, Asp or Glu; but when position 208 is substituted the variant is not a double, triple, quadruple, quintuple, sextuple, or septuple mutation variant having substitutions at positions selected from the group consisting of 102, 153, 154, 160, 183, and 211;

q. when a substitution occurs at position 209, the substituting amino acid His, Thr, Pro, Gly, Gln, Asn, Ser, Asp or Glu; but when position 209 is substituted the variant is not a double, triple quadruple quintuple, sextuple, or septuple mutation variant having substitutions at positions selected from the group consisting of 102, 153, 154, 160, 183, and 211;

r. when a substitution occurs at position 210, the substituting amino acid Asp or Glu;

s. when a substitution occurs at position 211, the substituting amino acid Ile, Val, Met, Cys, Ala, His, Thr, Pro, Gly, Gln, Asn, Ser, Glu or Asp; wherein when position 211 is substituted with Glu, the variant is not a double mutation variant having a substitution at position 127 with Glu;

t. when a substitution occurs at position 212, the substituting amino acid Gln, Ser, Asp, or Glu; but when position 212 is substituted the variant is not a double mutation variant having a substitution at position 211; and wherein when position 212 is substituted with Asp, the variant is not a double mutation variant having a substitution at position 160 with Asp;

u. when a substitution occurs at position 213, the substituting amino acid is Pro, Gln, Asn, Ser, Asp or Glu; and v. when a substitution occurs at position 214, the substituting amino acid is Pro, Gly, Gln, Asn, Asp, Ser or Glu;

whereby the subtilisin 309 variant has decreased adsorption to, and increased hydrolysis, of an insoluble substrate as compared to wild-type subtilisin 309.

41. The subtilisin 309 variant of claim 40, wherein two or more substitutions occur in the sixth loop region.

42. The subtilisin 309 variant of claim 40, wherein two or more substitutions occur in the first loop region.

43. The subtilisin 309 variant of claim 40, wherein two or more substitutions occur in the second loop region.

44. The subtilisin 309 variant of claim 40, wherein two or more substitutions occur in the third loop region.

45. The subtilisin 309 variant of claim 40, wherein two or more substitutions occur in the fourth loop region.

46. The subtilisin 309 variant of claim 40, wherein two or more substitutions occur in the fifth loop region.

47. An isolated subtilisin 309 variant having a modified amino acid sequence of subtilisin 309 wild-type amino acid sequence set forth in SEQ NO:1, the wild-type amino acid sequence comprising a first loop region, a second loop region, a third loop region, a fourth loop region, a fifth loop region, and a sixth loop region; wherein the modified amino acid sequence comprises a substitution at two or more positions in one or more of the loop regions; wherein A. when a substitution occurs in the first loop region, the substitution occurs at one or more of positions 57, 58, 59, 60, 61, 63, or 64; wherein a. when a substitution occurs at position 57, the substituting amino acid is Asn, Asp, Glu or Ser;

b. when a substitution occurs at position 58, the substituting amino acid is Glu;

c. when a substitution occurs at position 59, the substituting amino acid is Asn, Asp, Gln, Glu, Pro or Ser;

d. when a substitution occurs at position 60, the substituting amino acid is Asp, Gln, Glu or Ser;

e. when a substitution occurs at position 61, the substituting amino acid is Asn, Asp, Gln, Glu, Pro or Ser;

f. when a substitution occurs at position 63, the substituting amino acid is Asn, Asp, Gln, Glu, Pro or Ser; and g. when a substitution occurs at position 64, the substituting amino acid is Asn, Asp, Gln, Glu, Gly, Pro or Ser;

B. when a substitution occurs in the second loop region, the substitution occurs at one or more of positions 93, 94, 95, 96, 97, 98, 99, 100, 101, 102, 103, 104 or 105; wherein a. when a substitution occurs at position 93, the substituting amino acid is Ala, Asn, Asp, Cys, Gln, Glu, Gly, His, Met, Pro, Ser or Thr;

b. when a substitution occurs at position 94, the substituting amino acid is Ala, Asn, Asp, Cys, Gln, Glu, Gly, His, Ile, Met, Pro, Ser, Thr or Val;

c. when a substitution occurs at position 95, the substituting amino acid is Asn, Asp, Gln, Glu, Pro Ser; provided that if position 96 or position 207 is substituted with Asp, and the variant is a double mutation variant, then position 95 is not substituted with Asp; and when position 95 is substituted the variant is not a double, triple, quadruple, quintuple, sextuple, or septuple mutation variant having substitutions at positions selected from the group consisting of 102, 153, 154, 160, 183, and 211;

d. when a substitution occurs at position 96, the substituting amino acid is Asn, Asp, Gln, Glu, Gly, His, Pro, Ser or Thr; provided that if position 207 is substituted with Asp, and the variant is a double mutation variant, then position 96 is not substituted with Asp; and when position 96 is substituted the variant is not a double, triple, quadruple, quintuple, or sextuple mutation variant having substitutions at positions selected from the group consisting of 102, 154, 160, 183, and 211;

e. when a substitution occurs at position 97, the substituting amino acid is Asp or Glu; but when position 97 is substituted the variant is not a double, triple, quadruple, quintuple, or sextuple mutation variant having substitutions at positions selected from the group consisting of 102, 154, 160, 183, and 211;

f. when a substitution occurs at position 98, the substituting amino acid is Asn, Asp, Gln, Glu, Pro or Ser; but when position 98 is substituted the variant is not a double, triple, quadruple, quintuple, or sextuple mutation variant having substitutions at positions selected from the group consisting of 102, 154, 160, 183, and 211;

g. when a substitution occurs at position 99, the substituting amino acid is Asp or Glu; but when position 99 is substituted the variant is not a double, triple, quadruple, quintuple, or sextuple mutation variant having substitutions at positions selected from the group consisting of 102, 154, 160, 183, and 211;

h. when a substitution occurs at position 100, the substituting amino acid is Asn, Asp, Gln, Glu, Pro or Ser; but when position 100 is substituted the variant is not a double, triple, quadruple, quintuple, or sextuple mutation variant having substitutions at positions selected from the group consisting of 102, 154, 160, 183, and 211;

i. when a substitution occurs at position 101, the substituting amino acid is Asp or Glu; but when position 101 is substituted the variant is not a double, triple, quadruple, quintuple, or sextuple mutation variant having substitutions at positions selected from the group consisting of 102, 154, 160, 183, and 211;

j. when a substitution occurs at position 102, the substituting amino acid is Ala, Asn, Asp, Cys, Gln, Glu, Gly, His, Met, Pro, Ser or Thr;

k. when a substitution occurs at position 103, the substituting amino acid is Asp or Glu;

l. when a substitution occurs at position 104, the substituting amino acid is Asp or Glu; and m. when a substitution occurs at position 105, the substituting amino acid is Ala, Asn, Asp, Cys, Gln, Glu, Gly, His, Leu, Met, Pro, Ser, Thr or Val; but when position 105 is substituted the variant is not a double, triple, quadruple, quintuple, sextuple, or septuple mutation variant having substitutions at positions selected from the group consisting of 102, 153, 154, 160, 183, and 211;

C. when a substitution occurs in the third loop region, the substitution occurs at one or more of positions 124, 125 or 131; wherein a. when a substitution occurs at position 124, the substituting amino acid is Ala, Asn, Cys, Gln, Gly, His, Ile, Met, Pro, Ser, Thr or Val; but when position 124 is substituted the variant is not a double, triple, quadruple, quintuple, sextuple, or septuple mutation variant having substitutions at positions selected from the group consisting of 102, 153, 154, 160, 183, and 211;
b. when a substitution occurs at position 125, the substituting amino acid is Asn, Asp, Glu, Pro or Ser; but when position 125 is substituted the variant is not a double, triple, quadruple, quintuple, sextuple, or septuple mutation variant having substitutions at positions selected from the group consisting of 102, 153, 154, 160, 183, and 211; and
c. when a substitution occurs at position 131, the substituting amino acid is Asn, Gly, Gly, His, Pro, Ser or Thr;

D. when a substitution occurs in the fourth loop region, the substitution occurs at one or more of positions 152, 153, 154, 155, 156, 157, 158, 159, 160 or 161; wherein
a. when a substitution occurs at position 152, the substituting amino acid is Asn, Asp, Gln, Glu, Pro or Ser; but when position 152 is substituted the variant is not a double, triple, quadruple, quintuple, or sextuple mutation variant having substitutions at positions selected from the group consisting of 102, 154, 160, 183, and 211;
b. when a substitution occurs at position 153, the substituting amino acid is Asp, Gln, Glu, Pro or Ser;
c. when a substitution occurs at position 154, the substituting amino acid is Asp or Glu; but when position 154 is substituted the variant is not a double, triple, quadruple, or quintuple mutation variant having substitutions at positions selected from the group consisting of 102, 160, 183, and 211;
d. when a substitution occurs at position 155, the substituting amino acid is Asn, Asp, Gln, Glu, Pro or Ser; but when position 155 is substituted the variant is not a double, triple, quadruple, quintuple, or sextuple mutation variant having substitutions at positions selected from the group consisting of 102, 154, 160, 183, and 211;
e. when a substitution occurs at position 156, the substituting amino acid is Asn, Asp, Gln, Glu, Gly, His, Pro, Ser or Thr; but when position 156 is substituted the variant is not a double, triple, quadruple, quintuple, or sextuple mutation variant having substitutions at positions selected from the group consisting of 102, 154, 160, 183, and 211;
f. when a substitution occurs at position 157, the substituting amino acid is Asn, Asp, Gln, Glu, Pro or Ser; but when position 157 is substituted the variant is not a double, triple, quadruple, quintuple, or sextuple mutation variant having substitutions at positions selected from the group consisting of 102, 154, 160, 183, and 211;
g. when a substitution occurs at position 158, the substituting amino acid is Asp or Glu; but when position 158 is substituted the variant is not a double, triple, quadruple, quintuple, or sextuple mutation variant having substitutions at position selected from the group consisting of 102, 154, 160, 183, and 211;
h. when a substitution occurs at position 159, the substituting amino acid is Ala, Asn, Asp, Cys, Gln, Glu, Gly, His, Leu, Met, Pro, Ser, Thr or Val; but when position 159 is substituted with Leu, the variant is not a double mutation variant having a substitution at position 158 with Glu; and when position 159 is substituted the variant is not a double, triple, quadruple, quintuple, or sextuple mutation variant having substitutions at position selected from the group consisting of 102, 154, 160, 183, a and 211;
i. when a substitution occurs at position 160, the substituting amino acid is Asp or Glu; but when position 160 is substituted the variant is not a double mutation variant having a substitution at position 60 with Asp or Glu; and
j. when a substitution occurs at position 161, the substituting amino acid is Ala, Asn, Asp, Cys, Gln, Glu, Gly, His, Ile, Leu, Met, Pro, Ser, Thr or Val; but when position 161 is substituted the variant is not a double, triple, quadruple, quintuple, or sextuple mutation variant having substitutions at positions selected from the group consisting of 102, 154, 160, 183, and 211;

E. when a substitution occurs in the fifth loop region, the substitution occurs at one or more of positions 181, 182, 183, 184 or 185; wherein
a. when a substitution occurs at position 181, the substituting amino acid is Asn, Asp, Gln, Glu, Gly, His, Pro, Ser or Thr;
b. when a substitution occurs at position 182, the substituting amino acid is Asp or Glu;
c. when a substitution occurs at position 183, the substituting amino acid is Ala, Asn, Asp, Cys, Gln, Glu, Gly, His, Ile, Leu, Met, Pro, Ser, Thr, Tyr or Val;
d. when a substitution occurs at position 184, the substituting amino acid is Asp or Glu; and
e. when a substitution occurs at position 185, the substituting amino acid is Asn, Asp, Glu or Ser; and F. when a substitution occurs in the sixth loop region, the substitution occurs at one or more of positions 193, 194, 195, 196, 197, 198, 199, 200, 201, 202, 203, 204, 205, 206, 207, 208, 209, 210, 211, 212, 213 or 214; wherein
a. when a substitution occurs at position 193, the substituting amino acid is Met, Cys, Ala, His, Thr, Pro, Gly, Gln, Asn, Ser, Asp or Glu;
b. when a substitution occurs at position 194, the substituting amino acid is His, Thr, Pro, Gly, Gln, Asn, Ser, Asp or Glu;
c. when a substitution occurs at position 195, the substituting amino acid is Gly, Gln, Asn, Ser, Asp or Glu;
d. when a substitution occurs at position 196, the substituting amino acid is Pro, Gln, Asn, Ser, Asp or Glu;
e. when a substitution occurs at position 197, the substituting amino acid is Met, Cys, Ala, His, Thr, Pro, Gly, Gln, Asn, Ser, Asp or Glu;
f. when a substitution occurs at position 198, the substituting amino acid is Glu, Gln, Asp or Ser;
g. when a substitution occurs at position 199, the substituting amino acid is Met, Cys, Ala, His, Thr, Pro, Gly, Gln, Asn, Ser, Asp or Glu;
h. when a substitution occurs at position 200, the substituting amino acid is Asn, Ser, Glu or Asp;
i. when a substitution occurs at position 201, the substituting amino acid is Asp or Glu;
j. when a substitution occurs at position 202, the substituting amino acid is Pro, Gly, Gln, Asn, Ser, Asp or Glu;
k. when a substitution occurs at position 203, the substituting amino acid is Leu, Ile, Val, Met, Cys, Ala, His, Thr, Pro, Gly, Gln, Asn, Ser, Asp or Glu;
l. when a substitution occurs at position 204, the substituting amino acid is Gly, Gln, Asn, Ser, Asp or Glu;

m. when a substitution occurs at position 205, the substituting amino acid Pro, Gln, Asn, Ser, Asp or Glu;
n. when a substitution occurs at position 206, the substituting amino acid Asp or Glu;
o. when a substitution occurs at position 207, the substituting amino acid Pro, Gly, Gln, Asn, Ser, Asp or Glu; but when position 207 is substituted the variant is not a double, triple, quadruple, quintuple, sextuple or septuple mutation variant having substitutions at positions selected from the group consisting of 102, 153, 154, 160, 183, and 211;
p. when a substitution occurs at position 208, the substituting amino acid Leu, Ile, Val, Met, Cys, Thr, Ala, His, Pro, Gly, Gln, Asn, Asp or Glu; but when position 208 is substituted the variant is not a double, triple, quadruple, quintuple, sextuple, or septuple mutation variant having substitutions at positions selected from the group consisting of 102, 153, 154, 160, 183, and 211;
q. when a substitution occurs at position 209, the substituting amino acid His, Thr, Pro, Gly, Gln, Asn, Ser, Asp or Glu; but when position 209 is substituted the variant is not a double, triple, quadruple, quintuple, sextuple, or septuple mutation variant having substitutions at positions selected from the group consisting of 102, 153, 154, 160, 183, and 211;
r. when a substitution occurs at position 210, the substituting amino acid Asp or Glu;
s. when a substitution occurs at position 211, the substituting amino acid Ile, Val, Met, Cys, Ala, His, Thr, Pro, Gly, Gln, Asn, Ser, Glu or Asp; wherein when position 211 is substituted with Glu, the variant is not a double mutation variant having a substitution at position 102 with Asn;
t. when a substitution occurs at position 212, the substituting amino acid Gln, Ser, Asp, or Glu; but when position 212 is substituted the variant is not a double mutation variant having a substitution at position 211; and wherein when position 212 is substituted with Asp, the variant is not a double mutation variant having a substitution at position 160 with Asp;
u. when a substitution occurs at position 213, the substituting amino acid is Pro, Gln, Asn, Ser, Asp or Glu; and
v. when a substitution occurs at position 214, the substituting amino acid is Pro, Gly, Gln, Asn, Asp, Ser or Glu;
whereby the subtilisin 309 variant has decreased adsorption to, and increased hydrolysis of, an insoluble substrate as compared to wild-type subtilisin 309.

48. The subtilisin 309 variant of claim 47, wherein two or more substitutions occur in the sixth loop region.

49. The subtilisin 309 variant of claim 47, wherein two or more substitutions occur in the first loop region.

50. The subtilisin 309 variant of claim 47, wherein two or more substitutions occur in the second loop region.

51. The subtilisin 309 variant of claim 47, wherein two or more substitutions occur in the third loop region.

52. The subtilisin 309 variant of claim 47, wherein two or more substitutions occur in the fifth loop region.

53. The subtilisin 309 variant of claim 47, wherein two or more substitutions occur in the fifth loop region.

54. An isolated subtilisin 309 variant having a modified amino acid sequence of subtilisin 309 wild-type amino acid sequence set forth in SEQ ID NO:1, the wild-type amino acid sequence comprising a first loop region, a second loop region, a third loop region, a fourth loop region, a fifth loop region, and a sixth loop region; wherein the modified amino acid sequence comprises a substitution at two or more positions in one or more of the loop regions; wherein
A. when a substitution occurs in the first loop region, the substitution occurs at one or more of positions 57, 58, 59, 60, 61, 63, or 64; wherein
a. when substitution occurs at position 57, the substituting amino acid is Asn, Asp, Glu or Ser;
b. when a substitution occurs at position 58, the substituting amino acid is Glu;
c. when a substitution occurs at position 59, the substituting amino acid is Asn, Asp, Gln, Glu, Pro or Ser;
d. when a substitution occurs at position 60, the substituting amino acid is Asp, Gln, Glu or Ser;
e. when a substitution occurs at position 61, the substituting amino acid is Asn, Asp, Gln, Glu, Pro or Ser;
f. when a substitution occurs at position 63, the substituting amino acid is Asn, Asp, Gln, Glu, Pro or Ser; and
g. when a substitution occurs at position 64, the substituting amino acid is Asn, Asp, Gln, Glu, Gly, Pro or Ser;
B. when a substitution occurs in the second loop region, the substitution occurs at one or more of positions 93, 94, 95, 96, 97, 98, 99, 100, 101, 102, 103, 104 or 105; wherein
a. when a substitution occurs at position 93, the substituting amino acid is Ala, Asn, Asp, Cys, Gln, Glu, Gly, His, Met, Pro, Ser or Thr;
b. when a substitution occurs at position 94, the substituting amino acid is Ala, Asn, Asp, Cys, Gln, Glu, Gly, His, Ile, Met, Pro, Ser, Thr or Val;
c. when a substitution occurs at position 95, the substituting amino acid is Asn, Asp, Gln, Glu, Pro or Ser; provided that if position 96 or position 207 is substituted with Asp, and the variant is a double mutation variant, then position 95 is not substituted with Asp; and when position 95 is substituted the variant is not a double, triple, or quadruple mutation variant having substitutions at positions selected from the group consisting of 102, 183, and 211;
d. when a substitution occurs at position 96, the substituting amino acid is Asn, Asp, Gln, Glu, Gly, His, Pro, Ser or Thr; provided that if position 207 is substituted with Asp, and the variant is a double mutation variant, then position 96 is not substituted with Asp; and when position 96 is substituted the variant is not a double, triple, or quadruple mutation variant having a substitutions at positions selected from the group consisting of 102, 183, and 211;
e. when substitution occurs at position 97, the substituting amino acid is Asp or Glu; but when position 97 is substituted the variant is not a double, triple, or quadruple mutation variant having substitutions at positions selected from the group consisting of 102, 183, and 211;
f. when a substitution occurs at position 98, the substituting amino acid is Asn, Asp, Gln, Glu, Pro or Ser; but when position 98 is substituted the variant is not a double, triple, or quadruple mutation variant having substitutions at positions selected from the group consisting of 102, 183, and 211;
g. when a substitution occurs at position 99, the substituting amino acid is Asp or Glu; but when position 99 is substituted the variant is not a double, triple, or quadruple mutation variant having substitutions at positions selected from the group consisting of 102, 183, and 211;
h. when a substitution occurs at position 100, the substituting amino acid is Asn, Asp, Gln, Glu, Pro or Ser; but when position 100 is substituted the variant is not a double, triple, or quadruple mutation variant having substitutions at positions selected from the group consisting of 102, 183, and 211;
i. when a substitution occurs at position 101, the substituting amino acid is Asp or Glu; but when position 101 is substituted the variant is not a double, triple, or quadruple mutation variant having substitutions at positions selected from the group consisting of 102, 183, and 211;
j. when a substitution occurs at position 102, the substituting amino acid is Ala, Asn, Asp, Cys, Gln, Glu, Gly, His, Met, Pro, Ser or Thr;
k. when a substitution occurs at position 103, the substituting amino acid is Asp or Glu;
l. when a substitution occurs at position 104, the substituting amino acid is Asp or Glu; and
m. when a substitution occurs at position 105, the substituting amino acid is Ala, Asn, Asp, Cys, Gln, Glu, Gly, His, Leu, Met, Pro, Ser, Thr or Val; but when position 105 is substituted the variant is not a double, triple, or quadruple mutation variant having substitutions at positions selected from the group consisting of 102, 183, and 211;

C. when a substitution occurs in the third loop region, the substitution occurs at one or more of positions 124, 125, 126, 127, 128, 129, 130 or 131; wherein
a. when a substitution occurs at position 124, the substituting amino acid is Ala, Asn, Asp, Cys, Gln, Glu, Gly, His, Ile, Met, Pro, Ser, Thr or Val; but when position 124 is substituted the variant is not a double, triple, or quadruple mutation variant having substitutions at positions selected from the group consisting of 102, 183, and 211;
b. when a substitution occurs at position 125, the substituting amino acid is Asn, Asp, Gln, Glu, Pro or Ser; but when position 125 is substituted the variant is not a double, triple, or quadruple mutation variant having substitutions at positions selected from the group consisting of 102, 183, and 211;
c. when a substitution occurs at position 126, the substituting amino acid is Asp or Glu; but when position 126 is substituted the variant is not a double, triple, or quadruple mutation variant having substitutions at positions selected from the group consisting of 102, 183, and 211;
d. when a substitution occurs at position 127, the substituting amino acid is Asn, Asp, Gln, Glu, Gly or Ser; but when position 127 is substituted the variant is not a double, triple, or quadruple mutation variant having substitutions at positions selected from the group consisting of 102, 183, and 211;
e. when a substitution occurs at position 128, the substituting amino acid is Asp or Glu;
f. when a substitution occurs at position 129, the substituting amino acid is Asn, Asp, Gln, Glu, Gly or Ser;
g. when a substitution occurs at position 130, the substituting amino acid is Asp or Glu; and
h. when a substitution occurs at position 131, the substituting amino acid is Asn, Asp, Gln, Glu, Gly, His, Pro, Ser or Thr;

D. when a substitution occurs in the fifth loop region, the substitution occurs at one or more of positions 181, 182, 183, 184 or 185; wherein
a. when a substitution occurs at position 181, the substituting amino acid is Asn, Asp, Gln, Glu, Gly, His, Pro, Ser or Thr;
b. when a substitution occurs at position 182, the substituting amino acid is Asp or Glu;
c. when a substitution occurs at position 183, the substituting amino acid is Ala, Asn, Asp, Cys, Gln, Glu, Gly, His, Ile, Leu, Met, Pro, Ser, Thr, Tyr or Val;
d. when a substitution occurs at position 184, the substituting amino acid is Asp or Glu; and
e. when a substitution occurs at position 185, the substituting amino acid is Asn, Asp, Glu or Ser; and E. when a substitution occurs in the sixth loop region, the substitution occurs at one or more of positions 193, 194, 195, 196, 197, 198, 199, 200, 201, 202, 203, 204, 205, 206, 207, 208, 209, 210, 211, 212, 213 or 214; wherein
a. when a substitution occurs at position 193, the substituting amino acid is Met, Cys, Ala, His, Thr, Pro, Gly, Gln, Asn, Ser, Asp or Glu;
b. when a substitution occurs at position 194, the substituting amino acid is His, Thr, Pro, Gly, gln, Asn, Ser, Asp or Glu;
c. when a substitution occurs at position 195, the substituting amino acid is Gly, Gln, Asn, Ser, Asp or Glu;
d. when a substitution occurs at position 196, the substituting amino acid is Pro, Gln, Asn, Ser, Asp or Glu;
e. when a substitution occurs at position 197, the substituting amino acid is Met, Cys, Ala, His, Thr, Pro, Gly, Asn, Ser, Asp or Glu;
f. when a substitution occurs at position 198, the substituting amino acid is Glu, Gln, Asp or Ser;
g. when a substitution occurs at position 199, the substituting amino acid is Met, Cys, Ala, His, Thr, Pro, Gly, Gln, Asn, Ser, Asp or Glu;
h. when a substitution occurs at position 200, the substituting amino acid is Asn, Ser, Glu or Asp;
i. when a substitution occurs at position 201, the substituting amino acid is Asp or Glu;
j. when a substitution occurs at position 202, the substituting amino acid is Pro, Gly, Gln, Asn, Asn, Ser, Asp or Glu;
k. when a substitution occurs at position 203, the substituting amino acid is Leu, Ile, Val, Met, Cys, Ala, His, Thr, Pro, Gly, Gln, Asn, Ser, Asp or Glu;
l. when a substitution occurs at position 204, the substituting amino acid is Gly, Gln, Asn, Ser, Asp or Glu;
m. when a substitution occurs at position 205, the substituting amino acid Pro, Gln, Asn, Ser, Asp or Glu;
n. when a substitution occurs at position 206, the substituting amino acid Asp or Glu;
o. when a substitution occurs at positions 207, the substituting amino acid Pro, Gly, Gln, Asn, Ser, Asp or Glu; but when position 207 is substituted the variant is not a double triple, or quadruple mutation variant having substitutions at positions selected from the group consisting of 102, 183, and 211;
p. when a substitution occurs at position 208, the substituting amino acid Leu, Ile, Val, Met, Cys, Thr, Ala, His, Pro, Gly, Gln, Asn, Asp or Glu; but when position 208 is substituted the variant is not a double, triple, or quadruple mutation variant having substitutions at positions selected from the group consisting of 102, 183, and 211;
q. when a substitution occurs at position 209, the substituting amino acid His, Thr, Pro, Gly, Gln, Asn, Ser, Asp or Glu; but when position 209 is substituted the variant is not a double, triple, or quadruple mutation variant having substitutions at positions selected from the group consisting of 102, 183, and 211;
r. when a substitution occurs at position 210, the substituting amino acid Asp or Glu;
s. when a substitution occurs at position 211, the substituting amino acid Ile, Val, Met, Cys, Ala, His, Thr, Pro, Gly, Gln, Asn, Ser, Glu or Asp; but when position 211 is substituted with Glu, the variant is not a double mutation variant having a substitution of Glu at position 127 or a substitution of Asn at position 102;
t. when a substitution occurs at position 212, the substituting amino acid Gln, Ser, Asp, or Glu; but when a substitution occurs at position 212 the variant is not a double mutation variant having a substitution at position 211;
u. when a substitution occurs at position 213, the substituting amino acid is Pro, Gln, Asn, Ser, Asp or Glu; and
v. when a substitution occurs at position 214, the substituting amino acid is Pro, Gly, Gln, Asn, Asp, Ser or Glu;

whereby the subtilisin 309 variant has decreased adsorption to, and increased hydrolysis of, an insoluble substrate as compared to wild-type subtilisin 309.

55. The subtilisin 309 variant of claim 54, wherein two or more substitutions occur in the sixth loop region.

56. The subtilisin 309 variant of claim 54, wherein two or more substitutions occur in the first loop region.

57. The subtilisin 309 variant of claim 54, wherein two or more substitutions occur in the second loop region.

58. The subtilisin 309 variant of claim 54, wherein two or more substitutions occur in the third loop region.

59. The subtilisin 309 variant of claim 54, wherein two or more substitutions occur in the fifth loop region.

60. An isolated subtilisin 309 variant having a modified amino acid sequence of subtilisin 309 wild-type amino acid sequence set forth in SEQ ID NO:1, the wild-type amino acid sequence comprising a first loop region, a second loop region, a third loop region, a fourth loop region, a fifth loop region, and a sixth loop region; wherein the modified amino acid sequence comprises a substitution at two or more positions in one or more of the loop regions; wherein
A. when a substitution occurs in the first loop region, the substitution occurs at one or more of positions 57, 58, 59, 60, 61, 63, or 64; wherein
  a. when a substitution occurs at position 57, the substituting amino acid is Asn, Asp, Glu or Ser;
  b. when a substitution occurs at position 58, the substituting amino acid is Glu;
  c. when a substitution occurs at position 59, the substituting amino acid is Asn, Asp, Gln, Glu, Pro or Ser;
  d. when a substitution occurs at position 60, the substituting amino acid is Asp, Gln, Glu or Ser;
  e. when a substitution occurs at position 61, the substituting amino acid is Asn, Asp, Gln, Glu, Pro or Ser;
  f. when a substitution occurs at position 63, the substituting amino acid is Asn, Asp, Gln, Glu, Pro or Ser; and
  g. when a substitution occurs at position 64, the substituting amino acid is Asn, Asp, Gln, Glu, Gly, Pro or Ser;
B. when a substitution occurs in the second loop region, the substitution occurs at one or more of positions 93, 94, 95, 96, 97, 98. 99, 100, 101, 102, 103, 104 or 105; wherein
  a. when a substitution occurs at position 93, the substituting amino acid is Ala, Asn, Asp, Cys, Gln, Glu, Gly, His, Met, Pro, Ser or Thr;
  b. when a substitution occurs at position 94, the substituting amino acid is Ala, Asn, Asp, Cys, Gln, Glu, Gly, His Ile, Met, Pro, Ser, Thr or Val;
  c. when a substitution occurs at position 95, the substituting amino acid is Asn, Asp, Gln, Glu, Pro or Ser; provided that if position 96 or position 207 is substituted with Asp, and the variant is a double mutation variant, then position 95 is not substituted with Asp; and when position 95 is substituted the variant is not a double, triple, quadruple, quintuple, sextuple, or septuple mutation variant having substitutions at positions selected from the group consisting of 102, 153, 154, 160, 183, and 211;
  d. when a substitution occurs at position 96, the substituting amino acid is Asn, Asp, Gln, Glu, Gly, His, Pro, Ser or Thr; provided that if position 207 is substituted with Asp, and the variant is a double mutation variant, then position 96 is not substituted with Asp; and when position 96 is substituted the variant is not a double, triple, quadruple, quintuple, or sextuple mutation variant having substitutions at positions selected from the group consisting of 102, 154, 160, 183, and 211;
  e. when a substitution occurs at position 97, the substituting amino acid is Asp or Glu; but when position 97 is substituted the variant is not a double, triple, quadruple, quintuple, or sextuple mutation variant having substitutions at positions selected from the group consisting of 102, 154, 160, 183, and 211;
  f. when a substitution occurs at position 98, the substituting amino acid is Asn, Asp, Gln, Glu, Pro or Ser; but when position 98 is substituted the variant is not a double, triple, quadruple, quintuple, or sextuple mutation variant having substitutions at positions selected from the group consisting of 102, 154, 160, 183, and 211;
  g. when a substitution occurs at position 99, the substituting amino acid is Asp or Glu; but when position 99 is substituted the variant is not a double, triple, quadruple, quintuple, or sextuple mutation variant having substitutions at positions selected from the group consisting of 102, 154, 160, 183, and 211;
  h. when a substitution occurs at position 100, the substituting amino acid is Asn, Asp, Gln, Glu, Pro or Ser; but when position 100 is substituted the variant is not a double, triple, quadruple, quintuple, or sextuple mutation variant having substitutions at positions selected from the group consisting of 102, 154, 160, 183, and 211;
  i. when a substitution occurs at position 101, the substituting amino acid is Asp or Glu; but when position 101 is substituted the variant is not a double, triple, quadruple, quintuple, or sextuple mutation variant having substitutions at positions selected from the group consisting of 102, 154, 160, 183, and 211;

j. when a substitution occurs at position 102, the substituting amino acid is Ala, Asn, Asp, Cys, Gln, Glu, Gly, His, Met, Pro, Ser or Thr;
k. when a substitution occurs at position 103, the substituting amino acid is Asp or Glu;
l. when a substitution occurs at position 104, the substituting amino acid is Asp or Glu; and
m. when a substitution occurs at position 105, the substituting amino acid is Ala, Asn, Asp, Cys, Gln, Glu, Gly, His, Leu, Met, Pro, Ser, Thr or Val; but when position 105 is substituted the variant is not a double, triple, quadruple, quintuple, sextuple, or septuple mutation variant having substitutions at position selected from the group consisting of 102, 153, 154, 160, 183, and 211;

C. when substitution occurs in the third loop region, the substitution occurs at one or more of positions 124, 125, 126, 127, 128, 129, 130 or 131; wherein
a. when substitution occurs at position 124, the substituting amino acid is Ala, Asn, Asp, Cys, Gln, Glu, Gly, His, Ile, Met, Pro, Ser, Thr or Val; but when position 124 is substituted the variant is not a double, triple, quadruple, quintuple, sextuple, or septuple mutation variant having substitutions at positions selected from the group consisting of 102, 153, 154, 160, 183, and 211;
b. when a substitution occurs at position 125, the substituting amino acid is Asn, Asp, Gln, Glu, Pro or Ser; but when position 125 is substituted the variant is not a double, triple, quadruple, quintuple, sextuple, or septuple mutation variant having substitutions at position selected from the group consisting of 102, 153, 154, 160, 183, and 211;
c. when a substitution occurs at position 126, the substituting amino acid is Asp or Glu; but when position 126 is substituted the variant is not a double, triple, quadruple, quintuple, sextuple, or septuple mutation variant having substitutions at positions selected from the group consisting of 102, 153, 154, 160, 183, and 211;
d. when a substitution occurs at position 127, the substituting amino acid is Asn, Asp, Gln, Gly or Ser; but when position 127 is substituted the variant is not a double, triple, quadruple, quintuple, sextuple, or septuple mutation variant having substitutions at positions selected from the group consisting of 102, 153, 154, 160, 183, and 211;
e. when a substitution occurs at position 128, the substituting amino acid is Asp or Glu;
f. when a substitution occurs at position 129, the substituting amino acid is Asn, Asp, Gln, Glu, Gly or Ser;
g. when a substitution occurs at position 130, the substituting amino acid is Asp or Glu; and
h. when a substitution occurs at position 131, the substituting amino acid is Asn, Asp, Gln, Glu, Gly, His, Pro, Ser or Thr;

D. when a substitution occurs in the fourth loop region, the substitution occurs at one or more of positions 152, 153, 154, 155, 156, 157, 158, 159, 160, or 161; wherein
a. when a substitution occurs at position 152, the substituting amino acid is Asn, Asp, Gln, Glu, Pro or Ser; but when position 152 is substituted the variant is not a double, triple, quadruple, quintuple, or sextuple mutation variant having substitutions at positions selected from the group consisting of 102, 154, 160, 183, and 211;
b. when a substitution occurs at position 153, the substituting amino acid is Asp, Gln, Glu, Pro or Ser;
c. when a substitution occurs at position 154, the substituting amino acid is Asp or Glu; but when position 154 is substituted the variant is not a double, triple, quadruple, or quintuple mutation variant having substitutions at positions selected from the group consisting of 102, 160, 183, and 211;
d. when a substitution occurs at position 155, the substituting amino acid is Asn, Asp, Gln, Glu, Pro or Ser; but when position 155 is substituted the variant is not a double, triple, quadruple, quintuple, or sextuple mutation variant having substitutions at positions selected from the group consisting of 102, 154, 160, 183, and 211;
e. when a substitution occurs at position 156, the substituting amino acid is Asn, Asp, Gln, Glu, Gly, His, Pro, Ser or Thr; but when position 156 is substituted the variant is not a double, triple, quadruple, quintuple, or sextuple mutation variant having substitutions at positions selected from the group consisting of 102, 154, 160, 183, and 211;
f. when a substitution occurs at position 157, the substituting amino acid is Asn, Asp, Gln, Glu, Pro or Ser; but when position 157 is substituted the variant is not a double, triple, quadruple, quintuple, or sextuple mutation variant having substitutions at positions selected from the group consisting of 102, 154, 160, 183, and 211;
g. when a substitution occurs at position 158, the substituting amino acid is Asp or Glu; but when position 158 is substituted the variant is not a double, triple, quadruple, quintuple, or sextuple mutation variant having substitutions at positions selected from the group consisting of 102, 154, 160, 183, and 211;
h. when a substitution occurs at position 159, the substituting amino acid is Ala, Asn, Asp, Cys, Gln, Glu, Gly, His, Leu, Met, Pro, Ser, Thr or Val; but when position 159 is substituted with Leu, the variant is not a double mutation variant having a substitution at position 158 with Glu; and when position 159 is substituted the variant is not a double, triple, quadruple, quintuple, or sextuple mutation variant having substitutions at positions selected from the group consisting of 102, 154, 160, 183, and 211;
i. when a substitution occurs at position 160, the substituting amino acid is Asp or Glu; but when position 160 is substituted the variant is not a double mutation variant having a substitution at position 60 with Asp or Glu; and
j. when a substitution occurs at position 161, the substituting amino acid is Ala, Asn, Asp, Cys, Gln, Glu, Gly, His, Ile, Leu, Met, Pro, Ser, Thr or Val; but when position 161 is substituted the variant is not a double, triple, quadruple, quintuple, or sextuple mutation variant having substitutions at positions selected from the group consisting of 102, 154, 160, 183, and 211;

E. when the substitution occurs in the fifth loop region, the substitution occurs at one of positions 181, 183, 184 or 185; wherein
a. when a substitution occurs at position 181, the substituting amino acid is Asn, Asp, Gln, Glu, Gly, His, Ser or Thr;
b. when a substitution occurs at position 183, the substituting amino acid is Ala, Asn, Cys, Gln, Gly, His, Ile, Leu, Met, Ser, Thr, Tyr or Val;

c. when a substitution occurs at position 184, the substituting amino acid is Asp or Glu; and
d. when a substitution occurs at position 185, the substituting amino acid is Asn or Ser; and F. when a substitution occurs in the sixth loop region, the substitution occurs at one or more of positions 193, 194, 195, 196, 197, 198, 199, 200, 201, 202, 203, 204, 205, 206, 207, 208, 209, 210, 211, 212, 213 or 214; wherein
  a. when a substitution occurs at position 193, the substituting amino acid is Met, Cys, Ala, His, Thr, Pro, Gly, Gln, Asn, Ser, Asp or Glu;
  b. when a substitution occurs at position 194, the substituting amino acid is His, Thr, Pro, Gly, Gln, Asn, Ser, Asp or Glu;
  c. when a substitution occurs at position 195, the substituting amino acid is Gly, Gln, Asn, Ser, Asp or Glu;
  d. when a substitution occurs at position 196, the substituting amino acid is Pro, Gln, Asn, Ser, Asp or Glu;
  e. when a substitution occurs at position 197, the substituting amino acid is Met, Cys, Ala, His, Thr, Pro, Gly, Gln, Asn, Ser, Asp or Glu;
  f. when a substitution occurs at position 198, the substituting amino acid is Glu, Gln, Asp or Ser;
  g. when a substitution occurs at position 199, the substituting amino acid is Met, Cys, Ala, His, Thr, Pro, Gly, Gln, Asn, Ser, Asp or Glu;
  h. when a substitution occurs at position 200, the substituting amino acid is Asn, Ser, Glu or Asp;
  i. when a substitution occurs at position 201, the substituting amino acid is Asp or Glu;
  j. when a substitution occurs at position 202, the substituting amino acid is Pro, Gly, Gln, Asn, Ser, Asp or Glu;
  k. when a substitution occurs at position 203, the substituting amino acid is Leu, Ile, Val, Met, Cys, Ala, His, Thr, Pro, Gly, Gln, Asn, Ser, Asp or Glu;
  l. when a substitution occurs at position 204, the substituting amino acid is Gly, Gln, Asn, Ser, Asp or Glu;
  m. when a substitution occurs at position 205, the substituting amino acid Pro, Gln, Asn, Ser, Asp or Glu;
  n. when a substitution occurs at position 206, the substituting amino acid Asp or Glu;
  o. when a substitution occurs at position 207, the substituting amino acid Pro, Gly, Gln, Asn, Ser, Asp or Glu; but when position 207 is substituted the variant is not a double, triple, quadruple, quintuple, sextuple, or septuple mutation variant having substitutions at positions selected from the group consisting of 102, 153, 154, 160, 183, and 211;
  p. when a substitution occurs at position 208, the substituting amino acid Leu, Ile, Val, Met, Cys, Thr, Ala, His, Pro, Gly, Gln, Asn, Asp or Glu; but when position 208 is substituted the variant is not a double, triple, quadruple, quintuple, sextuple, r septuple mutation variant having substitutions at positions selected from the group consisting of 102, 153, 154, 160, 183, and 211;
  q. when a substitution occurs at position 209, the substituting amino acid His, Thr, Pro, Gly, Gln, Asn, Ser, Asp or Glu; but when position 209 is substituted the variant is not a double, triple, quadruple, quintuple, sextuple, or septuple mutation variant having substitutions at positions selected from the group consisting of 102, 153, 154, 160, 183 and 211;
  r. when a substitution occurs at position 210, the substituting amino acid Asp or Glu;
  s. when a substitution occurs at position 211, the substituting amino acid Ile, Val, Met, Cys, Ala, His, Thr, Pro, Gly, Gln, Asn, Ser, Glu or Asp; but when position 211 is substituted with Glu, the variant is not a double mutation variant having a substitution of Glu or position 127 or a substitution of Asn at position 102;
  t. when a substitution occurs at position 212, the substituting amino acid Gln, Ser, Asp, or Glu; but when a substitution occurs at position 212 the variant is not a double mutation variant having a substitution at position 211; and wherein when position 212 is substituted wit Asp, the variant is not a double mutation variant having a substitution at position 160 with Asp;
  u. when a substitution occurs at position 213, the substituting amino acid is Pro, Gln, Asn, Ser, Asp or Glu; and
  v. when a substitution occurs at position 214, the substituting amino acid is Pro, Gly, Gln, Asn, Asp, Ser or Glu;

whereby the subtilisin 309 variant has decreased adsorption to, and increased hydrolysis of, an insoluble substrate as compared to wild-type subtilisin 309.

61. The subtilisin 309 variant of claim 60, wherein two or more substitutions occur in the sixth loop region.

62. The subtilisin 309 variant of claim 60, wherein two or more substitutions occur in the first loop region.

63. The subtilisin 309 variant of claim 60, wherein two or more substitutions occur in the second loop region.

64. The subtilisin 309 variant of claim 60, wherein two or more substitutions occur in the third loop region.

65. The subtilisin 309 variant of claim 60, wherein two or more substitutions occur in the fourth loop region.

66. The subtilisin 300 variant of claim 60, wherein two or more substitutions occur in the fifth loop region.

67. An isolated subtilisin 309 variant having a modified amino acid sequence of subtilisin 309 wild-type amino acid sequence set forth in SEQ ID NO:1, the wild-type amino acid sequence comprising a first loop region, a second loop region, a third loop region, a fourth loop region, a fifth loop region, and a sixth loop region; wherein the modified amino acid sequence comprises a substitution at two or more positions in one or more of the loop regions; and
  A. when a substitution occurs in the first loop region, the substitution occurs at one or more of positions 57, 58, 59, 60, 61, 63, or 64; wherein
    a. when a substitution occurs at position 57, the substituting amino acid is Asn, Asp, Glu or Ser;
    b. when a substitution occurs at position 58, the substituting amino acid is Glu;
    c. when a substitution occurs at position 59, the substituting amino acid is Asn, Asp, Gln, Glu, Pro or Ser;
    d. when a substitution occurs at position 60, the substituting amino acid is Asp, Gln, Glu or Ser;
    e. when a substitution occurs at position 61, the substituting amino acid is Asn, Asp, Gln, Glu, Pro or Ser;
    f. when a substitution occurs at position 63, the substituting amino acid is Asn, Asp, Gln, Glu, Pro or Ser; and
    g. when a substitution occurs at position 64, the substituting amino acid is Asn, Asp, Gln, Glu, Gly, Pro or Ser;

B. when a substitution occurs in the second loop region, the substitution occurs at one or more of positions 93, 94, 95, 96, 97, 98, 99, 100, 101, 102, 103, 104 or 105; wherein
  a. when a substitution occurs at position 93, the substituting amino acid is Ala, Asn, Asp, Cys, Gln, Glu, Gly, His, Met, Pro, Ser or Thr;
  b. when a substitution occurs at position 94, the substituting amino acid is Ala, Asn, Asp, Cys, Gln, Glu, Gly, His, Ile, Met, Pro, Ser, Thr or Val;
  c. when a substitution occurs at position 95, the substituting amino acid is Asn, Asp, Gln, Glu, Pro or Ser; provided that if position 96 is substituted with Asp, and the variant is a double mutation variant, then position 95 is not substituted with Asp; and when position 95 is substituted the variant is not a double, triple, quadruple, quintuple, sextuple, or septuple mutation variant having a substitutions at positions selected from the group consisting of 102, 153, 154, 160, 183, and 211;
  d. when a substitution occurs at position 96, the substituting amino acid is Asn, Asp, Gln, Glu, Gly, His, Pro, Ser or Thr; but when position 96 is substituted the variant is not a double, triple, quadruple, quintuple, or sextuple mutation variant having substitutions at positions selected from the group consisting of 105, 154, 160, 183, and 211;
  e. when a substitution occurs at position 97, the substituting amino acid is Asp or Glu; but when position 97 is substituted the variant is not a double, triple, quadruple, quintuple, or sextuple mutation variant having substitutions at positions selected from the group consisting of 102, 154, 160, 183, and 211;
  f. when a substitution occurs at position 98, the substituting amino acid is Asn, Asp, Gln, Glu, Pro or Ser; but when position 98 is substituted the variant is not a double, triple, quadruple, quintuple, or sextuple mutation variant having substitutions at positions selected from the group consisting of 102, 154, 160, 183, and 211;
  g. when a substitution occurs at position 99, the substituting amino acid is Asp or Glu; but when position 99 is substituted the variant is not a double, triple, quadruple, quintuple, or sextuple mutation variant having substitutions at positions selected the group consisting of 102, 154, 160, 183, and 211;
  h. when a substitution occurs at position 100, the substituting amino acid is Asn, Asp, Gln, Glu, Pro or Ser; but when position 100 is substituted the variant is not a double, triple, quadruple, quintuple, or sextuple mutation variant having substitutions at positions selected from the group consisting of 102, 154, 160, 183, and 211;
  i. when a substitution occurs at position 101, the substituting amino acid is Asp or Glu; but when position 101 is substituted the variant is not a double, triple, quadruple, quintuple, or sextuple mutation variant having substitutions at positions selected from the group consisting of 102, 154, 160, 183, and 211;
  j. when a substitution occurs at position 102, the substituting amino acid is Ala, Asn, Asp, Cys, Gln, Glu, Gly, His, Met, Pro, Ser or Thr;
  k. when a substitution occurs at position 103, the substituting amino acid is Asp or Glu;
  l. when a substitution occurs at position 104, the substituting amino acid is Asp or Glu; and
  m. when a substitution occurs at position 105, the substituting amino acid is Ala, Asn, Asp, Cys, Gln, Glu, Gly, His, Leu, Met, Pro, Ser, Thr or Val; but when position 105 is substituted the variant is not a double, triple, quadruple, quintuple, sextuple, or septuple mutation variant having substitutions at position selected from the group consisting of 102, 153, 154, 160, 183, and 211;
C. when a substitution occurs in the third loop region, the substitution occurs at one or more of positions 124, 125, 126, 127, 128, 129, 130 or 131; wherein
  a. when a substitution occurs at position 124, the substituting amino acid is Ala, Asn, Asp, Cys, Gln, Glu, Gly, His, Ile, Met, Pro, Ser, Thr or Val; but when position 124 is substituted the variant is not a double, triple, quadruple, quintuple, sextuple, or septuple mutation variant having substitutions at positions selected from the group consisting of 102, 153, 154, 160, 183, and 211;
  b. when a substitution occurs at position 125, the substituting amino acid is Asn, Asp, Gln, Glu, Pro or Ser; but when position 125 is substituted the variant is not a double, triple, quadruple, quintuple, sextuple, or septuple mutation variant having a substitutions at positions selected from the group consisting of 102, 153, 154, 160, 183, and 211;
  c. when a substitution occurs at position 126, the substituting amino acid is Asp or Glu; but when position 126 is substituted the variant is not a double, triple, quadruple, quintuple, sextuple, or septuple mutation variant having substitutions at positions selected from the group consisting of 102, 153, 154, 160, 183, and 211;
  d. when a substitution occurs at position 127, the substituting amino acid is Asn, Asp, Gln, Glu, Gly or Ser; but when position 127 is substituted the variant is not a double, triple, quadruple, quintuple, sextuple, or septuple mutation variant having substitutions at positions selected from the group consisting of 102, 153, 154, 160, 183, and 211;
  e. when a substitution occurs at position 128, the substituting amino acid is Asp or Glu;
  f. when a substitution occurs at position 129, the substituting amino acid is Asn, Asp, Gln, Glu, Gly or Ser;
  g. when substitution occurs at position 130, the substituting amino acid is Asp or Glu; and
  h. when a substitution occurs at position 131, the substituting amino acid is Asn, Asp, Gln, Glu, Gly, His, Pro, Ser or Thr;
D. when a substitution occurs in the fourth loop region, the substitution occurs at one or more of positions 152, 153, 154, 155, 156, 157, 158, 159, 160 or 161; wherein
  a. when a substitution occurs at position 152, the substituting amino acid is Asn, Asp, Gln, Glu, Pro or Ser; but when position 152 is substituted the variant is not a double, triple, quadruple, quintuple, or sextuple mutation variant having substitutions at positions selected from the group consisting of 102, 154, 160, 183, and 211;
  b. when a substitution occurs at position 153, the substituting amino acid is Asp, Gln, Glu, Pro or Ser;
  c. when a substitution occurs at position 154, the substituting amino acid is Asp or Glu; but when position 154 is substituted the variant is not a double, triple, quadruple, or quintuple mutation variant having substitutions at positions selected from the group consisting of 102, 160, 183, and 211;

d. when a substitution occurs at position 155, the substituting amino acid is Asn, Asp, Gln, Pro or Ser; but when position 155 is substituted the variant is not a double, triple, quadruple, quintuple, or sextuple mutation variant having substitutions at positions selected from the group consisting of 102, 154, 160, 183, and 211;

e. when a substitution occurs at position 156, the substituting amino acid is Asn, Asp, Gln, Glu, Gly, His, Pro, Ser or Thr; but when position 156 is substituted the variant is not a double, triple, quadruple, quintuple, or sextuple mutation variant having substitutions at positions selected from the group consisting of 102, 154, 160, 183, and 211;

f. when a substitution occurs at position 157, the substituting amino acid is Asn, Asp, Gln, Glu, Pro or Ser; but when position 157 is substituted the variant is not a double, triple, quadruple, quintuple, or sextuple mutation variant having substitutions at positions selected from the group consisting of 102, 154, 160, 183, and 211;

g. when a substitution occurs at position 158, the substituting amino acid is Asp or Glu; but when position 158 is substituted the variant is not a double, triple, quadruple, quintuple, or sextuple mutation variant having substitutions at positions from the group consisting of 102, 154, 160, 183, and 211;

h. when a substitution occurs at position 159, the substituting amino acid is Ala, Asn, Asp, Cys, Gln, Glu, Gly, His, Leu, Met, Pro, Ser, Thr or Val; but when position 159 is substituted with Leu, the variant is not a double mutation variant having a substitution at position 158 with Glu; and when position 159 is substituted the variant is not a double, triple, quadruple, quintuple, or sextuple mutation variant having substitutions at positions selected from the group consisting of 102, 154, 160, 183, and 211;

i. when a substitution occurs at position 160, the substituting amino acid is Asp or Glu; but when position 160 is substituted the variant is not a double mutation variant having a substitution at position 60 with Asp or Glu; and j. when a substitution occurs at position 161, the substituting amino acid is Ala, Asn, Asp, Cys, Gln, Glu, Gly, His, Ile, Leu, Met, Pro, Ser, Thr or Val; but when position 161 is substituted the variant is not a double, triple, quadruple, quintuple, or sextuple mutation variant having substitutions at positions selected from the group consisting of 120, 154, 160, 183, and 211;

E. when a substitution occurs in the fifth loop region, the substitution occurs at one or more of positions 181, 182, 183, 184 or 185; wherein a. when a substitution occurs at position 181, the substituting amino acid is Asn, Asp, Gln, Glu, Gly, His, Pro, Ser or Thr;

b. when a substitution occurs at position 182, the substituting amino acid is Asp or Glu;

c. when a substitution occurs at position 183, the substituting amino acid is Ala, Asn, Asp, Cys, Gln, Glu, Gly, His, Ile, Leu, Met, Pro, Ser, Thr, Tyr or Val;

d. when a substitution occurs at position 184, the substituting amino acid is Asp or Glu; and e. when a substitution occurs at position 185, the substituting amino acid is Asn, Asp, Glu or Ser; and F. when the substitution occurs in the sixth loop region, the substitution occurs at one of positions 194, 195, 196, 197, 198, 199, 200, 201, 202, 203, 204, 205, 207, 208, 209, 211 or 214; wherein a. when a substitution occurs at position 194, the substituting amino acid is His, Thr, Pro, Gly, Gln, Asn, Ser, Asp or Gln;

b. when a substitution occurs at position 195, the substituting amino acid is Gly, Gln, Asn, Ser, Asp or Glu;

c. when a substitution occurs at position 196, the substituting amino acid is Pro, Gln, Asn, Ser, Asp or Glu;

d. when a substitution occurs at position 197, the substituting amino acid is Met, Cys, Ala, His, Pro, Gly, Gln or Ser;

e. when a substitution occurs at position 199, the substituting amino acid is Met, Cys, Ala, His, Pro, Gly, Gln, Asn or Ser;

f. when a substitution occurs at position 200, the substituting amino acid is Asn or Ser;

g. when a substitution occurs at position 201, the substituting amino acid is Asp or Glu;

h. when a substitution occurs at position 202, the substituting amino acid is Pro, Gly, Gln, Asn, Ser, Asp or Glu;

i. when a substitution occurs at position 203, the substituting amino acid is Ile, Met, Ala, His, Pro, Gln, Asn or Ser;

j. when a substitution occurs at position 204, the substituting amino acid is Gly, Gln, Asn or Ser;

k. when a substitution occurs at position 205, the substituting amino acid is Pro, Gln, Asn or Ser;

l. when a substitution occurs at position 207, the substituting amino acid is Pro, Gly, Gln, Asn or Ser; but when position 207 is substituted the variant is not a double, triple, quadruple, quintuple, sextuple, or septuple mutation variant having substitutions at positions selected from the group consisting of 102, 153, 154, 160, 183, and 211;

m. when a substitution occurs at position 208, the substituting amino acid is Leu, Ile, Met, Cys, Ala, His, Pro, Gly, Gln or Asn; but when position 208 is substituted the variant is not a double, triple, quadruple, quintuple, sextuple, or septuple mutation variant having a substitutions at positions selected from the group consisting of 102, 153, 154, 160, 183, and 211;

n. when a substitution occurs at position 209, the substituting amino acid is His, Thr, Pro, Gly, Gln, Asn or Ser; but when position 209 is substituted the variant is not a double, triple, quadruple, quintuple, sextuple, or septuple mutation variant having substitutions at positions selected from the group consisting of 102, 153, 154, 160, 183, and 211;

o. when a substitution occurs at position 211, the substituting amino acid is Ile, Val, met, Cys, Ala, His, Thr, Pro, Gly, Gln, Asn or Ser; and p. when a substitution occurs at position 214, the substituting amino acid is Pro, Gly, Gln, Asn, Asp, Ser or Glu;

whereby the subtilisin 309 variant has decreased adsorption to, and increased hydrolysis of, an insoluble substrate as compared to wild-type subtilisin 309.

68. The subtilisin 309 variant of claim 67, wherein two or more substitutions occur in the sixth loop region.

69. The subtilisin 309 variant of claim 67, wherein two or more substitutions occur in the third loop region.

70. The subtilisin 309 variant of claim 67, wherein two or more substitutions occur in the second loop region.

71. The subtilisin 309 variant of claim 67, wherein two or more substitutions occur in the third loop region.

72. The subtilisin 309 variant of claim 67, wherein two or more substitutions occur in the fourth loop region.

73. The subtilisin 309 variant of claim 67, wherein two or more substitutions occur in the fifth loop region.

74. A clearing composition selected from the group consisting of a hard surface cleaning composition, a detergent composition for cleaning fabrics, a dishwashing composition, an oral cleaning composition, a denture cleaning composition and a contact lens cleaning composition, wherein the cleaning composition comprises the subtilisin 309 variant of claim 1 and a cleaning composition carrier.

75. A hard surface cleaning composition comprising the subtilisin 309 variant of claim 1 and a hard surface cleaning carrier.

76. A detergent composition for cleaning fabrics comprising the subtilisin 309 variant of claim 1 and one or more cleaning composition materials compatable with the subtilisin 309 variant.

77. A cleaning composition selected from the group consisting of a hard surface cleaning composition, a detergent composition for cleaning fabrics, a dishwashing composition, an oral cleaning composition, a denture cleansing composition and a contact lens cleaning composition, wherein the cleaning composition comprises the subtilisin 309 variant of claim 7 and a cleaning composition carrier.

78. A hard surface cleaning composition comprising the subtilisin 309 variant of claim 7 and a hard surface cleaning carrier.

79. A detergent composition for cleaning fabrics comprising the subtilisin 309 variant of claim 7 and one or more cleaning composition materials compatable ti the subtilisin 309 variant.

80. A cleaning composition selected from the group consisting of a hard surface cleaning composition, a detergent composition for cleaning fabrics a dishwashing composition, an oral cleaning composition, a denture cleaning composition and a contact lens cleaning composition, wherein the cleaning composition comprises the subtilisin 309 variant of claim 13 and a cleaning composition carrier.

81. A hard surface cleaning composition comprising the subtilisin 309 variant of claim 13 and a hard surface cleaning carrier.

82. A detergent composition for cleaning fabrics comprising the subtilisin 309 variant of claim 13 and one or more cleaning composition materials compatible with the subtilisin 309 variant.

83. A cleaning composition selected from the group consisting of a hard surface cleaning composition, a dishwashing composition, an oral cleaning composition, a denture cleaning composition, a contact lens cleaning composition and a fabric cleaning composition, wherein the cleaning composition comprises the subtilisin 309 variant of claim 19, and a cleaning composition carrier.

84. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the subtilisin 309 variant of claim 20 and a cleaning composition carrier.

85. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the subtilisin 309 variant of claim 33 and a cleaning composition carrier.

86. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the subtilisin 309 variant of claim 40 and a cleaning composition carrier.

87. A cleaning composition selected from the group consisting of hard surface cleaning composition, a dishwashing composition, an oral cleaning composition, a denture cleansing composition, a contact lens cleaning composition and a fabric cleaning composition, wherein the cleaning composition comprises the subtilisin 309 variant of claim 47 and a cleaning composition carrier.

88. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the subtilisin 309 variant of claim 54 and a cleaning composition carrier.

89. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the subtilisin 309 variant of claim 60 and a cleaning composition carrier.

90. A cleaning composition selected from the group consisting of a hard surface cleaning composition, a dishwashing composition, an oral cleaning composition, a denture cleansing composition, a contact lens cleaning composition and a fabric cleaning composition, wherein the cleaning composition comprises the subtilisin 309 variant of claim 67 and a cleaning composition carrier.

91. A n-isolated DNA sequence encoding the subtilisin 309 variant of claim 1.

92. A n-isolated DNA sequence encoding the subtilisin 309 variant of claim 7.

93. A n-isolated DNA sequence encoding the subtilisin 309 variant of claim 13.

94. An isolated DNA sequence encoding the subtilisin 309 variant of claim 26.

* * * * *